US009102759B2

(12) United States Patent
Pieczykolan et al.

(10) Patent No.: US 9,102,759 B2
(45) Date of Patent: Aug. 11, 2015

(54) ANTICANCER FUSION PROTEIN COMPRISING TRAIL

(75) Inventors: Jerzy Szczepan Pieczykolan, Radecznica (PL); Sebastian Pawlak, Warsaw (PL); Bartlomiej Zerek, Dabrowa (PL); Krzysztof Kazimierz Lemke, Gdynia (PL)

(73) Assignee: ADAMED SP. Z O.O., Czosnow k/Warszawy (PL)

(*) Notice: Subject to any disclaimer, the term of this patent is extended or adjusted under 35 U.S.C. 154(b) by 98 days.

(21) Appl. No.: 13/806,072

(22) PCT Filed: Jun. 24, 2011

(86) PCT No.: PCT/EP2011/060666
§ 371 (c)(1), (2), (4) Date: Mar. 7, 2013

(87) PCT Pub. No.: WO2011/161260
PCT Pub. Date: Dec. 29, 2011

(65) Prior Publication Data
US 2013/0164254 A1 Jun. 27, 2013

(30) Foreign Application Priority Data
Jun. 25, 2010 (PL) ........................................ 391627

(51) Int. Cl.

| | |
|---|---|
| ***C07K 14/47*** | (2006.01) |
| ***C07K 14/525*** | (2006.01) |
| ***A61K 38/00*** | (2006.01) |
| ***A61K 38/16*** | (2006.01) |
| ***A61K 38/17*** | (2006.01) |
| ***A61K 38/19*** | (2006.01) |
| ***A61K 38/43*** | (2006.01) |
| ***C07K 19/00*** | (2006.01) |
| ***C07K 14/705*** | (2006.01) |
| ***C12N 9/10*** | (2006.01) |
| ***C07K 14/80*** | (2006.01) |
| ***C07K 14/00*** | (2006.01) |
| ***C07K 7/06*** | (2006.01) |
| ***C07K 7/08*** | (2006.01) |
| ***C12N 9/50*** | (2006.01) |
| ***C07K 14/52*** | (2006.01) |

(52) U.S. Cl.
CPC ........... *C07K 14/70575* (2013.01); *A61K 38/19* (2013.01); *A61K 38/191* (2013.01); *C07K 7/06* (2013.01); *C07K 7/08* (2013.01); *C07K 14/00* (2013.01); *C07K 14/47* (2013.01); *C07K 14/4747* (2013.01); *C07K 14/52* (2013.01); *C07K 14/525* (2013.01); *C07K 14/80* (2013.01); *C12N 9/10* (2013.01); *C12N 9/50* (2013.01); *A61K 38/17* (2013.01); *A61K 38/43* (2013.01); *C07K 2319/00* (2013.01); *C07K 2319/01* (2013.01); *C07K 2319/036* (2013.01); *C07K 2319/04* (2013.01); *C07K 2319/07* (2013.01); *C07K 2319/09* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 6,284,236 | B1 * | 9/2001 | Wiley et al. | 424/85.1 |
| 6,962,696 | B1 * | 11/2005 | Bermudes et al. | 424/93.4 |
| 8,039,437 | B2 * | 10/2011 | Tykocinski et al. | 514/12.2 |

OTHER PUBLICATIONS

Wu et al. Regression of human mammary adenocarcinoma by systemic administration of a recombinant gene encoding the hFLEX-TRAIL fusion protein.Mol Therapy 3(3): 368-374, 2001.*

Pieczykolan et al. TRAIL\Apo2L-Smac\Diablo fusion molecule with high cytotoxic activity against cancer cells. Eur J Cancer 48 (Suppl 2): p. 29, abstract #91, 2012.*

Pieczykolan et al. Novel chimeric TRAIL-based protein overcomes resistance to TRAIL-induced apoptosis in cancer cells in vitro and in vivo by activation of mitochondrial pathway of apoptosis independently of TRAIL. Eur J Cancer 48 (Suppl 2): p. 29, abstract #92.*

Pieczykolan et al. TRAIL/Apo2L resistant cancer cells can be sensitized to TRAIL by targeted delivery of peptides derived from BH3 domain of human Bid. Eur J Cancer 49 (Suppl 2): p. S108, #538, Sep. 2013.*

Pieczykolan et al. AD-O53.2—a novel recombinant fusion protein combining the activities of TRAIL/Apo2L and Smac/Diablo, overcomes resistance of human cancer cells to TRAIL/Apo2L. Invest New Drugs, 12 pages, Sep. 2014.*

Abdulghani et al. TRAIL receptor signaling and therapeutics. Expert Opin Ther Targets 14(10): 1091-1108, 2010.*

Ashkenazi et al. Ligand-based targeting of apoptosis in cancer: the potential of recombinant human apoptosis ligand 2/tumor necrosis factor-related apoptosis-inducing ligand (rhApo2L/TRAIL). J Clin Oncol 26(21): 3621-3630, 2008.*

PCT International Patent Application Publication No. W0 2010/005519 A1, (University of Pennsylvania), published Jan. 14, 2010.

(Continued)

*Primary Examiner* — Bridget E Bunner
(74) *Attorney, Agent, or Firm* — Gary J. Gershik; Cooper & Dunham LLP

(57) ABSTRACT

The fusion protein, especially recombinant, comprising domain (a) which is a functional fragment of soluble hTRAIL protein sequence beginning with an amino acid at a position not lower than hTRAIL95 or a sequence having at least 70% homology thereto; and domain (b) which is a sequence of pro-apoptotic effector peptide, wherein the sequence of domain (b) is attached at C-terminus and/or N-terminus of domain (a). The fusion protein has anticancer activity. The nucleotide sequence coding the fusion protein, expression vector and host cell for the preparation of the fusion protein, and the use of the fusion protein for treating cancer diseases.

20 Claims, 16 Drawing Sheets

(56) References Cited

OTHER PUBLICATIONS

International Search Report issued by the International Searching Authority (ISA/O.E.P.M.) on Sep. 29, 2011 in connection with International Application No. PCT/EP2011/060666.
Written Opinion of the International Searching Authority issued on Sep. 29, 2011 in connection with International Application No. PCT/EP2011/060666.
EP 0 835 305 B1 (Immunex corp [US]) Nov. 23, 2005.
Dong F. et al., "Degradation of the proapoptotic proteins Bik, Puma, and Bim with Bcl-2 doamin 3 homology in *Chlamydia trachomatis*-infected cells", Infection and Immunity, vol. 73, No. 3, (2005), pp. 1861-1864.
Fulda S. et al., "Extrinsic versus intrinsic apaptosis pathways in anticancer chemotherapy", Oncogene, vol. 25, No. 34, (2006), pp. 4789-8411.
Kruyt et al., "Trail and cancer therapy", Cancer letters, New York, NY, US, 263, No. 1., (2008), pp. 14-25.
Reed, J.C., "Proapoptotic multidomain Bcl-2/Bax-family proteins: mechanisms, physiological roles, and therapeutic opportunities", Cell Death and Differentiation, vol. 13, No. 8, (2006), pp. 1378-1386.
Zhang, H.M. et al., "BNips: A group of pro-apoptotic proteins in the Ccl-2 family", Apoptosis, vol. 8, No. 3, (2003), pp. 229-236.
Zhang, H-Y at al., "Tumor-targeted delivery of biologically active TRAIL protein", Cancer Gene Therapy, vol. 17, No. 5, (2010), pp. 334-343.

* cited by examiner

Ex. 1

Ex. 2

Ex. 3

Ex. 4

Ex. 5

Ex. 6

Ex. 7

Ex. 8

Ex. 9

Ex. 10

Ex. 16

Ex. 17

Ex. 18

Ex. 19

Ex. 20

Ex. 21

Ex. 22

Ex. 23

Ex. 24

Ex. 25

Ex. 26

Ex. 27 459 aa

213 aa

Ex. 28

204 aa

Ex. 29

205 aa

Ex. 30

207 aa

Ex. 31

247 aa

Ex. 37

212 aa

Ex. 38

221 aa

Ex. 39

435 aa

Ex.40

580 aa

Ex. 41 rhTRAIL114-281

Ex. 24

Ex. 2

EX. 1

Ex. 42

Ex. 14

Ex. 51

SEQUENCE LISTING

```
<160> NUMBER OF SEQ ID NOS: 186

<210> SEQ ID NO 1
<211> LENGTH: 194
<212> TYPE: PRT
<213> ORGANISM: Artificial Sequence
<220> FEATURE:
<223> OTHER INFORMATION: synthesized, fusion protein comprising fragment
      of TRAIL protein, peptide derived from the BH3 domain of Bax
      protein, polyarginine sequence and fragments recognized by
      urokinase and metalloprotease MMP

<400> SEQUENCE: 1

Lys Lys Leu Ser Glu Cys Leu Lys Arg Ile Gly Asp Glu Leu Asp Ser
1               5                   10                  15

Arg Arg Arg Arg Arg Arg Arg Arg Val Val Arg Pro Leu Gly Leu Ala
            20                  25                  30

Gly Arg Val Ala Ala His Ile Thr Gly Thr Arg Gly Arg Ser Asn Thr
        35                  40                  45

Leu Ser Ser Pro Asn Ser Lys Asn Glu Lys Ala Leu Gly Arg Lys Ile
    50                  55                  60

Asn Ser Trp Glu Ser Ser Arg Ser Gly His Ser Phe Leu Ser Asn Leu
65                  70                  75                  80

His Leu Arg Asn Gly Glu Leu Val Ile His Glu Lys Gly Phe Tyr Tyr
                85                  90                  95

Ile Tyr Ser Gln Thr Tyr Phe Arg Phe Gln Glu Glu Ile Lys Glu Asn
            100                 105                 110

Thr Lys Asn Asp Lys Gln Met Val Gln Tyr Ile Tyr Lys Tyr Thr Ser
        115                 120                 125

Tyr Pro Asp Pro Ile Leu Leu Met Lys Ser Ala Arg Asn Ser Cys Trp
    130                 135                 140
```

Ser Lys Asp Ala Glu Tyr Gly Leu Tyr Ser Ile Tyr Gln Gly Gly Ile
145 150 155 160

Phe Glu Leu Lys Glu Asn Asp Arg Ile Phe Val Ser Val Thr Asn Glu
165 170 175

His Leu Ile Asp Met Asp His Glu Ala Ser Phe Phe Gly Ala Phe Leu
180 185 190

Val Gly

<210> SEQ ID NO 2
<211> LENGTH: 193
<212> TYPE: PRT
<213> ORGANISM: Artificial Sequence
<220> FEATURE:
<223> OTHER INFORMATION: synthesized, comprising a fragment of TRAIL protein, peptide derived from the Bid protein, polyarginine sequence and fragments recognized by urokinase and metalloproteinase

<400> SEQUENCE: 2

Arg Asn Ile Ala Arg His Leu Ala Gln Val Gly Asp Ser Met Asp Arg
1 5 10 15

Arg Arg Arg Arg Arg Arg Arg Val Val Arg Pro Leu Gly Leu Ala Gly
20 25 30

Arg Val Ala Ala His Ile Thr Gly Thr Arg Gly Arg Ser Asn Thr Leu
35 40 45

Ser Ser Pro Asn Ser Lys Asn Glu Lys Ala Leu Gly Arg Lys Ile Asn
50 55 60

Ser Trp Glu Ser Ser Arg Ser Gly His Ser Phe Leu Ser Asn Leu His
65 70 75 80

Leu Arg Asn Gly Glu Leu Val Ile His Glu Lys Gly Phe Tyr Tyr Ile
85 90 95

Tyr Ser Gln Thr Tyr Phe Arg Phe Gln Glu Glu Ile Lys Glu Asn Thr
100 105 110

Lys Asn Asp Lys Gln Met Val Gln Tyr Ile Tyr Lys Tyr Thr Ser Tyr
115 120 125

Pro Asp Pro Ile Leu Leu Met Lys Ser Ala Arg Asn Ser Cys Trp Ser
130 135 140

Lys Asp Ala Glu Tyr Gly Leu Tyr Ser Ile Tyr Gln Gly Gly Ile Phe
145 150 155 160

Glu Leu Lys Glu Asn Asp Arg Ile Phe Val Ser Val Thr Asn Glu His
165 170 175

Leu Ile Asp Met Asp His Glu Ala Ser Phe Phe Gly Ala Phe Leu Val
180 185 190

Gly

<210> SEQ ID NO 3
<211> LENGTH: 303
<212> TYPE: PRT
<213> ORGANISM: Artificial Sequence
<220> FEATURE:
<223> OTHER INFORMATION: synthesized, comprising a fragment of TRAIL protein, homologue of ribonuclease RNase A, fragments recognized by urokinase and metalloproteinase, and a sequence directing to the endoplasmic reticulum

<400> SEQUENCE: 3

Arg Val Ala Ala His Ile Thr Gly Thr Arg Gly Arg Ser Asn Thr Leu
1 5 10 15

Ser Ser Pro Asn Ser Lys Asn Glu Lys Ala Leu Gly Arg Lys Ile Asn

```
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Ser Gly Pro Leu Gly Leu Ala Gly Arg Val Val Arg Lys
                165                 170                 175

Glu Thr Ala Ala Ala Lys Phe Glu Arg Gln His Met Asp Ser Ser Thr
            180                 185                 190

Ser Ala Ala Ser Ser Ser Asn Tyr Cys Asn Gln Met Met Lys Ser Arg
        195                 200                 205

Asn Leu Thr Lys Asp Arg Cys Lys Pro Val Asn Thr Phe Val His Glu
    210                 215                 220

Ser Leu Ala Asp Val Gln Ala Val Cys Ser Gln Lys Asn Val Ala Cys
225                 230                 235                 240

Lys Asn Gly Gln Thr Asn Cys Tyr Gln Ser Tyr Ser Thr Met Ser Ile
                245                 250                 255

Thr Asp Cys Arg Glu Thr Gly Ser Ser Lys Tyr Pro Asn Cys Ala Tyr
            260                 265                 270

Lys Thr Thr Gln Ala Asn Lys His Ile Ile Val Ala Cys Glu Gly Asn
        275                 280                 285

Pro Tyr Val Pro Val His Phe Asp Ala Ser Val Lys Glu Asp Leu
    290                 295                 300


<210> SEQ ID NO 4
<211> LENGTH: 293
<212> TYPE: PRT
<213> ORGANISM: Artificial Sequence
<220> FEATURE:
<223> OTHER INFORMATION: synthesized, fusion protein comprising a
      fragment of TRAIL protein, a homologue of ribonuclease RNase A
      and a steric linker

<400> SEQUENCE: 4

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80
```

```
Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Ser Gly Gly Gly Ser Lys Glu Thr Ala Ala Ala Lys
                165                 170                 175

Phe Glu Arg Gln His Met Asp Ser Ser Thr Ser Ala Ala Ser Ser Ser
            180                 185                 190

Asn Tyr Cys Asn Gln Met Met Lys Ser Arg Asn Leu Thr Lys Asp Arg
        195                 200                 205

Cys Lys Pro Val Asn Thr Phe Val His Glu Ser Leu Ala Asp Val Gln
    210                 215                 220

Ala Val Cys Ser Gln Lys Asn Val Ala Cys Lys Asn Gly Gln Thr Asn
225                 230                 235                 240

Cys Tyr Gln Ser Tyr Ser Thr Met Ser Ile Thr Asp Cys Arg Glu Thr
                245                 250                 255

Gly Ser Ser Lys Tyr Pro Asn Cys Ala Tyr Lys Thr Thr Gln Ala Asn
            260                 265                 270

Lys His Ile Ile Val Ala Cys Glu Gly Asn Pro Tyr Val Pro Val His
        275                 280                 285

Phe Asp Ala Ser Val
    290


<210> SEQ ID NO 5
<211> LENGTH: 283
<212> TYPE: PRT
<213> ORGANISM: Artificial Sequence
<220> FEATURE:
<223> OTHER INFORMATION: synthesized, fusion protein comprising a
      fragment of TRAIL protein, a sequence of cytochrome C, sequences
      recognized by metalloprotease MMP and urokinase, a steric linker
      and a sequence directing to the endoplasmic reticulum

<400> SEQUENCE: 5

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125
```

```
Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Ser Gly Pro Leu Gly Leu Ala Gly Arg Val Val Arg Gly
                165                 170                 175

Asp Val Glu Lys Gly Lys Lys Ile Phe Ile Met Lys Cys Ser Gln Cys
            180                 185                 190

His Thr Val Glu Lys Gly Gly Lys His Lys Thr Gly Pro Asn Leu His
        195                 200                 205

Gly Leu Phe Gly Arg Lys Thr Gly Gln Ala Pro Gly Tyr Ser Tyr Thr
    210                 215                 220

Ala Ala Asn Lys Asn Lys Gly Ile Ile Trp Gly Glu Asp Thr Leu Met
225                 230                 235                 240

Glu Tyr Leu Glu Asn Pro Lys Lys Tyr Ile Pro Gly Thr Lys Met Ile
                245                 250                 255

Phe Val Gly Ile Lys Lys Lys Glu Glu Arg Ala Asp Leu Ile Ala Tyr
            260                 265                 270

Leu Lys Lys Ala Thr Asn Glu Lys Glu Asp Leu
        275                 280


<210> SEQ ID NO 6
<211> LENGTH: 407
<212> TYPE: PRT
<213> ORGANISM: Artificial Sequence
<220> FEATURE:
<223> OTHER INFORMATION: synthesized, fusion protein comprising a
      fragment of TRAIL protein, a sequence of cytochrome C, a sequence
      recognized by furin, steric linker, a sequence directing to the
      endoplasmic reticulum and translocation domain from Pseudomonas
      aeruginosa

<400> SEQUENCE: 6

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Ser Arg Lys Lys Arg Ala Ser Gly Gly Pro Glu Gly
                165                 170                 175

Gly Ser Leu Ala Ala Leu Thr Ala His Gln Ala Cys His Leu Pro Leu
```

```
            180                 185                 190

Glu Thr Phe Thr Arg His Arg Gln Pro Arg Gly Trp Glu Gln Leu Glu
        195                 200                 205

Gln Cys Gly Tyr Pro Val Gln Arg Leu Val Ala Leu Tyr Leu Ala Ala
    210                 215                 220

Arg Leu Ser Trp Asn Gln Val Asp Gln Val Ile Ala Asn Ala Leu Ala
225                 230                 235                 240

Ser Pro Gly Ser Gly Gly Asp Leu Gly Glu Ala Ile Arg Glu Ser Pro
                245                 250                 255

Glu Gln Ala Arg Leu Ala Leu Thr Leu Ala Ala Ala Glu Ser Glu Arg
            260                 265                 270

Phe Val Arg Gln Gly Thr Gly Asn Asp Glu Ala Gly Ala Ala Asn Gly
        275                 280                 285

Pro Ala Asp Gly Gly Gly Ser Gly Gly Gly Met Gly Asp Val Glu Lys
    290                 295                 300

Gly Lys Lys Ile Phe Ile Met Lys Cys Ser Gln Cys His Thr Val Glu
305                 310                 315                 320

Lys Gly Gly Lys His Lys Thr Gly Pro Asn Leu His Gly Leu Phe Gly
                325                 330                 335

Arg Lys Thr Gly Gln Ala Pro Gly Tyr Ser Tyr Thr Ala Ala Asn Lys
            340                 345                 350

Asn Lys Gly Ile Ile Trp Gly Glu Asp Thr Leu Met Glu Tyr Leu Glu
        355                 360                 365

Asn Pro Lys Lys Tyr Ile Pro Gly Thr Lys Met Ile Phe Val Gly Ile
    370                 375                 380

Lys Lys Lys Glu Glu Arg Ala Asp Leu Ile Ala Tyr Leu Lys Lys Ala
385                 390                 395                 400

Thr Asn Glu Lys Asp Glu Leu
                405


<210> SEQ ID NO 7
<211> LENGTH: 409
<212> TYPE: PRT
<213> ORGANISM: Artificial Sequence
<220> FEATURE:
<223> OTHER INFORMATION: synthesized, fusion protein comprising a
      fragment of TRAIL protein, a sequence of granzyme B, a sequence
      recognized by furin and sequences of steric linkers

<400> SEQUENCE: 7

Ile Ile Gly Gly His Val Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125
```

```
Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Gly Gly Gly Gly Ser Arg Lys Lys Arg Gly Gly Gly Gly
225                 230                 235                 240

Ser Val Arg Glu Arg Gly Pro Gln Arg Val Ala Ala His Ile Thr Gly
                245                 250                 255

Thr Arg Gly Arg Ser Asn Thr Leu Ser Ser Pro Asn Ser Lys Asn Glu
            260                 265                 270

Lys Ala Leu Gly Arg Lys Ile Asn Ser Trp Glu Ser Ser Arg Ser Gly
        275                 280                 285

His Ser Phe Leu Ser Asn Leu His Leu Arg Asn Gly Glu Leu Val Ile
    290                 295                 300

His Glu Lys Gly Phe Tyr Tyr Ile Tyr Ser Gln Thr Tyr Phe Arg Phe
305                 310                 315                 320

Gln Glu Glu Ile Lys Glu Asn Thr Lys Asn Asp Lys Gln Met Val Gln
                325                 330                 335

Tyr Ile Tyr Lys Tyr Thr Ser Tyr Pro Asp Pro Ile Leu Leu Met Lys
            340                 345                 350

Ser Ala Arg Asn Ser Cys Trp Ser Lys Asp Ala Glu Tyr Gly Leu Tyr
        355                 360                 365

Ser Ile Tyr Gln Gly Gly Ile Phe Glu Leu Lys Glu Asn Asp Arg Ile
    370                 375                 380

Phe Val Ser Val Thr Asn Glu His Leu Ile Asp Met Asp His Glu Ala
385                 390                 395                 400

Ser Phe Phe Gly Ala Phe Leu Val Gly
                405


<210> SEQ ID NO 8
<211> LENGTH: 405
<212> TYPE: PRT
<213> ORGANISM: Artificial Sequence
<220> FEATURE:
<223> OTHER INFORMATION: synthesized, fusion protein comprising a
      fragment of TRAIL protein, a sequence of granzyme B, a sequence
      recognized by furin, sequences of steric linkers and a sequence
      directing to the endoplasmic reticulum

<400> SEQUENCE: 8

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60
```

```
Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Ser Arg Lys Lys Arg Gly Gly Gly Gly Ser Ile Ile
                165                 170                 175

Gly Gly His Val Ala Lys Pro His Ser Arg Pro Tyr Met Ala Tyr Leu
            180                 185                 190

Met Ile Trp Asp Gln Lys Ser Leu Lys Arg Cys Gly Gly Phe Leu Ile
        195                 200                 205

Arg Asp Asp Phe Val Leu Thr Ala Ala His Cys Trp Gly Ser Ser Ile
    210                 215                 220

Asn Val Thr Leu Gly Ala His Asn Ile Lys Glu Gln Glu Pro Thr Gln
225                 230                 235                 240

Gln Phe Ile Pro Val Lys Arg Ala Ile Pro His Pro Ala Tyr Asn Pro
                245                 250                 255

Lys Asn Phe Ser Asn Asp Ile Met Leu Leu Gln Leu Glu Arg Lys Ala
            260                 265                 270

Lys Arg Thr Arg Ala Val Gln Pro Leu Arg Leu Pro Ser Asn Lys Ala
        275                 280                 285

Gln Val Lys Pro Gly Gln Thr Cys Ser Val Ala Gly Trp Gly Gln Thr
    290                 295                 300

Ala Pro Leu Gly Lys His Ser His Thr Leu Gln Glu Val Lys Met Thr
305                 310                 315                 320

Val Gln Glu Asp Arg Lys Cys Glu Ser Asp Leu Arg His Tyr Tyr Asp
                325                 330                 335

Ser Thr Ile Glu Leu Cys Val Gly Asp Pro Glu Ile Lys Lys Thr Ser
            340                 345                 350

Phe Lys Gly Asp Ser Gly Gly Pro Leu Val Cys Asn Lys Val Ala Gln
        355                 360                 365

Gly Ile Val Ser Tyr Gly Arg Asn Asn Gly Met Pro Pro Arg Ala Cys
    370                 375                 380

Thr Lys Val Ser Ser Phe Val His Trp Ile Lys Lys Thr Met Lys Arg
385                 390                 395                 400

Tyr Lys Asp Glu Leu
                405
```

<210> SEQ ID NO 9
<211> LENGTH: 187
<212> TYPE: PRT
<213> ORGANISM: Artificial Sequence
<220> FEATURE:
<223> OTHER INFORMATION: synthesized, fusion protein comprising a fragment of TRAIL protein, a peptide derived from Nur77 protein, a polyarginine sequence and sequences recognized by metalloprotease and urokinase

<400> SEQUENCE: 9

```
Phe Ser Arg Ser Leu His Ser Leu Leu Arg Arg Arg Arg Arg Arg Arg
1               5                   10                  15

Arg Val Val Arg Pro Leu Gly Leu Ala Gly Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185


<210> SEQ ID NO 10
<211> LENGTH: 193
<212> TYPE: PRT
<213> ORGANISM: Artificial Sequence
<220> FEATURE:
<223> OTHER INFORMATION: synthesized, fusion protein comprising a
      fragment of TRAIL protein, a peptide containing the BH3 domain
      of Bak, a polyarginine sequence and sequences recognized by
      metalloprotease and urokinase

<400> SEQUENCE: 10

Gly Gln Val Gly Arg Gln Leu Ala Ile Ile Gly Asp Asp Ile Asn Arg
1               5                   10                  15

Arg Arg Arg Arg Arg Arg Arg Val Val Arg Pro Leu Gly Leu Ala Gly
            20                  25                  30

Arg Val Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
    130                 135                 140

Lys Asp Ala Glu Tyr Gly Leu Tyr Ser Ile Tyr Gln Gly Gly Ile Phe
145                 150                 155                 160
```

```
Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

Gly
```

<210> SEQ ID NO 11
<211> LENGTH: 204
<212> TYPE: PRT
<213> ORGANISM: Artificial Sequence
<220> FEATURE:
<223> OTHER INFORMATION: synthesized, fusion protein comprising a fragment of TRAIL protein, a BH3 domain of the PUMA/BBC3, a polyarginine sequence and sequences recognized by metalloprotease and urokinase

<400> SEQUENCE: 11

```
Glu Glu Gln Trp Ala Arg Glu Ile Gly Ala Gln Leu Arg Arg Met Ala
1               5                   10                  15

Asp Asp Leu Asn Ala Gln Tyr Glu Arg Arg Arg Arg Arg Arg Arg Arg
            20                  25                  30

Arg Arg Val Val Arg Pro Leu Gly Leu Ala Gly Arg Val Ala Ala His
        35                  40                  45

Ile Thr Gly Thr Arg Gly Arg Ser Asn Thr Leu Ser Ser Pro Asn Ser
    50                  55                  60

Lys Asn Glu Lys Ala Leu Gly Arg Lys Ile Asn Ser Trp Glu Ser Ser
65                  70                  75                  80

Arg Ser Gly His Ser Phe Leu Ser Asn Leu His Leu Arg Asn Gly Glu
                85                  90                  95

Leu Val Ile His Glu Lys Gly Phe Tyr Tyr Ile Tyr Ser Gln Thr Tyr
            100                 105                 110

Phe Arg Phe Gln Glu Glu Ile Lys Glu Asn Thr Lys Asn Asp Lys Gln
        115                 120                 125

Met Val Gln Tyr Ile Tyr Lys Tyr Thr Ser Tyr Pro Asp Pro Ile Leu
    130                 135                 140

Leu Met Lys Ser Ala Arg Asn Ser Cys Trp Ser Lys Asp Ala Glu Tyr
145                 150                 155                 160

Gly Leu Tyr Ser Ile Tyr Gln Gly Gly Ile Phe Glu Leu Lys Glu Asn
                165                 170                 175

Asp Arg Ile Phe Val Ser Val Thr Asn Glu His Leu Ile Asp Met Asp
            180                 185                 190

His Glu Ala Ser Phe Phe Gly Ala Phe Leu Val Gly
        195                 200
```

<210> SEQ ID NO 12
<211> LENGTH: 372
<212> TYPE: PRT
<213> ORGANISM: Artificial Sequence
<220> FEATURE:
<223> OTHER INFORMATION: synthesized, fusion protein comprising a fragment of TRAIL protein, a PUMA protein, sequences recognized by metalloprotease and urokinase, a sequence directing to endoplasmic reticulum and a flexible linker

<400> SEQUENCE: 12

```
Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30
```

Ser Trp Glu Ser Ser Arg Ser Gly His Ser Phe Leu Ser Asn Leu His
35 40 45

Leu Arg Asn Gly Glu Leu Val Ile His Glu Lys Gly Phe Tyr Tyr Ile
50 55 60

Tyr Ser Gln Thr Tyr Phe Arg Phe Gln Glu Glu Ile Lys Glu Asn Thr
65 70 75 80

Lys Asn Asp Lys Gln Met Val Gln Tyr Ile Tyr Lys Tyr Thr Ser Tyr
85 90 95

Pro Asp Pro Ile Leu Leu Met Lys Ser Ala Arg Asn Ser Cys Trp Ser
100 105 110

Lys Asp Ala Glu Tyr Gly Leu Tyr Ser Ile Tyr Gln Gly Gly Ile Phe
115 120 125

Glu Leu Lys Glu Asn Asp Arg Ile Phe Val Ser Val Thr Asn Glu His
130 135 140

Leu Ile Asp Met Asp His Glu Ala Ser Phe Phe Gly Ala Phe Leu Val
145 150 155 160

Gly Gly Gly Ser Gly Gly Pro Leu Gly Leu Ala Gly Arg Val Val Arg
165 170 175

Ala Arg Ala Arg Gln Glu Gly Ser Ser Pro Glu Pro Val Glu Gly Leu
180 185 190

Ala Arg Asp Gly Pro Arg Pro Phe Pro Leu Gly Arg Leu Val Pro Ser
195 200 205

Ala Val Ser Cys Gly Leu Cys Glu Pro Gly Leu Ala Ala Ala Pro Ala
210 215 220

Ala Pro Thr Leu Leu Pro Ala Ala Tyr Leu Cys Ala Pro Thr Ala Pro
225 230 235 240

Pro Ala Val Thr Ala Ala Leu Gly Gly Ser Arg Trp Pro Gly Gly Pro
245 250 255

Arg Ser Arg Pro Arg Gly Pro Arg Pro Asp Gly Pro Gln Pro Ser Leu
260 265 270

Ser Leu Ala Glu Gln His Leu Glu Ser Pro Val Pro Ser Ala Pro Gly
275 280 285

Ala Leu Ala Gly Gly Pro Thr Gln Ala Ala Pro Gly Val Arg Gly Glu
290 295 300

Glu Glu Gln Trp Ala Arg Glu Ile Gly Ala Gln Leu Arg Arg Met Ala
305 310 315 320

Asp Asp Leu Asn Ala Gln Tyr Glu Arg Arg Arg Gln Glu Glu Gln Gln
325 330 335

Arg His Arg Pro Ser Pro Trp Arg Val Leu Tyr Asn Leu Ile Met Gly
340 345 350

Leu Leu Pro Leu Pro Arg Gly His Arg Ala Pro Glu Met Glu Pro Asn
355 360 365

Lys Glu Asp Leu
370

<210> SEQ ID NO 13
<211> LENGTH: 493
<212> TYPE: PRT
<213> ORGANISM: Artificial Sequence
<220> FEATURE:
<223> OTHER INFORMATION: synthesized, fusion protein comprising a fragment of TRAIL protein, a PUMA protein, translocation domain from Pseudomonas aeruginosa, flexible linkers, furin cleavage site and a sequence directing to the endoplasmic reticulum

<400> SEQUENCE: 13

```
Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Ser Arg Lys Lys Arg Ala Ser Gly Gly Pro Glu Gly
                165                 170                 175

Gly Ser Leu Ala Ala Leu Thr Ala His Gln Ala Cys His Leu Pro Leu
            180                 185                 190

Glu Thr Phe Thr Arg His Arg Gln Pro Arg Gly Trp Glu Gln Leu Glu
        195                 200                 205

Gln Cys Gly Tyr Pro Val Gln Arg Leu Val Ala Leu Tyr Leu Ala Ala
    210                 215                 220

Arg Leu Ser Trp Asn Gln Val Asp Gln Val Ile Ala Asn Ala Leu Ala
225                 230                 235                 240

Ser Pro Gly Ser Gly Gly Asp Leu Gly Glu Ala Ile Arg Glu Ser Pro
                245                 250                 255

Glu Gln Ala Arg Leu Ala Leu Thr Leu Ala Ala Ala Glu Ser Glu Arg
            260                 265                 270

Phe Val Arg Gln Gly Thr Gly Asn Asp Glu Ala Gly Ala Ala Asn Gly
        275                 280                 285

Pro Ala Asp Gly Gly Ser Gly Gly Gly Ala Arg Ala Arg Gln Glu Gly
    290                 295                 300

Ser Ser Pro Glu Pro Val Glu Gly Leu Ala Arg Asp Gly Pro Arg Pro
305                 310                 315                 320

Phe Pro Leu Gly Arg Leu Val Pro Ser Ala Val Ser Cys Gly Leu Cys
                325                 330                 335

Glu Pro Gly Leu Ala Ala Ala Pro Ala Ala Pro Thr Leu Leu Pro Ala
            340                 345                 350

Ala Tyr Leu Cys Ala Pro Thr Ala Pro Pro Ala Val Thr Ala Ala Leu
        355                 360                 365

Gly Gly Ser Arg Trp Pro Gly Gly Pro Arg Ser Arg Pro Arg Gly Pro
    370                 375                 380

Arg Pro Asp Gly Pro Gln Pro Ser Leu Ser Leu Ala Glu Gln His Leu
385                 390                 395                 400

Glu Ser Pro Val Pro Ser Ala Pro Gly Ala Leu Ala Gly Gly Pro Thr
                405                 410                 415
```

```
Gln Ala Ala Pro Gly Val Arg Gly Glu Glu Glu Gln Trp Ala Arg Glu
            420                 425                 430

Ile Gly Ala Gln Leu Arg Arg Met Ala Asp Asp Leu Asn Ala Gln Tyr
        435                 440                 445

Glu Arg Arg Arg Gln Glu Glu Gln Gln Arg His Arg Pro Ser Pro Trp
    450                 455                 460

Arg Val Leu Tyr Asn Leu Ile Met Gly Leu Leu Pro Leu Pro Arg Gly
465                 470                 475                 480

His Arg Ala Pro Glu Met Glu Pro Asn Lys Asp Glu Leu
                485                 490


<210> SEQ ID NO 14
<211> LENGTH: 186
<212> TYPE: PRT
<213> ORGANISM: Artificial Sequence
<220> FEATURE:
<223> OTHER INFORMATION: synthesized, fusion protein comprising a
      fragment of TRAIL protein, SMAC/Diablo peptide, a polyarginine
      sequence and sequences of cleavage sites recognized by protease
      uPA and MMP.

<400> SEQUENCE: 14

Ala Val Pro Ile Ala Gln Lys Pro Arg Arg Arg Arg Arg Arg Arg Arg
1               5                   10                  15

Val Val Arg Pro Leu Gly Leu Ala Gly Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly
            180                 185


<210> SEQ ID NO 15
<211> LENGTH: 191
<212> TYPE: PRT
<213> ORGANISM: Artificial Sequence
<220> FEATURE:
<223> OTHER INFORMATION: synthesized, fusion protein comprising a
      fragment of TRAIL protein, buforin IIb peptide, and sequences of
      cleavage sites recognized by protease uPA and MMP.

<400> SEQUENCE: 15

Arg Ala Gly Leu Gln Phe Pro Val Gly Arg Leu Leu Arg Arg Leu Leu
1               5                   10                  15
```

```
Arg Arg Leu Leu Arg Val Val Arg Pro Leu Gly Leu Ala Gly Arg Val
            20                  25                  30

Ala Ala His Ile Thr Gly Thr Arg Gly Arg Ser Asn Thr Leu Ser Ser
        35                  40                  45

Pro Asn Ser Lys Asn Glu Lys Ala Leu Gly Arg Lys Ile Asn Ser Trp
    50                  55                  60

Glu Ser Ser Arg Ser Gly His Ser Phe Leu Ser Asn Leu His Leu Arg
65                  70                  75                  80

Asn Gly Glu Leu Val Ile His Glu Lys Gly Phe Tyr Tyr Ile Tyr Ser
                85                  90                  95

Gln Thr Tyr Phe Arg Phe Gln Glu Glu Ile Lys Glu Asn Thr Lys Asn
            100                 105                 110

Asp Lys Gln Met Val Gln Tyr Ile Tyr Lys Tyr Thr Ser Tyr Pro Asp
        115                 120                 125

Pro Ile Leu Leu Met Lys Ser Ala Arg Asn Ser Cys Trp Ser Lys Asp
    130                 135                 140

Ala Glu Tyr Gly Leu Tyr Ser Ile Tyr Gln Gly Gly Ile Phe Glu Leu
145                 150                 155                 160

Lys Glu Asn Asp Arg Ile Phe Val Ser Val Thr Asn Glu His Leu Ile
                165                 170                 175

Asp Met Asp His Glu Ala Ser Phe Phe Gly Ala Phe Leu Val Gly
            180                 185                 190


<210> SEQ ID NO 16
<211> LENGTH: 279
<212> TYPE: PRT
<213> ORGANISM: Artificial Sequence
<220> FEATURE:
<223> OTHER INFORMATION: synthesized, fusion protein comprising a
      fragment of TRAIL protein, onconase peptide, a steric linker and
      sequences of cleavage sites recognized by protease uPA and MMP.

<400> SEQUENCE: 16

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Ser Gly Pro Leu Gly Leu Ala Gly Arg Val Val Arg Gln
                165                 170                 175

Asp Trp Leu Thr Phe Gln Lys Lys His Ile Thr Asn Thr Arg Asp Val
```

```
            180                 185                 190

Asp Cys Asp Asn Ile Met Ser Thr Asn Leu Phe His Cys Lys Asp Lys
        195                 200                 205

Asn Thr Phe Ile Tyr Ser Arg Pro Glu Pro Val Lys Ala Ile Cys Lys
    210                 215                 220

Gly Ile Ile Ala Ser Lys Asn Val Leu Thr Thr Ser Glu Phe Tyr Leu
225                 230                 235                 240

Ser Asp Cys Asn Val Thr Ser Arg Pro Cys Lys Tyr Lys Leu Lys Lys
                245                 250                 255

Ser Thr Asn Lys Phe Cys Val Thr Cys Glu Asn Gln Ala Pro Val His
            260                 265                 270

Phe Val Gly Val Gly Ser Cys
        275


<210> SEQ ID NO 17
<211> LENGTH: 274
<212> TYPE: PRT
<213> ORGANISM: Artificial Sequence
<220> FEATURE:
<223> OTHER INFORMATION: synthesized, fusion protein comprising a
      fragment of TRAIL protein, onconase peptide and a steric linker

<400> SEQUENCE: 17

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Ser Gly Gly Gly Gly Ser Gln Asp Trp Leu Thr Phe
                165                 170                 175

Gln Lys Lys His Ile Thr Asn Thr Arg Asp Val Asp Cys Asp Asn Ile
            180                 185                 190

Met Ser Thr Asn Leu Phe His Cys Lys Asp Lys Asn Thr Phe Ile Tyr
        195                 200                 205

Ser Arg Pro Glu Pro Val Lys Ala Ile Cys Lys Gly Ile Ile Ala Ser
    210                 215                 220

Lys Asn Val Leu Thr Thr Ser Glu Phe Tyr Leu Ser Asp Cys Asn Val
225                 230                 235                 240

Thr Ser Arg Pro Cys Lys Tyr Lys Leu Lys Lys Ser Thr Asn Lys Phe
                245                 250                 255
```

```
Cys Val Thr Cys Glu Asn Gln Ala Pro Val His Phe Val Gly Val Gly
            260                 265                 270

Ser Cys


<210> SEQ ID NO 18
<211> LENGTH: 197
<212> TYPE: PRT
<213> ORGANISM: Artificial Sequence
<220> FEATURE:
<223> OTHER INFORMATION: synthesized, fusion protein comprising a
      fragment of TRAIL protein, N-terminal domain of the protein
      p14ARF, a polyarginine sequence and protease cleavage sites uPA
      and MMP

<400> SEQUENCE: 18

Val Arg Arg Phe Leu Val Thr Leu Arg Ile Arg Arg Ala Cys Gly Pro
1               5                   10                  15

Pro Arg Val Arg Arg Arg Arg Arg Arg Arg Arg Val Val Arg Pro Leu
            20                  25                  30

Gly Leu Ala Gly Arg Val Ala Ala His Ile Thr Gly Thr Arg Gly Arg
        35                  40                  45

Ser Asn Thr Leu Ser Ser Pro Asn Ser Lys Asn Glu Lys Ala Leu Gly
    50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125

Tyr Thr Ser Tyr Pro Asp Pro Ile Leu Leu Met Lys Ser Ala Arg Asn
    130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Leu Val Gly
        195


<210> SEQ ID NO 19
<211> LENGTH: 189
<212> TYPE: PRT
<213> ORGANISM: Artificial Sequence
<220> FEATURE:
<223> OTHER INFORMATION: synthesized, fusion protein comprising a
      fragment of TRAIL protein, peptide binding to Mdm2, a polyarginine
      sequence and protease cleavage sites uPA and MMP

<400> SEQUENCE: 19

Pro Arg Phe Met Asp Thr Trp Glu Gly Leu Asn Arg Arg Arg Arg Arg
1               5                   10                  15

Arg Arg Arg Val Val Arg Pro Leu Gly Leu Ala Gly Arg Val Ala Ala
            20                  25                  30

His Ile Thr Gly Thr Arg Gly Arg Ser Asn Thr Leu Ser Ser Pro Asn
        35                  40                  45

Ser Lys Asn Glu Lys Ala Leu Gly Arg Lys Ile Asn Ser Trp Glu Ser
```

-continued 50 55 60

Ser Arg Ser Gly His Ser Phe Leu Ser Asn Leu His Leu Arg Asn Gly
65 70 75 80

Glu Leu Val Ile His Glu Lys Gly Phe Tyr Tyr Ile Tyr Ser Gln Thr
85 90 95

Tyr Phe Arg Phe Gln Glu Glu Ile Lys Glu Asn Thr Lys Asn Asp Lys
100 105 110

Gln Met Val Gln Tyr Ile Tyr Lys Tyr Thr Ser Tyr Pro Asp Pro Ile
115 120 125

Leu Leu Met Lys Ser Ala Arg Asn Ser Cys Trp Ser Lys Asp Ala Glu
130 135 140

Tyr Gly Leu Tyr Ser Ile Tyr Gln Gly Gly Ile Phe Glu Leu Lys Glu
145 150 155 160

Asn Asp Arg Ile Phe Val Ser Val Thr Asn Glu His Leu Ile Asp Met
165 170 175

Asp His Glu Ala Ser Phe Phe Gly Ala Phe Leu Val Gly
180 185

<210> SEQ ID NO 20
<211> LENGTH: 195
<212> TYPE: PRT
<213> ORGANISM: Artificial Sequence
<220> FEATURE:
<223> OTHER INFORMATION: synthesized, fusion protein comprising a fragment of TRAIL protein, lunasin peptide, a polyarginine sequence and protease cleavage sites uPA and MMP

<400> SEQUENCE: 20

Cys Glu Lys His Ile Met Glu Lys Ile Gln Gly Arg Gly Asp Asp Asp
1 5 10 15

Asp Arg Arg Arg Arg Arg Arg Arg Arg Val Val Arg Pro Leu Gly Leu
20 25 30

Ala Gly Arg Val Ala Ala His Ile Thr Gly Thr Arg Gly Arg Ser Asn
35 40 45

Thr Leu Ser Ser Pro Asn Ser Lys Asn Glu Lys Ala Leu Gly Arg Lys
50 55 60

Ile Asn Ser Trp Glu Ser Ser Arg Ser Gly His Ser Phe Leu Ser Asn
65 70 75 80

Leu His Leu Arg Asn Gly Glu Leu Val Ile His Glu Lys Gly Phe Tyr
85 90 95

Tyr Ile Tyr Ser Gln Thr Tyr Phe Arg Phe Gln Glu Glu Ile Lys Glu
100 105 110

Asn Thr Lys Asn Asp Lys Gln Met Val Gln Tyr Ile Tyr Lys Tyr Thr
115 120 125

Ser Tyr Pro Asp Pro Ile Leu Leu Met Lys Ser Ala Arg Asn Ser Cys
130 135 140

Trp Ser Lys Asp Ala Glu Tyr Gly Leu Tyr Ser Ile Tyr Gln Gly Gly
145 150 155 160

Ile Phe Glu Leu Lys Glu Asn Asp Arg Ile Phe Val Ser Val Thr Asn
165 170 175

Glu His Leu Ile Asp Met Asp His Glu Ala Ser Phe Phe Gly Ala Phe
180 185 190

Leu Val Gly
195

<210> SEQ ID NO 21

<211> LENGTH: 218
<212> TYPE: PRT
<213> ORGANISM: Artificial Sequence
<220> FEATURE:
<223> OTHER INFORMATION: synthesized, fusion protein comprising a fragment of TRAIL protein, Smac/Diablo protein BH3 domain of Bik protein, a polyarginine sequence and protease cleavage sites uPA and MMP

<400> SEQUENCE: 21

Ala Val Pro Ile Ala Gln Lys Pro Arg Arg Arg Arg Arg Arg Arg Arg
1               5                   10                  15

Val Val Arg Pro Leu Gly Leu Ala Gly Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Pro Leu Gly Leu Ala Gly
            180                 185                 190

Arg Val Val Arg Arg Arg Arg Arg Arg Arg Arg Leu Ala Leu Arg Leu
        195                 200                 205

Ala Cys Ile Gly Asp Glu Met Asp Val Ser
    210                 215

<210> SEQ ID NO 22
<211> LENGTH: 199
<212> TYPE: PRT
<213> ORGANISM: Artificial Sequence
<220> FEATURE:
<223> OTHER INFORMATION: synthesized, fusion protein comprising a fragment of TRAIL protein, peptide consisting of Gly - Ala repetitions, a polyarginine sequence and protease cleavage sites uPA and MMP

<400> SEQUENCE: 22

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr

-continued

```
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Arg Val Val Arg Pro Leu Gly Leu Ala Gly Ala Gly Ala Gly Gly
                165                 170                 175

Gly Ala Gly Gly Ala Gly Ala Gly Gly Gly Ala Gly Gly Ala Gly Arg
            180                 185                 190

Arg Arg Arg Arg Arg Arg Arg
        195


<210> SEQ ID NO 23
<211> LENGTH: 289
<212> TYPE: PRT
<213> ORGANISM: Artificial Sequence
<220> FEATURE:
<223> OTHER INFORMATION: synthesized, fusion protein comprising a
      fragment of TRAIL protein, proteasome component S5a containing
      UIMs motifs, a furin cleavage site, a steric linker and a sequence
      directing to endoplasmic reticulum

<400> SEQUENCE: 23

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Ser Gly Gly Arg Lys Lys Arg Met Thr Ile Ser Gln
                165                 170                 175

Gln Glu Phe Gly Arg Thr Gly Leu Pro Asp Leu Ser Ser Met Thr Glu
            180                 185                 190

Glu Glu Gln Ile Ala Tyr Ala Met Gln Met Ser Leu Gln Gly Ala Glu
        195                 200                 205

Phe Gly Gln Ala Glu Ser Ala Asp Ile Asp Ala Ser Ser Ala Met Asp
```

```
    210                 215                 220

Thr Ser Glu Pro Ala Lys Glu Glu Asp Asp Tyr Asp Val Met Gln Asp
225                 230                 235                 240

Pro Glu Phe Leu Gln Ser Val Leu Glu Asn Leu Pro Gly Val Asp Pro
                245                 250                 255

Asn Asn Glu Ala Ile Arg Asn Ala Met Gly Ser Leu Ala Ser Gln Ala
            260                 265                 270

Thr Lys Asp Gly Lys Lys Asp Lys Lys Glu Glu Asp Lys Lys Glu Asp
        275                 280                 285

Leu


<210> SEQ ID NO 24
<211> LENGTH: 183
<212> TYPE: PRT
<213> ORGANISM: Artificial Sequence
<220> FEATURE:
<223> OTHER INFORMATION: synthesized, fusion protein comprising a
      fragment of TRAIL protein, peptide derived from the TNF ligand and
      cleavage sites recognized by proteases uPA and MMP

<400> SEQUENCE: 24

Val Ala Asn Pro Gln Ala Glu Gly Gln Leu Arg Val Val Arg Pro Leu
1               5                   10                  15

Gly Leu Ala Gly Pro Gln Arg Val Ala Ala His Ile Thr Gly Thr Arg
            20                  25                  30

Gly Arg Ser Asn Thr Leu Ser Ser Pro Asn Ser Lys Asn Glu Lys Ala
        35                  40                  45

Leu Gly Arg Lys Ile Asn Ser Trp Glu Ser Ser Arg Ser Gly His Ser
    50                  55                  60

Phe Leu Ser Asn Leu His Leu Arg Asn Gly Glu Leu Val Ile His Glu
65                  70                  75                  80

Lys Gly Phe Tyr Tyr Ile Tyr Ser Gln Thr Tyr Phe Arg Phe Gln Glu
                85                  90                  95

Glu Ile Lys Glu Asn Thr Lys Asn Asp Lys Gln Met Val Gln Tyr Ile
            100                 105                 110

Tyr Lys Tyr Thr Ser Tyr Pro Asp Pro Ile Leu Leu Met Lys Ser Ala
        115                 120                 125

Arg Asn Ser Cys Trp Ser Lys Asp Ala Glu Tyr Gly Leu Tyr Ser Ile
    130                 135                 140

Tyr Gln Gly Gly Ile Phe Glu Leu Lys Glu Asn Asp Arg Ile Phe Val
145                 150                 155                 160

Ser Val Thr Asn Glu His Leu Ile Asp Met Asp His Glu Ala Ser Phe
                165                 170                 175

Phe Gly Ala Phe Leu Val Gly
            180


<210> SEQ ID NO 25
<211> LENGTH: 179
<212> TYPE: PRT
<213> ORGANISM: Artificial Sequence
<220> FEATURE:
<223> OTHER INFORMATION: synthesized, fusion protein comprising a
      fragment of TRAIL protein, a peptide derived from the TNF and
      cleavage sites recognized by proteases uPA and MMP.

<400> SEQUENCE: 25

Leu Ala Asn Gly Val Glu Arg Val Val Arg Pro Leu Gly Leu Ala Gly
1               5                   10                  15
```

-continued

Pro Gln Arg Val Ala Ala His Ile Thr Gly Thr Arg Gly Arg Ser Asn
20 25 30

Thr Leu Ser Ser Pro Asn Ser Lys Asn Glu Lys Ala Leu Gly Arg Lys
35 40 45

Ile Asn Ser Trp Glu Ser Ser Arg Ser Gly His Ser Phe Leu Ser Asn
50 55 60

Leu His Leu Arg Asn Gly Glu Leu Val Ile His Glu Lys Gly Phe Tyr
65 70 75 80

Tyr Ile Tyr Ser Gln Thr Tyr Phe Arg Phe Gln Glu Glu Ile Lys Glu
85 90 95

Asn Thr Lys Asn Asp Lys Gln Met Val Gln Tyr Ile Tyr Lys Tyr Thr
100 105 110

Ser Tyr Pro Asp Pro Ile Leu Leu Met Lys Ser Ala Arg Asn Ser Cys
115 120 125

Trp Ser Lys Asp Ala Glu Tyr Gly Leu Tyr Ser Ile Tyr Gln Gly Gly
130 135 140

Ile Phe Glu Leu Lys Glu Asn Asp Arg Ile Phe Val Ser Val Thr Asn
145 150 155 160

Glu His Leu Ile Asp Met Asp His Glu Ala Ser Phe Phe Gly Ala Phe
165 170 175

Leu Val Gly

<210> SEQ ID NO 26
<211> LENGTH: 180
<212> TYPE: PRT
<213> ORGANISM: Artificial Sequence
<220> FEATURE:
<223> OTHER INFORMATION: synthesized, fusion protein comprising a fragment of TRAIL protein, a fragment of the TNF cytokine and cleavage sites recognized by proteases uPA and MMP.

<400> SEQUENCE: 26

Cys Pro Ser Glu Gly Leu Cys Arg Val Val Arg Pro Leu Gly Leu Ala
1 5 10 15

Gly Pro Gln Arg Val Ala Ala His Ile Thr Gly Thr Arg Gly Arg Ser
20 25 30

Asn Thr Leu Ser Ser Pro Asn Ser Lys Asn Glu Lys Ala Leu Gly Arg
35 40 45

Lys Ile Asn Ser Trp Glu Ser Ser Arg Ser Gly His Ser Phe Leu Ser
50 55 60

Asn Leu His Leu Arg Asn Gly Glu Leu Val Ile His Glu Lys Gly Phe
65 70 75 80

Tyr Tyr Ile Tyr Ser Gln Thr Tyr Phe Arg Phe Gln Glu Glu Ile Lys
85 90 95

Glu Asn Thr Lys Asn Asp Lys Gln Met Val Gln Tyr Ile Tyr Lys Tyr
100 105 110

Thr Ser Tyr Pro Asp Pro Ile Leu Leu Met Lys Ser Ala Arg Asn Ser
115 120 125

Cys Trp Ser Lys Asp Ala Glu Tyr Gly Leu Tyr Ser Ile Tyr Gln Gly
130 135 140

Gly Ile Phe Glu Leu Lys Glu Asn Asp Arg Ile Phe Val Ser Val Thr
145 150 155 160

Asn Glu His Leu Ile Asp Met Asp His Glu Ala Ser Phe Phe Gly Ala
165 170 175

Phe Leu Val Gly
180

-continued

<210> SEQ ID NO 27
<211> LENGTH: 168
<212> TYPE: PRT
<213> ORGANISM: Homo sapiens
<300> PUBLICATION INFORMATION:
<308> DATABASE ACCESSION NUMBER: P50591
<309> DATABASE ENTRY DATE: 1996-10-01
<313> RELEVANT RESIDUES IN SEQ ID NO: (114)..(281)

<400> SEQUENCE: 27

```
Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165
```

<210> SEQ ID NO 28
<211> LENGTH: 163
<212> TYPE: PRT
<213> ORGANISM: Homo sapiens
<300> PUBLICATION INFORMATION:
<308> DATABASE ACCESSION NUMBER: P50591
<309> DATABASE ENTRY DATE: 1996-10-01
<313> RELEVANT RESIDUES IN SEQ ID NO: (119)..(281)

<400> SEQUENCE: 28

```
Pro Gln Arg Val Ala Ala His Ile Thr Gly Thr Arg Gly Arg Ser Asn
1               5                   10                  15

Thr Leu Ser Ser Pro Asn Ser Lys Asn Glu Lys Ala Leu Gly Arg Lys
            20                  25                  30

Ile Asn Ser Trp Glu Ser Ser Arg Ser Gly His Ser Phe Leu Ser Asn
        35                  40                  45

Leu His Leu Arg Asn Gly Glu Leu Val Ile His Glu Lys Gly Phe Tyr
    50                  55                  60

Tyr Ile Tyr Ser Gln Thr Tyr Phe Arg Phe Gln Glu Glu Ile Lys Glu
65                  70                  75                  80

Asn Thr Lys Asn Asp Lys Gln Met Val Gln Tyr Ile Tyr Lys Tyr Thr
                85                  90                  95

Ser Tyr Pro Asp Pro Ile Leu Leu Met Lys Ser Ala Arg Asn Ser Cys
            100                 105                 110
```

```
Trp Ser Lys Asp Ala Glu Tyr Gly Leu Tyr Ser Ile Tyr Gln Gly Gly
        115                 120                 125

Ile Phe Glu Leu Lys Glu Asn Asp Arg Ile Phe Val Ser Val Thr Asn
    130                 135                 140

Glu His Leu Ile Asp Met Asp His Glu Ala Ser Phe Phe Gly Ala Phe
145                 150                 155                 160

Leu Val Gly


<210> SEQ ID NO 29
<211> LENGTH: 161
<212> TYPE: PRT
<213> ORGANISM: Homo sapiens
<300> PUBLICATION INFORMATION:
<308> DATABASE ACCESSION NUMBER: P50591
<309> DATABASE ENTRY DATE: 1996-10-01
<313> RELEVANT RESIDUES IN SEQ ID NO: (121)..(281)

<400> SEQUENCE: 29

Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly


<210> SEQ ID NO 30
<211> LENGTH: 16
<212> TYPE: PRT
<213> ORGANISM: Homo sapiens
<300> PUBLICATION INFORMATION:
<308> DATABASE ACCESSION NUMBER: GenBank/ AAF71267.1
<309> DATABASE ENTRY DATE: 2000-05-21
<313> RELEVANT RESIDUES IN SEQ ID NO: (57)..(72)

<400> SEQUENCE: 30

Lys Lys Leu Ser Glu Cys Leu Lys Arg Ile Gly Asp Glu Leu Asp Ser
1               5                   10                  15


<210> SEQ ID NO 31
<211> LENGTH: 15
<212> TYPE: PRT
<213> ORGANISM: Homo sapiens
<300> PUBLICATION INFORMATION:
<308> DATABASE ACCESSION NUMBER: GenBank/ AAH22072.2
<309> DATABASE ENTRY DATE: 2005-07-21
<313> RELEVANT RESIDUES IN SEQ ID NO: (141)..(155)
```

<400> SEQUENCE: 31

```
Arg Asn Ile Ala Arg His Leu Ala Gln Val Gly Asp Ser Met Asp
1               5                   10                  15
```

<210> SEQ ID NO 32
<211> LENGTH: 124
<212> TYPE: PRT
<213> ORGANISM: Homo sapiens
<300> PUBLICATION INFORMATION:
<308> DATABASE ACCESSION NUMBER: GenBank/ AAA72757.1
<309> DATABASE ENTRY DATE: 1993-08-30
<313> RELEVANT RESIDUES IN SEQ ID NO: (33)..(156)

<400> SEQUENCE: 32

```
Lys Glu Thr Ala Ala Ala Lys Phe Glu Arg Gln His Met Asp Ser Ser
1               5                   10                  15

Thr Ser Ala Ala Ser Ser Ser Asn Tyr Cys Asn Gln Met Met Lys Ser
            20                  25                  30

Arg Asn Leu Thr Lys Asp Arg Cys Lys Pro Val Asn Thr Phe Val His
        35                  40                  45

Glu Ser Leu Ala Asp Val Gln Ala Val Cys Ser Gln Lys Asn Val Ala
    50                  55                  60

Cys Lys Asn Gly Gln Thr Asn Cys Tyr Gln Ser Tyr Ser Thr Met Ser
65                  70                  75                  80

Ile Thr Asp Cys Arg Glu Thr Gly Ser Ser Lys Tyr Pro Asn Cys Ala
                85                  90                  95

Tyr Lys Thr Thr Gln Ala Asn Lys His Ile Ile Val Ala Cys Glu Gly
            100                 105                 110

Asn Pro Tyr Val Pro Val His Phe Asp Ala Ser Val
        115                 120
```

<210> SEQ ID NO 33
<211> LENGTH: 104
<212> TYPE: PRT
<213> ORGANISM: Homo sapiens
<300> PUBLICATION INFORMATION:
<308> DATABASE ACCESSION NUMBER: GenBank/ AAH67222.1
<309> DATABASE ENTRY DATE: 2006-07-15
<313> RELEVANT RESIDUES IN SEQ ID NO: (2)..(105)

<400> SEQUENCE: 33

```
Gly Asp Val Glu Lys Gly Lys Lys Ile Phe Ile Met Lys Cys Ser Gln
1               5                   10                  15

Cys His Thr Val Glu Lys Gly Gly Lys His Lys Thr Gly Pro Asn Leu
            20                  25                  30

His Gly Leu Phe Gly Arg Lys Thr Gly Gln Ala Pro Gly Tyr Ser Tyr
        35                  40                  45

Thr Ala Ala Asn Lys Asn Lys Gly Ile Ile Trp Gly Glu Asp Thr Leu
    50                  55                  60

Met Glu Tyr Leu Glu Asn Pro Lys Lys Tyr Ile Pro Gly Thr Lys Met
65                  70                  75                  80

Ile Phe Val Gly Ile Lys Lys Lys Glu Glu Arg Ala Asp Leu Ile Ala
                85                  90                  95

Tyr Leu Lys Lys Ala Thr Asn Glu
            100
```

<210> SEQ ID NO 34
<211> LENGTH: 227
<212> TYPE: PRT

<213> ORGANISM: Homo sapiens
<300> PUBLICATION INFORMATION:
<308> DATABASE ACCESSION NUMBER: GenBank/ CAA01810.1
<309> DATABASE ENTRY DATE: 1995-10-17
<313> RELEVANT RESIDUES IN SEQ ID NO: (1)..(227)

<400> SEQUENCE: 34

```
Ile Ile Gly Gly His Val Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225
```

<210> SEQ ID NO 35
<211> LENGTH: 9
<212> TYPE: PRT
<213> ORGANISM: Homo sapiens
<300> PUBLICATION INFORMATION:
<308> DATABASE ACCESSION NUMBER: GenBank/ EAW58223.1
<309> DATABASE ENTRY DATE: 2006-12-18
<313> RELEVANT RESIDUES IN SEQ ID NO: (561)..(569)

<400> SEQUENCE: 35

```
Phe Ser Arg Ser Leu His Ser Leu Leu
1               5
```

<210> SEQ ID NO 36
<211> LENGTH: 15
<212> TYPE: PRT
<213> ORGANISM: Homo sapiens
<300> PUBLICATION INFORMATION:
<308> DATABASE ACCESSION NUMBER: GenBank/ AAI10338.1
<309> DATABASE ENTRY DATE: 2009-03-18
<313> RELEVANT RESIDUES IN SEQ ID NO: (72)..(86)

<400> SEQUENCE: 36

Gly Gln Val Gly Arg Gln Leu Ala Ile Ile Gly Asp Asp Ile Asn
1 5 10 15

<210> SEQ ID NO 37
<211> LENGTH: 24
<212> TYPE: PRT
<213> ORGANISM: Homo sapiens
<300> PUBLICATION INFORMATION:
<308> DATABASE ACCESSION NUMBER: GenBank/ AAB51243.2
<309> DATABASE ENTRY DATE: 2001-09-26
<313> RELEVANT RESIDUES IN SEQ ID NO: (130)..(153)

<400> SEQUENCE: 37

Glu Glu Gln Trp Ala Arg Glu Ile Gly Ala Gln Leu Arg Arg Met Ala
1 5 10 15

Asp Asp Leu Asn Ala Gln Tyr Glu
20

<210> SEQ ID NO 38
<211> LENGTH: 192
<212> TYPE: PRT
<213> ORGANISM: Homo sapiens
<300> PUBLICATION INFORMATION:
<308> DATABASE ACCESSION NUMBER: GenBank/ AAB51243.2
<309> DATABASE ENTRY DATE: 2001-09-26
<313> RELEVANT RESIDUES IN SEQ ID NO: (2)..(193)

<400> SEQUENCE: 38

Ala Arg Ala Arg Gln Glu Gly Ser Ser Pro Glu Pro Val Glu Gly Leu
1 5 10 15

Ala Arg Asp Gly Pro Arg Pro Phe Pro Leu Gly Arg Leu Val Pro Ser
20 25 30

Ala Val Ser Cys Gly Leu Cys Glu Pro Gly Leu Ala Ala Ala Pro Ala
35 40 45

Ala Pro Thr Leu Leu Pro Ala Ala Tyr Leu Cys Ala Pro Thr Ala Pro
50 55 60

Pro Ala Val Thr Ala Ala Leu Gly Gly Ser Arg Trp Pro Gly Gly Pro
65 70 75 80

Arg Ser Arg Pro Arg Gly Pro Arg Pro Asp Gly Pro Gln Pro Ser Leu
85 90 95

Ser Leu Ala Glu Gln His Leu Glu Ser Pro Val Pro Ser Ala Pro Gly
100 105 110

Ala Leu Ala Gly Gly Pro Thr Gln Ala Ala Pro Gly Val Arg Gly Glu
115 120 125

Glu Glu Gln Trp Ala Arg Glu Ile Gly Ala Gln Leu Arg Arg Met Ala
130 135 140

Asp Asp Leu Asn Ala Gln Tyr Glu Arg Arg Arg Gln Glu Glu Gln Gln
145 150 155 160

Arg His Arg Pro Ser Pro Trp Arg Val Leu Tyr Asn Leu Ile Met Gly
165 170 175

Leu Leu Pro Leu Pro Arg Gly His Arg Ala Pro Glu Met Glu Pro Asn
180 185 190

<210> SEQ ID NO 39
<211> LENGTH: 8
<212> TYPE: PRT
<213> ORGANISM: Homo sapiens
<300> PUBLICATION INFORMATION:
<308> DATABASE ACCESSION NUMBER: GenBank/ EAW98311.1
<309> DATABASE ENTRY DATE: 2006-12-18
<313> RELEVANT RESIDUES IN SEQ ID NO: (132)..(138)

<400> SEQUENCE: 39

Ala Val Pro Ile Ala Gln Lys Pro
1               5

<210> SEQ ID NO 40
<211> LENGTH: 20
<212> TYPE: PRT
<213> ORGANISM: Homo sapiens
<300> PUBLICATION INFORMATION:
<308> DATABASE ACCESSION NUMBER: GenBank/ BAG35060.1
<309> DATABASE ENTRY DATE: 2008-05-24
<313> RELEVANT RESIDUES IN SEQ ID NO: (21)..(36)

<400> SEQUENCE: 40

Arg Ala Gly Leu Gln Phe Pro Val Gly Arg Leu Leu Arg Arg Leu Leu
1               5                   10                  15

Arg Arg Leu Leu
            20

<210> SEQ ID NO 41
<211> LENGTH: 104
<212> TYPE: PRT
<213> ORGANISM: Homo sapiens
<300> PUBLICATION INFORMATION:
<308> DATABASE ACCESSION NUMBER: Swiss-Prot/ P22069.2
<309> DATABASE ENTRY DATE: 2010-03-02
<313> RELEVANT RESIDUES IN SEQ ID NO: (1)..(104)

<400> SEQUENCE: 41

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 42
<211> LENGTH: 19
<212> TYPE: PRT
<213> ORGANISM: Homo sapiens
<300> PUBLICATION INFORMATION:
<308> DATABASE ACCESSION NUMBER: GenBank/ AAH15960.3
<309> DATABASE ENTRY DATE: 2008-11-30
<313> RELEVANT RESIDUES IN SEQ ID NO: (18)..(36)

<400> SEQUENCE: 42

Val Arg Arg Phe Leu Val Thr Leu Arg Ile Arg Arg Ala Cys Gly Pro
1               5                   10                  15

Pro Arg Val

<210> SEQ ID NO 43
<211> LENGTH: 11
<212> TYPE: PRT
<213> ORGANISM: Homo sapiens -continued <300> PUBLICATION INFORMATION:
<301> AUTHORS: Bvttger
<303> JOURNAL: Oncogene
<304> VOLUME: 13
<306> PAGES: 2141-2147
<307> DATE: 1996

<400> SEQUENCE: 43

Pro Arg Phe Met Asp Thr Trp Glu Gly Leu Asn
1 5 10

<210> SEQ ID NO 44
<211> LENGTH: 17
<212> TYPE: PRT
<213> ORGANISM: Glycine max
<300> PUBLICATION INFORMATION:
<308> DATABASE ACCESSION NUMBER: GenBank/ ACE36683.1
<309> DATABASE ENTRY DATE: 2008-07-10
<313> RELEVANT RESIDUES IN SEQ ID NO: (43)..(59)

<400> SEQUENCE: 44

Cys Glu Lys His Ile Met Glu Lys Ile Gln Gly Arg Gly Asp Asp Asp
1 5 10 15

Asp

<210> SEQ ID NO 45
<211> LENGTH: 15
<212> TYPE: PRT
<213> ORGANISM: Homo sapiens
<300> PUBLICATION INFORMATION:
<308> DATABASE ACCESSION NUMBER: GenBank/ EAW98311.1
<309> DATABASE ENTRY DATE: 2006-12-18
<313> RELEVANT RESIDUES IN SEQ ID NO: (132)..(138)

<400> SEQUENCE: 45

Leu Ala Leu Arg Leu Ala Cys Ile Gly Asp Glu Met Asp Val Ser
1 5 10 15

<210> SEQ ID NO 46
<211> LENGTH: 20
<212> TYPE: PRT
<213> ORGANISM: Artificial Sequence
<220> FEATURE:
<223> OTHER INFORMATION: synthesized, derived from Human herpesvirus 4 fragment
<300> PUBLICATION INFORMATION:
<308> DATABASE ACCESSION NUMBER: GenBank/ AAY41125.1
<309> DATABASE ENTRY DATE: 2006-01-06
<313> RELEVANT RESIDUES IN SEQ ID NO: (148)..(167)

<400> SEQUENCE: 46

Ala Gly Ala Gly Gly Gly Ala Gly Gly Ala Gly Ala Gly Gly Gly Ala
1 5 10 15

Gly Gly Ala Gly
20

<210> SEQ ID NO 47
<211> LENGTH: 114
<212> TYPE: PRT
<213> ORGANISM: Homo sapiens
<300> PUBLICATION INFORMATION:
<308> DATABASE ACCESSION NUMBER: GenBank/ CAO72169.1
<309> DATABASE ENTRY DATE: 2009-01-13
<313> RELEVANT RESIDUES IN SEQ ID NO: (79)..(191)

<400> SEQUENCE: 47

Met Thr Ile Ser Gln Gln Glu Phe Gly Arg Thr Gly Leu Pro Asp Leu
1 5 10 15

```
Ser Ser Met Thr Glu Glu Glu Gln Ile Ala Tyr Ala Met Gln Met Ser
            20                  25                  30

Leu Gln Gly Ala Glu Phe Gly Gln Ala Glu Ser Ala Asp Ile Asp Ala
        35                  40                  45

Ser Ser Ala Met Asp Thr Ser Glu Pro Ala Lys Glu Glu Asp Asp Tyr
    50                  55                  60

Asp Val Met Gln Asp Pro Glu Phe Leu Gln Ser Val Leu Glu Asn Leu
65                  70                  75                  80

Pro Gly Val Asp Pro Asn Asn Glu Ala Ile Arg Asn Ala Met Gly Ser
                85                  90                  95

Leu Ala Ser Gln Ala Thr Lys Asp Gly Lys Lys Asp Lys Lys Glu Glu
            100                 105                 110

Asp Lys


<210> SEQ ID NO 48
<211> LENGTH: 10
<212> TYPE: PRT
<213> ORGANISM: Homo sapiens
<300> PUBLICATION INFORMATION:
<308> DATABASE ACCESSION NUMBER: GenBank/ AAO21132.1
<309> DATABASE ENTRY DATE: 2003-01-18
<313> RELEVANT RESIDUES IN SEQ ID NO: (93)..(102)

<400> SEQUENCE: 48

Val Ala Asn Pro Gln Ala Glu Gly Gln Leu
1               5                   10


<210> SEQ ID NO 49
<211> LENGTH: 6
<212> TYPE: PRT
<213> ORGANISM: Homo sapiens
<300> PUBLICATION INFORMATION:
<308> DATABASE ACCESSION NUMBER: GenBank/ AAO21132.1
<309> DATABASE ENTRY DATE: 2003-01-18
<313> RELEVANT RESIDUES IN SEQ ID NO: (113)..(118)

<400> SEQUENCE: 49

Leu Ala Asn Gly Val Glu
1               5


<210> SEQ ID NO 50
<211> LENGTH: 7
<212> TYPE: PRT
<213> ORGANISM: Homo sapiens
<300> PUBLICATION INFORMATION:
<308> DATABASE ACCESSION NUMBER: GenBank/ AAO21132.1
<309> DATABASE ENTRY DATE: 2003-01-18
<313> RELEVANT RESIDUES IN SEQ ID NO: (127)..(131)

<400> SEQUENCE: 50

Cys Pro Ser Glu Gly Leu Cys
1               5


<210> SEQ ID NO 51
<211> LENGTH: 6
<212> TYPE: PRT
<213> ORGANISM: Artificial Sequence
<220> FEATURE:
<223> OTHER INFORMATION: synthesized, a fragment recognized by
      metalloprotease MMP

<400> SEQUENCE: 51

Pro Leu Gly Leu Ala Gly
1               5
```

<210> SEQ ID NO 52
<211> LENGTH: 4
<212> TYPE: PRT
<213> ORGANISM: Artificial Sequence
<220> FEATURE:
<223> OTHER INFORMATION: synthesized, a fragment recognized by urokinase

<400> SEQUENCE: 52

Arg Val Val Arg
1

<210> SEQ ID NO 53
<211> LENGTH: 4
<212> TYPE: PRT
<213> ORGANISM: Artificial Sequence
<220> FEATURE:
<223> OTHER INFORMATION: synthesized, a fragment recognized by furin

<400> SEQUENCE: 53

Arg Lys Lys Arg
1

<210> SEQ ID NO 54
<211> LENGTH: 118
<212> TYPE: PRT
<213> ORGANISM: Pseudomonas aeruginosa

<400> SEQUENCE: 54

```
Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Ala Asn
    50                  55                  60

Ala Leu Ala Ser Pro Gly Ser Gly Gly Asp Leu Gly Glu Ala Ile Arg
65                  70                  75                  80

Glu Ser Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Gly Pro Ala Asp
        115
```

<210> SEQ ID NO 55
<211> LENGTH: 4
<212> TYPE: PRT
<213> ORGANISM: Homo sapiens

<400> SEQUENCE: 55

Lys Asp Glu Leu
1

<210> SEQ ID NO 56
<211> LENGTH: 4
<212> TYPE: PRT
<213> ORGANISM: Homo sapiens

<400> SEQUENCE: 56

Lys Glu Asp Leu

1

<210> SEQ ID NO 57
<211> LENGTH: 4
<212> TYPE: PRT
<213> ORGANISM: Artificial Sequence
<220> FEATURE:
<223> OTHER INFORMATION: synthesized, steric linker

<400> SEQUENCE: 57

Gly Gly Ser Gly
1

<210> SEQ ID NO 58
<211> LENGTH: 4
<212> TYPE: PRT
<213> ORGANISM: Artificial Sequence
<220> FEATURE:
<223> OTHER INFORMATION: synthesized, steric linker

<400> SEQUENCE: 58

Gly Gly Gly Ser
1

<210> SEQ ID NO 59
<211> LENGTH: 5
<212> TYPE: PRT
<213> ORGANISM: Artificial Sequence
<220> FEATURE:
<223> OTHER INFORMATION: synthesized, steric linker

<400> SEQUENCE: 59

Gly Gly Gly Gly Ser
1 5

<210> SEQ ID NO 60
<211> LENGTH: 5
<212> TYPE: PRT
<213> ORGANISM: Artificial Sequence
<220> FEATURE:
<223> OTHER INFORMATION: synthesized, steric linker

<400> SEQUENCE: 60

Gly Gly Ser Gly Gly
1 5

<210> SEQ ID NO 61
<211> LENGTH: 6
<212> TYPE: PRT
<213> ORGANISM: Artificial Sequence
<220> FEATURE:
<223> OTHER INFORMATION: synthesized, steric linker

<400> SEQUENCE: 61

Gly Gly Gly Ser Gly Gly
1 5

<210> SEQ ID NO 62
<211> LENGTH: 7
<212> TYPE: PRT
<213> ORGANISM: Artificial Sequence
<220> FEATURE:
<223> OTHER INFORMATION: synthesized, steric linker

<400> SEQUENCE: 62

Gly Gly Gly Ser Gly Gly Gly
1 5

<210> SEQ ID NO 63
<211> LENGTH: 8
<212> TYPE: PRT
<213> ORGANISM: Artificial Sequence
<220> FEATURE:
<223> OTHER INFORMATION: synthesized, steric linker

<400> SEQUENCE: 63

Gly Gly Gly Ser Gly Gly Gly Ser
1               5

<210> SEQ ID NO 64
<211> LENGTH: 9
<212> TYPE: PRT
<213> ORGANISM: Artificial Sequence
<220> FEATURE:
<223> OTHER INFORMATION: synthesized, steric linker

<400> SEQUENCE: 64

Gly Gly Gly Ser Gly Gly Gly Gly Ser
1               5

<210> SEQ ID NO 65
<211> LENGTH: 4
<212> TYPE: PRT
<213> ORGANISM: Artificial Sequence
<220> FEATURE:
<223> OTHER INFORMATION: synthesized, steric linker

<400> SEQUENCE: 65

Ala Ser Gly Gly
1

<210> SEQ ID NO 66
<211> LENGTH: 8
<212> TYPE: PRT
<213> ORGANISM: Artificial Sequence
<220> FEATURE:
<223> OTHER INFORMATION: synthesized, steric linker

<400> SEQUENCE: 66

Gly Gly Gly Ser Ala Ser Gly Gly
1               5

<210> SEQ ID NO 67
<211> LENGTH: 582
<212> TYPE: DNA
<213> ORGANISM: Artificial Sequence
<220> FEATURE:
<223> OTHER INFORMATION: synthesized, encoding a fusion protein
      comprising a fragment of TRAIL protein, a peptide derived from
      the BH3 domain of Bax protein, polyarginine sequence and fragments
      recognized by urokinase and metalloprotease MMP

<400> SEQUENCE: 67
gcccaccaga aatgcaccaa aaaagctggc ttcatgatcc atatcaatca gatgttcatt     60
ggtcacgctc acaaaaatgc gatcattttc tttcagttca aaaatgccac cctgataaat    120
gctatacagg ccatattctg catctttgct ccaacagcta ttacgtgcgc ttttcatcag    180
cagaatcgga tccggatagc tggtatattt ataaatgtac tgcaccattt gtttatcatt    240
tttggtattt tctttaattt cttcctgaaa gcgaaaatag gtctggctat aaatataata    300
aaagcctttt tcatgaatca ccagttcacc attacgcaga tgcagattgc tcagaaagct    360
atgaccgcta cggctgcttt cccagctatt aattttgcga cccagggctt tttcattttt    420

```
gctattcggg ctgctcaggg tattgctacg accacgggtg ccggtaatat gtgctgcaac    480

acgacctgcc agacccagcg gacgaacaac acgacgacgg cgacgacgac gacggctatc    540

cagttcatca ccaatacgtt tcaggcattc gctcagtttt tt                       582


<210> SEQ ID NO 68
<211> LENGTH: 579
<212> TYPE: DNA
<213> ORGANISM: Artificial Sequence
<220> FEATURE:
<223> OTHER INFORMATION: synthesized, encoding a fusion protein
      comprising a fragment of TRAIL protein, a peptide derived from
      the Bid protein, polyarginine sequence and fragments recognized
      by urokinase and metalloproteinase

<400> SEQUENCE: 68

cgtaatattg cacgtcatct ggcacaggtt ggtgatagca tggaccgtcg tcgtcgtcgc     60

cgtcgtcgtg ttgttcgtcc gctgggtctg gcaggtcgtg ttgcagcaca tattaccggc    120

acccgtggtc gtagcaatac cctgagcagc ccgaatagca aaaatgaaaa agccctgggt    180

cgcaaaatta atagctggga aagcagccgt agcggtcata gctttctgag caatctgcat    240

ctgcgtaatg gtgaactggt gattcatgaa aaaggctttt attatattta tagccagacc    300

tattttcgct ttcaggaaga aattaaagaa aataccaaaa atgataaaca aatggtgcag    360

tacatttata aatataccag ctatccggat ccgattctgc tgatgaaaag cgcacgtaat    420

agctgttgga gcaaagatgc agaatatggc ctgtatagca tttatcaggg tggcattttt    480

gaactgaaag aaaatgatcg catttttgtg agcgtgacca atgaacatct gattgatatg    540

gatcatgaag ccagcttttt tggtgcattt ctggtgggc                           579


<210> SEQ ID NO 69
<211> LENGTH: 909
<212> TYPE: DNA
<213> ORGANISM: Artificial Sequence
<220> FEATURE:
<223> OTHER INFORMATION: synthesized, encoding a fusion protein
      comprising a fragment of TRAIL protein, homologue of ribonuclease
      RNase A, fragments recognized by urokinase and metalloproteinase,
      and sequence directing to the endoplasmic reticulum

<400> SEQUENCE: 69

cgtgttgcag cacatattac cggcacccgt ggtcgtagca ataccctgag cagcccgaat     60

agcaaaaatg aaaaagccct gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcagg aagaaattaa agaaaatacc    240

aaaaatgaca aacaaatggt gcagtatatc tacaaataca ccagctatcc ggatccgatt    300

ctgctgatga aaagcgcacg taatagctgt tggagcaaag atgcagaata tggcctgtat    360

agcatttatc agggtggcat ttttgaactg aaagaaaatg atcgcatttt tgtgagcgtg    420

accaatgaac atctgattga tatggatcat gaagccagct tttttggtgc atttctggtt    480

ggtggtggta gcggtccgct gggtctggca ggtcgtgttg ttcgtaaaga aaccgcagca    540

gccaaatttg aacgtcagca catggatagc agcaccagcg cagcaagcag cagcaattat    600

tgcaatcaga tgatgaaaag ccgcaatctg accaaagatc gttgtaaacc ggtgaatacc    660

tttgttcatg aaagcctggc agatgttcag gcagtttgca gccagaaaaa tgtggcctgt    720

aaaaatggtc agaccaattg ctatcagagc tatagcacca tgagcattac cgattgtcgt    780
```

```
gaaaccggta gcagcaaata tccgaattgc gcctataaaa ccacccaggc caataaacat    840

attattgtgg cctgtgaagg caatccgtat gttccggttc attttgatgc cagcgtgaaa    900

gaagatctg                                                            909
```

<210> SEQ ID NO 70
<211> LENGTH: 879
<212> TYPE: DNA
<213> ORGANISM: Artificial Sequence
<220> FEATURE:
<223> OTHER INFORMATION: synthesized, encoding fusion protein comprising a fragment of TRAIL protein, a homologue of ribonuclease RNase A and a steric linker

<400> SEQUENCE: 70

```
cgtgttgcag cacatattac cggcacccgt ggtcgtagca ataccctgag cagcccgaat     60

agcaaaaatg aaaaagcact gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcaag aagaaattaa agaaaatacc    240

aaaaatgata agcagatggt gcagtatatc tataaatata ccagctatcc ggatccgatt    300

ctgctgatga aaagcgcacg taatagctgt tggagcaaag atgcagaata tggtctgtat    360

agcatttatc agggtggcat tttgaactg aaagaaaatg atcgcatttt tgtgagcgtg    420

accaatgaac atctgattga tatggatcat gaagccagct tttttggtgc atttctggtt    480

ggtggtggtg gtagcggtgg tggtagtaaa gaaaccgcag cagcaaaatt tgaacgtcag    540

cacatggata gcagcaccag cgcagcaagc agcagcaatt attgtaatca gatgatgaaa    600

agccgcaatc tgaccaaaga tcgttgtaaa ccggtgaata cctttgttca tgaaagcctg    660

gcagatgttc aggcagtttg tagccagaaa aatgttgcct gtaaaaatgg tcagaccaat    720

tgctatcaga gctatagcac catgagcatt accgattgtc gtgaaaccgg tagcagcaaa    780

tatccgaatt gtgcatataa aaccacccag gccaataaac atattattgt tgcctgtgaa    840

ggcaatccgt atgttccggt tcattttgat gcaagcgtt                           879
```

<210> SEQ ID NO 71
<211> LENGTH: 852
<212> TYPE: DNA
<213> ORGANISM: Artificial Sequence
<220> FEATURE:
<223> OTHER INFORMATION: synthesized, encoding fusion protein comprising a fragment of TRAIL protein, a sequence of cytochrome C, sequences recognized by metalloprotease MMP and urokinase, a steric linker and a sequence directing to the endoplasmic reticulum

<400> SEQUENCE: 71

```
cagatcttct ttttcattgg tggctttttt cagataggca atcagatctg cgcgttcttc     60

ttttttttta atgcccacaa aaatcatttt cgtacccgga atatattttt tcggattttc    120

cagatattcc atcagggtat cttcacccca aataatgcct ttgtttttat tggctgcggt    180

atagctataa cccggtgcct gaccggtttt acgaccaaac agaccatgca gattcggacc    240

ggttttatgt ttgccacctt tttcaacggt atgacactgg ctgcatttca taataaaaat    300

ttttttgcct ttttccacat caccacgaac aacacgacct gccagaccca gcggaccgct    360

accaccacca accagaaatg caccaaaaaa gctggcttca tgatccatat caatcagatg    420

ttcattggtc acgctcacaa aaatgcgatc attttctttc agttcaaaaa tgccaccctg    480

ataaatgcta tacaggccat attctgcatc tttgctccaa cagctattac gtgcgctttt    540
```

-continued

```
catcagcaga atcggatccg gatagctggt atatttataa atgtactgca ccatttgttt    600

atcgtttttg gtattttctt taatttcttc ctgaaagcga aaataggtct ggctataaat    660

ataataaaag cctttttcat gaatcaccag ttcaccatta cgcagatgca gattgctcag    720

aaagctatga ccgctacggc tgctttccca gctattaatt ttgcgaccca gggctttttc    780

atttttgcta ttcgggctgc tcagggtatt gctacgacca cgggtgccgg taatatgtgc    840

tgcaacacgc at                                                        852
```

<210> SEQ ID NO 72
<211> LENGTH: 800
<212> TYPE: DNA
<213> ORGANISM: Artificial Sequence
<220> FEATURE:
<223> OTHER INFORMATION: synthesized, encoding fusion protein comprising a fragment of TRAIL protein, a sequence of cytochrome C, a sequence recognized by furin, steric linker, a sequence directing to the endoplasmic reticulum and translocation domain from Pseudomonas aeruginosa

<400> SEQUENCE: 72

```
cgtgttgcag cacatattac cggcacccgt ggtcgtagca ataccctgag cagcccgaat     60

agcaaaaatg aaaaagcact gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcaag aagaaattaa agaaaatacc    240

aaaaatgaca aacaaatggt gcagtatatc tataaatata ccagctatcc ggatccgatt    300

ctgctgatga aaagcgcacg taatagctgt tggagcaaag atgcagaata tggtctgtat    360

agcatttatc agggtggcat ttttgaactg aaagaaaatg atcgcatttt tgtgagcgtg    420

accaatgaac atctgattga tatggatcat gaagccagct tttttggtgc atttctggtt    480

ggtggtggtg gtagccgtaa aaaacgtgca agcggtggtc cggaaggtgg tagcctggca    540

gcactgaccg cacatcaggc atgtcatctg ccgctggaaa cctttacccg tcatcgtcag    600

cctcgtggtt gggaacagct ggaacagtgt ggttatccgg ttcagcgtct ggttgcactg    660

tatctggcag cacgtctgag ctggaatcag gttgatcagg ttattgcaaa tgcactggca    720

agtccgggta gcggtggtga tctgggtgaa gcaattcgtg aaagtccgga acaggcacgt    780

ctggcactga ccctggcagc                                                800
```

<210> SEQ ID NO 73
<211> LENGTH: 1215
<212> TYPE: DNA
<213> ORGANISM: Artificial Sequence
<220> FEATURE:
<223> OTHER INFORMATION: synthesized, encoding fusion protein comprising a fragment of TRAIL protein, a sequence of granzyme B, a sequence recognized by furin and sequences of steric linkers

<400> SEQUENCE: 73

```
cgtgttgcag cacatattac cggcacccgt ggtcgtagca ataccctgag cagcccgaat     60

agcaaaaatg aaaaagccct gggtcgtaaa attaatagct gggaaagcag ccgtagcggt    120

catagctttc tgagcaatct gcatctgcgt aatggcgaac tggtgattca tgaaaaaggc    180

ttttattata tttatagcca gacctatttt cgctttcagg aagaaattaa agaaaatacc    240

aaaaatgata aacaaatggt gcagtatatc tataaatata ccagctatcc ggatccgatt    300

ctgctgatga aaagcgcacg taatagctgt tggagcaaag atgccgaata tggtctgtat    360

agcatttatc agggtggcat ttttgaactg aaagaaaatg atcgcatttt tgtgagcgtg    420
```

```
accaatgaac atctgattga tatggatcat gaagccagct tttttggtgc atttctggtt    480

ggtggtggtg gtagccgtaa aaaacgtggt ggtggcggtt ctattattgg tggtcatgtt    540

gcaaaaccgc atagccgtcc gtatatggca tatctgatga tttgggatca gaaaagcctg    600

aaacgttgtg gtggctttct gattcgtgat gattttgttc tgaccgcagc acattgttgg    660

ggtagcagca ttaatgttac cctgggtgcc cataatatta aagaacagga accgacccag    720

cagtttattc cggttaaacg tgcaattccg catccggcat ataatccgaa aaattttagc    780

aatgatatca tgctgctgca gctggaacgt aaagcaaaac gtacccgtgc agttcagccg    840

ctgcgtctgc cgagcaataa agcacaggtt aaaccgggtc agacctgtag cgttgcaggt    900

tggggtcaga ccgcaccgct gggtaaacat tctcataccc tgcaagaggt taaaatgacc    960

gtccaagagg atcgtaaatg cgaaagcgat ctgcgccatt attatgatag caccattgaa   1020

ctgtgtgtgg gcgatccgga aatcaaaaaa accagcttta aaggtgatag cggtggtccg   1080

ctggtttgta ataaagttgc ccagggtatt gttagctatg gtcgtaataa tggtatgccg   1140

ccgcgtgcat gtaccaaagt tagcagcttt gtgcattgga ttaaaaaaac gatgaaacgc   1200

tataaagatg aactg                                                    1215
```

```
<210> SEQ ID NO 74
<211> LENGTH: 1215
<212> TYPE: DNA
<213> ORGANISM: Artificial Sequence
<220> FEATURE:
<223> OTHER INFORMATION: synthesized, encoding fusion protein comprising
      a fragment of TRAIL protein, a sequence of granzyme B, a sequence
      recognized by furin, sequences of steric linkers and a sequence
      directing to the endoplasmic reticulum

<400> SEQUENCE: 74

cgtgttgcag cacatattac cggcacccgt ggtcgtagca ataccctgag cagcccgaat     60

agcaaaaatg aaaaagcact gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcaag aagaaattaa agaaaacacc    240

aaaaatgata aacaaatggt gcagtatatt tacaaatata ccagctatcc ggatccgatt    300

ctgctgatga aaagcgcacg taatagctgt tggagcaaag atgcagaata tggtctgtat    360

agcatttatc agggtggcat ttttgaactg aaagaaaatg atcgcatttt tgtgagcgtg    420

accaatgaac atctgattga tatggatcat gaagccagct tttttggtgc atttctggtt    480

ggtggtggtg gtagccgtaa aaaacgtggt ggtggcggta gtattattgg tggtcatgtt    540

gcaaaaccgc atagccgtcc gtatatggca tatctgatga tttgggatca gaaaagcctg    600

aaacgttgtg gtggttttct gattcgtgat gattttgttc tgaccgcagc acattgttgg    660

ggtagcagca ttaatgttac cctgggtgcc cataatatta aagaacaaga accgacccag    720

cagtttattc cggttaaacg tgcaattccg catccggcat ataatccgaa aaattttagc    780

aatgatatta tgctgctgca gctggaacgc aaagcaaaac gtacccgtgc agttcagccg    840

ctgcgtctgc cgagcaataa agcacaggtt aaaccgggtc agacctgtag cgttgcaggt    900

tggggtcaga ccgcaccgct gggtaaacat tcacataccc tgcaagaggt gaaaatgacc    960

gttcaagagg atcgtaaatg cgaaagcgat ctgcgccatt attatgatag caccattgaa   1020

ctgtgtgttg gtgatccgga aattaaaaaa accagcttta aaggcgatag cggtggtccg   1080

ctggtttgta ataaagttgc acagggtatt gtgagctatg gtcgtaataa tggtatgcct   1140
```

ccgcgtgcat gtaccaaagt tagcagcttt gtgcattgga ttaaaaaaac gatgaaacgc 1200
tataaagatg aactg 1215

<210> SEQ ID NO 75
<211> LENGTH: 561
<212> TYPE: DNA
<213> ORGANISM: Artificial Sequence
<220> FEATURE:
<223> OTHER INFORMATION: synthesized, encoding fusion protein comprising a fragment of TRAIL protein, a peptide derived from Nur77 protein, a polyarginine sequence and sequences recognized by metalloprotease and urokinase

<400> SEQUENCE: 75
tttagccgta gcctgcatag cctgctgcgt cgtcgtcgtc gccgtcgtcg tgttgttcgt 60
ccgctgggtc tggcaggtcg tgttgcagca catattaccg gcacccgtgg tcgtagcaat 120
accctgagca gcccgaatag caaaaatgaa aaagccctgg gtcgcaaaat taatagctgg 180
gaaagcagcc gtagcggtca tagctttctg agcaatctgc atctgcgtaa tggtgaactg 240
gtgattcatg aaaaaggctt ttattatatt tatagccaga cctattttcg ctttcaggaa 300
gaaattaaag aaaataccaa aaatgataaa caaatggtgc agtacattta taaatatacc 360
agctatccgg atccgattct gctgatgaaa agcgcacgta atagctgttg gagcaaagat 420
gcagaatatg gcctgtatag catttatcag ggtggcattt ttgaactgaa agaaaatgat 480
cgcatttttg tgagcgtgac caatgaacat ctgattgata tggatcatga agccagcttt 540
tttggtgcat ttctggtggg c 561

<210> SEQ ID NO 76
<211> LENGTH: 579
<212> TYPE: DNA
<213> ORGANISM: Artificial Sequence
<220> FEATURE:
<223> OTHER INFORMATION: synthesized, encoding fusion protein comprising a fragment of TRAIL protein, a peptide containing the BH3 domain of Bak, a polyarginine sequence and sequences recognized by metalloprotease and urokinase

<400> SEQUENCE: 76
ggtcaggttg gtcgtcagct ggcaattatt ggtgatgata ttaaccgtcg tcgtcgtcgc 60
cgtcgtcgtg ttgttcgtcc gctgggtctg gcaggtcgtg ttgcagcaca tattaccggc 120
acccgtggtc gtagcaatac cctgagcagc ccgaatagca aaaatgaaaa agccctgggt 180
cgcaaaatta atagctggga aagcagccgt agcggtcata gctttctgag caatctgcat 240
ctgcgtaatg gtgaactggt gattcatgaa aaaggctttt attatattta tagccagacc 300
tattttcgct ttcaggaaga aattaaagaa aataccaaaa atgataaaca aatggtgcag 360
tacatttata aatataccag ctatccggat ccgattctgc tgatgaaaag cgcacgtaat 420
agctgttgga gcaaagatgc agaatatggc ctgtatagca tttatcaggg tggcattttt 480
gaactgaaag aaaatgatcg catttttgtg agcgtgacca atgaacatct gattgatatg 540
gatcatgaag ccagcttttt tggtgcattt ctggtgggc 579

<210> SEQ ID NO 77
<211> LENGTH: 666
<212> TYPE: DNA
<213> ORGANISM: Artificial Sequence
<220> FEATURE:
<223> OTHER INFORMATION: synthesized, encoding fusion protein comprising a fragment of TRAIL protein, a BH3 domain of the PUMA/BBC3, a polyarginine sequence and sequences recognized by metalloprotease and urokinase

<400> SEQUENCE: 77
gaagaacagt gggcacgtga aattggtgca cagctgcgtc gtatggcaga tgatctgaat 60
gcacagtatg aacgtcgtcg tcgtcgccgt cggcgtcgtc gtgttgttcg tccgctgggt 120
ctggcaggtc gtgttgcagc acatattacc ggcacccgtg gtcgtagcaa taccctgagc 180
agcccgaata gcaaaaatga aaaagcactg ggtcgcaaaa tcaatagctg ggaaagcagc 240
cgtagcggtc atagctttct gagcaatctg catctgcgta atggtgaact ggtgattcat 300
gaaaaaggct tttattatat ttatagccag acctattttc gctttcaaga agagattaaa 360
gaaaatacca aaaatgataa acaaatggtg cagtatattt acaaatacac cagctatccg 420
gacccgattc tgctgatgaa aagcgcacgt aatagctgtt ggagcaaaga tgcagaatat 480
ggtctgtata gcatttatca gggtggcatc tttgagctga aagaaaatga tcgcatcttt 540
gttagcgtga ccaacgaaca tctgatcgat atggatcatg aagccagctt ttttggtgca 600
tttctggtgg gtctggttcc gcgtggtagc ggtagcagcc atcatcatca tcaccatagc 660
agcggt 666

<210> SEQ ID NO 78
<211> LENGTH: 1116
<212> TYPE: DNA
<213> ORGANISM: Artificial Sequence
<220> FEATURE:
<223> OTHER INFORMATION: synthesized, encoding fusion protein comprising a fragment of TRAIL protein, a PUMA protein, sequences recognized by metalloprotease and urokinase, a sequence directing to endoplasmic reticulum and a flexible linker

<400> SEQUENCE: 78
cgtgttgcag cacatattac cggcacccgt ggtcgtagca ataccctgag cagcccgaat 60
agcaaaaatg aaaaagcact gggtcgcaaa atcaatagct gggaaagcag ccgtagcggt 120
catagctttc tgagcaatct gcatctgcgt aatggtgaac tggtgattca tgaaaaaggc 180
ttttattata tttatagcca gacctatttt cgctttcaag aagagattaa agaaaatacc 240
aaaaatgata aacaaatggt gcagtacatt tacaaatata ccagctatcc ggacccgatt 300
ctgctgatga aaagcgcacg taatagctgt tggagcaaag atgcagaata tggtctgtat 360
agcatttatc agggtggcat ctttgagctg aaagaaaatg atcgcatctt tgttagcgtg 420
accaacgaac atctgatcga tatggatcat gaagccagct tttttggtgc atttctggtt 480
ggtggtggta gcggtggtcc gctgggtctg gcaggtcgtg ttgttcgtgc ccgtgcgcgt 540
caagaaggta gcagtccgga accggttgaa ggtctggcac gtgatggtcc gcgtccgttt 600
ccgctgggtc gtctggttcc gagcgcagtt agctgtggtc tgtgtgaacc gggtctggca 660
gccgcaccgg cagcaccgac actgctgcct gcagcatatc tgtgtgcacc gaccgcaccg 720
cctgcagtta ccgcagcact gggtggtagc cgttggcctg gtggtccgcg tagtcgtccg 780
cgtggtcctc gtccggatgg tccgcagccg agcctgagcc tggcagaaca gcatctggaa 840
agtccggtgc cgagcgcacc gggtgcactg gcaggcggtc ctacacaggc agcaccgggt 900
gttcgtggtg aagaggaaca gtgggcacgt gaaattggtg cacagctgcg tcgtatggca 960
gatgatctga atgcacagta tgaacgtcgt cgtcaagaag aacagcagcg tcatcgtccg 1020
agcccgtggc gtgttctgta taatctgatt atgggtctgc tgccgctgcc tcgtggtcat 1080
cgtgcaccgg aaatggaacc gaataaagaa gatctg 1116

<210> SEQ ID NO 79
<211> LENGTH: 1479
<212> TYPE: DNA
<213> ORGANISM: Artificial Sequence
<220> FEATURE:
<223> OTHER INFORMATION: synthesized, encoding fusion protein comprising a fragment of TRAIL protein, a PUMA protein, translocation domain from Pseudomonas aeruginosa, flexible linkers, furin cleavage site and a sequence directing to the endoplasmic reticulum

<400> SEQUENCE: 79

```
cgtgttgcag cacatattac cggcacccgt ggtcgtagca ataccctgag cagcccgaat     60

agcaaaaatg aaaaagcact gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcaag aagaaattaa agaaaatacc    240

aaaaatgata agcagatggt gcagtatatc tataaatata ccagctatcc ggatccgatt    300

ctgctgatga aaagcgcacg taatagctgt tggagcaaag atgcagaata tggtctgtat    360

agcatttatc agggtggcat ttttgaactg aaagaaaatg atcgcatttt tgtgagcgtg    420

accaatgaac atctgattga tatggatcat gaagccagct tttttggtgc atttctggtt    480

ggtggtggtg gtagccgtaa aaaacgtgca agcggtggtc cggaaggtgg tagcctggca    540

gcactgaccg cacatcaggc atgtcatctg ccgctggaaa cctttacccg tcatcgtcag    600

cctcgtggtt gggaacagct ggaacagtgt ggttatccgg ttcagcgtct ggttgcactg    660

tatctggcag cacgtctgag ctggaatcag gttgatcagg ttattgcaaa tgcactggca    720

agtccgggta gcggtggtga tctgggtgaa gcaattcgtg aaagtccgga acaggcacgt    780

ctggcactga ccctggcagc agcagaaagc gaacgttttg ttcgtcaggg caccggtaat    840

gatgaagccg gtgcagcaaa tggtccggca gatggtggta gtggtggtgg tgcacgtgct    900

cgtcaagaag gtagcagtcc ggaaccggtt gaaggtctgg cacgtgacgg tccgcgtccg    960

tttccgctgg gtcgtctggt tccgagcgca gttagctgtg gtctgtgtga accgggtctg   1020

gcagccgcac cggcagcacc gacactgctg cctgcagcat atctgtgtgc accgaccgca   1080

ccgcctgcag ttaccgcagc actgggtggt agtcgttggc ctggtggtcc gcgtagtcgt   1140

ccgcgtggtc cgcgtccgga tggtccgcag ccgagtctga gcctggcaga acagcatctg   1200

gaaagtcctg tgccgagcgc accgggtgca ctggcaggcg gtccgacaca ggcagcacct   1260

ggtgttcgtg gtgaagaaga acagtgggca cgcgaaattg gtgcacagct gcgtcgtatg   1320

gcagatgatc tgaatgcaca gtatgaacgt cgtcgtcaag aagaacagca gcgtcatcgt   1380

ccgagcccgt ggcgtgttct gtataatctg attatgggtc tgctgccgct gcctcgtggt   1440

catcgtgcac cggaaatgga accgaataaa gatgaactg                          1479
```

<210> SEQ ID NO 80
<211> LENGTH: 558
<212> TYPE: DNA
<213> ORGANISM: Artificial Sequence
<220> FEATURE:
<223> OTHER INFORMATION: synthesized, encoding fusion protein comprising a fragment of TRAIL protein, SMAC/Diablo peptide, a polyarginine sequence and
sequences of cleavage sites recognized by protease uPA and MMP.

<400> SEQUENCE: 80

```
gcagttccga ttgcacagaa accgcgtcgt cgtcgtcgcc gtcgtcgtgt tgttcgtccg     60
```

```
ctgggtctgg caggtcgtgt tgcagcacat attaccggca cccgtggtcg tagcaatacc    120

ctgagcagcc cgaatagcaa aaatgaaaaa gccctgggtc gcaaaatcaa tagctgggaa    180

agcagccgta gcggtcatag ctttctgagc aatctgcatc tgcgtaatgg tgaactggtg    240

attcatgaaa aaggctttta ctatatctat agccagacct acttccgctt tcaggaagaa    300

attaaagaaa ataccaaaaa tgataaacaa atggtgcagt atatctataa atataccagc    360

tatccggatc cgattctgct gatgaaaagc gcacgtaata gctgttggag caaagatgca    420

gaatatggcc tgtatagcat ttatcagggt ggcatttttg aactgaaaga aaatgatcgc    480

atttttgtga gcgtgaccaa tgaacatctg attgatatgg atcatgaagc cagctttttt    540

ggtgcatttc tggtgggt                                                  558
```

```
<210> SEQ ID NO 81
<211> LENGTH: 627
<212> TYPE: DNA
<213> ORGANISM: Artificial Sequence
<220> FEATURE:
<223> OTHER INFORMATION: synthesized, encoding fusion protein comprising
      a fragment of TRAIL protein, buforin IIb peptide, and sequences of
      cleavage sites recognized by protease uPA and MMP.

<400> SEQUENCE: 81

cgtgcaggtc tgcagtttcc ggttggacgt ctgttacgtc gcctgctgcg tcgtctgctg     60

cgcgttgttc gtccgctggg tctggcaggt cgtgttgcag cacatattac cggcacccgt    120

ggtcgtagca ataccctgag cagcccgaat agcaaaaatg aaaaagcact gggtcgcaaa    180

atcaatagct gggaaagcag ccgtagcggt catagctttc tgagcaatct gcatctgcgt    240

aatggtgaac tggtgattca tgaaaaaggc ttttattata tttatagcca gacctatttt    300

cgctttcaag aagagattaa agaaaatacc aaaaatgata aacaaatggt gcagtacatt    360

tacaaatata ccagctatcc ggacccgatt ctgctgatga aaagcgcacg taatagctgt    420

tggagcaaag atgcagaata tggtctgtat agcatttatc agggtggcat ctttgagctg    480

aaagaaaatg atcgcatctt tgttagcgtg accaacgaac atctgatcga tatggatcat    540

gaagccagct tttttggtgc atttctggtg ggtctggttc cgcgtggtag cggtagcagc    600

catcatcatc atcaccatag cagcggt                                        627
```

```
<210> SEQ ID NO 82
<211> LENGTH: 837
<212> TYPE: DNA
<213> ORGANISM: Artificial Sequence
<220> FEATURE:
<223> OTHER INFORMATION: synthesized, encoding fusion protein comprising
      a fragment of TRAIL protein, onconase peptide, a steric linker and
      sequences of cleavage sites recognized by protease uPA and MMP.

<400> SEQUENCE: 82

cgtgttgcag cacatattac cggcacccgt ggtcgtagca ataccctgag cagcccgaat     60

agcaaaaatg aaaaagcact gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcaag aagaaattaa agaaaatacc    240

aaaaatgata agcagatggt gcagtatatc tataaatata ccagctatcc ggatccgatt    300

ctgctgatga aaagcgcacg taatagctgt tggagcaaag atgcagaata tggtctgtat    360

agcatttatc agggtggcat tttgaactg aaagaaaatg atcgcatttt tgtgagcgtg    420

accaatgaac atctgattga tatggatcat gaagccagct tttttggtgc atttctggtt    480
```

```
ggtggtggta gcggtccgct gggtctggca ggtcgtgttg ttcgtcagga ttggctgacc    540

tttcagaaaa aacatattac caatacccgt gatgtggatt gcgataatat tatgagcacc    600

aacctgtttc attgcaaaga taaaaatacc tttatttata gccgtccgga accggttaaa    660

gcaatttgta aaggtattat tgccagcaaa aatgtgctga ccacgagcga attctatctg    720

agcgattgta atgttaccag ccgtccgtgt aaatataaac tgaaaaaaag caccaataaa    780

ttttgcgtga cctgcgaaaa tcaggcaccg gttcattttg ttggtgttgg tagctgt       837
```

<210> SEQ ID NO 83
<211> LENGTH: 822
<212> TYPE: DNA
<213> ORGANISM: Artificial Sequence
<220> FEATURE:
<223> OTHER INFORMATION: synthesized, encoding fusion protein comprising a fragment of TRAIL protein, onconase peptide and a steric linker

<400> SEQUENCE: 83

```
cgtgttgcag cacatattac cggcacccgt ggtcgtagca ataccctgag cagcccgaat     60

agcaaaaatg aaaaagcact gggtcgcaaa attaatagct gggaaagcag ccgtagcggt    120

catagctttc tgagcaatct gcatctgcgt aatggtgaac tggtgattca tgaaaaaggc    180

ttttattata tttatagcca gacctatttt cgctttcaag aagaaattaa agaaaatacc    240

aaaaatgata agcagatggt gcagtatatc tataaatata ccagctatcc ggatccgatt    300

ctgctgatga aaagcgcacg taatagctgt tggagcaaag atgcagaata tggtctgtat    360

agcatttatc agggtggcat ttttgaactg aaagaaaatg atcgcatttt tgtgagcgtg    420

accaatgaac atctgattga tatggatcat gaagccagct tttttggtgc atttctggtt    480

ggtggtggtg gtagcggtgg tggtggcagc caggattggc tgacctttca gaaaaaacat    540

attaccaata cccgtgatgt ggattgcgat aatattatga gcaccaacct gtttcattgc    600

aaagataaaa atacctttat ttatagccgt ccggaaccgg ttaaagcaat ttgtaaaggt    660

attattgcca gcaaaaatgt gctgaccacg agcgaattct atctgagcga ttgtaatgtt    720

accagccgtc cgtgtaaata taaactgaaa aaaagcacca ataaattttg cgtgacctgc    780

gaaaatcagg caccggttca ttttgttggt gttggtagct gt                       822
```

<210> SEQ ID NO 84
<211> LENGTH: 591
<212> TYPE: DNA
<213> ORGANISM: Artificial Sequence
<220> FEATURE:
<223> OTHER INFORMATION: synthesized, encoding fusion protein comprising a fragment of TRAIL protein, N-terminal domain of the protein p14ARF, a polyarginine sequence and protease cleavage sites uPA and MMP

<400> SEQUENCE: 84

```
gttcgtcgtt ttctggttac cctgcgtatt cgtcgtgcat gtggtcctcc gcgtgtgcgt     60

cgtcgtcgtc gccgtcgtcg tgttgttcgt cctctgggtc tggcaggtcg cgttgcagca    120

catattaccg gcacccgtgg tcgtagcaat accctgagca gcccgaatag caaaaatgaa    180

aaagccctgg gtcgcaaaat taatagctgg gaaagcagcc gtagcggtca tagctttctg    240

agcaatctgc atctgcgtaa tggtgaactg gtgattcatg aaaaaggctt ttattatatt    300

tatagccaga cctattttcg ctttcaggaa gaaattaaag aaaataccaa aaatgataaa    360

caaatggtgc agtatatcta taaatatacc agctatccgg atccgattct gctgatgaaa    420
```

```
agcgcacgta atagctgttg gagcaaagat gcagaatatg gcctgtatag catttatcag    480

ggtggcattt ttgaactgaa agaaaatgat cgcatttttg tgagcgtgac caatgaacat    540

ctgattgata tggatcatga agccagcttt tttggtgcat ttctggttgg t             591
```

<210> SEQ ID NO 85
<211> LENGTH: 567
<212> TYPE: DNA
<213> ORGANISM: Artificial Sequence
<220> FEATURE:
<223> OTHER INFORMATION: synthesized, encoding fusion protein comprising a fragment of TRAIL protein, peptide binding to Mdm2, a polyarginine sequence and protease cleavage sites uPA and MMP

<400> SEQUENCE: 85

```
cctcgtttta tggatacctg ggaaggtctg aatcgccgtc ggcgtcgtcg gcgtcgtgtt     60

gttcgtccgc tgggtctggc aggtcgtgtt gcagcacata ttaccggcac ccgtggtcgt    120

agcaataccc tgagcagccc gaatagcaaa aatgaaaaag cactgggtcg caaaattaat    180

agctgggaaa gcagccgtag cggtcatagc tttctgagca atctgcatct gcgtaatggt    240

gaactggtga ttcatgaaaa aggcttttat tatatttata gccagaccta ttttcgcttt    300

caggaagaaa ttaaagaaaa taccaaaaat gataaacaaa tggtgcagta catttacaaa    360

tataccagct atccggatcc gattctgctg atgaaaagcg cacgtaatag ctgttggagc    420

aaagatgcag aatatggtct gtatagcatt tatcagggtg gcatttttga actgaaagaa    480

aatgatcgca tttttgtgag cgtgaccaat gaacatctga ttgatatgga tcatgaagcc    540

agcttttttg gtgcatttct ggttggt                                        567
```

<210> SEQ ID NO 86
<211> LENGTH: 585
<212> TYPE: DNA
<213> ORGANISM: Artificial Sequence
<220> FEATURE:
<223> OTHER INFORMATION: synthesized, encoding fusion protein comprising a fragment of TRAIL protein, lunasin peptide, a polyarginine sequence and protease cleavage sites uPA and MMP

<400> SEQUENCE: 86

```
tgtgaaaaac atattatgga aaaaattcag ggtcgcggtg atgatgatga tcgccgtcgg     60

cgtcgtcggc gtcgtgttgt tcgtccgctg ggtctggcag gtcgtgttgc agcacatatt    120

accggcaccc gtggtcgtag caataccctg agcagcccga atagcaaaaa tgaaaaagca    180

ctgggtcgca aaattaatag ctgggaaagc agccgtagcg gtcatagctt tctgagcaat    240

ctgcatctgc gtaatggtga actggtgatt catgaaaaag gcttttatta tatttatagc    300

cagacctatt ttcgctttca ggaagaaatt aaagaaaata ccaaaaatga taaacaaatg    360

gtgcagtaca tttacaaata taccagctat ccggatccga ttctgctgat gaaaagcgca    420

cgtaatagct gttggagcaa agatgcagaa tatggtctgt atagcattta tcagggtggc    480

atttttgaac tgaaagaaaa tgatcgcatt tttgtgagcg tgaccaatga acatctgatt    540

gatatggatc atgaagccag cttttttggt gcatttctgg ttggt                    585
```

<210> SEQ ID NO 87
<211> LENGTH: 654
<212> TYPE: DNA
<213> ORGANISM: Artificial Sequence
<220> FEATURE:
<223> OTHER INFORMATION: synthesized, encoding fusion protein comprising a fragment of TRAIL protein, Smac/Diablo protein BH3 domain of Bik protein, a polyarginine sequence and protease cleavage sites uPA and MMP

<400> SEQUENCE: 87
gcagttccga ttgcacagaa accgcgtcgt cgtcgtcgcc gtcgtcgtgt tgttcgtcct 60
ctgggtctgg caggtcgcgt tgcagcacat attaccggca cccgtggtcg tagcaatacc 120
ctgagcagcc cgaatagcaa aaatgaaaaa gccctgggtc gcaaaattaa tagctgggaa 180
agcagccgta gcggtcatag ctttctgagc aatctgcatc tgcgtaatgg tgaactggtg 240
attcatgaaa aaggctttta ttatatttat agccagacct attttcgctt tcaggaagaa 300
attaaagaaa ataccaaaaa tgataaacaa atggtgcagt atatctataa atataccagc 360
tatccggatc cgattctgct gatgaaaagc gcacgtaata gctgttggag caaagatgca 420
gaatatggcc tgtatagcat ttatcagggt ggcatttttg aactgaaaga aaatgatcgc 480
atttttgtga gcgtgaccaa tgaacatctg attgatatgg atcatgaagc cagctttttt 540
ggtgcatttc tggttggtcc gctgggcctg gctggccgtg tggttcgccg gcgccgtcgc 600
cgtcgccgcc tggcactgcg tctggcatgt attggtgatg aaatggatgt gagc 654

<210> SEQ ID NO 88
<211> LENGTH: 618
<212> TYPE: DNA
<213> ORGANISM: Artificial Sequence
<220> FEATURE:
<223> OTHER INFORMATION: synthesized, encoding fusion protein comprising a fragment of TRAIL protein, peptide consisting of Gly - Ala repetitions, a polyarginine sequence and protease cleavage sites uPA and MMP

<400> SEQUENCE: 88
cgtgttgcag cacatattac cggcacccgt ggtcgtagca ataccctgag cagcccgaat 60
agcaaaaatg aaaaagcact gggtcgcaaa attaatagct gggaaagcag ccgtagcggt 120
catagctttc tgagcaatct gcatctgcgt aatggtgaac tggtgattca tgaaaaaggc 180
ttttattata tttatagcca gacctatttt cgctttcaag aagaaattaa agaaaacacc 240
aaaaatgata aacaaatggt gcagtatatt tacaaatata ccagctatcc ggatccgatt 300
ctgctgatga aaagcgcacg taatagctgt tggagcaaag atgcagaata tggtctgtat 360
agcatttatc agggtggcat tttgaactg aaagaaaatg atcgcatttt tgtgagcgtg 420
accaatgaac atctgattga tatggatcat gaagccagct tttttggtgc atttctggtt 480
ggtggtggtg gtagcggtgg tggtcgtgtt gttcgtccgc tgggtctggc tggtgccggt 540
gccggtggtg gtgcaggcgg tgctggtgcg ggtggcggag ccggtggtgc aggtcgtcgt 600
cgtcgccgtc gtcggcgt 618

<210> SEQ ID NO 89
<211> LENGTH: 867
<212> TYPE: DNA
<213> ORGANISM: Artificial Sequence
<220> FEATURE:
<223> OTHER INFORMATION: synthesized, encoding fusion protein comprising a fragment of TRAIL protein, proteasome component S5a containing UIMs motifs, a furin cleavage site, a steric linker and a sequence directing to endoplasmic reticulum

<400> SEQUENCE: 89
cgtgttgcag cacatattac cggcacccgt ggtcgtagca ataccctgag cagcccgaat 60
agcaaaaatg aaaaagcact gggtcgcaaa attaatagct gggaaagcag ccgtagcggt 120
catagctttc tgagcaatct gcatctgcgt aatggtgaac tggtgattca tgaaaaaggc 180

```
ttttattata tttatagcca gacctatttt cgctttcaag aagaaattaa agaaaacacc    240

aaaaatgata aacaaatggt gcagtatatt tacaaatata ccagctatcc ggatccgatt    300

ctgctgatga aaagcgcacg taatagctgt tggagcaaag atgcagaata tggtctgtat    360

agcatttatc agggtggcat ttttgaactg aaagaaaatg atcgcatttt tgtgagcgtg    420

accaatgaac atctgattga tatggatcat gaagccagct tttttggtgc atttctggtt    480

ggtggtggtg gtagcggtgg tcgtaaaaaa cgtatgacca ttagccagca agaatttggt    540

cgtaccggtc tgccggatct gagcagcatg accgaagaag aacaaattgc ctacgcaatg    600

cagatgagcc tgcagggtgc agaatttggt caggcagaaa gcgcagatat tgatgcaagc    660

agcgcaatgg ataccagcga accggcaaaa gaagaagacg attacgacgt tatgcaggat    720

ccggaatttc tgcagagcgt tctggaaaat ctgccgggtg ttgatccgaa taatgaagca    780

attcgtaatg caatgggtag cctggcaagc caagcaacca aagatggcaa aaaagataaa    840

aaagaggaag acaaaaaaga agatctg                                        867
```

<210> SEQ ID NO 90
<211> LENGTH: 549
<212> TYPE: DNA
<213> ORGANISM: Artificial Sequence
<220> FEATURE:
<223> OTHER INFORMATION: synthesized, encoding fusion protein comprising a fragment of TRAIL protein, peptide derived from the TNF ligand and cleavage sites recognized by proteases uPA and MMP

<400> SEQUENCE: 90

```
gttgcaaatc cgcaggcaga aggtcagctg cgcgttgttc gtccgctggg tctggcaggt     60

ccgcagcgtg ttgcagcaca tattaccggc acccgtggtc gtagcaatac cctgagcagc    120

ccgaatagca aaaatgaaaa agccctgggt cgtaaaatta atagctggga aagcagccgt    180

agcggtcata gctttctgag caatctgcat ctgcgtaatg gcgaactggt gattcatgaa    240

aaaggctttt attatattta tagccagacc tattttcgct ttcaggaaga aattaaagaa    300

aataccaaaa atgataaaca aatggtgcag tatatctata aatataccag ctatccggat    360

ccgattctgc tgatgaaaag cgcacgtaat agctgttgga gcaaagatgc cgaatatggt    420

ctgtatagca tttatcaggg tggcattttt gaactgaaag aaaatgatcg catttttgtg    480

agcgtgacca atgaacatct gattgatatg gatcatgaag ccagcttttt tggtgcattt    540

ctggttggt                                                            549
```

<210> SEQ ID NO 91
<211> LENGTH: 537
<212> TYPE: DNA
<213> ORGANISM: Artificial Sequence
<220> FEATURE:
<223> OTHER INFORMATION: synthesized, fusion protein comprising a fragment of TRAIL protein, a peptide derived from the TNF and cleavage sites recognized by proteases uPA and MMP.

<400> SEQUENCE: 91

```
ctggcaaatg gtgttgaacg tgttgttcgt ccgctgggtc tggcaggtcc gcagcgtgtt     60

gcagcacata ttaccggcac ccgtggtcgt agcaataccc tgagcagccc gaatagcaaa    120

aatgaaaaag ccctgggtcg taaaattaat agctgggaaa gcagccgtag cggtcatagc    180

tttctgagca atctgcatct gcgtaatggc gaactggtga ttcatgaaaa aggcttttat    240

tatatttata gccagaccta ttttcgcttt caggaagaaa ttaaagaaaa taccaaaaat    300
```

gataaacaaa tggtgcagta tatctataaa tataccagct atccggatcc gattctgctg 360
atgaaaagcg cacgtaatag ctgttggagc aaagatgccg aatatggtct gtatagcatt 420
tatcagggtg gcatttttga actgaaagaa aatgatcgca tttttgtgag cgtgaccaat 480
gaacatctga ttgatatgga tcatgaagcc agctttttg gtgcatttct ggttggt 537

<210> SEQ ID NO 92
<211> LENGTH: 540
<212> TYPE: DNA
<213> ORGANISM: Artificial Sequence
<220> FEATURE:
<223> OTHER INFORMATION: synthesized, encoding fusion protein comprising a fragment of TRAIL protein, a fragment of the TNF cytokine and cleavage sites recognized by proteases uPA and MMP.

<400> SEQUENCE: 92
tgtccgagcg aaggtctgtg tcgtgttgtt cgtccgctgg gtctggcagg tccgcagcgt 60
gttgcagcac atattaccgg cacccgtggt cgtagcaata ccctgagcag cccgaatagc 120
aaaaatgaaa aagccctggg tcgtaaaatt aatagctggg aaagcagccg tagcggtcat 180
agctttctga gcaatctgca tctgcgtaat ggcgaactgg tgattcatga aaaaggcttt 240
tattatattt atagccagac ctattttcgc tttcaggaag aaattaaaga aaataccaaa 300
aatgataaac aaatggtgca gtatatctat aaatatacca gctatccgga tccgattctg 360
ctgatgaaaa gcgcacgtaa tagctgttgg agcaaagatg ccgaatatgg tctgtatagc 420
atttatcagg gtggcatttt tgaactgaaa gaaaatgatc gcatttttgt gagcgtgacc 480
aatgaacatc tgattgatat ggatcatgaa gccagctttt ttggtgcatt tctggttggt 540

<210> SEQ ID NO 93
<211> LENGTH: 459
<212> TYPE: PRT
<213> ORGANISM: Artificial Sequence
<220> FEATURE:
<223> OTHER INFORMATION: synthesized, fusion protein comprising a fragment of TRAIL protein, RNAse A, a sequence directing to endoplasmic reticulum, steric, pegylation and stabilizing linkers, sequence of furincleavage site and a fragment of P.aeruginosa translocation

<400> SEQUENCE: 93

Gly Cys Ala Ala Ala Cys Ala Ala Cys Thr Ser Glu Glu Thr Ile Ser
1 5 10 15

Thr Val Gln Glu Lys Gln Gln Asn Ile Ser Pro Leu Val Arg Glu Arg
20 25 30

Gly Pro Gln Arg Val Ala Ala His Ile Thr Gly Thr Arg Gly Arg Ser
35 40 45

Asn Thr Leu Ser Ser Pro Asn Ser Lys Asn Glu Lys Ala Leu Gly Arg
50 55 60

Lys Ile Asn Ser Trp Glu Ser Ser Arg Ser Gly His Ser Phe Leu Ser
65 70 75 80

Asn Leu His Leu Arg Asn Gly Glu Leu Val Ile His Glu Lys Gly Phe
85 90 95

Tyr Tyr Ile Tyr Ser Gln Thr Tyr Phe Arg Phe Gln Glu Glu Ile Lys
100 105 110

Glu Asn Thr Lys Asn Asp Lys Gln Met Val Gln Tyr Ile Tyr Lys Tyr
115 120 125

Thr Ser Tyr Pro Asp Pro Ile Leu Leu Met Lys Ser Ala Arg Asn Ser
130 135 140

```
Cys Trp Ser Lys Asp Ala Glu Tyr Gly Leu Tyr Ser Ile Tyr Gln Gly
145                 150                 155                 160

Gly Ile Phe Glu Leu Lys Glu Asn Asp Arg Ile Phe Val Ser Val Thr
                165                 170                 175

Asn Glu His Leu Ile Asp Met Asp His Glu Ala Ser Phe Phe Gly Ala
            180                 185                 190

Phe Leu Val Gly Gly Gly Gly Ser Ala Ser Gly Cys Gly Pro Glu Arg
        195                 200                 205

Lys Lys Arg Ala Ser Gly Gly Pro Glu Gly Gly Ser Leu Ala Ala Leu
    210                 215                 220

Thr Ala His Gln Ala Cys His Leu Pro Leu Glu Thr Phe Thr Arg His
225                 230                 235                 240

Arg Gln Pro Arg Gly Trp Glu Gln Leu Glu Gln Cys Gly Tyr Pro Val
                245                 250                 255

Gln Arg Leu Val Ala Leu Tyr Leu Ala Ala Arg Leu Ser Trp Asn Gln
            260                 265                 270

Val Asp Gln Val Ile Arg Asn Ala Leu Ala Ser Pro Gly Ser Gly Gly
        275                 280                 285

Asp Leu Gly Glu Ala Ile Arg Glu Gln Pro Glu Gln Ala Arg Leu Ala
    290                 295                 300

Leu Thr Leu Ala Ala Ala Glu Ser Glu Arg Phe Val Arg Gln Gly Thr
305                 310                 315                 320

Gly Asn Gly Gly Gly Gly Ser Gly Gly Gly Ser Lys Glu Thr Ala Ala
                325                 330                 335

Ala Lys Phe Glu Arg Gln His Met Asp Ser Ser Thr Ser Ala Ala Ser
            340                 345                 350

Ser Ser Asn Tyr Cys Asn Gln Met Met Lys Ser Arg Asn Leu Thr Lys
        355                 360                 365

Asp Arg Cys Lys Pro Val Asn Thr Phe Val His Glu Ser Leu Ala Asp
    370                 375                 380

Val Gln Ala Val Cys Ser Gln Lys Asn Val Ala Cys Lys Asn Gly Gln
385                 390                 395                 400

Thr Asn Cys Tyr Gln Ser Tyr Ser Thr Met Ser Ile Thr Asp Cys Arg
                405                 410                 415

Glu Thr Gly Ser Ser Lys Tyr Pro Asn Cys Ala Tyr Lys Thr Thr Gln
            420                 425                 430

Ala Asn Lys His Ile Ile Val Ala Cys Glu Gly Asn Pro Tyr Val Pro
        435                 440                 445

Val His Phe Asp Ala Ser Val Lys Asp Glu Leu
    450                 455


<210> SEQ ID NO 94
<211> LENGTH: 213
<212> TYPE: PRT
<213> ORGANISM: Artificial Sequence
<220> FEATURE:
<223> OTHER INFORMATION: synthesized, fusion protein comprising a
      fragment of TRAIL protein, Nur77 derived peptide , poly-arginine
      transporting domain and sequence of cleavage sites recognized by
      proteases MMP and uPA

<400> SEQUENCE: 94

Phe Ser Arg Ser Leu His Ser Leu Leu Arg Arg Arg Arg Arg Arg Arg
1               5                   10                  15

Arg Val Val Arg Pro Leu Gly Leu Ala Gly Thr Ser Glu Glu Thr Ile
            20                  25                  30
```

```
Ser Thr Val Gln Glu Lys Gln Gln Asn Ile Ser Pro Leu Val Arg Glu
        35                  40                  45

Arg Gly Pro Gln Arg Val Ala Ala His Ile Thr Gly Thr Arg Gly Arg
    50                  55                  60

Ser Asn Thr Leu Ser Ser Pro Asn Ser Lys Asn Glu Lys Ala Leu Gly
65                  70                  75                  80

Arg Lys Ile Asn Ser Trp Glu Ser Ser Arg Ser Gly His Ser Phe Leu
                85                  90                  95

Ser Asn Leu His Leu Arg Asn Gly Glu Leu Val Ile His Glu Lys Gly
            100                 105                 110

Phe Tyr Tyr Ile Tyr Ser Gln Thr Tyr Phe Arg Phe Gln Glu Glu Ile
        115                 120                 125

Lys Glu Asn Thr Lys Asn Asp Lys Gln Met Val Gln Tyr Ile Tyr Lys
    130                 135                 140

Tyr Thr Ser Tyr Pro Asp Pro Ile Leu Leu Met Lys Ser Ala Arg Asn
145                 150                 155                 160

Ser Cys Trp Ser Lys Asp Ala Glu Tyr Gly Leu Tyr Ser Ile Tyr Gln
                165                 170                 175

Gly Gly Ile Phe Glu Leu Lys Glu Asn Asp Arg Ile Phe Val Ser Val
            180                 185                 190

Thr Asn Glu His Leu Ile Asp Met Asp His Glu Ala Ser Phe Phe Gly
        195                 200                 205

Ala Phe Leu Val Gly
    210


<210> SEQ ID NO 95
<211> LENGTH: 204
<212> TYPE: PRT
<213> ORGANISM: Artificial Sequence
<220> FEATURE:
<223> OTHER INFORMATION: synthesized, fusion protein comprising a
      fragment of TRAIL protein, azurin derived peptide and sequence
      of cleavage sites recognized by proteases MMP  and uPA

<400> SEQUENCE: 95

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp Pro Leu Gly Leu
            20                  25                  30

Ala Gly Arg Val Val Arg Glu Arg Gly Pro Gln Arg Val Ala Ala His
        35                  40                  45

Ile Thr Gly Thr Arg Gly Arg Ser Asn Thr Leu Ser Ser Pro Asn Ser
    50                  55                  60

Lys Asn Glu Lys Ala Leu Gly Arg Lys Ile Asn Ser Trp Glu Ser Ser
65                  70                  75                  80

Arg Ser Gly His Ser Phe Leu Ser Asn Leu His Leu Arg Asn Gly Glu
                85                  90                  95

Leu Val Ile His Glu Lys Gly Phe Tyr Tyr Ile Tyr Ser Gln Thr Tyr
            100                 105                 110

Phe Arg Phe Gln Glu Glu Ile Lys Glu Asn Thr Lys Asn Asp Lys Gln
        115                 120                 125

Met Val Gln Tyr Ile Tyr Lys Tyr Thr Ser Tyr Pro Asp Pro Ile Leu
    130                 135                 140

Leu Met Lys Ser Ala Arg Asn Ser Cys Trp Ser Lys Asp Ala Glu Tyr
145                 150                 155                 160

Gly Leu Tyr Ser Ile Tyr Gln Gly Gly Ile Phe Glu Leu Lys Glu Asn
```

-continued

```
                165                 170                 175

Asp Arg Ile Phe Val Ser Val Thr Asn Glu His Leu Ile Asp Met Asp
            180                 185                 190

His Glu Ala Ser Phe Phe Gly Ala Phe Leu Val Gly
        195                 200


<210> SEQ ID NO 96
<211> LENGTH: 205
<212> TYPE: PRT
<213> ORGANISM: Artificial Sequence
<220> FEATURE:
<223> OTHER INFORMATION: synthesized, fusion protein comprising a
      fragment of TRAIL protein, azurin derived peptide, cleavage site
      recognized by furin, steric linker and a sequence directing to
      endoplasmic reticulum

<400> SEQUENCE: 96

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Gly Gly Ser Arg Lys Lys Arg Val Lys Arg Leu Ser Thr
                165                 170                 175

Ala Ala Asp Met Gln Gly Val Val Thr Asp Gly Met Ala Ser Gly Leu
            180                 185                 190

Asp Lys Asp Tyr Leu Lys Pro Asp Asp Lys Asp Glu Leu
        195                 200                 205


<210> SEQ ID NO 97
<211> LENGTH: 207
<212> TYPE: PRT
<213> ORGANISM: Artificial Sequence
<220> FEATURE:
<223> OTHER INFORMATION: synthesized, fusion protein comprising a
      fragment of TRAIL protein, azurin derived peptide, cleavage site
      recognized by proteases MMP and uPA and steric linker

<400> SEQUENCE: 97

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
```

```
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Gly Gly Ser Gly Gly Gly Pro Leu Gly Leu Ala Gly Arg
                165                 170                 175

Val Val Arg Leu Ser Thr Ala Ala Asp Met Gln Gly Val Val Thr Asp
            180                 185                 190

Gly Met Ala Ser Gly Leu Asp Lys Asp Tyr Leu Lys Pro Asp Asp
        195                 200                 205


<210> SEQ ID NO 98
<211> LENGTH: 327
<212> TYPE: PRT
<213> ORGANISM: Artificial Sequence
<220> FEATURE:
<223> OTHER INFORMATION: synthesized, fusion protein comprising a
      fragment of TRAIL protein, azurin derived peptide, cleavage site
      recognized by proteases MMP and uPA and steric linker

<400> SEQUENCE: 98

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Gly Gly Ser Gly Gly Gly Pro Leu Gly Leu Ala Gly Arg
                165                 170                 175

Val Val Arg Met Leu Arg Lys Leu Ala Ala Val Ser Leu Leu Ser Leu
            180                 185                 190
```

```
Leu Ser Ala Pro Leu Leu Ala Ala Glu Cys Ser Val Asp Ile Gln Gly
        195                 200                 205

Asn Asp Gln Met Gln Phe Asn Thr Asn Ala Ile Thr Val Asp Lys Ser
    210                 215                 220

Cys Lys Gln Phe Thr Val Asn Leu Ser His Pro Gly Asn Leu Pro Lys
225                 230                 235                 240

Asn Val Met Gly His Asn Trp Val Leu Ser Thr Ala Ala Asp Met Gln
                245                 250                 255

Gly Val Val Thr Asp Gly Met Ala Ser Gly Leu Asp Lys Asp Tyr Leu
            260                 265                 270

Lys Pro Asp Asp Ser Arg Val Ile Ala His Thr Lys Leu Ile Gly Ser
        275                 280                 285

Gly Glu Lys Asp Ser Val Thr Phe Asp Val Ser Lys Leu Lys Glu Gly
    290                 295                 300

Glu Gln Tyr Met Phe Phe Cys Thr Phe Pro Gly His Ser Ala Leu Met
305                 310                 315                 320

Lys Gly Thr Leu Thr Leu Lys
                325


<210> SEQ ID NO 99
<211> LENGTH: 193
<212> TYPE: PRT
<213> ORGANISM: Artificial Sequence
<220> FEATURE:
<223> OTHER INFORMATION: synthesized, fusion protein comprising a
      fragment of TRAIL protein, a Smac/DIABLO derived peptide,
      poly-arginine transporting domain and cleavage sites recognized
      by proteases uPA and MMP

<400> SEQUENCE: 99

Ala Val Pro Ile Ala Gln Lys Pro Arg Arg Arg Arg Arg Arg Arg Arg
1               5                   10                  15

Val Val Arg Pro Leu Gly Leu Ala Gly Val Arg Glu Arg Gly Pro Gln
            20                  25                  30

Arg Val Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
    130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

Gly
```

<210> SEQ ID NO 100
<211> LENGTH: 221
<212> TYPE: PRT
<213> ORGANISM: Artificial Sequence
<220> FEATURE:
<223> OTHER INFORMATION: synthesized, fusion protein comprising a fragment of TRAIL protein, a Smac/DIABLO derived peptide, poly-arginine transporting domain, cleavage sites recognized by proteases uPA and MMP and polycysteine linker.

<400> SEQUENCE: 100

```
Ala Val Pro Ile Ala Gln Lys Pro Arg Arg Arg Arg Arg Arg Arg Arg
1               5                   10                  15

Val Val Arg Pro Leu Gly Leu Ala Gly Gly Cys Ala Ala Ala Cys Ala
            20                  25                  30

Ala Cys Thr Ser Glu Glu Thr Ile Ser Thr Val Gln Glu Lys Gln Gln
        35                  40                  45

Asn Ile Ser Pro Leu Val Arg Glu Arg Gly Pro Gln Arg Cys Ala Ala
    50                  55                  60

His Ile Thr Gly Thr Arg Gly Arg Ser Asn Thr Leu Ser Ser Pro Asn
65                  70                  75                  80

Ser Lys Asn Glu Lys Ala Leu Gly Arg Lys Ile Asn Ser Trp Glu Ser
                85                  90                  95

Ser Arg Ser Gly His Ser Phe Leu Ser Asn Leu His Leu Arg Asn Gly
            100                 105                 110

Glu Leu Val Ile His Glu Lys Gly Phe Tyr Tyr Ile Tyr Ser Gln Thr
        115                 120                 125

Tyr Phe Arg Phe Gln Glu Glu Ile Lys Glu Asn Thr Lys Asn Asp Lys
    130                 135                 140

Gln Met Val Gln Tyr Ile Tyr Lys Tyr Thr Ser Tyr Pro Asp Pro Ile
145                 150                 155                 160

Leu Leu Met Lys Ser Ala Arg Asn Ser Cys Trp Ser Lys Asp Ala Glu
                165                 170                 175

Tyr Gly Leu Tyr Ser Ile Tyr Gln Gly Gly Ile Phe Glu Leu Lys Glu
            180                 185                 190

Asn Asp Arg Ile Phe Val Ser Val Thr Asn Glu His Leu Ile Asp Met
        195                 200                 205

Asp His Glu Ala Ser Phe Phe Gly Ala Phe Leu Val Gly
    210                 215                 220
```

<210> SEQ ID NO 101
<211> LENGTH: 212
<212> TYPE: PRT
<213> ORGANISM: Artificial Sequence
<220> FEATURE:
<223> OTHER INFORMATION: synthesized, fusion protein comprising a fragment of TRAIL protein, a Smac/DIABLO derived peptide, poly-arginine transporting domain and cleavage sites recognized by proteases uPA and MMP.

<400> SEQUENCE: 101

```
Ala Val Pro Ile Ala Gln Lys Pro Arg Arg Arg Arg Arg Arg Arg Arg
1               5                   10                  15

Val Val Arg Pro Leu Gly Leu Ala Gly Thr Ser Glu Glu Thr Ile Ser
            20                  25                  30

Thr Val Gln Glu Lys Gln Gln Asn Ile Ser Pro Leu Val Arg Glu Arg
        35                  40                  45

Gly Pro Gln Arg Val Ala Ala His Ile Thr Gly Thr Arg Gly Arg Ser
    50                  55                  60
```

Asn Thr Leu Ser Ser Pro Asn Ser Lys Asn Glu Lys Ala Leu Gly Arg
65 70 75 80

Lys Ile Asn Ser Trp Glu Ser Ser Arg Ser Gly His Ser Phe Leu Ser
85 90 95

Asn Leu His Leu Arg Asn Gly Glu Leu Val Ile His Glu Lys Gly Phe
100 105 110

Tyr Tyr Ile Tyr Ser Gln Thr Tyr Phe Arg Phe Gln Glu Glu Ile Lys
115 120 125

Glu Asn Thr Lys Asn Asp Lys Gln Met Val Gln Tyr Ile Tyr Lys Tyr
130 135 140

Thr Ser Tyr Pro Asp Pro Ile Leu Leu Met Lys Ser Ala Arg Asn Ser
145 150 155 160

Cys Trp Ser Lys Asp Ala Glu Tyr Gly Leu Tyr Ser Ile Tyr Gln Gly
165 170 175

Gly Ile Phe Glu Leu Lys Glu Asn Asp Arg Ile Phe Val Ser Val Thr
180 185 190

Asn Glu His Leu Ile Asp Met Asp His Glu Ala Ser Phe Phe Gly Ala
195 200 205

Phe Leu Val Gly
210

<210> SEQ ID NO 102
<211> LENGTH: 212
<212> TYPE: PRT
<213> ORGANISM: Artificial Sequence
<220> FEATURE:
<223> OTHER INFORMATION: synthesized, fusion protein comprising a fragment of TRAIL protein, a protein derived from aPP protein and BH3 domain of Bax, poly-arginine domain and sequences of cleavage sites recognized by proteases uPA and MMP.

<400> SEQUENCE: 102

Gly Pro Ser Gln Pro Thr Tyr Pro Gly Asp Asp Ala Pro Val Glu Asp
1 5 10 15

Leu Ile Arg Phe Val Gly Arg Leu Leu Ala Tyr Phe Gly Asp Thr Ile
20 25 30

Asn Arg Arg Arg Arg Arg Arg Arg Arg Arg Val Val Arg Pro Leu Gly
35 40 45

Leu Ala Gly Arg Val Ala Ala His Ile Thr Gly Thr Arg Gly Arg Ser
50 55 60

Asn Thr Leu Ser Ser Pro Asn Ser Lys Asn Glu Lys Ala Leu Gly Arg
65 70 75 80

Lys Ile Asn Ser Trp Glu Ser Ser Arg Ser Gly His Ser Phe Leu Ser
85 90 95

Asn Leu His Leu Arg Asn Gly Glu Leu Val Ile His Glu Lys Gly Phe
100 105 110

Tyr Tyr Ile Tyr Ser Gln Thr Tyr Phe Arg Phe Gln Glu Glu Ile Lys
115 120 125

Glu Asn Thr Lys Asn Asp Lys Gln Met Val Gln Tyr Ile Tyr Lys Tyr
130 135 140

Thr Ser Tyr Pro Asp Pro Ile Leu Leu Met Lys Ser Ala Arg Asn Ser
145 150 155 160

Cys Trp Ser Lys Asp Ala Glu Tyr Gly Leu Tyr Ser Ile Tyr Gln Gly
165 170 175

Gly Ile Phe Glu Leu Lys Glu Asn Asp Arg Ile Phe Val Ser Val Thr
180 185 190

```
Asn Glu His Leu Ile Asp Met Asp His Glu Ala Ser Phe Phe Gly Ala
        195                 200                 205

Phe Leu Val Gly
    210


<210> SEQ ID NO 103
<211> LENGTH: 247
<212> TYPE: PRT
<213> ORGANISM: Artificial Sequence
<220> FEATURE:
<223> OTHER INFORMATION: synthesized, fusion protein comprising a
      fragment of TRAIL protein, a protein derived from aPP protein
      and BH3 domain of Bax, poly-arginine domain, polycysteine linker
      and sequences of cleavage sites recognized by proteases uPA and
      MMP.

<400> SEQUENCE: 103

Gly Pro Ser Gln Pro Thr Tyr Pro Gly Asp Asp Ala Pro Val Glu Asp
1               5                   10                  15

Leu Ile Arg Phe Val Gly Arg Leu Leu Ala Tyr Phe Gly Asp Thr Ile
            20                  25                  30

Asn Arg Arg Arg Arg Arg Arg Arg Arg Arg Val Val Arg Pro Leu Gly
        35                  40                  45

Leu Ala Gly Gly Cys Ala Ala Ala Cys Ala Ala Cys Thr Ser Glu Glu
    50                  55                  60

Thr Ile Ser Thr Val Gln Glu Lys Gln Gln Asn Ile Ser Pro Leu Val
65                  70                  75                  80

Arg Glu Arg Gly Pro Gln Arg Val Ala Ala His Ile Thr Gly Thr Arg
                85                  90                  95

Gly Arg Ser Asn Thr Leu Ser Ser Pro Asn Ser Lys Asn Glu Lys Ala
            100                 105                 110

Leu Gly Arg Lys Ile Asn Ser Trp Glu Ser Ser Arg Ser Gly His Ser
        115                 120                 125

Phe Leu Ser Asn Leu His Leu Arg Asn Gly Glu Leu Val Ile His Glu
    130                 135                 140

Lys Gly Phe Tyr Tyr Ile Tyr Ser Gln Thr Tyr Phe Arg Phe Gln Glu
145                 150                 155                 160

Glu Ile Lys Glu Asn Thr Lys Asn Asp Lys Gln Met Val Gln Tyr Ile
                165                 170                 175

Tyr Lys Tyr Thr Ser Tyr Pro Asp Pro Ile Leu Leu Met Lys Ser Ala
            180                 185                 190

Arg Asn Ser Cys Trp Ser Lys Asp Ala Glu Tyr Gly Leu Tyr Ser Ile
        195                 200                 205

Tyr Gln Gly Gly Ile Phe Glu Leu Lys Glu Asn Asp Arg Ile Phe Val
    210                 215                 220

Ser Val Thr Asn Glu His Leu Ile Asp Met Asp His Glu Ala Ser Phe
225                 230                 235                 240

Phe Gly Ala Phe Leu Val Gly
                245


<210> SEQ ID NO 104
<211> LENGTH: 212
<212> TYPE: PRT
<213> ORGANISM: Artificial Sequence
<220> FEATURE:
<223> OTHER INFORMATION: synthesized, fusion protein comprising a
      fragment of TRAIL protein, a protein derived from aPP protein and
      BH3 domain of Bax and sequences of cleavage sites recognized by
      proteases uPA and MMP.
```

<400> SEQUENCE: 104

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly Pro Leu Gly Leu Ala Gly Arg Val
                165                 170                 175

Val Arg Gly Pro Arg Arg Pro Arg Arg Pro Gly Asp Asp Ala Pro Val
            180                 185                 190

Glu Asp Leu Ile Arg Phe Val Gly Arg Leu Leu Ala Tyr Phe Gly Asp
        195                 200                 205

Thr Ile Asn Arg
    210

<210> SEQ ID NO 105
<211> LENGTH: 221
<212> TYPE: PRT
<213> ORGANISM: Artificial Sequence
<220> FEATURE:
<223> OTHER INFORMATION: synthesized, fusion protein comprising a fragment of TRAIL reticulon RTN1-C derived peptide, a nucleus localizing sequence, a polycysteine linker and cleavage sites recognized by proteases uPA and MMP

<400> SEQUENCE: 105

Arg Thr His Ile Asn Thr Val Val Ala Lys Ile Gln Ala Lys Ile Pro
1               5                   10                  15

Gly Ala Lys Arg His Ala Glu Glu Glu Glu Ala Ala Gly Arg Lys Arg
            20                  25                  30

Lys Lys Arg Thr Arg Val Val Arg Pro Leu Gly Leu Ala Gly Gly Gly
        35                  40                  45

Cys Ala Ala Ala Cys Ala Ala Cys Gly Gly Gly Gln Arg Val Ala Ala
    50                  55                  60

His Ile Thr Gly Thr Arg Gly Arg Ser Asn Thr Leu Ser Ser Pro Asn
65                  70                  75                  80

Ser Lys Asn Glu Lys Ala Leu Gly Arg Lys Ile Asn Ser Trp Glu Ser
                85                  90                  95

Ser Arg Ser Gly His Ser Phe Leu Ser Asn Leu His Leu Arg Asn Gly
            100                 105                 110

```
Glu Leu Val Ile His Glu Lys Gly Phe Tyr Tyr Ile Tyr Ser Gln Thr
        115                 120                 125

Tyr Phe Arg Phe Gln Glu Glu Ile Lys Glu Asn Thr Lys Asn Asp Lys
    130                 135                 140

Gln Met Val Gln Tyr Ile Tyr Lys Tyr Thr Ser Tyr Pro Asp Pro Ile
145                 150                 155                 160

Leu Leu Met Lys Ser Ala Arg Asn Ser Cys Trp Ser Lys Asp Ala Glu
                165                 170                 175

Tyr Gly Leu Tyr Ser Ile Tyr Gln Gly Gly Ile Phe Glu Leu Lys Glu
            180                 185                 190

Asn Asp Arg Ile Phe Val Ser Val Thr Asn Glu His Leu Ile Asp Met
        195                 200                 205

Asp His Glu Ala Ser Phe Phe Gly Ala Phe Leu Val Gly
    210                 215                 220


<210> SEQ ID NO 106
<211> LENGTH: 435
<212> TYPE: PRT
<213> ORGANISM: Artificial Sequence
<220> FEATURE:
<223> OTHER INFORMATION: synthesized, fusion protein comprising a
      fragment of TRAIL reticulon RTN1-C derived peptide, a poly-
      arginine domain, a polycysteine linker, steric linker and cleavage
      sites recognized by proteases uPA and MMP

<400> SEQUENCE: 106

Ala Glu Pro Ser Ala Ala Thr Gln Ser His Ser Ile Ser Ser Ser Ser
1               5                   10                  15

Phe Gly Ala Glu Pro Ser Ala Pro Gly Gly Gly Gly Ser Pro Gly Ala
            20                  25                  30

Cys Pro Ala Leu Gly Thr Lys Ser Cys Ser Ser Ser Cys Ala Val His
        35                  40                  45

Asp Leu Ile Phe Trp Arg Asp Val Lys Lys Thr Gly Phe Val Phe Gly
    50                  55                  60

Thr Thr Leu Ile Met Leu Leu Ser Leu Ala Ala Phe Ser Val Ile Ser
65                  70                  75                  80

Val Val Ser Tyr Leu Ile Leu Ala Leu Leu Ser Val Thr Ile Ser Phe
                85                  90                  95

Arg Ile Tyr Lys Ser Val Ile Gln Ala Val Gln Lys Ser Glu Glu Gly
            100                 105                 110

His Pro Phe Lys Ala Tyr Leu Asp Val Asp Ile Thr Leu Ser Ser Glu
        115                 120                 125

Ala Phe His Asn Tyr Met Asn Ala Ala Met Val His Ile Asn Arg Ala
    130                 135                 140

Leu Lys Leu Ile Ile Arg Leu Phe Leu Val Glu Asp Leu Val Asp Ser
145                 150                 155                 160

Leu Lys Leu Ala Val Phe Met Trp Leu Met Thr Tyr Val Gly Ala Val
                165                 170                 175

Phe Asn Gly Ile Thr Leu Leu Ile Leu Ala Glu Leu Leu Ile Phe Ser
            180                 185                 190

Val Pro Ile Val Tyr Glu Lys Tyr Lys Thr Gln Ile Asp His Tyr Val
        195                 200                 205

Gly Ile Ala Arg Asp Gln Thr Lys Ser Ile Val Glu Lys Ile Gln Ala
    210                 215                 220

Lys Leu Pro Gly Ile Ala Lys Lys Lys Ala Glu Arg Arg Arg Arg Arg
225                 230                 235                 240
```

-continued

```
Arg Arg Arg Gly Gly Ser Gly Gly Arg Val Val Arg Pro Leu Gly Leu
                245                 250                 255

Ala Gly Gly Gly Ser Gly Gly Cys Ala Ala Glu Cys Ala Ala Ala Cys
            260                 265                 270

Pro Gln Arg Val Ala Ala His Ile Thr Gly Thr Arg Gly Arg Ser Asn
        275                 280                 285

Thr Leu Ser Ser Pro Asn Ser Lys Asn Glu Lys Ala Leu Gly Arg Lys
    290                 295                 300

Ile Asn Ser Trp Glu Ser Ser Arg Ser Gly His Ser Phe Leu Ser Asn
305                 310                 315                 320

Leu His Leu Arg Asn Gly Glu Leu Val Ile His Glu Lys Gly Phe Tyr
                325                 330                 335

Tyr Ile Tyr Ser Gln Thr Tyr Phe Arg Phe Gln Glu Glu Ile Lys Glu
            340                 345                 350

Asn Thr Lys Asn Asp Lys Gln Met Val Gln Tyr Ile Tyr Lys Tyr Thr
        355                 360                 365

Ser Tyr Pro Asp Pro Ile Leu Leu Met Lys Ser Ala Arg Asn Ser Cys
    370                 375                 380

Trp Ser Lys Asp Ala Glu Tyr Gly Leu Tyr Ser Ile Tyr Gln Gly Gly
385                 390                 395                 400

Ile Phe Glu Leu Lys Glu Asn Asp Arg Ile Phe Val Ser Val Thr Asn
                405                 410                 415

Glu His Leu Ile Asp Met Asp His Glu Ala Ser Phe Phe Gly Ala Phe
            420                 425                 430

Leu Val Gly
        435
```

<210> SEQ ID NO 107
<211> LENGTH: 580
<212> TYPE: PRT
<213> ORGANISM: Artificial Sequence
<220> FEATURE:
<223> OTHER INFORMATION: synthesized, fusion protein comprising a fragment of TRAIL, a caspase-3 peptide, a transporting domain derived from Pseudomonas, steric linkers and cleavage site recognized by furin

<400> SEQUENCE: 107

```
Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140
```

-continued

```
Leu Ile Asp Met Asp His Glu Ala Ser Phe Phe Gly Ala Phe Leu Val
145                 150                 155                 160

Gly Gly Gly Gly Ser Arg Lys Lys Arg Ala Ser Gly Gly Pro Glu Gly
                165                 170                 175

Gly Ser Leu Ala Ala Leu Thr Ala His Gln Ala Cys His Leu Pro Leu
            180                 185                 190

Glu Thr Phe Thr Arg His Arg Gln Pro Arg Gly Trp Glu Gln Leu Glu
        195                 200                 205

Gln Cys Gly Tyr Pro Val Gln Arg Leu Val Ala Leu Tyr Leu Ala Ala
    210                 215                 220

Arg Leu Ser Trp Asn Gln Val Asp Gln Val Ile Ala Asn Ala Leu Ala
225                 230                 235                 240

Ser Pro Gly Ser Gly Gly Asp Leu Gly Glu Ala Ile Arg Glu Ser Pro
                245                 250                 255

Glu Gln Ala Arg Leu Ala Leu Thr Leu Ala Ala Ala Glu Ser Glu Arg
            260                 265                 270

Phe Val Arg Gln Gly Thr Gly Asn Asp Glu Ala Gly Ala Ala Asn Gly
        275                 280                 285

Pro Ala Asp Gly Gly Gly Ser Gly Gly Gly Met Ile Glu Thr Asp Ser
    290                 295                 300

Gly Val Asp Asp Asp Met Ala Cys His Lys Ile Pro Val Asp Ala Asp
305                 310                 315                 320

Phe Leu Tyr Ala Tyr Ser Thr Ala Pro Gly Tyr Tyr Ser Trp Arg Asn
                325                 330                 335

Ser Lys Asp Gly Ser Trp Phe Ile Gln Ser Leu Cys Ala Met Leu Lys
            340                 345                 350

Gln Tyr Ala Asp Lys Leu Glu Phe Met His Ile Leu Thr Arg Val Asn
        355                 360                 365

Arg Lys Val Ala Thr Glu Phe Glu Ser Phe Ser Phe Asp Ala Thr Phe
    370                 375                 380

His Ala Lys Lys Gln Ile Pro Cys Ile Val Ser Met Leu Thr Lys Glu
385                 390                 395                 400

Leu Tyr Phe Tyr His Asp Val Asp Gly Met Glu Asn Thr Glu Asn Ser
                405                 410                 415

Val Asp Ser Lys Ser Ile Lys Asn Leu Glu Pro Lys Ile Ile His Gly
            420                 425                 430

Ser Glu Ser Met Asp Ser Gly Met Ser Trp Asp Thr Gly Tyr Lys Met
        435                 440                 445

Asp Tyr Pro Glu Met Gly Leu Cys Ile Ile Ile Asn Asn Lys Asn Phe
    450                 455                 460

His Lys Ser Thr Gly Met Thr Ser Arg Ser Gly Thr Asp Val Asp Ala
465                 470                 475                 480

Ala Asn Leu Arg Glu Thr Phe Arg Asn Leu Lys Tyr Glu Val Arg Asn
                485                 490                 495

Lys Asn Asp Leu Thr Arg Glu Glu Ile Val Glu Leu Met Arg Asp Val
            500                 505                 510

Ser Lys Glu Asp His Ser Lys Arg Ser Ser Phe Val Cys Val Leu Leu
        515                 520                 525

Ser His Gly Glu Glu Gly Ile Ile Phe Gly Thr Asn Gly Pro Val Asp
    530                 535                 540

Leu Lys Lys Ile Thr Asn Phe Phe Arg Gly Asp Arg Cys Arg Ser Leu
545                 550                 555                 560

Thr Gly Lys Pro Lys Leu Phe Ile Ile Gln Ala Cys Arg Gly Thr Glu
```

565 570 575

Leu Asp Cys Gly
580

<210> SEQ ID NO 108
<211> LENGTH: 247
<212> TYPE: PRT
<213> ORGANISM: Artificial Sequence
<220> FEATURE:
<223> OTHER INFORMATION: synthesized, fusion protein comprising a fragment of TRAIL, SAC domain from Par-4, apoly-arginine domain, a steric linker and cleavage sites recognized by proteases uPA and MMP.

<400> SEQUENCE: 108

Ala Arg Lys Gly Lys Gly Gln Ile Glu Lys Arg Lys Leu Arg Glu Lys
1 5 10 15

Arg Arg Ser Thr Gly Val Val Asn Ile Pro Ala Ala Glu Cys Leu Asp
20 25 30

Glu Tyr Glu Asp Asp Glu Ala Gly Gln Lys Glu Arg Lys Arg Glu Asp
35 40 45

Ala Ile Thr Gln Gln Asn Thr Ile Gln Asn Glu Ala Arg Arg Arg Arg
50 55 60

Arg Arg Arg Arg Val Val Arg Pro Leu Gly Leu Ala Gly Gln Gly Gly
65 70 75 80

Ser Gly Gly Ser Pro Gln Arg Val Ala Ala His Ile Thr Gly Thr Arg
85 90 95

Gly Arg Ser Asn Thr Leu Ser Ser Pro Asn Ser Lys Asn Glu Lys Ala
100 105 110

Leu Gly Arg Lys Ile Asn Ser Trp Glu Ser Ser Arg Ser Gly His Ser
115 120 125

Phe Leu Ser Asn Leu His Leu Arg Asn Gly Glu Leu Val Ile His Glu
130 135 140

Lys Gly Phe Tyr Tyr Ile Tyr Ser Gln Thr Tyr Phe Arg Phe Gln Glu
145 150 155 160

Glu Ile Lys Glu Asn Thr Lys Asn Asp Lys Gln Met Val Gln Tyr Ile
165 170 175

Tyr Lys Tyr Thr Ser Tyr Pro Asp Pro Ile Leu Leu Met Lys Ser Ala
180 185 190

Arg Asn Ser Cys Trp Ser Lys Asp Ala Glu Tyr Gly Leu Tyr Ser Ile
195 200 205

Tyr Gln Gly Gly Ile Phe Glu Leu Lys Glu Asn Asp Arg Ile Phe Val
210 215 220

Ser Val Thr Asn Glu His Leu Ile Asp Met Asp His Glu Ala Ser Phe
225 230 235 240

Phe Gly Ala Phe Leu Val Gly
245

<210> SEQ ID NO 109
<211> LENGTH: 260
<212> TYPE: PRT
<213> ORGANISM: Artificial Sequence
<220> FEATURE:
<223> OTHER INFORMATION: synthesized, fusion protein comprising a fragment of TRAIL, SAC domain from Par-4, apoly-arginine domain, a Nuclear Localization Signal) sequence from Oct6 transcription factor, a steric linker and cleavage sites recognized by proteases uPA and MMP.

<400> SEQUENCE: 109

```
Glu Glu Glu Ala Ala Gly Arg Lys Arg Lys Lys Arg Thr Ala Arg Lys
1               5                   10                  15

Gly Lys Gly Gln Ile Glu Lys Arg Lys Leu Arg Glu Lys Arg Arg Ser
            20                  25                  30

Thr Gly Val Val Asn Ile Pro Ala Ala Glu Cys Leu Asp Glu Tyr Glu
        35                  40                  45

Asp Asp Glu Ala Gly Gln Lys Glu Arg Lys Arg Glu Asp Ala Ile Thr
    50                  55                  60

Gln Gln Asn Thr Ile Gln Asn Glu Ala Arg Arg Arg Arg Arg Arg Arg
65                  70                  75                  80

Arg Val Val Arg Pro Leu Gly Leu Ala Gly Gln Gly Gly Ser Gly Gly
                85                  90                  95

Ser Pro Gln Arg Val Ala Ala His Ile Thr Gly Thr Arg Gly Arg Ser
            100                 105                 110

Asn Thr Leu Ser Ser Pro Asn Ser Lys Asn Glu Lys Ala Leu Gly Arg
        115                 120                 125

Lys Ile Asn Ser Trp Glu Ser Ser Arg Ser Gly His Ser Phe Leu Ser
    130                 135                 140

Asn Leu His Leu Arg Asn Gly Glu Leu Val Ile His Glu Lys Gly Phe
145                 150                 155                 160

Tyr Tyr Ile Tyr Ser Gln Thr Tyr Phe Arg Phe Gln Glu Glu Ile Lys
                165                 170                 175

Glu Asn Thr Lys Asn Asp Lys Gln Met Val Gln Tyr Ile Tyr Lys Tyr
            180                 185                 190

Thr Ser Tyr Pro Asp Pro Ile Leu Leu Met Lys Ser Ala Arg Asn Ser
        195                 200                 205

Cys Trp Ser Lys Asp Ala Glu Tyr Gly Leu Tyr Ser Ile Tyr Gln Gly
    210                 215                 220

Gly Ile Phe Glu Leu Lys Glu Asn Asp Arg Ile Phe Val Ser Val Thr
225                 230                 235                 240

Asn Glu His Leu Ile Asp Met Asp His Glu Ala Ser Phe Phe Gly Ala
                245                 250                 255

Phe Leu Val Gly
            260


<210> SEQ ID NO 110
<211> LENGTH: 270
<212> TYPE: PRT
<213> ORGANISM: Artificial Sequence
<220> FEATURE:
<223> OTHER INFORMATION: synthesized, fusion protein comprising a
      fragment of TRAIL, Noxa protein, poly-arginine domain, a
      polycysteine linker, a steric linker and cleavage sites
      recognized by proteases MMP and uPA.

<400> SEQUENCE: 110

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80
```

-continued

```
Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly Gly Gly Ser Gly Cys
            180                 185                 190

Ala Ala Cys Ala Ala Ala Cys Pro Leu Gly Leu Ala Gly Arg Val Val
        195                 200                 205

Arg Arg Arg Arg Arg Arg Arg Arg Met Pro Gly Lys Lys Ala Arg Lys
    210                 215                 220

Asn Ala Gln Pro Ser Pro Ala Arg Ala Pro Ala Glu Leu Glu Val Glu
225                 230                 235                 240

Cys Ala Thr Gln Leu Arg Arg Phe Gly Asp Lys Leu Asn Phe Arg Gln
                245                 250                 255

Lys Leu Leu Asn Leu Ile Ser Lys Leu Phe Cys Ser Gly Thr
            260                 265                 270


<210> SEQ ID NO 111
<211> LENGTH: 207
<212> TYPE: PRT
<213> ORGANISM: Artificial Sequence
<220> FEATURE:
<223> OTHER INFORMATION: synthesized, fusion protein comprising a
      fragment of TRAIL, MTD/CKP peptide derived from Noxa protein,
      poly-arginine domain, a polycysteine linker, steric linker and
      sequence of cleavage sites recognized by proteases MMP  and uPA

<400> SEQUENCE: 111

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160
```

```
Phe Phe Gly Ala Phe Leu Val Gly Gly Gly Ser Gly Cys Ala Ala Cys
                165                 170                 175

Ala Ala Ala Cys Pro Leu Gly Leu Ala Gly Arg Val Val Arg Arg Arg
            180                 185                 190

Arg Arg Arg Arg Arg Lys Leu Leu Asn Leu Ile Ser Lys Leu Phe
        195                 200                 205


<210> SEQ ID NO 112
<211> LENGTH: 311
<212> TYPE: PRT
<213> ORGANISM: Artificial Sequence
<220> FEATURE:
<223> OTHER INFORMATION: synthesized, fusion protein comprising a
      fragment of TRAIL, onconase, sequence of cleavage sites recognized
      by proteases uPA and steric linkers

<400> SEQUENCE: 112

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys Arg Val Val Arg Pro Leu Gly Leu
            100                 105                 110

Ala Gly Gly Gly Gly Gly Ser Gly Gly Gly Gly Ser Thr Ser Glu Glu
        115                 120                 125

Thr Ile Ser Thr Val Gln Glu Lys Gln Gln Asn Ile Ser Pro Leu Val
    130                 135                 140

Arg Glu Arg Gly Pro Gln Arg Val Ala Ala His Ile Thr Gly Thr Arg
145                 150                 155                 160

Gly Arg Ser Asn Thr Leu Ser Ser Pro Asn Ser Lys Asn Glu Lys Ala
                165                 170                 175

Leu Gly Arg Lys Ile Asn Ser Trp Glu Ser Ser Arg Ser Gly His Ser
            180                 185                 190

Phe Leu Ser Asn Leu His Leu Arg Asn Gly Glu Leu Val Ile His Glu
        195                 200                 205

Lys Gly Phe Tyr Tyr Ile Tyr Ser Gln Thr Tyr Phe Arg Phe Gln Glu
    210                 215                 220

Glu Ile Lys Glu Asn Thr Lys Asn Asp Lys Gln Met Val Gln Tyr Ile
225                 230                 235                 240

Tyr Lys Tyr Thr Ser Tyr Pro Asp Pro Ile Leu Leu Met Lys Ser Ala
                245                 250                 255

Arg Asn Ser Cys Trp Ser Lys Asp Ala Glu Tyr Gly Leu Tyr Ser Ile
            260                 265                 270

Tyr Gln Gly Gly Ile Phe Glu Leu Lys Glu Asn Asp Arg Ile Phe Val
        275                 280                 285

Ser Val Thr Asn Glu His Leu Ile Asp Met Asp His Glu Ala Ser Phe
    290                 295                 300
```

```
Phe Gly Ala Phe Leu Val Gly
305                 310


<210> SEQ ID NO 113
<211> LENGTH: 230
<212> TYPE: PRT
<213> ORGANISM: Artificial Sequence
<220> FEATURE:
<223> OTHER INFORMATION: synthesized, fusion protein comprising a
      fragment of TRAIL, BH3 domain from PUMA protein, a poly-arginine
      and sequence of cleavage sites recognized by proteases uPA and MMP

<400> SEQUENCE: 113

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg Arg Arg Arg Arg Arg Arg
            20                  25                  30

Arg Arg Val Val Arg Pro Leu Gly Leu Ala Gly Thr Ser Glu Glu Thr
        35                  40                  45

Ile Ser Thr Val Gln Glu Lys Gln Gln Asn Ile Ser Pro Leu Val Arg
    50                  55                  60

Glu Arg Gly Pro Gln Arg Val Ala Ala His Ile Thr Gly Thr Arg Gly
65                  70                  75                  80

Arg Ser Asn Thr Leu Ser Ser Pro Asn Ser Lys Asn Glu Lys Ala Leu
                85                  90                  95

Gly Arg Lys Ile Asn Ser Trp Glu Ser Ser Arg Ser Gly His Ser Phe
            100                 105                 110

Leu Ser Asn Leu His Leu Arg Asn Gly Glu Leu Val Ile His Glu Lys
        115                 120                 125

Gly Phe Tyr Tyr Ile Tyr Ser Gln Thr Tyr Phe Arg Phe Gln Glu Glu
    130                 135                 140

Ile Lys Glu Asn Thr Lys Asn Asp Lys Gln Met Val Gln Tyr Ile Tyr
145                 150                 155                 160

Lys Tyr Thr Ser Tyr Pro Asp Pro Ile Leu Leu Met Lys Ser Ala Arg
                165                 170                 175

Asn Ser Cys Trp Ser Lys Asp Ala Glu Tyr Gly Leu Tyr Ser Ile Tyr
            180                 185                 190

Gln Gly Gly Ile Phe Glu Leu Lys Glu Asn Asp Arg Ile Phe Val Ser
        195                 200                 205

Val Thr Asn Glu His Leu Ile Asp Met Asp His Glu Ala Ser Phe Phe
    210                 215                 220

Gly Ala Phe Leu Val Gly
225                 230


<210> SEQ ID NO 114
<211> LENGTH: 225
<212> TYPE: PRT
<213> ORGANISM: Artificial Sequence
<220> FEATURE:
<223> OTHER INFORMATION: synthesized, fusion protein comprising a
      fragment of TRAIL, a peptide derived from Bid protein, a
      transporting domain KPRRPY, a polycysteine linker and sequence of
      cleavage sites recognized by proteases MMP and uPA

<400> SEQUENCE: 114

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30
```

Thr Gly Thr Arg Gly Arg Ser Asn Thr Leu Ser Ser Pro Asn Ser Lys
35 40 45

Asn Glu Lys Ala Leu Gly Arg Lys Ile Asn Ser Trp Glu Ser Ser Arg
50 55 60

Ser Gly His Ser Phe Leu Ser Asn Leu His Leu Arg Asn Gly Glu Leu
65 70 75 80

Val Ile His Glu Lys Gly Phe Tyr Tyr Ile Tyr Ser Gln Thr Tyr Phe
85 90 95

Arg Phe Gln Glu Glu Ile Lys Glu Asn Thr Lys Asn Asp Lys Gln Met
100 105 110

Val Gln Tyr Ile Tyr Lys Tyr Thr Ser Tyr Pro Asp Pro Ile Leu Leu
115 120 125

Met Lys Ser Ala Arg Asn Ser Cys Trp Ser Lys Asp Ala Glu Tyr Gly
130 135 140

Leu Tyr Ser Ile Tyr Gln Gly Gly Ile Phe Glu Leu Lys Glu Asn Asp
145 150 155 160

Arg Ile Phe Val Ser Val Thr Asn Glu His Leu Ile Asp Met Asp His
165 170 175

Glu Ala Ser Phe Phe Gly Ala Phe Leu Val Gly Cys Ala Ala Cys Ala
180 185 190

Ala Ala Cys Pro Leu Gly Leu Ala Gly Arg Val Val Arg Asn Ile Ala
195 200 205

Arg His Leu Ala Gln Val Gly Asp Ser Met Asp Lys Pro Arg Arg Pro
210 215 220

Tyr
225

<210> SEQ ID NO 115
<211> LENGTH: 234
<212> TYPE: PRT
<213> ORGANISM: Artificial Sequence
<220> FEATURE:
<223> OTHER INFORMATION: synthesized, fusion protein comprising a fragment of TRAIL, a hybrid peptide Antp-TPR, sequences of cleavage sites recognized by proteases MMP and uPA and a polycysteine linker

<400> SEQUENCE: 115

Thr Ser Glu Glu Thr Ile Ser Thr Val Gln Glu Lys Gln Gln Asn Ile
1 5 10 15

Ser Pro Leu Val Arg Glu Arg Gly Pro Gln Arg Val Ala Ala His Ile
20 25 30

Thr Gly Thr Arg Gly Arg Ser Asn Thr Leu Ser Ser Pro Asn Ser Lys
35 40 45

Asn Glu Lys Ala Leu Gly Arg Lys Ile Asn Ser Trp Glu Ser Ser Arg
50 55 60

Ser Gly His Ser Phe Leu Ser Asn Leu His Leu Arg Asn Gly Glu Leu
65 70 75 80

Val Ile His Glu Lys Gly Phe Tyr Tyr Ile Tyr Ser Gln Thr Tyr Phe
85 90 95

Arg Phe Gln Glu Glu Ile Lys Glu Asn Thr Lys Asn Asp Lys Gln Met
100 105 110

Val Gln Tyr Ile Tyr Lys Tyr Thr Ser Tyr Pro Asp Pro Ile Leu Leu
115 120 125

Met Lys Ser Ala Arg Asn Ser Cys Trp Ser Lys Asp Ala Glu Tyr Gly
130 135 140

```
Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly Cys Ala Ala Cys Ala
            180                 185                 190

Ala Ala Cys Gly Gly Pro Leu Gly Leu Ala Gly Arg Val Val Arg Gln
        195                 200                 205

Ile Lys Ile Trp Phe Gln Asn Arg Arg Met Lys Trp Lys Lys Lys Ala
    210                 215                 220

Tyr Ala Ala Ala Gly Asn Ser Tyr Phe Lys
225                 230


<210> SEQ ID NO 116
<211> LENGTH: 216
<212> TYPE: PRT
<213> ORGANISM: Artificial Sequence
<220> FEATURE:
<223> OTHER INFORMATION: synthesized, fusion protein comprising a
      fragment of TRAIL, a peptide inhibitor of the SH2 domain of Stat3
      protein, a polycysteine linker, a steric linker and sequence of
      cleavage sites recognized by proteases uPA and MMP

<400> SEQUENCE: 116

Phe Ile Ser Lys Glu Arg Arg Glu Arg Ala Ile Leu Ser Thr Lys Pro
1               5                   10                  15

Pro Gly Thr Phe Leu Leu Arg Phe Ser Glu Ser Ser Lys Arg Val Val
            20                  25                  30

Arg Pro Leu Gly Ile Ala Gly Glu Gly Gly Gly Cys Ala Ala Ala Cys
        35                  40                  45

Ala Ala Cys Gly Ser Gly Gln Arg Val Ala Ala His Ile Thr Gly Thr
    50                  55                  60

Arg Gly Arg Ser Asn Thr Leu Ser Ser Pro Asn Ser Lys Asn Glu Lys
65                  70                  75                  80

Ala Leu Gly Arg Lys Ile Asn Ser Trp Glu Ser Ser Arg Ser Gly His
                85                  90                  95

Ser Phe Leu Ser Asn Leu His Leu Arg Asn Gly Glu Leu Val Ile His
            100                 105                 110

Glu Lys Gly Phe Tyr Tyr Ile Tyr Ser Gln Thr Tyr Phe Arg Phe Gln
        115                 120                 125

Glu Glu Ile Lys Glu Asn Thr Lys Asn Asp Lys Gln Met Val Gln Tyr
    130                 135                 140

Ile Tyr Lys Tyr Thr Ser Tyr Pro Asp Pro Ile Leu Leu Met Lys Ser
145                 150                 155                 160

Ala Arg Asn Ser Cys Trp Ser Lys Asp Ala Glu Tyr Gly Leu Tyr Ser
                165                 170                 175

Ile Tyr Gln Gly Gly Ile Phe Glu Leu Lys Glu Asn Asp Arg Ile Phe
            180                 185                 190

Val Ser Val Thr Asn Glu His Leu Ile Asp Met Asp His Glu Ala Ser
        195                 200                 205

Phe Phe Gly Ala Phe Leu Val Gly
    210                 215


<210> SEQ ID NO 117
<211> LENGTH: 194
<212> TYPE: PRT
<213> ORGANISM: Artificial Sequence
<220> FEATURE:
```

<223> OTHER INFORMATION: synthesized, fusion protein comprising a fragment of TRAIL, a peptide derived from BH3 domain of Bak protein, a poly-arginine domain and sequence of cleavage sites recognized by proteases uPA and MMP

<400> SEQUENCE: 117

```
Gly Gln Val Gly Arg Gln Leu Ala Ile Ile Gly Asp Asp Ile Asn Arg
1               5                   10                  15

Arg Arg Arg Arg Arg Arg Arg Arg Val Val Arg Pro Leu Gly Leu Ala
            20                  25                  30

Gly Arg Val Ala Ala His Ile Thr Gly Thr Arg Gly Arg Ser Asn Thr
        35                  40                  45

Leu Ser Ser Pro Asn Ser Lys Asn Glu Lys Ala Leu Gly Arg Lys Ile
    50                  55                  60

Asn Ser Trp Glu Ser Ser Arg Ser Gly His Ser Phe Leu Ser Asn Leu
65                  70                  75                  80

His Leu Arg Asn Gly Glu Leu Val Ile His Glu Lys Gly Phe Tyr Tyr
                85                  90                  95

Ile Tyr Ser Gln Thr Tyr Phe Arg Phe Gln Glu Glu Ile Lys Glu Asn
            100                 105                 110

Thr Lys Asn Asp Lys Gln Met Val Gln Tyr Ile Tyr Lys Tyr Thr Ser
        115                 120                 125

Tyr Pro Asp Pro Ile Leu Leu Met Lys Ser Ala Arg Asn Ser Cys Trp
    130                 135                 140

Ser Lys Asp Ala Glu Tyr Gly Leu Tyr Ser Ile Tyr Gln Gly Gly Ile
145                 150                 155                 160

Phe Glu Leu Lys Glu Asn Asp Arg Ile Phe Val Ser Val Thr Asn Glu
                165                 170                 175

His Leu Ile Asp Met Asp His Glu Ala Ser Phe Phe Gly Ala Phe Leu
            180                 185                 190

Val Gly
```

<210> SEQ ID NO 118
<211> LENGTH: 243
<212> TYPE: PRT
<213> ORGANISM: Artificial Sequence
<220> FEATURE:
<223> OTHER INFORMATION: synthesized, fusion protein comprising a fragment of TRAIL, a peptide derived from BH3 domain of Bad protein, a poly-arginine domain, sequence of cleavage sites recognized by proteases uPA and MMP, a flexible linker and sequence o recognized by thrombin

<400> SEQUENCE: 118

```
Lys Asn Leu Trp Ala Ala Gln Arg Tyr Gly Arg Glu Leu Arg Arg Met
1               5                   10                  15

Ser Asp Glu Phe Glu Gly Ser Phe Lys Gly Leu Arg Arg Arg Arg Arg
            20                  25                  30

Arg Arg Arg Arg Val Val Arg Pro Leu Gly Leu Ala Gly Arg Val Ala
        35                  40                  45

Ala His Ile Thr Gly Thr Arg Gly Arg Ser Asn Thr Leu Ser Ser Pro
    50                  55                  60

Asn Ser Lys Asn Glu Lys Ala Leu Gly Arg Lys Ile Asn Ser Trp Glu
65                  70                  75                  80

Ser Ser Arg Ser Gly His Ser Phe Leu Ser Asn Leu His Leu Arg Asn
                85                  90                  95

Gly Glu Leu Val Ile His Glu Lys Gly Phe Tyr Tyr Ile Tyr Ser Gln
            100                 105                 110
```

Thr Tyr Phe Arg Phe Gln Glu Glu Ile Lys Glu Asn Thr Lys Asn Asp
115 120 125

Lys Gln Met Val Gln Tyr Ile Tyr Lys Tyr Thr Ser Tyr Pro Asp Pro
130 135 140

Ile Leu Leu Met Lys Ser Ala Arg Asn Ser Cys Trp Ser Lys Asp Ala
145 150 155 160

Glu Tyr Gly Leu Tyr Ser Ile Tyr Gln Gly Gly Ile Phe Glu Leu Lys
165 170 175

Glu Asn Asp Arg Ile Phe Val Ser Val Thr Asn Glu His Leu Ile Asp
180 185 190

Met Asp His Glu Ala Ser Phe Phe Gly Ala Phe Leu Val Gly Gly Gly
195 200 205

Ser His Gly Leu Val Pro Arg Gly Ser Thr Ser Glu Glu Thr Ile Ser
210 215 220

Thr Val Gln Glu Lys Gln Gln Asn Ile Ser Pro Leu Val Arg Glu Arg
225 230 235 240

Gly Pro Gln

<210> SEQ ID NO 119
<211> LENGTH: 236
<212> TYPE: PRT
<213> ORGANISM: Artificial Sequence
<220> FEATURE:
<223> OTHER INFORMATION: synthesized, fusion protein comprising a fragment of TRAIL, a peptide derived from BH3 domain of Bad protein, a poly-arginine domain, a sequence of cleavage sites recognized by proteases MMP and uPA and a steric linker.

<400> SEQUENCE: 119

Thr Ser Glu Glu Thr Ile Ser Thr Val Gln Glu Lys Gln Gln Asn Ile
1 5 10 15

Ser Pro Leu Val Arg Glu Arg Gly Pro Gln Arg Val Ala Ala His Ile
20 25 30

Thr Gly Thr Arg Gly Arg Ser Asn Thr Leu Ser Ser Pro Asn Ser Lys
35 40 45

Asn Glu Lys Ala Leu Gly Arg Lys Ile Asn Ser Trp Glu Ser Ser Arg
50 55 60

Ser Gly His Ser Phe Leu Ser Asn Leu His Leu Arg Asn Gly Glu Leu
65 70 75 80

Val Ile His Glu Lys Gly Phe Tyr Tyr Ile Tyr Ser Gln Thr Tyr Phe
85 90 95

Arg Phe Gln Glu Glu Ile Lys Glu Asn Thr Lys Asn Asp Lys Gln Met
100 105 110

Val Gln Tyr Ile Tyr Lys Tyr Thr Ser Tyr Pro Asp Pro Ile Leu Leu
115 120 125

Met Lys Ser Ala Arg Asn Ser Cys Trp Ser Lys Asp Ala Glu Tyr Gly
130 135 140

Leu Tyr Ser Ile Tyr Gln Gly Gly Ile Phe Glu Leu Lys Glu Asn Asp
145 150 155 160

Arg Ile Phe Val Ser Val Thr Asn Glu His Leu Ile Asp Met Asp His
165 170 175

Glu Ala Ser Phe Phe Gly Ala Phe Leu Val Gly Gly Gly Ser Pro Leu
180 185 190

Gly Leu Ala Gly Cys Arg Val Val Arg Arg Arg Arg Arg Arg Arg Arg
195 200 205

```
Arg Lys Asn Leu Trp Ala Ala Gln Arg Tyr Gly Arg Glu Leu Arg Arg
    210                 215                 220

Met Ser Asp Glu Phe Glu Gly Ser Phe Lys Gly Leu
225                 230                 235
```

<210> SEQ ID NO 120
<211> LENGTH: 216
<212> TYPE: PRT
<213> ORGANISM: Artificial Sequence
<220> FEATURE:
<223> OTHER INFORMATION: synthesized, fusion protein comprising a fragment of TRAIL, a ATAP peptide from Bfl1 protein, a membrane transporting domain KPRRPYR, a sequence of cleavage sites recognized by proteases MMP and uPA and a steric linker.

<400> SEQUENCE: 120

```
Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
    50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
    130                 135                 140

Leu Ile Asp Met Asp His Glu Ala Ser Phe Phe Gly Ala Phe Leu Val
145                 150                 155                 160

Gly Gly Gly Gly Gly Ser Gly Gly Gly Gly Pro Leu Gly Leu Ala Gly
                165                 170                 175

Arg Val Val Arg Lys Phe Glu Pro Lys Ser Gly Trp Met Thr Phe Leu
            180                 185                 190

Glu Val Thr Gly Lys Ile Cys Glu Met Leu Ser Leu Leu Lys Gln Tyr
        195                 200                 205

Cys Lys Pro Arg Arg Pro Tyr Arg
    210                 215
```

<210> SEQ ID NO 121
<211> LENGTH: 237
<212> TYPE: PRT
<213> ORGANISM: Artificial Sequence
<220> FEATURE:
<223> OTHER INFORMATION: synthesized, fusion protein comprising a fragment of TRAIL, a ATAP peptide from Bfl1 protein, a mitochondrial targeting sequence, a sequence of cleavage sites recognized by proteases MMP and uPA and a steric linker.

<400> SEQUENCE: 121

```
Arg Val Ser Phe Cys Arg Pro Gly Trp Ser Ala Met Ala Arg Ser Arg
1               5                   10                  15

Leu Thr Ala Thr Ser Val Ser Gln Val Gln Glu Asn Gly Phe Val Lys
            20                  25                  30
```

```
Lys Phe Glu Pro Lys Ser Gly Trp Met Thr Phe Leu Glu Val Thr Gly
        35                  40                  45

Lys Ile Cys Glu Met Leu Ser Leu Leu Lys Gln Tyr Cys Arg Val Val
    50                  55                  60

Arg Pro Leu Gly Leu Ala Gly Gly Gly Ser Gly Gly Arg Val Ala Ala
65                  70                  75                  80

His Ile Thr Gly Thr Arg Gly Arg Ser Asn Thr Leu Ser Ser Pro Asn
                85                  90                  95

Ser Lys Asn Glu Lys Ala Leu Gly Arg Lys Ile Asn Ser Trp Glu Ser
            100                 105                 110

Ser Arg Ser Gly His Ser Phe Leu Ser Asn Leu His Leu Arg Asn Gly
        115                 120                 125

Glu Leu Val Ile His Glu Lys Gly Phe Tyr Tyr Ile Tyr Ser Gln Thr
    130                 135                 140

Tyr Phe Arg Phe Gln Glu Glu Ile Lys Glu Asn Thr Lys Asn Asp Lys
145                 150                 155                 160

Gln Met Val Gln Tyr Ile Tyr Lys Tyr Thr Ser Tyr Pro Asp Pro Ile
                165                 170                 175

Leu Leu Met Lys Ser Ala Arg Asn Ser Cys Trp Ser Lys Asp Ala Glu
            180                 185                 190

Tyr Gly Leu Tyr Ser Ile Tyr Gln Gly Gly Ile Phe Glu Leu Lys Glu
        195                 200                 205

Asn Asp Arg Ile Phe Val Ser Val Thr Asn Glu His Leu Ile Asp Met
    210                 215                 220

Asp His Glu Ala Ser Phe Phe Gly Ala Phe Leu Val Gly
225                 230                 235
```

<210> SEQ ID NO 122
<211> LENGTH: 1377
<212> TYPE: DNA
<213> ORGANISM: Artificial Sequence
<220> FEATURE:
<223> OTHER INFORMATION: synthesized, encoding fusion protein comprising a fragment of TRAIL protein, RNAse A, a sequence directing to endoplasmic reticulum, steric, pegylation and stabilizing linkers, sequence of furincleavage site and a fragment of P.aeruginosa translocation

<400> SEQUENCE: 122

```
ggttgtgcag cagcatgtgc agcctgtacc agcgaagaaa ccattagcac cgttcaagaa      60

aaacagcaga atattagtcc gctggttcgt gaacgtggtc cgcagcgtgt tgcagcacat     120

attaccggca cccgtggtcg tagcaatacc ctgagcagcc cgaatagcaa aaatgaaaaa     180

gccctgggtc gcaaaattaa cagctgggaa agcagccgta gcggtcatag ctttctgagc     240

aatctgcatc tgcgtaatgg tgaactggtg attcacgaga aaggcttcta ttatatctat     300

agccagacct atttccgctt ccaagaagag atcaaagaga acaccaaaaa cgacaaacaa     360

atggtgcagt acatctataa atacaccagc tatccggatc cgattctgct gatgaaaagc     420

gcacgtaata gctgttggag caaagatgca gaatatggcc tgtatagcat ctatcagggt     480

ggcatttttg aactgaaaga aaacgatcgc atctttgtga gcgtgaccaa tgaacatctg     540

attgatatgg atcacgaagc cagctttttt ggtgcatttc tggttggtgg tggtggtagc     600

gcaagcggtt gtggtccgga acgtaaaaaa cgtgcaagcg gtggtccgga aggtggtagt     660

ctggcagcac tgaccgcaca tcaggcatgt catctgccgc tggaaacctt tacccgtcat     720

cgtcagcctc gtggttggga acagctggaa cagtgtggtt atccggttca gcgtctggtt     780
```

gcactgtatc tggcagctcg tctgagctgg aatcaggttg atcaggttat tcgtaatgca 840
ctggcaagtc cgggtagcgg tggcgatctg ggtgaagcaa ttcgtgaaca gccggaacag 900
gcacgtctgg cactgaccct ggcagcagca gaaagcgaac gttttgttcg tcaaggcacc 960
ggtaatggtg gtggcggtag tggtggtggt tcaaaagaaa ccgcagcagc caaatttgaa 1020
cgtcagcaca tggatagcag caccagcgca gcaagcagca gcaattattg caatcagatg 1080
atgaaaagcc gcaatctgac caaagatcgt tgtaaaccgg tgaatacctt tgttcatgaa 1140
agcctggcag atgttcaggc agtttgcagc cagaaaaatg tggcctgtaa aaatggtcag 1200
accaattgct atcagagcta tagcaccatg agcattaccg attgtcgtga aaccggtagc 1260
agcaaatatc cgaattgcgc ctataaaacc acccaggcca ataaacatat tattgtggcc 1320
tgtgaaggca atccgtatgt tccggttcat tttgatgcca gcgtgaaaga tgaactg 1377

<210> SEQ ID NO 123
<211> LENGTH: 639
<212> TYPE: DNA
<213> ORGANISM: Artificial Sequence
<220> FEATURE:
<223> OTHER INFORMATION: synthesized, encoding fusion protein comprising a fragment of TRAIL protein, Nur77 derived peptide , poly-arginine transporting domain and sequence of cleavage sites recognized by proteases MMP and uPA

<400> SEQUENCE: 123
tttagccgta gcctgcatag cctgctgcgt cgtcgtcgcc gtcgtcggcg tgttgttcgt 60
ccgctgggtc tggcaggcac cagcgaagaa accattagca ccgttcaaga aaaacagcag 120
aatattagtc cgctggttcg tgaacgtggt ccgcagcgtg ttgcagcaca tattaccggc 180
acccgtggtc gtagcaatac cctgagcagc ccgaatagca aaaatgaaaa agccctgggt 240
cgcaaaatta acagctggga aagcagccgt agcggtcata gctttctgag caatctgcat 300
ctgcgtaatg gtgaactggt gattcacgag aaaggcttct attatatcta tagccagacc 360
tatttccgct tccaagaaga gatcaaagag aacaccaaaa acgacaaaca aatggtgcag 420
tacatctata aatacaccag ctatccggat ccgattctgc tgatgaaaag cgcacgtaat 480
agctgttgga gcaaagatgc agaatatggc ctgtatagca tctatcaggg tggcattttt 540
gaactgaaag aaaacgatcg catctttgtg agcgtgacca atgaacatct gattgatatg 600
gatcacgaag ccagcttttt tggtgccttt ctggttggt 639

<210> SEQ ID NO 124
<211> LENGTH: 612
<212> TYPE: DNA
<213> ORGANISM: Artificial Sequence
<220> FEATURE:
<223> OTHER INFORMATION: synthesized, encoding fusion protein comprising a fragment of TRAIL protein, azurin derived peptide and sequence of cleavage sites recognized by proteases MMP and uPA

<400> SEQUENCE: 124
ctgtctaccg cagcagatat gcagggtgtt gttaccgatg gtatggcaag cggtctggat 60
aaagattatc tgaaaccgga tgatccgctg ggtctggcag gtcgtgttgt tcgtgaacgt 120
ggtccgcagc gtgttgcagc acatattacc ggcacccgtg gtcgtagcaa taccctgagc 180
agcccgaata gcaaaaatga aaaagccctg ggtcgcaaaa ttaatagctg ggaaagcagc 240
cgtagcggtc atagctttct gagcaatctg catctgcgta atggtgaact ggtgattcat 300
gaaaaaggct tttattatat ttatagccag acctattttc gctttcagga agaaattaaa 360

-continued

```
gaaaacacca aaaatgataa acaaatggtg cagtatatct ataaatatac cagctatccg    420

gatccgattc tgctgatgaa aagcgcacgt aatagctgtt ggagcaaaga tgcagaatat    480

ggcctgtata gcatttatca gggtggcatt tttgaactga aagaaaatga tcgcattttt    540

gtgagcgtga ccaatgaaca tctgattgat atggatcatg aagccagctt ttttggtgca    600

tttctggttg gt                                                        612


<210> SEQ ID NO 125
<211> LENGTH: 615
<212> TYPE: DNA
<213> ORGANISM: Artificial Sequence
<220> FEATURE:
<223> OTHER INFORMATION: synthesized, encoding fusion protein comprising
      a fragment of TRAIL protein, azurin derived peptide, cleavage site
      recognized by furin, steric linker and a sequence directing to
      endoplasmic reticulum

<400> SEQUENCE: 125

cagcgtgttg cagcacatat taccggcacc cgtggtcgta gcaataccct gagcagcccg     60

aatagcaaaa atgaaaaagc actgggtcgc aaaattaaca gctgggaaag cagccgtagc    120

ggtcatagct ttctgagcaa tctgcatctg cgtaatggtg aactggtgat tcatgaaaaa    180

ggcttctact atatctacag ccagacctat tttcgcttcc aagaagagat taaagaaaac    240

accaaaaacg ataaacaaat ggtgcagtac atctataaat acaccagcta tccggatccg    300

attctgctga tgaaaagcgc acgtaatagc tgttggagca aagatgcaga atatggcctg    360

tatagcattt atcagggtgg catctttgaa ctgaaagaaa acgatcgtat tttcgtgagc    420

gtgaccaatg aacatctgat cgatatggat catgaagcca gctttttttgg tgcatttctg    480

gtgggtggtg gtggtagccg taaaaaacgt gttaaacgtc tgagcaccgc agcagatatg    540

cagggtgttg ttaccgatgg tatggcaagc ggtctggata aagattatct gaaaccggat    600

gataaagatg aactg                                                     615


<210> SEQ ID NO 126
<211> LENGTH: 621
<212> TYPE: DNA
<213> ORGANISM: Artificial Sequence
<220> FEATURE:
<223> OTHER INFORMATION: synthesized, encoding fusion protein comprising
      a fragment of TRAIL protein, azurin derived peptide, cleavage site
      recognized by proteases MMP and uPA and steric linker

<400> SEQUENCE: 126

cagcgtgttg cagcacatat taccggcacc cgtggtcgta gcaataccct gagcagcccg     60

aatagcaaaa atgaaaaagc actgggtcgc aaaatcaata gctgggaaag cagccgtagc    120

ggtcatagct ttctgagcaa tctgcatctg cgtaatggtg aactggtgat tcatgaaaaa    180

ggcttttatt atatttatag ccagacctat tttcgctttc aagaagagat taaagaaaat    240

accaaaaatg ataaacaaat ggtgcagtac atttataaat ataccagcta tccggacccg    300

attctgctga tgaaaagcgc acgtaatagc tgttggagca aagatgcaga atatggtctg    360

tatagcattt atcagggtgg catctttgag ctgaaagaaa atgatcgcat ctttgttagc    420

gtgaccaacg aacatctgat cgatatggat catgaagcca gctttttttgg tgcatttctg    480

gttggtggtg gtggtagcgg tggtggtccg ctgggtctgg caggtcgtgt tgttcgtctg    540

agcaccgcag cagatatgca gggtgttgtt accgatggta tggcaagcgg tctggataaa    600

gattatctga aaccggatga t                                              621
```

<210> SEQ ID NO 127
<211> LENGTH: 981
<212> TYPE: DNA
<213> ORGANISM: Artificial Sequence
<220> FEATURE:
<223> OTHER INFORMATION: synthesized, encoding fusion protein comprising a fragment of TRAIL protein, azurin derived peptide, cleavage site recognized by proteases MMP and uPA and steric linker

<400> SEQUENCE: 127

```
cagcgtgttg cagcacatat taccggcacc cgtggtcgta gcaataccct gagcagcccg     60

aatagcaaaa atgaaaaagc actgggtcgc aaaatcaata gctgggaaag cagccgtagc    120

ggtcatagct ttctgagcaa tctgcatctg cgtaatggtg aactggtgat tcatgaaaaa    180

ggcttttatt atatttatag ccagacctat tttcgctttc aagaagagat taaagaaaat    240

accaaaaatg ataaacaaat ggtgcagtac atttataaat ataccagcta tccggacccg    300

attctgctga tgaaaagcgc acgtaatagc tgttggagca aagatgcaga atatggtctg    360

tatagcattt atcagggtgg catctttgag ctgaaagaaa atgatcgcat ctttgttagc    420

gtgaccaacg aacatctgat cgatatggat catgaagcca gctttttttgg tgcatttctg    480

gttggtggtg gtggtagcgg tggtggtccg ctgggtctgg caggtcgtgt tgttcgtatg    540

ctgcgtaaac tggcagcagt tagcctgctg agtctgctga gcgcaccgct gctggcagca    600

gaatgtagcg ttgatattca gggtaatgat cagatgcagt ttaacaccaa tgccattacc    660

gttgacaaaa gctgtaaaca gtttaccgtg aatctgagcc atccgggtaa tctgccgaaa    720

aatgttatgg gtcataattg ggttctgagc accgcagcag atatgcaggg tgttgttacc    780

gatggtatgg caagcggtct ggataaagat tatctgaaac cggatgatag ccgtgttatt    840

gcacatacca aactgattgg tagcggtgaa aaagatagcg ttacctttga tgtgagcaaa    900

ctgaaagaag gcgagcagta tatgttcttt tgtacctttc cgggtcatag cgcactgatg    960

aaaggcaccc tgaccctgaa a                                              981
```

<210> SEQ ID NO 128
<211> LENGTH: 579
<212> TYPE: DNA
<213> ORGANISM: Artificial Sequence
<220> FEATURE:
<223> OTHER INFORMATION: synthesized, encoding fusion protein comprising a fragment of TRAIL protein, a Smac/DIABLO derived peptide, poly-arginine transporting domain and cleavage sites recognized by proteases uPA and MMP

<400> SEQUENCE: 128

```
gcagttccga ttgcacagaa accgcgtcgt cgtcgtcgcc gtcggcgtgt tgttcgtccg     60

ctgggtctgg caggcgttcg tgaacgtggt ccgcagcgtg ttgcagcaca tattaccggc    120

acccgtggtc gtagcaatac cctgagcagc ccgaatagca aaaatgaaaa agcactgggt    180

cgcaaaatca atagctggga aagcagccgt agcggtcata gctttctgag caatctgcat    240

ctgcgtaatg gtgaactggt gattcatgaa aaaggctttt attatattta tagccagacc    300

tattttcgct ttcaagaaga gattaaagaa aataccaaaa atgataaaca aatggtgcag    360

tatatctata aatataccag ctatccggac ccgattctgc tgatgaaaag cgcacgtaat    420

agctgttgga gcaaagatgc agaatatggt ctgtatagca tttatcaggg tggcatcttt    480

gagctgaaag aaaatgatcg catctttgtt agcgtgacca acgaacatct gatcgatatg    540

gatcatgaag ccagcttttt tggtgcattt ctggttggt                           579
```

<210> SEQ ID NO 129
<211> LENGTH: 663
<212> TYPE: DNA
<213> ORGANISM: Artificial Sequence
<220> FEATURE:
<223> OTHER INFORMATION: synthesized, encoding fusion protein comprising a fragment of TRAIL protein, a Smac/DIABLO derived peptide, poly-arginine transporting domain, cleavage sites recognized by proteases uPA and MMP and polycysteine linker.

<400> SEQUENCE: 129

```
gcagttccga ttgcacagaa accgcgtcgt cgtcgtcgcc gtcggcgtgt tgttcgtccg     60
ctgggtctgg caggcggttg tgcagcagca tgtgcagcct gtaccagcga agaaaccatt    120
agcaccgttc aagaaaaaca gcagaatatt agtccgctgg ttcgtgaacg tggtccgcag    180
cgttgtgcag cacatattac cggcacccgt ggtcgtagca ataccctgag cagcccgaat    240
agcaaaaatg aaaaagcact gggtcgcaaa atcaatagct gggaaagcag ccgtagcggt    300
catagctttc tgagcaatct gcatctgcgt aatggtgaac tggtgattca tgaaaaaggc    360
ttctactata tctatagcca gacctatttc cgcttccaag aagaaatcaa agaaaatacc    420
aaaaatgata aacaaatggt gcagtatatt tacaaatata ccagctatcc ggatccgatt    480
ctgctgatga aagcgcacg taatagctgt tggagcaaag atgcagaata tggtctgtat    540
agcatttatc agggtggcat ctttgagctg aaagaaaatg atcgcatctt tgttagcgtg    600
accaacgaac atctgatcga tatggatcat gaagccagct tttttggtgc atttctggtg    660
ggt                                                                  663
```

<210> SEQ ID NO 130
<211> LENGTH: 636
<212> TYPE: DNA
<213> ORGANISM: Artificial Sequence
<220> FEATURE:
<223> OTHER INFORMATION: synthesized, encoding fusion protein comprising a fragment of TRAIL protein, a Smac/DIABLO derived peptide, poly-arginine transporting domain and cleavage sites recognized by proteases uPA and MMP.

<400> SEQUENCE: 130

```
gcagttccga ttgcacagaa accgcgtcgt cgtcgtcgcc gtcggcgtgt tgttcgtccg     60
ctgggtctgg caggcaccag tgaagaaacc attagcaccg ttcaagaaaa acagcagaat    120
attagtccgc tggttcgtga acgtggtccg cagcgtgttg cagcacatat taccggcacc    180
cgtggtcgta gcaataccct gagcagcccg aatagcaaaa atgaaaaagc actgggtcgc    240
aaaatcaata gctgggaaag cagccgtagc ggtcatagct ttctgagcaa tctgcatctg    300
cgtaatggtg aactggtgat tcatgaaaaa ggcttctact atatctacag ccagacctat    360
tttcgcttcc aagaagaaat caaagagaac accaaaaacg acaaacaaat ggtgcagtac    420
atctacaaat ataccagcta tccggatccg attctgctga tgaaaagcgc acgtaatagc    480
tgttggagca aagatgcaga atatggtctg tatagcattt atcagggtgg catctttgag    540
ctgaaagaaa atgatcgcat ctttgttagc gtgaccaacg aacatctgat cgatatggat    600
catgaagcca gctttttttgg tgcatttctg gtgggt                             636
```

<210> SEQ ID NO 131
<211> LENGTH: 636
<212> TYPE: DNA
<213> ORGANISM: Artificial Sequence
<220> FEATURE:

<223> OTHER INFORMATION: synthesized, encoding fusion protein comprising a fragment of TRAIL protein, a protein derived from aPP protein and BH3 domain of Bax, poly-arginine domain and sequences of cleavage sites recognized by proteases uPA and MMP.

<400> SEQUENCE: 131

```
ggtccgagcc agccgaccta tccgggtgat gatgcaccgg ttgaagatct gattcgtttt     60

gttggtcgtc tgctggcata ttttggcgat accattaatc gtcgtcgtag acgtcgtcgg    120

cgtcgtgttg ttcgtccgct gggtctggca ggtcgtgttg cagcacatat taccggcacc    180

cgtggtcgta gcaataccct gagcagcccg aatagcaaaa atgaaaaagc actgggtcgc    240

aaaatcaata gctgggaaag cagccgtagc ggtcatagct ttctgagcaa tctgcatctg    300

cgtaatggtg aactggtgat tcatgaaaaa ggcttttatt atatttatag ccagacctat    360

tttcgctttc aagaagagat taaagaaaat accaaaaatg ataaacaaat ggtgcagtat    420

atctataaat ataccagcta tccggacccg attctgctga tgaaaagcgc acgtaatagc    480

tgttggagca aagatgcaga atatggtctg tatagcattt atcagggtgg catctttgag    540

ctgaaagaaa atgatcgcat ctttgttagc gtgaccaacg aacatctgat cgatatggat    600

catgaagcca gctttttggt tgcatttctg gtgggt                              636
```

<210> SEQ ID NO 132
<211> LENGTH: 741
<212> TYPE: DNA
<213> ORGANISM: Artificial Sequence
<220> FEATURE:
<223> OTHER INFORMATION: synthesized, encoding fusion protein comprising a fragment of TRAIL protein, a protein derived from aPP protein and BH3 domain of Bax, poly-arginine domain, polycysteine linker and sequences of cleavage sites recognized by proteases uPA and MMP.

<400> SEQUENCE: 132

```
ggtccgagcc agccgaccta tccgggtgat gatgcaccgg ttgaagatct gattcgtttt     60

gttggtcgtc tgctggcata ttttggcgat accattaatc gtcgtcgtcg ccgtcgtaga    120

cgtcgtgttg ttcgtccgct gggtctggca ggcggttgtg cagcagcatg tgcagcctgt    180

accagcgaag aaaccattag caccgttcaa gaaaaacagc agaatattag tccgctggtt    240

cgtgaacgtg gtccgcagcg ttgtgcagca catattaccg gcacccgtgg tcgtagcaat    300

accctgagca gcccgaatag caaaaatgaa aaagcactgg gtcgcaaaat caatagctgg    360

gaaagcagcc gtagcggtca tagctttctg agcaatctgc atctgcgtaa tggtgaactg    420

gtgattcatg aaaaaggctt ttattatatc tatagccaga cctatttccg cttccaagaa    480

gaaatcaaag aaaataccaa aaatgataaa caaatggtgc agtatattta caaatatacc    540

agctatccgg atccgattct gctgatgaaa agcgcacgta atagctgttg gagcaaagat    600

gcagaatatg gtctgtatag catttatcag ggtggcatct ttgagctgaa agaaaatgat    660

cgcatctttg ttagcgtgac caacgaacat ctgatcgata tggatcatga agccagcttt    720

tttggtgcat ttctggtggg t                                              741
```

<210> SEQ ID NO 133
<211> LENGTH: 686
<212> TYPE: DNA
<213> ORGANISM: Artificial Sequence
<220> FEATURE:
<223> OTHER INFORMATION: synthesized,encoding fusion protein comprising a fragment of TRAIL protein, a protein derived from aPP protein and BH3 domain of Bax and sequences of cleavage sites recognized by proteases uPA and MMP.

-continued

<400> SEQUENCE: 133

```
ggtccgagcc agccgaccta tccgggtgat gatgcaccgg ttgaagatct gttcgtgaac     60
gtggtccgca gcgtgttgca gcacatatta ccggcacccg tggtcgtagc aataccctga    120
gcagcccgaa tagcaaaaat gaaaaagcac tgggtcgcaa aatcaatagc tgggaaagca    180
gccgtagcgg tcatagcttt ctgagcaatc tgcatctgcg taatggtgaa ctggtgattc    240
atgaaaaagg cttttattat atttatagcc agacctattt tcgctttcaa gaagagatta    300
aagaaaatac caaaaatgat aaacaaatgg tgcagtatat ctataaatat accagctatc    360
cggacccgat tctgctgatg aaaagcgcac gtaatagctg ttggagcaaa gatgcagaat    420
atggtctgta tagcatttat cagggtggca tctttgagct gaaagaaaat gatcgcatct    480
ttgttagcgt gaccaacgaa catctgatcg atatggatca tgaagccagc ttttttggtg    540
catttctggt tggtccgctg ggtctggcag gtcgtgttgt tcgtggtccg cgtcgtcctc    600
gtcgtccggg tgatgatgca ccggttgaag atctgattcg ttttgttggt cgtctgctgg    660
catattttgg cgataccatt aaccgc                                         686
```

<210> SEQ ID NO 134
<211> LENGTH: 663
<212> TYPE: DNA
<213> ORGANISM: Artificial Sequence
<220> FEATURE:
<223> OTHER INFORMATION: synthesized, encoding fusion protein comprising a fragment of TRAIL reticulon RTN1-C derived peptide, a nucleus localizing sequence, a polycysteine linker and cleavage sites recognized by proteases uPA and MMP

<400> SEQUENCE: 134

```
cgcacccata ttaacaccgt tgttgcaaaa attcaggcca aaattccggg tgcaaaacgt     60
catgccgaag aagaagaggc agcaggtcgt aaacgtaaaa aacgtacccg tgttgttcgt    120
ccgctgggtc tggcaggcgg tggttgtgca gcagcatgtg cagcctgtgg tggtggtcag    180
cgtgttgcag cacatattac cggcacccgt ggtcgtagca ataccctgag cagcccgaat    240
agcaaaaatg aaaaagcact gggtcgcaaa attaacagct gggaaagcag ccgtagcggt    300
catagctttc tgagcaatct gcatctgcgt aatggtgaac tggtgattca tgaaaaaggc    360
ttctactata tctacagcca gacctatttt cgcttccaag aagagattaa agaaaacacc    420
aaaaacgata aacaaatggt gcagtacatc tataaataca ccagctatcc ggatccgatt    480
ctgctgatga aaagcgcacg taatagctgt tggagcaaag atgcagaata tggcctgtat    540
agcatttatc agggtggcat ctttgaactg aaagaaaacg atcgtatttt cgtgagcgtg    600
accaatgaac atctgatcga tatggatcat gaagccagct tttttggtgc atttctggtg    660
ggt                                                                  663
```

<210> SEQ ID NO 135
<211> LENGTH: 1305
<212> TYPE: DNA
<213> ORGANISM: Artificial Sequence
<220> FEATURE:
<223> OTHER INFORMATION: synthesized, encoding fusion protein comprising a fragment of TRAIL reticulon RTN1-C derived peptide, a poly-arginine domain, a polycysteine linker, steric linker and cleavage sites recognized by proteases uPA and MMP

<400> SEQUENCE: 135

```
gcagaaccga gcgcagcaac ccagagccat agcattagca gcagcagctt tggtgcagaa     60
```

-continued ccgtcagcac cgggtggtgg tggtagtccg ggtgcatgtc cggcactggg caccaaaagc 120
tgtagcagca gttgtgcagt tcatgatctg attttttggc gtgacgtgaa aaaaaccggc 180
tttgtttttg gcaccaccct gattatgctg ctgagcctgg cagcatttag cgttattagc 240
gttgtgagct atctgattct ggcactgctg agcgttacca ttagctttcg tatctataaa 300
agcgttattc aggccgtgca gaaaagcgaa gaaggtcatc cgtttaaagc atatctggat 360
gttgatatta ccctgagcag cgaagcattt cacaattata tgaatgcagc catggtgcac 420
attaatcgtg ccctgaaact gattattcgt ctgtttctgg ttgaagatct ggtggatagt 480
ctgaaactgg cagtttttat gtggctgatg acctatgttg gtgccgtgtt taatggcatt 540
accctgctga tcctggccga actgctgatt tttagcgttc cgattgtgta tgaaaaatac 600
aaaacccaga tcgatcacta tgtgggtatt gcacgtgatc agaccaaaag cattgtggaa 660
aaaattcagg caaaactgcc tgggatcgca aaaaaaaaag cagaacgtcg tcgtcgccgt 720
cgtcggcgtg gtggttcagg tggtcgtgtt gttcgtccgc tgggtctggc aggcggtggt 780
agcggtggtt gtgcagcaga atgtgcagcc gcatgtccgc agcgtgttgc agcacatatt 840
accggcaccc gtggtcgtag caataccctg agtagcccga atagcaaaaa tgaaaaagca 900
ctgggtcgta aaatcaacag ctgggaaagc agccgtagcg gtcatagctt tctgagcaat 960
ctgcatctgc gtaatggtga actggtgatt catgaaaaag gcttctacta tatctacagc 1020
cagacctatt ttcgcttcca agaagagatt aaagaaaaca ccaaaaacga taaacaaatg 1080
gtgcagtaca tctataaata caccagctat ccggatccga ttctgctgat gaaaagcgca 1140
cgtaatagct gttggagcaa agatgcagaa tatggcctgt atagcattta ccagggtggt 1200
atctttgaac tgaaagaaaa cgatcgcatt tttgtgagcg tgaccaatga acatctgatc 1260
gatatggatc atgaagccag ctttttttggt gcatttctgg tgggt 1305

<210> SEQ ID NO 136
<211> LENGTH: 1740
<212> TYPE: DNA
<213> ORGANISM: Artificial Sequence
<220> FEATURE:
<223> OTHER INFORMATION: synthesized,encoding fusion protein comprising a fragment of TRAIL, a caspase-3 peptide, a transporting domain derived from Pseudomonas, steric linkers and cleavage site recognized by furin

<400> SEQUENCE: 136
cgtgtggcag cacatattac cggcacccgt ggtcgtagca ataccctgag cagcccgaat 60
agcaaaaatg aaaaagcact gggtcgcaaa atcaatagct gggaaagcag ccgtagcggt 120
catagctttc tgagcaatct gcatctgcgt aatggtgaac tggtgattca tgaaaaaggc 180
ttttattata tttatagcca gacctatttt cgctttcaag aagagattaa agaaaatacc 240
aaaaatgata aacaaatggt gcagtacatc tataaatata ccagctatcc ggacccgatt 300
ctgctgatga aaagcgcacg taatagctgt tggagcaaag atgcagaata tggtctgtat 360
agcatttatc agggtggcat ctttgagctg aaagaaaatg atcgcatctt tgttagcgtg 420
accaacgaac atctgatcga tatggatcat gaagccagct tttttggtgc atttctggtt 480
ggtggtggtg gtagccgtaa aaaacgtgca agcggtggtc cggaaggtgg tagcctggca 540
gcactgaccg cacatcaggc atgtcatctg ccgctggaaa cctttacccg tcatcgtcag 600
cctcgtggtt gggaacagct ggaacagtgt ggttatccgg ttcagcgtct ggttgcactg 660
tatctggcag cacgtctgag ctggaatcag gttgatcagg ttattgcaaa tgcactggca 720
agtccgggta gcggtggtga tctgggtgaa gcaattcgtg aaagtccgga acaggcacgt 780
ctggcactga ccctggcagc agcagaaagc gaacgttttg ttcgtcaggg caccggtaat 840
gatgaagccg gtgcagcaaa tggtccggca gatggtggtg gttcaggtgg tggtatgatt 900
gaaaccgata gcggtgttga tgatgatatg gcctgtcata aaattccggt tgatgccgat 960
ttcctgtatg catatagcac cgcaccgggt tattatagct ggcgtaatag caaagatggc 1020
agctggttta ttcagagcct gtgtgcaatg ctgaaacagt atgcagataa actggaattc 1080
atgcatattc tgacccgtgt taatcgtaaa gttgcaaccg aatttgagag ctttagcttt 1140
gatgcaacct tccatgccaa aaaacaaatt ccgtgcattg ttagcatgct gaccaaagaa 1200
ctgtatttct atcatgatgt ggatggcatg gaaaataccg aaaatagcgt tgatagcaaa 1260
agcattaaaa atctggaacc gaaaatcatc catggtagcg aaagcatgga tagcggtatg 1320
agctgggata ccggttataa aatggattat ccggaaatgg gcctgtgcat tatcatcaac 1380
aacaaaaact ttcataaaag caccggtatg accagccgta gtggcaccga tgttgatgca 1440
gcaaatctgc gtgaaacctt tcgcaatctg aaatatgaag tgcgcaacaa aaacgatctg 1500
acccgtgaag aaattgttga actgatgcgt gatgtgagca aagaagatca tagcaaacgt 1560
agcagctttg tttgtgttct gctgagccat ggtgaagaag gtattatttt tggcaccaat 1620
ggtccggtgg acctgaaaaa aatcaccaat ttttttcgtg gtgatcgttg tcgtagcctg 1680
accggtaaac cgaaactgtt tatcattcag gcatgtcgtg gcaccgaact ggattgtggt 1740

<210> SEQ ID NO 137
<211> LENGTH: 741
<212> TYPE: DNA
<213> ORGANISM: Artificial Sequence
<220> FEATURE:
<223> OTHER INFORMATION: synthesized, encoding fusion protein comprising a fragment of TRAIL, SAC domain from Par-4, apoly-arginine domain, a steric linker and cleavage sites recognized by proteases uPA and MMP.

<400> SEQUENCE: 137
gcacgtaaag gtaaaggcca gattgaaaaa cgtaaactgc gtgaaaaacg tcgtagcacc 60
ggtgttgtta atattccggc agcagaatgt ctggatgaat atgaagatga tgaagccggt 120
cagaaagaac gtaaacgtga agatgcaatt acccagcaga ataccattca gaatgaagca 180
cgtcgtcgtc gtcgccgtcg tcgtgttgtt cgtccgctgg gtctggcagg tcagggtggt 240
agcggtggta gtccgcagcg tgttgcagca catattaccg gcacccgtgg tcgtagcaat 300
accctgagca gcccgaatag caaaaatgaa aaagcactgg gtcgcaaaat taatagctgg 360
gaaagcagcc gtagcggtca tagctttctg agcaatctgc atctgcgtaa tggtgaactg 420
gtgattcatg aaaaaggctt ttattatatt tatagccaga cctattttcg ctttcaggaa 480
gaaattaaag aaaataccaa aaacgataaa caaatggtgc agtatatcta taaatatacc 540
agctatccgg atccgattct gctgatgaaa agcgcacgta atagctgttg gagcaaagat 600
gcagaatatg gtctgtatag catttatcag ggtggcattt ttgaactgaa agaaaatgat 660
cgcatttttg tgagcgtgac caatgaacat ctgattgata tggatcatga agccagcttt 720
tttggtgcat ttctggtggg t 741

<210> SEQ ID NO 138
<211> LENGTH: 780
<212> TYPE: DNA
<213> ORGANISM: Artificial Sequence
<220> FEATURE:

<223> OTHER INFORMATION: synthesized, encoding fusion protein comprising a fragment of TRAIL, SAC domain from Par-4, apoly-arginine domain, a Nuclear Localization Signal) sequence from Oct6 transcription factor, a steric linker and cleavage sites recognized by proteases uPA and

<400> SEQUENCE: 138

```
gaagaagaag cagcaggtcg taaacgtaaa aaacgtaccg cacgtaaagg taaaggccag     60

attgaaaaac gtaaactgcg tgaaaaacgc cgtagcaccg gtgttgttaa tattccggca    120

gcagaatgtc tggatgaata tgaagatgat gaagccggtc agaaagaacg caaacgtgaa    180

gatgcaatta cccagcagaa taccattcag aatgaagcac gtcgtcgtcg ccgtcgtcgg    240

cgtgttgttc gtccgctggg tctggcaggt cagggtggta gcggtggtag tccgcagcgt    300

gttgcagcac atattaccgg cacccgtggt cgtagcaata ccctgagcag cccgaatagc    360

aaaaatgaaa aagcactggg tcgcaaaatt aacagctggg aaagcagccg tagcggtcat    420

agctttctga gcaatctgca tctgcgtaat ggtgaactgg tgattcatga aaaaggcttc    480

tactatatct acagccagac ctattttcgc ttccaagaag agattaaaga aaacaccaaa    540

aacgataaac aaatggtgca gtacatctat aaatacacca gctatccgga tccgattctg    600

ctgatgaaaa gcgcacgtaa tagctgttgg agcaaagatg cagaatatgg cctgtatagc    660

atttatcagg gtggcatctt tgaactgaaa gaaaacgatc gtattttcgt gagcgtgacc    720

aatgaacatc tgatcgatat ggatcatgaa gccagctttt ttggtgcatt tctggtgggt    780
```

<210> SEQ ID NO 139
<211> LENGTH: 810
<212> TYPE: DNA
<213> ORGANISM: Artificial Sequence
<220> FEATURE:
<223> OTHER INFORMATION: synthesized, encoding fusion protein comprising a fragment of TRAIL, Noxa protein, poly-arginine domain, a polycysteine linker, a steric linker and cleavage sites recognized by proteases MMP and uPA.

<400> SEQUENCE: 139

```
accagcgaag aaaccattag caccgttcaa gaaaaacagc agaatattag tccgctggtt     60

cgtgaacgtg gtccgcagcg tgttgcagca catattaccg gcacccgtgg tcgtagcaat    120

accctgagca gcccgaatag caaaaatgaa aaagcactgg gtcgcaaaat caatagctgg    180

gaaagcagcc gtagcggtca tagctttctg agcaatctgc atctgcgtaa tggtgaactg    240

gtgattcatg aaaaaggctt ctactatatc tatagccaga cctatttccg cttccaagaa    300

gaaatcaaag aaaataccaa aaatgataaa caaatggtgc agtatattta caaatatacc    360

agctatccgg atccgattct gctgatgaaa agcgcacgta atagctgttg gagcaaagat    420

gcagaatatg gtctgtatag catttatcag ggtggcatct ttgagctgaa agaaaatgat    480

cgcatctttg ttagcgtgac caacgaacat ctgatcgata tggatcatga agccagcttt    540

tttggtgcat ttctggttgg tggtggtagc ggttgtgcag catgtgcagc cgcatgtccg    600

ctgggtctgg caggtcgtgt tgttcgtcgg cgtcgtcgcc gtcgtcgtat gcctggtaaa    660

aaagcacgta aaaatgcaca gccgagtccg gcacgtgcac cggcagaact ggaagttgaa    720

tgtgcaaccc agctgcgtcg ttttggtgat aaactgaatt ttcgtcagaa actgctgaat    780

ctgattagca aactgttttg tagcggcacc                                     810
```

<210> SEQ ID NO 140
<211> LENGTH: 621
<212> TYPE: DNA

<213> ORGANISM: Artificial Sequence
<220> FEATURE:
<223> OTHER INFORMATION: synthesized, encoding fusion protein comprising
a fragment of TRAIL, MTD/CKP peptide derived from Noxa protein,
poly-arginine domain, a polycysteine linker, steric linker and
sequence of cleavage sites recognized by proteases MMP and uPA

<400> SEQUENCE: 140
gttcgtgaac gtggtccgca gcgtgttgca gcacatatta ccggcacccg tggtcgtagc 60
aataccctga gcagcccgaa tagcaaaaat gaaaaagcac tgggtcgcaa aattaacagc 120
tgggaaagca gccgtagcgg tcatagcttt ctgagcaatc tgcatctgcg taatggtgaa 180
ctggtgattc atgaaaaagg cttctactat atctacagcc agacctattt tcgcttccaa 240
gaagagatta aagaaaacac caaaaacgat aaacaaatgg tgcagtacat ctataaatac 300
accagctatc cggatccgat tctgctgatg aaaagcgcac gtaatagctg ttggagcaaa 360
gatgcagaat atggcctgta tagcatttat cagggtggca tctttgaact gaaagaaaac 420
gatcgtattt tcgtgagcgt gaccaatgaa catctgatcg atatggatca tgaagccagc 480 tttttggtg catttctggt tggtggtggt agcggttgtg cagcatgtgc agccgcatgt 540
ccgctgggtc tggcaggtcg tgttgttcgt cgtcgtcgcc gtcgtcggcg taaactgctg 600
aatctgatta gcaaactgtt t 621

<210> SEQ ID NO 141
<211> LENGTH: 933
<212> TYPE: DNA
<213> ORGANISM: Artificial Sequence
<220> FEATURE:
<223> OTHER INFORMATION: synthesized, encoding fusion protein comprising
a fragment of TRAIL, onconase, sequence of cleavage sites
recognized by proteases uPA and steric linkers

<400> SEQUENCE: 141
caggattggc tgacctttca gaaaaaacat attaccaaca cccgtgatgt ggattgcgat 60
aacattatga gcaccaacct gtttcactgc aaagataaaa acaccttcat ctatagccgt 120
ccggaaccgg ttaaagcaat ttgtaaaggt attatcgcca gcaaaaatgt tctgaccacg 180
agcgagtttt atctgagcga ttgtaatgtt accagccgtc cgtgtaaata caaactgaaa 240
aaaagcacca acaaattctg cgtgacctgt gaaaatcagg caccggttca ttttgttggt 300
gttggtagct gtcgtgttgt tcgtccgctg ggtctggcag gcggtggtgg tggtagtggt 360
ggcggtggta gcaccagcga agaaaccatt agcaccgttc aagaaaaaca gcagaatatt 420
agtccgctgg ttcgtgaacg tggtccgcag cgtgttgcag cacatattac cggtacacgt 480
ggtcgtagca ataccctgag cagcccgaat agcaaaaatg aaaaagcact gggtcgcaaa 540
atcaatagct gggaaagcag ccgtagcggt catagctttc tgagcaatct gcatctgcgt 600
aatggtgaac tggtgattca tgaaaaaggc ttctactata tctatagcca gacctatttc 660
cgcttccaag aagaaatcaa agagaacacc aaaaacgata aacaaatggt gcagtacatc 720
tataaataca ccagctatcc ggatccgatt ctgctgatga aaagcgcacg taatagctgt 780
tggagcaaag atgcagaata tggtctgtat agcatttatc agggtggcat ctttgagctg 840
aaagaaaatg atcgcatctt tgttagcgtg accaacgaac atctgatcga tatggatcat 900
gaagccagct tttttggtgc atttctggtg ggt 933

<210> SEQ ID NO 142
<211> LENGTH: 690
<212> TYPE: DNA

<213> ORGANISM: Artificial Sequence
<220> FEATURE:
<223> OTHER INFORMATION: synthesized, encoding fusion protein comprising a fragment of TRAIL, BH3 domain from PUMA protein, a poly-arginine and sequence of cleavage sites recognized by proteases uPA and MMP

<400> SEQUENCE: 142
gaagaacagt gggcacgtga aattggtgca cagctgcgtc gtatggcaga tgatctgaat 60
gcacagtatg aacgccgtcg tcgtcgccgt agacgtcgtc gtgttgttcg tccgctgggt 120
ctggcaggca ccagtgaaga aaccattagc accgttcaag aaaaacagca gaatattagt 180
ccgctggttc gtgaacgtgg tccgcagcgt gttgcagcac atattaccgg cacccgtggt 240
cgtagcaata ccctgagcag cccgaatagc aaaaatgaaa aagccctggg tcgcaaaatt 300
aacagctggg aaagcagccg tagcggtcat agctttctga gcaatctgca tctgcgtaat 360
ggtgaactgg tgattcacga gaaaggcttc tattatatct atagccagac ctatttccgc 420
ttccaagaag agatcaaaga gaacaccaaa aacgacaaac aaatggtgca gtacatctat 480
aaatacacca gctatccgga tccgattctg ctgatgaaaa gcgcacgtaa tagctgttgg 540
agcaaagatg cagaatatgg cctgtatagc atctatcagg gtggcatttt tgaactgaaa 600
gaaaacgatc gcatctttgt gagcgtgacc aatgaacatc tgattgatat ggatcacgaa 660
gccagctttt ttggtgcctt tctggttggt 690

<210> SEQ ID NO 143
<211> LENGTH: 675
<212> TYPE: DNA
<213> ORGANISM: Artificial Sequence
<220> FEATURE:
<223> OTHER INFORMATION: synthesized, encoding fusion protein comprising a fragment of TRAIL, a peptide derived from Bid protein, a transporting domain KPRRPY, a polycysteine linker and sequence of cleavage sites recognized by proteases MMP and uPA

<400> SEQUENCE: 143
accagcgaag aaaccattag caccgttcaa gaaaaacagc agaatattag tccgctggtt 60
cgtgaacgtg gtccgcagcg tgttgcagca catattaccg gcacccgtgg tcgtagcaat 120
accctgagca gcccgaatag caaaaatgaa aaagcactgg gtcgcaaaat caatagctgg 180
gaaagcagcc gtagcggtca tagctttctg agcaatctgc atctgcgtaa tggtgaactg 240
gtgattcatg aaaaaggctt ctactatatc tatagccaga cctatttccg cttccaagaa 300
gaaatcaaag aaaataccaa aaatgataaa caaatggtgc agtatattta caaatatacc 360
agctatccgg atccgattct gctgatgaaa agcgcacgta atagctgttg gagcaaagat 420
gcagaatatg gtctgtatag catttatcag ggtggcatct ttgagctgaa agaaaatgat 480
cgcatctttg ttagcgtgac caacgaacat ctgatcgata tggatcatga agccagcttt 540
tttggtgcat ttctggttgg ttgtgcagca tgtgcagccg catgtccgct gggtctggca 600
ggtcgtgttg ttcgtaatat tgcacgtcat ctggcacagg ttggtgatag catggataaa 660
ccgcgtcgtc cgtat 675

<210> SEQ ID NO 144
<211> LENGTH: 702
<212> TYPE: DNA
<213> ORGANISM: Artificial Sequence
<220> FEATURE:
<223> OTHER INFORMATION: synthesized, encoding fusion protein comprising a fragment of TRAIL, a hybrid peptide Antp-TPR, sequences of cleavage sites recognized by proteases MMP and uPA and a polycysteine linker

<400> SEQUENCE: 144
accagcgaag aaaccattag caccgttcaa gaaaaacagc agaatattag tccgctggtt 60
cgtgaacgtg gtccgcagcg tgttgcagca catattaccg gcacccgtgg tcgtagcaat 120
accctgagca gcccgaatag caaaaatgaa aaagcactgg gtcgcaaaat taacagctgg 180
gaaagcagcc gtagcggtca tagctttctg agcaatctgc atctgcgtaa tggtgaactg 240
gtgattcatg aaaaaggctt ctactatatc tacagccaga cctattttcg cttccaagaa 300
gagattaaag aaaacaccaa aaacgataaa caaatggtgc agtacatcta taaatacacc 360
agctatccgg atccgattct gctgatgaaa agcgcacgta atagctgttg gagcaaagat 420
gcagaatatg gcctgtatag catttatcag ggtggcatct ttgaactgaa agaaaacgat 480
cgtattttcg tgagcgtgac caatgaacat ctgatcgata tggatcatga agccagcttt 540
tttggtgcat ttctggttgg ttgtgcagca tgtgcagccg catgtggtgg tccgctgggt 600
ctggcaggtc gtgttgttcg tcagattaaa atctggtttc agaaccgtcg catgaaatgg 660
aaaaaaaaag cctatgcagc agccggtaac agctacttta aa 702

<210> SEQ ID NO 145
<211> LENGTH: 648
<212> TYPE: DNA
<213> ORGANISM: Artificial Sequence
<220> FEATURE:
<223> OTHER INFORMATION: synthesized, encoding fusion protein comprising a fragment of TRAIL, a peptide inhibitor of the SH2 domain of Stat3 protein, a polycysteine linker, a steric linker and sequence of cleavage sites recognized by proteases uPA and MMP

<400> SEQUENCE: 145
ttcatcagca aagaacgtcg tgaacgtgca attctgagca ccaaaccgcc tggcaccttt 60
ctgctgcgtt ttagcgaaag cagcaaacgt gttgttcgtc cgctgggtat tgccggtgaa 120
ggtggtggtt gtgcagcagc atgtgcagcc tgtggtagcg gtcagcgtgt tgcagcacat 180
attaccggca cccgtggtcg tagcaatacc ctgagcagcc cgaatagcaa aaatgaaaaa 240
gcactgggtc gcaaaattaa cagctgggaa agcagccgta gtggtcatag ctttctgagc 300
aatctgcatc tgcgtaatgg tgaactggtg attcatgaaa aaggcttcta ctatatctac 360
agccagacct attttcgctt ccaagaagag attaaagaaa acaccaaaaa cgataaacaa 420
atggtgcagt acatctataa atacaccagc tatccggatc cgattctgct gatgaaaagc 480
gcacgtaata gctgttggag caaagatgca gaatatggcc tgtatagcat ttatcagggt 540
ggcatctttg aactgaaaga aaacgatcgt attttcgtga gcgtgaccaa tgaacatctg 600
atcgatatgg atcatgaagc cagctttttt ggtgcatttc tggtgggt 648

<210> SEQ ID NO 146
<211> LENGTH: 582
<212> TYPE: DNA
<213> ORGANISM: Artificial Sequence
<220> FEATURE:
<223> OTHER INFORMATION: synthesized, encoding fusion protein comprising a fragment of TRAIL, a peptide derived from BH3 domain of Bak protein, a poly-arginine domain and sequence of cleavage sites recognized by proteases uPA and MMP

<400> SEQUENCE: 146
ggacaggttg gtcgtcagct ggcaattatt ggtgatgata ttaatcgtcg tcgtcggcgt 60
cgtagacgtc gtgttgttcg tccgctgggt ctggcaggtc gtgttgcagc acatattacc 120

```
ggcacccgtg gtcgtagcaa taccctgagc agcccgaata gcaaaaatga aaaagcactg    180

ggtcgcaaaa tcaatagctg ggaaagcagc cgtagcggtc atagctttct gagcaatctg    240

catctgcgta atggtgaact ggtgattcat gaaaaaggct tttattatat ttatagccag    300

acctattttc gctttcaaga agagattaaa gaaaatacca aaaatgataa acaaatggtg    360

cagtacatct ataaatatac cagctatccg gacccgattc tgctgatgaa aagcgcacgt    420

aatagctgtt ggagcaaaga tgcagaatat ggtctgtata gcatttatca gggtggcatc    480

tttgagctga aagaaaatga tcgcatcttt gttagcgtga ccaacgaaca tctgatcgat    540

atggatcatg aagccagctt ttttggtgca tttctggttg gt                       582
```

<210> SEQ ID NO 147
<211> LENGTH: 729
<212> TYPE: DNA
<213> ORGANISM: Artificial Sequence
<220> FEATURE:
<223> OTHER INFORMATION: synthesized, fusion protein comprising a fragment of TRAIL, a peptide derived from BH3 domain of Bad protein, a poly-arginine domain, sequence of cleavage sites recognized by proteases uPA and MMP, a flexible linker and sequence o recognized by thrombin

<400> SEQUENCE: 147

```
aaaaatctgt gggcagcaca gcgttatggt cgtgaactgc gtcgtatgag tgatgaattt     60

gaaggtagct ttaaaggtct gcgtcgtcgt cgtcgccgtc gtcggcgtgt tgttcgtccg    120

ctgggtctgg caggtcgtgt tgcagcacat attaccggca cccgtggtcg tagcaatacc    180

ctgagcagcc cgaatagcaa aaatgaaaaa gcactgggtc gcaaaatcaa tagctgggaa    240

agcagccgta gcggtcatag ctttctgagc aatctgcatc tgcgtaatgg tgaactggtg    300

attcatgaaa aaggctttta ttatatttat agccagacct attttcgctt tcaagaagag    360

attaaagaaa ataccaaaaa tgataaacaa atggtgcagt acatctataa atataccagc    420

tatccggacc cgattctgct gatgaaaagc gcacgtaata gctgttggag caaagatgca    480

gaatatggtc tgtatagcat ttatcagggt ggcatctttg agctgaaaga aaatgatcgc    540

atctttgtta gcgtgaccaa cgaacatctg atcgatatgg atcatgaagc cagctttttt    600

ggtgcatttc tggttggtgg tggtagccat ggtctggttc cgcgtggtag caccagcgaa    660

gaaaccatta gcaccgttca agaaaaacag cagaatatta gtccgctggt tcgtgaacgt    720

ggtccgcag                                                            729
```

<210> SEQ ID NO 148
<211> LENGTH: 708
<212> TYPE: DNA
<213> ORGANISM: Artificial Sequence
<220> FEATURE:
<223> OTHER INFORMATION: synthesized, encoding fusion protein comprising a fragment of TRAIL, a peptide derived from BH3 domain of Bad protein, a poly-arginine domain, a sequence of cleavage sites recognized by proteases MMP and uPA and a steric linker.

<400> SEQUENCE: 148

```
accagcgaag aaaccattag caccgttcaa gaaaaacagc agaatattag tcctctggtt     60

cgtgaacgtg gtccgcagcg tgttgcagca catattaccg gcacccgtgg tcgtagcaat    120

accctgagca gcccgaatag caaaaatgaa aaagcactgg gtcgcaaaat caatagctgg    180

gaaagcagcc gtagcggtca tagctttctg agcaatctgc atctgcgtaa tggtgaactg    240

gtgattcatg aaaaaggctt ttattatatt tatagccaga cctattttcg ctttcaagaa    300
```

-continued gagattaaag aaaataccaa aaatgataaa caaatggtgc agtacatcta taaatatacc 360
agctatccgg acccgattct gctgatgaaa agcgcacgta atagctgttg gagcaaagat 420
gcagaatatg gtctgtatag catttatcag ggtggcatct ttgagctgaa agaaaatgat 480
cgcatctttg ttagcgtgac caacgaacat ctgatcgata tggatcatga agccagcttt 540
tttggtgcat ttctggttgg tggtggtagt ccgctgggtc tggcaggttg tcgtgttgtt 600
cgtcgtcgtc gccgtcgtcg gcgtcgtaaa aatctgtggg cagcacagcg ttatggtcgt 660
gaactgcgtc gtatgagtga tgaatttgaa ggtagcttta aaggcctg 708

<210> SEQ ID NO 149
<211> LENGTH: 648
<212> TYPE: DNA
<213> ORGANISM: Artificial Sequence
<220> FEATURE:
<223> OTHER INFORMATION: synthesized, encoding fusion protein comprising a fragment of TRAIL, a ATAP peptide from Bfl1 protein, a membrane transporting domain KPRRPYR, a sequence of cleavage sites recognized by proteases MMP and uPA and a steric linker.

<400> SEQUENCE: 149
cgtgttgcag cacatattac cggcacccgt ggtcgtagca ataccctgag cagcccgaat 60
agcaaaaatg aaaaagcact gggtcgcaaa attaacagct gggaaagcag ccgtagcggt 120
catagctttc tgagcaatct gcatctgcgt aatggtgaac tggtgattca tgaaaaaggc 180
ttctactata tctacagcca gacctatttt cgcttccaag aagagattaa agaaaacacc 240
aaaaacgata aacaaatggt gcagtacatc tataaataca ccagctatcc ggatccgatt 300
ctgctgatga aaagcgcacg taatagctgt tggagcaaag atgcagaata tggcctgtat 360
agcatttatc agggtggcat ctttgaactg aaagaaaacg atcgtatttt cgtgagcgtg 420
accaatgaac atctgatcga tatggatcat gaagccagct tttttggtgc atttctggtg 480
ggtggtggtg gcggtagtgg cggtggtggt cctctgggtc tggcaggtcg tgttgttcgt 540
aaatttgaac cgaaaagcgg ttggatgacc tttctggaag ttaccggcaa aatttgtgaa 600
atgctgagcc tgctgaaaca gtattgtaaa ccgcgtcgtc cgtatcgc 648

<210> SEQ ID NO 150
<211> LENGTH: 711
<212> TYPE: DNA
<213> ORGANISM: Artificial Sequence
<220> FEATURE:
<223> OTHER INFORMATION: synthesized, encoding fusion protein comprising a fragment of TRAIL, a ATAP peptide from Bfl1 protein, a mitochondrial targeting sequence, a sequence of cleavage sites recognized by proteases MMP and uPA and a steric linker.

<400> SEQUENCE: 150
cgtgttagct tttgtcgtcc gggttggagc gcaatggcac gtagccgtct gaccgcaacc 60
agcgttagcc aggttcaaga aaatggtttc gtgaaaaaat tcgaaccgaa aagcggttgg 120
atgacctttc tggaagttac cggcaaaatt tgtgaaatgc tgagcctgct gaaacagtat 180
tgtcgtgttg ttcgtccgct gggtctggca ggcggtggta gcggtggtcg tgttgcagca 240
catattaccg gcacccgtgg tcgtagcaat accctgagca gcccgaatag caaaaatgaa 300
aaagcactgg gtcgcaaaat taacagctgg gaaagcagcc gtagcggtca tagctttctg 360
agcaatctgc atctgcgtaa tggtgaactg gtgattcatg aaaaaggctt ctactatatc 420
tacagccaga cctattttcg cttccaagaa gagattaaag aaaacaccaa aaacgataaa 480
caaatggtgc agtacatcta taaatacacc agctatccgg atccgattct gctgatgaaa 540
agcgcacgta atagctgttg gagcaaagat gcagaatatg gcctgtatag catttatcag 600
ggtggcatct ttgaactgaa agaaaacgat cgtattttcg tgagcgtgac caatgaacat 660
ctgatcgata tggatcatga agccagcttt tttggtgcat ttctggtggg t 711

<210> SEQ ID NO 151
<211> LENGTH: 28
<212> TYPE: PRT
<213> ORGANISM: Pseudomonas aeruginosa
<300> PUBLICATION INFORMATION:
<308> DATABASE ACCESSION NUMBER: GenBankAAA25730.1
<309> DATABASE ENTRY DATE: 2000-03-19
<313> RELEVANT RESIDUES IN SEQ ID NO: (70)..(97)

<400> SEQUENCE: 151

Leu Ser Thr Ala Ala Asp Met Gln Gly Val Val Thr Asp Gly Met Ala
1 5 10 15

Ser Gly Leu Asp Lys Asp Tyr Leu Lys Pro Asp Asp
20 25

<210> SEQ ID NO 152
<211> LENGTH: 148
<212> TYPE: PRT
<213> ORGANISM: Pseudomonas aeruginosa
<300> PUBLICATION INFORMATION:
<308> DATABASE ACCESSION NUMBER: GenBank/AAA25730.1
<309> DATABASE ENTRY DATE: 2000-03-29
<313> RELEVANT RESIDUES IN SEQ ID NO: (1)..(148)

<400> SEQUENCE: 152

Met Leu Arg Lys Leu Ala Ala Val Ser Leu Leu Ser Leu Leu Ser Ala
1 5 10 15

Pro Leu Leu Ala Ala Glu Cys Ser Val Asp Ile Gln Gly Asn Asp Gln
20 25 30

Met Gln Phe Asn Thr Asn Ala Ile Thr Val Asp Lys Ser Cys Lys Gln
35 40 45

Phe Thr Val Asn Leu Ser His Pro Gly Asn Leu Pro Lys Asn Val Met
50 55 60

Gly His Asn Trp Val Leu Ser Thr Ala Ala Asp Met Gln Gly Val Val
65 70 75 80

Thr Asp Gly Met Ala Ser Gly Leu Asp Lys Asp Tyr Leu Lys Pro Asp
85 90 95

Asp Ser Arg Val Ile Ala His Thr Lys Leu Ile Gly Ser Gly Glu Lys
100 105 110

Asp Ser Val Thr Phe Asp Val Ser Lys Leu Lys Glu Gly Glu Gln Tyr
115 120 125

Met Phe Phe Cys Thr Phe Pro Gly His Ser Ala Leu Met Lys Gly Thr
130 135 140

Leu Thr Leu Lys
145

<210> SEQ ID NO 153
<211> LENGTH: 35
<212> TYPE: PRT
<213> ORGANISM: Artificial Sequence
<220> FEATURE:
<223> OTHER INFORMATION: synthesized, derived from aPP protein and BH3 domain of Bax protein
<300> PUBLICATION INFORMATION:
<301> AUTHORS: E. P. Holinger, T. Chittenden, R. J. Lutz, J.
<302> TITLE: Bak BH3 peptides antagonize Bcl-xL function and induce apoptosis through cytochrome c-independent activation of caspases.

<303> JOURNAL: Journal of Biological Chemistry
<304> VOLUME: 7
<305> ISSUE: 274
<306> PAGES: 13298-14304
<307> DATE: 1999-05-07

<400> SEQUENCE: 153

```
Gly Pro Ser Gln Pro Thr Tyr Pro Gly Asp Asp Ala Pro Val Glu Asp
1               5                   10                  15

Leu Ile Arg Phe Val Gly Arg Leu Leu Ala Tyr Phe Gly Asp Thr Ile
            20                  25                  30

Asn Arg Arg
        35
```

<210> SEQ ID NO 154
<211> LENGTH: 34
<212> TYPE: PRT
<213> ORGANISM: Artificial Sequence
<220> FEATURE:
<223> OTHER INFORMATION: synthesized, derived form aPP protein and BH3 domain of Bax protein
<300> PUBLICATION INFORMATION:
<301> AUTHORS: E. P. Holinger, T. Chittenden, R. J. Lutz
<302> TITLE: Bak BH3 Peptides Antagonize Bcl-xL Function and Induce Apoptosis through Cytochrome c-independent Activation of Caspases
<303> JOURNAL: Journal of Biological Chemistry
<304> VOLUME: 7
<305> ISSUE: 274
<306> PAGES: 13298-14304
<307> DATE: 1999-05-07

<400> SEQUENCE: 154

```
Gly Pro Arg Arg Pro Arg Arg Pro Gly Asp Asp Ala Pro Val Glu Asp
1               5                   10                  15

Leu Ile Arg Phe Val Gly Arg Leu Leu Ala Tyr Phe Gly Asp Thr Ile
            20                  25                  30

Asn Arg
```

<210> SEQ ID NO 155
<211> LENGTH: 23
<212> TYPE: PRT
<213> ORGANISM: Homo sapiens
<300> PUBLICATION INFORMATION:
<301> AUTHORS: Nepravishta R, Bellomaria A, Polizio F, Paci M, Melino S.
<302> TITLE: Reticulon RTN1-C(CT)peptide: a potential nuclease and inhibitor of histone deacetylase enzymes
<303> JOURNAL: Biochemistry
<304> VOLUME: 19
<305> ISSUE: 49(2)
<306> PAGES: 252-258
<307> DATE: 2010-01-19

<400> SEQUENCE: 155

```
Arg Thr His Ile Asn Thr Val Val Ala Lys Ile Gln Ala Lys Ile Pro
1               5                   10                  15

Gly Ala Lys Arg His Ala Glu
            20
```

<210> SEQ ID NO 156
<211> LENGTH: 235
<212> TYPE: PRT
<213> ORGANISM: Homo sapiens
<300> PUBLICATION INFORMATION:
<308> DATABASE ACCESSION NUMBER: GenBank/NP_006045
<309> DATABASE ENTRY DATE: 2011-06-01
<313> RELEVANT RESIDUES IN SEQ ID NO: (2)..(236)

<400> SEQUENCE: 156

```
Ala Glu Pro Ser Ala Ala Thr Gln Ser His Ser Ile Ser Ser Ser Ser
1               5                   10                  15

Phe Gly Ala Glu Pro Ser Ala Pro Gly Gly Gly Gly Ser Pro Gly Ala
            20                  25                  30

Cys Pro Ala Leu Gly Thr Lys Ser Cys Ser Ser Ser Cys Ala Val His
        35                  40                  45

Asp Leu Ile Phe Trp Arg Asp Val Lys Lys Thr Gly Phe Val Phe Gly
    50                  55                  60

Thr Thr Leu Ile Met Leu Leu Ser Leu Ala Ala Phe Ser Val Ile Ser
65                  70                  75                  80

Val Val Ser Tyr Leu Ile Leu Ala Leu Leu Ser Val Thr Ile Ser Phe
                85                  90                  95

Arg Ile Tyr Lys Ser Val Ile Gln Ala Val Gln Lys Ser Glu Glu Gly
            100                 105                 110

His Pro Phe Lys Ala Tyr Leu Asp Val Asp Ile Thr Leu Ser Ser Glu
        115                 120                 125

Ala Phe His Asn Tyr Met Asn Ala Ala Met Val His Ile Asn Arg Ala
    130                 135                 140

Leu Lys Leu Ile Ile Arg Leu Phe Leu Val Glu Asp Leu Val Asp Ser
145                 150                 155                 160

Leu Lys Leu Ala Val Phe Met Trp Leu Met Thr Tyr Val Gly Ala Val
                165                 170                 175

Phe Asn Gly Ile Thr Leu Leu Ile Leu Ala Glu Leu Leu Ile Phe Ser
            180                 185                 190

Val Pro Ile Val Tyr Glu Lys Tyr Lys Thr Gln Ile Asp His Tyr Val
        195                 200                 205

Gly Ile Ala Arg Asp Gln Thr Lys Ser Ile Val Glu Lys Ile Gln Ala
    210                 215                 220

Lys Leu Pro Gly Ile Ala Lys Lys Lys Ala Glu
225                 230                 235


<210> SEQ ID NO 157
<211> LENGTH: 282
<212> TYPE: PRT
<213> ORGANISM: Homo sapiens
<300> PUBLICATION INFORMATION:
<301> AUTHORS: Srinivasula SM, Ahmad M, MacFarlane M, Luo Z, Huang Z,
      Fernandes-Alnemri T, Alnemri ES
<302> TITLE: Generation of constitutively active recombinant caspases-3
      and -6 by rearrangement of their subunits
<303> JOURNAL: Journal of Biological Chemistry
<304> VOLUME: 273
<305> ISSUE: 17
<306> PAGES: 10107-11
<307> DATE: 1998-04-24

<400> SEQUENCE: 157

Met Ile Glu Thr Asp Ser Gly Val Asp Asp Asp Met Ala Cys His Lys
1               5                   10                  15

Ile Pro Val Asp Ala Asp Phe Leu Tyr Ala Tyr Ser Thr Ala Pro Gly
            20                  25                  30

Tyr Tyr Ser Trp Arg Asn Ser Lys Asp Gly Ser Trp Phe Ile Gln Ser
        35                  40                  45

Leu Cys Ala Met Leu Lys Gln Tyr Ala Asp Lys Leu Glu Phe Met His
    50                  55                  60

Ile Leu Thr Arg Val Asn Arg Lys Val Ala Thr Glu Phe Glu Ser Phe
65                  70                  75                  80
```

```
Ser Phe Asp Ala Thr Phe His Ala Lys Lys Gln Ile Pro Cys Ile Val
                85                  90                  95

Ser Met Leu Thr Lys Glu Leu Tyr Phe Tyr His Asp Val Asp Gly Met
            100                 105                 110

Glu Asn Thr Glu Asn Ser Val Asp Ser Lys Ser Ile Lys Asn Leu Glu
        115                 120                 125

Pro Lys Ile Ile His Gly Ser Glu Ser Met Asp Ser Gly Met Ser Trp
    130                 135                 140

Asp Thr Gly Tyr Lys Met Asp Tyr Pro Glu Met Gly Leu Cys Ile Ile
145                 150                 155                 160

Ile Asn Asn Lys Asn Phe His Lys Ser Thr Gly Met Thr Ser Arg Ser
                165                 170                 175

Gly Thr Asp Val Asp Ala Ala Asn Leu Arg Glu Thr Phe Arg Asn Leu
            180                 185                 190

Lys Tyr Glu Val Arg Asn Lys Asn Asp Leu Thr Arg Glu Glu Ile Val
        195                 200                 205

Glu Leu Met Arg Asp Val Ser Lys Glu Asp His Ser Lys Arg Ser Ser
    210                 215                 220

Phe Val Cys Val Leu Leu Ser His Gly Glu Glu Gly Ile Ile Phe Gly
225                 230                 235                 240

Thr Asn Gly Pro Val Asp Leu Lys Lys Ile Thr Asn Phe Phe Arg Gly
                245                 250                 255

Asp Arg Cys Arg Ser Leu Thr Gly Lys Pro Lys Leu Phe Ile Ile Gln
            260                 265                 270

Ala Cys Arg Gly Thr Glu Leu Asp Cys Gly
        275                 280
```

<210> SEQ ID NO 158
<211> LENGTH: 60
<212> TYPE: PRT
<213> ORGANISM: Homo sapiens
<300> PUBLICATION INFORMATION:
<308> DATABASE ACCESSION NUMBER: GenBank/AAC24947.1
<309> DATABASE ENTRY DATE: 1998-07-01
<313> RELEVANT RESIDUES IN SEQ ID NO: (146)..(205)

<400> SEQUENCE: 158

```
Ala Arg Lys Gly Lys Gly Gln Ile Glu Lys Arg Lys Leu Arg Glu Lys
1               5                   10                  15

Arg Arg Ser Thr Gly Val Val Asn Ile Pro Ala Ala Glu Cys Leu Asp
            20                  25                  30

Glu Tyr Glu Asp Asp Glu Ala Gly Gln Lys Glu Arg Lys Arg Glu Asp
        35                  40                  45

Ala Ile Thr Gln Gln Asn Thr Ile Gln Asn Glu Ala
    50                  55                  60
```

<210> SEQ ID NO 159
<211> LENGTH: 54
<212> TYPE: PRT
<213> ORGANISM: Homo sapiens
<300> PUBLICATION INFORMATION:
<308> DATABASE ACCESSION NUMBER: GenBank/NP_066950
<309> DATABASE ENTRY DATE: 2011-06-05
<313> RELEVANT RESIDUES IN SEQ ID NO: (1)..(54)

<400> SEQUENCE: 159

```
Met Pro Gly Lys Lys Ala Arg Lys Asn Ala Gln Pro Ser Pro Ala Arg
1               5                   10                  15

Ala Pro Ala Glu Leu Glu Val Glu Cys Ala Thr Gln Leu Arg Arg Phe
```

```
            20                  25                  30

Gly Asp Lys Leu Asn Phe Arg Gln Lys Leu Leu Asn Leu Ile Ser Lys
        35                  40                  45

Leu Phe Cys Ser Gly Thr
    50


<210> SEQ ID NO 160
<211> LENGTH: 9
<212> TYPE: PRT
<213> ORGANISM: Homo sapiens
<300> PUBLICATION INFORMATION:
<302> TITLE: CELL-KILLING PEPTIDE
<310> PATENT DOCUMENT NUMBER: WO2006001582
<311> PATENT FILING DATE: 2005-03-22
<312> PUBLICATION DATE: 2006-01-05

<400> SEQUENCE: 160

Lys Leu Leu Asn Leu Ile Ser Lys Leu
1               5


<210> SEQ ID NO 161
<211> LENGTH: 27
<212> TYPE: PRT
<213> ORGANISM: Homo sapiens
<300> PUBLICATION INFORMATION:
<302> TITLE: NOVEL HSP90-TARGETED ANTI-CANCER CHIMERIC PEPTIDE
<310> PATENT DOCUMENT NUMBER: WO2010055929
<311> PATENT FILING DATE: 2009-11-13
<312> PUBLICATION DATE: 2010-05-20

<400> SEQUENCE: 161

Gln Ile Lys Ile Trp Phe Gln Asn Arg Arg Met Lys Trp Lys Lys Lys
1               5                   10                  15

Ala Tyr Ala Ala Ala Gly Asn Ser Tyr Phe Lys
            20                  25


<210> SEQ ID NO 162
<211> LENGTH: 29
<212> TYPE: PRT
<213> ORGANISM: Homo sapiens
<300> PUBLICATION INFORMATION:
<301> AUTHORS: Zhao W, Jaganathan S, Turkson
<302> TITLE: A cell-permeable Stat3 SH2 domain mimetic inhibits Stat3
      activation and induces antitumor cell effects in vitro
<303> JOURNAL: Journal of Biological Chemistry
<304> VOLUME: 285
<305> ISSUE: 46
<306> PAGES: 35855-65.
<307> DATE: 2010-11-12
<308> DATABASE ACCESSION NUMBER: genBank/NP_644805
<309> DATABASE ENTRY DATE: 2011-06-05
<313> RELEVANT RESIDUES IN SEQ ID NO: (517)..(544)

<400> SEQUENCE: 162

Phe Ile Ser Lys Glu Arg Arg Glu Arg Ala Ile Leu Ser Thr Lys Pro
1               5                   10                  15

Pro Gly Thr Phe Leu Leu Arg Phe Ser Glu Ser Ser Lys
            20                  25


<210> SEQ ID NO 163
<211> LENGTH: 15
<212> TYPE: PRT
<213> ORGANISM: Homo sapiens
<300> PUBLICATION INFORMATION:
<308> DATABASE ACCESSION NUMBER: GenBank/AAA74466.1
<309> DATABASE ENTRY DATE: 1995-08-18
<313> RELEVANT RESIDUES IN SEQ ID NO: (72)..(86)
```

<400> SEQUENCE: 163

Gly Gln Val Gly Arg Gln Leu Ala Ile Ile Gly Asp Asp Ile Asn
1 5 10 15

<210> SEQ ID NO 164
<211> LENGTH: 27
<212> TYPE: PRT
<213> ORGANISM: Homo sapiens
<300> PUBLICATION INFORMATION:
<301> AUTHORS: Wang JL, Zhang ZJ, Choksi S, Shan S, Lu Z, Croce CM, Alnemri ES, Korngold R, Huang Z.
<302> TITLE: Cell permeable Bcl-2 binding peptides: a chemical approach to apoptosis induction in tumor cells
<303> JOURNAL: Cancer Research
<304> VOLUME: 60
<305> ISSUE: 6
<306> PAGES: 1498-502
<307> DATE: 2000-03-15

<400> SEQUENCE: 164

Lys Asn Leu Trp Ala Ala Gln Arg Tyr Gly Arg Glu Leu Arg Arg Met
1 5 10 15

Ser Asp Glu Phe Glu Gly Ser Phe Lys Gly Leu
20 25

<210> SEQ ID NO 165
<211> LENGTH: 29
<212> TYPE: PRT
<213> ORGANISM: Homo sapiens
<300> PUBLICATION INFORMATION:
<308> DATABASE ACCESSION NUMBER: GenBank/CAG46760.1
<309> DATABASE ENTRY DATE: 2004-06-29
<313> RELEVANT RESIDUES IN SEQ ID NO: (147)..(175)

<400> SEQUENCE: 165

Lys Phe Glu Pro Lys Ser Gly Trp Met Thr Phe Leu Glu Val Thr Gly
1 5 10 15

Lys Ile Cys Glu Met Leu Ser Leu Leu Lys Gln Tyr Cys
20 25

<210> SEQ ID NO 166
<211> LENGTH: 32
<212> TYPE: PRT
<213> ORGANISM: Homo sapiens
<300> PUBLICATION INFORMATION:
<301> AUTHORS: Ko JK, Choi KH, Pan Z, Lin P, Weisleder N, Kim CW, Ma J.
<302> TITLE: The tail-anchoring domain of Bfl1 and HCCS1 targets mitochondrial membrane permeability to induce apoptosis
<303> JOURNAL: J Cell Sci.
<304> VOLUME: 120
<305> ISSUE: 16
<306> PAGES: 2912-2923
<307> DATE: 2007-07-31

<400> SEQUENCE: 166

Arg Val Ser Phe Cys Arg Pro Gly Trp Ser Ala Met Ala Arg Ser Arg
1 5 10 15

Leu Thr Ala Thr Ser Val Ser Gln Val Gln Glu Asn Gly Phe Val Lys
20 25 30

<210> SEQ ID NO 167
<211> LENGTH: 6
<212> TYPE: PRT
<213> ORGANISM: Homo sapiens

<400> SEQUENCE: 167

Lys Pro Arg Arg Pro Tyr

```
1               5


<210> SEQ ID NO 168
<211> LENGTH: 13
<212> TYPE: PRT
<213> ORGANISM: Homo sapiens
<300> PUBLICATION INFORMATION:
<308> DATABASE ACCESSION NUMBER: NCBI Reference Sequence/NP_002690.3
<309> DATABASE ENTRY DATE: 2011-04-19
<313> RELEVANT RESIDUES IN SEQ ID NO: (334)..(344)

<400> SEQUENCE: 168

Glu Glu Glu Ala Ala Gly Arg Lys Arg Lys Lys Arg Thr
1               5                   10


<210> SEQ ID NO 169
<211> LENGTH: 5
<212> TYPE: PRT
<213> ORGANISM: Artificial Sequence
<220> FEATURE:
<223> OTHER INFORMATION: synthesized, steric linker

<400> SEQUENCE: 169

Ser Gly Cys Gly Ser
1               5


<210> SEQ ID NO 170
<211> LENGTH: 7
<212> TYPE: PRT
<213> ORGANISM: Artificial Sequence
<220> FEATURE:
<223> OTHER INFORMATION: synthesized, pegylation linker
<300> PUBLICATION INFORMATION:
<301> AUTHORS: Tsutsumi Y, Onda M, Nagata S, Lee B, Kreitman RJ, Pastan
      I.
<302> TITLE: Site-specific chemical modification with polyethylene
      glycol of
<303> JOURNAL: Proc Natl Acad Sci U S A
<304> VOLUME: 97
<305> ISSUE: 15
<306> PAGES: 8548-8553
<307> DATE: 2000-07-18

<400> SEQUENCE: 170

Ala Ser Gly Cys Gly Pro Glu
1               5


<210> SEQ ID NO 171
<211> LENGTH: 7
<212> TYPE: PRT
<213> ORGANISM: Artificial Sequence
<220> FEATURE:
<223> OTHER INFORMATION: synthesized, a fragment recognized by
      metalloprotease MMP

<400> SEQUENCE: 171

Pro Leu Gly Ile Ala Gly Glu
1               5


<210> SEQ ID NO 172
<211> LENGTH: 7
<212> TYPE: PRT
<213> ORGANISM: Artificial Sequence
<220> FEATURE:
<223> OTHER INFORMATION: synthesized, a fragment recognized by furin
<300> PUBLICATION INFORMATION:
<301> AUTHORS: chards RM, Lowy DR, Schiller JT, Day PM
<302> TITLE: Cleavage of the papillomavirus minor capsid protein, L2,
      at a furin consensus site is necessary for infection.
<303> JOURNAL: Proc Natl Acad Sci U S A
```

-continued

<304> VOLUME: 103
<305> ISSUE: 5
<306> PAGES: 1522-1527
<307> DATE: 2006-01-31

<400> SEQUENCE: 172

Arg Lys Lys Arg Val Lys Arg
1               5

<210> SEQ ID NO 173
<211> LENGTH: 7
<212> TYPE: PRT
<213> ORGANISM: Artificial Sequence
<220> FEATURE:
<223> OTHER INFORMATION: synthesized, a fragment recognized by metalloprotease MMP

<400> SEQUENCE: 173

Pro Leu Gly Leu Ala Gly Gln
1               5

<210> SEQ ID NO 174
<211> LENGTH: 6
<212> TYPE: PRT
<213> ORGANISM: Artificial Sequence
<220> FEATURE:
<223> OTHER INFORMATION: synthesized, a fragment recognized by thrombin

<400> SEQUENCE: 174

Leu Val Pro Arg Gly Ser
1               5

<210> SEQ ID NO 175
<211> LENGTH: 9
<212> TYPE: PRT
<213> ORGANISM: Artificial Sequence
<220> FEATURE:
<223> OTHER INFORMATION: synthesized, steric linker

<400> SEQUENCE: 175

Gly Gly Gly Gly Ser Gly Gly Gly Ser
1               5

<210> SEQ ID NO 176
<211> LENGTH: 107
<212> TYPE: PRT
<213> ORGANISM: Pseudomonas aeruginosa
<300> PUBLICATION INFORMATION:
<308> DATABASE ACCESSION NUMBER: GenBank/1IKQ_A
<309> DATABASE ENTRY DATE: 2008-08-24
<313> RELEVANT RESIDUES IN SEQ ID NO: (251)..(357)

<400> SEQUENCE: 176

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

```
Ser Glu Arg Phe Val Arg Gln Gly Thr Gly Asn
            100                 105


<210> SEQ ID NO 177
<211> LENGTH: 8
<212> TYPE: PRT
<213> ORGANISM: Artificial Sequence
<220> FEATURE:
<223> OTHER INFORMATION: synthesized, stabilizing linker

<400> SEQUENCE: 177

Cys Ala Ala Cys Ala Ala Ala Cys
1               5


<210> SEQ ID NO 178
<211> LENGTH: 9
<212> TYPE: PRT
<213> ORGANISM: Artificial Sequence
<220> FEATURE:
<223> OTHER INFORMATION: synthesized, stabilizing linker

<400> SEQUENCE: 178

Cys Ala Ala Glu Cys Ala Ala Ala Cys
1               5


<210> SEQ ID NO 179
<211> LENGTH: 8
<212> TYPE: PRT
<213> ORGANISM: Artificial Sequence
<220> FEATURE:
<223> OTHER INFORMATION: synthesized, stabilizing linker

<400> SEQUENCE: 179

Cys Ala Ala Ala Cys Ala Ala Cys
1               5


<210> SEQ ID NO 180
<211> LENGTH: 9
<212> TYPE: PRT
<213> ORGANISM: Artificial Sequence
<220> FEATURE:
<223> OTHER INFORMATION: synthesized, steric linker

<400> SEQUENCE: 180

Gly Gly Gly Gly Ser Gly Gly Gly Gly
1               5


<210> SEQ ID NO 181
<211> LENGTH: 7
<212> TYPE: PRT
<213> ORGANISM: Homo sapiens

<400> SEQUENCE: 181

Lys Pro Arg Arg Pro Tyr Arg
1               5


<210> SEQ ID NO 182
<211> LENGTH: 5
<212> TYPE: PRT
<213> ORGANISM: Artificial Sequence
<220> FEATURE:
<223> OTHER INFORMATION: synthesized, steric linker

<400> SEQUENCE: 182

Gly Gly Ser His Gly
1               5
```

-continued

```
<210> SEQ ID NO 183
<211> LENGTH: 7
<212> TYPE: PRT
<213> ORGANISM: Artificial Sequence
<220> FEATURE:
<223> OTHER INFORMATION: synthesized, steric linker

<400> SEQUENCE: 183

Ser Gly Gly Cys Gly Gly Ser
1               5


<210> SEQ ID NO 184
<211> LENGTH: 5
<212> TYPE: PRT
<213> ORGANISM: Artificial Sequence
<220> FEATURE:
<223> OTHER INFORMATION: synthesized, steric linker

<400> SEQUENCE: 184

Ala Ala Cys Ala Ala
1               5


<210> SEQ ID NO 185
<211> LENGTH: 19
<212> TYPE: DNA
<213> ORGANISM: Artificial Sequence
<220> FEATURE:
<223> OTHER INFORMATION: primer complementary to T7 promotor

<400> SEQUENCE: 185

taatacgact cactatagg                                              19


<210> SEQ ID NO 186
<211> LENGTH: 19
<212> TYPE: DNA
<213> ORGANISM: Artificial Sequence
<220> FEATURE:
<223> OTHER INFORMATION: primer complementary to T7 terminator

<400> SEQUENCE: 186

gctagttatt gctcagcgg                                              19
```

ANTICANCER FUSION PROTEIN COMPRISING TRAIL

RELATED APPLICATIONS

This application is a §371 national stage of PCT International Application No. PCT/EP2011/060666, filed Jun. 24, 2011, claiming priority of Polish Patent Application PL391627, filed Jun. 25, 2010, the contents of each of which are hereby incorporated by reference into this application.

REFERENCE TO A SEQUENCE LISTING

This application incorporates-by-reference nucleotide and/or amino acid sequences which are present in the file named "130307_1947_84732_Sequence_Listing_SC.txt," which is 245 kilobytes in size, and which was created Mar. 7, 2013 in the IBM-PC machine format, having an operating system compatibility with MS-Windows, which is contained in the text file filed Mar. 7, 2013 as part of this application.

The invention relates to the field of therapeutic fusion proteins, in particular recombinant fusion proteins. More particularly, the invention relates to fusion proteins containing the fragment of a sequence of soluble human TRAIL protein in combination with the sequence of a short proapoptotic peptide, pharmaceutical compositions containing them, their use in therapy, particularly as anticancer agents, and to polynucleotide sequences encoding the fusion proteins, expression vectors containing the polynucleotide sequences, and host cells containing these expression vectors.

Apoptosis (programmed cell death) is a process that plays important role in preventing cancer and in the treatment of cancer by using agents that induce apoptosis of abnormal cancer cells.

Signaling for apoptosis may initiated from outside a cell (extrinsic or death receptor pathway) or from inside a cell (intrinsic or mitochondrial pathway).

Activation of extrinsic apoptosis pathways in human cancer cells requires binding of a ligand by cell death receptors to activate receptors. Upon binding of a ligand, activated receptors induce apoptosis signals.

Initiation of intrinsic apoptosis inside a cell by mitochondrial pathway may be initiated on different levels of apoptotic cascade to finally cause induction or restoration of functions of proapoptogenic proteins (cytochrome c, SmacDiablo, AIF, p53, Bcl2 proteins family including BH3 domain family), nucleic acids degradation or activation of caspases.

TRAIL protein belonging to the cytokines family (Tumour Necrosis Factor-Related Apoptosis Inducing Ligand), also known as Apo2L (Apo2-ligand), is a potent activator of apoptosis in tumour cells and in cells infected by viruses. TRAIL is a ligand naturally occurring in the body. TRAIL protein, its amino acid sequence, coding DNA sequences and protein expression systems were disclosed for the first time in EP0835305A1.

TRAIL protein exerts its anticancer activity binding to pro-apoptotic TRAIL surface receptors 1 and 2 (TRAIL-R1/R2) and subsequent activation of these receptors. These receptors, also known as DR4 and DR5 (death receptor 4 and death receptor 5), belong to the TNF receptor family and are overexpressed by different types of cancer cells. Activation of the receptors can induce external signaling pathway of apoptosis independent from suppressor gene p53, which by activated caspase-8 leads to the activation of executive caspases and thereby degradation of nucleic acids. Caspase-8 released upon TRAIL activation may also cause the release of Bid protein and thereby indirect activation of mitochondrial pathway, Bid protein being translocated to mitochondria, where it stimulates the release of cytochrome c, thus indirectly amplifying the apoptotic signal from death receptors.

TRAIL acts selectively on tumour cells essentially without inducing apoptosis in healthy cells, which are resistant to this protein. Therefore, the enormous potential of TRAIL was recognized as an anticancer agent acting on a wide range of different types of tumour cells, including hematologic malignancies and solid tumours, and at the same time not influencing normal cells and exerting potentially relatively small side effects.

TRAIL protein is a type II membrane protein having the length of 281 amino acids, and its extracellular region comprising amino acid residues 114-281 upon cleavage by proteases forms soluble sTRAIL molecule of 20 kDa size, which is also biologically active. Both forms of TRAIL and sTRAIL are capable of triggering apoptosis via interaction with TRAIL receptors present on target cells. Strong antitumour activity and very low systemic toxicity of soluble part of TRAIL molecule was demonstrated using cell lines tests. Also, human clinical studies on recombinant human soluble TRAIL (rhTRAIL) having aminoacid sequence corresponding to amino acids 114-281 of hTRAIL, known under the INN dulanermin, showed its good tolerance and absence of dose-limiting toxicity.

Recent studies show that TRAIL protein can have a form shorter than aminoacids 114-281, and that also in such form is able to bind with membrane receptors of DR family (death receptors, DR1, DR2, DcR1, DcR2 and OPG) and induce apoptotic via these receptors (F., FANG, A., WANG, S., F., YANG, Antitumor activity of a novel recombinant mutant human tumor necrosis factor-related apoptosis-inducing ligand, *Acta Pharmacologica Sinica* 2005 November; 26 (11): 1373-1381).

Presently reported toxic effects of recombinant TRAIL protein on liver cells appear to be associated with the presence of modification, i.e. polyhistidine tags, untagged TRAIL showing no systemic toxicity.

However, in the course of further research and development, it appeared that many cancer cells also show primary or acquired resistance to TRAIL (see for example WO2007/022214). Although the mechanism of resistance to TRAIL is not fully understood, it is believed that it may manifest itself at different levels of by TRAIL-induced apoptosis pathway, ranging from the level of receptors on the cell surface to the executive caspases within the signalling pathway. This resistance limits the usefulness of TRAIL as an anticancer agent.

Furthermore, in clinical trials on patients the actual effectiveness of TRAIL as a monotherapy proved to be low. To overcome this low efficiency and the resistance of tumours to TRAIL, various combination therapies were designed with radio- and chemotherapeutic agents, which resulted in synergistic apoptotic effect. (WO2009/002947; A. Almasan and A. Ashkenazi, Cytokine Growth Factor Reviews 14 (2003) 337-348; R K Srivastava, Neoplasis, Vol 3, No 6, 2001, 535-546, Soria J C et al., J. Clin. Oncology, Vol 28, No 9 (2010), p. 1527-1533). The use of rhTRAIL for cancer treatment in combination with selected conventional chemotherapeutic agents (paclitaxel, carboplatin) and monoclonal anti-VEGF antibodies are described in WO2009/140469. However, such a combination necessarily implies well-known deficiencies of conventional chemotherapy or radiotherapy.

Constructed fusion protein containing sequences of an angiogenesis inhibitor vasostatin and TRAIL linked with a metalloprotease cleavage site linker was described as exhibiting apoptosis-inducing effect in tumor cells by A. I. Guo et al in Chinese Journal of Biochemistry and Molecular Biology 2008, vol. 24(10), 925-930.

Constructed fusion protein containing sequences Tumstatin183-230 of an angiogenesis inhibitor tumstatin and TRAIL114-281 was described as exhibiting induction of apoptosis of pancreatic cancer cells by N. Ren et al in Academic Journal of Second Military Medical University 2008, vol. 28(5), 676-478.

US2005/244370 and corresponding WO2004/035794 disclose the construct of TRAIL95-281 as an effector domain linked by a peptide linker with extracellular part of another member of TNF family ligands CD40 as a cell surface binding domain. It is stated that activation of the construct is via binding of its CD40 part.

Moreover, the problem connected with TRAIL therapy has proved to be its low stability and rapid elimination from the body after administration.

Although many clinical cancer therapies are currently available, they are often insufficiently effective and have many well-known disadvantages, of which one of the most distressing and restricting the treatment are the lack of selectivity towards cancer cells, severe side effects and resistance—primary or acquired during treatment. Currently, a limited number of anticancer agents that are both effective and selective to cancer cells is known. Therefore, there remains an urgent and unmet need for new anticancer agents that would allow both to broaden the range of available agents and to find agents that are more effective (cytotoxic) and selective. There is also a need for new selective agents with increased stability and improved pharmacokinetics.

The present invention proposes a solution of this problem by providing new fusion proteins that contain a domain derived from TRAIL and a short effector peptide domain not including TRAIL fragments having intrinsic (intracellular) or extrinsic (extracellular) proapoptotic activity, that potentiates or complements the action of TRAIL. Moreover, it turned out that in many cases the fusion proteins of the invention show more potent activity than soluble TRAIL and its variants, including a fragment of the sequence, and in many cases also overcome the resistance to TRAIL. Moreover, the addition of an effector peptide results in prolonged half-life and increased retention of protein in the tumour and finally increases its efficiency.

DESCRIPTION OF FIGURES

The invention will now be described in detail with reference to the Figures of the drawing.

DETAILED DESCRIPTION OF THE INVENTION

Figure 1:
FIG. 1 presents a schematic structure of fusion proteins of the invention according to Ex. 1, Ex. 2, Ex. 3, Ex. 4 and Ex. 5.
Figure 1:
Figure 1:
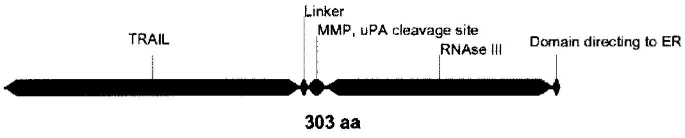
Figure 1:
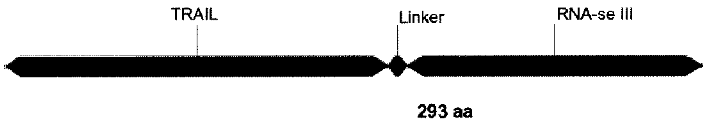
Figure 1:
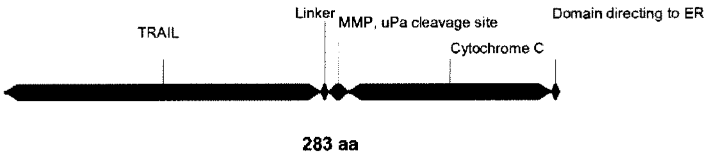

The invention relates to a fusion protein comprising:

domain (a) which is the functional fragment of a sequence of soluble hTRAIL protein, which fragment begins with an aminoacid at a position not lower than hTRAIL95, and domain (b) which is the sequence of a pro-apoptotic effector peptide, which effects its pro-apoptotic action via intrinsic apoptosis pathway, wherein the sequence of the domain (b) is attached at the C-terminus and/or N-terminus of domain (a).

The term "the functional soluble fragment of a sequence of soluble hTRAIL" should be understood as denoting any such fragment of soluble hTRAIL that is capable of inducing apoptotic signal.

The term "a peptide" in accordance with the invention should be understood as a molecule built from plurality of aminoacids linked together through a peptide bond. Thus, the term "peptide" according to the invention includes oligopeptides, polypeptides and proteins.

It should be understood that domain (b) of the effector peptide in the fusion protein of the invention is neither hTRAIL protein nor a part of hTRAIL protein.

In the present invention the aminoacid sequences of peptides will be presented in a conventional manner adopted in the art in the direction from N-terminus (N-end) of the peptide towards its C-terminus (C-end). Any sequence will thus have its N-terminus on the left side and C-terminus on the right side.

The fusion protein of the invention may comprise a single domain (b) of the effector peptide, attached at the C-terminus or N-terminus of domain (a).

The fusion protein of the invention may also contain two domains (b) of the effector peptide, in which case one of the domains (b) is attached at the C-terminus of domain (a) and the other is attached at the N-terminus of domain (a).

When the fusion protein of the invention comprises two domains (b) of the effector peptide, these domains may be the same or different. Preferably, in this case, the domains (b) are different.

In a particular embodiment, the domain (a) is a fragment of hTRAIL sequence, beginning with an aminoacid from the range of hTRAIL114 to hTRAIL121, inclusive, and ending on the aminoacid hTRAIL 281, or other functional fragments of hTRAIL sequence published in GenBank under Accession No P50591.

In particular, domain (a) may be selected from the group consisting of sequences corresponding to hTRAIL114-281 (SEQ. No. 27), hTRAIL119-281 (SEQ. No. 28), and hTRAIL121-281 (SEQ. No. 29), hTRAIL116-281 and hTRAIL120-281.

In another embodiment, domain (a) may be the sequence hTRAIL95-281.

The pro-apoptotic effector peptide of domain (b), which exerts its apoptotic activity via intrinsic apoptosis pathway (intracellularly), may induce apoptosis directly by activating signalling cascade components of mitochondrial pathway of apoptosis, or by direct induction of mitochondrial apoptosis in cells.

In one embodiment of the fusion protein of the invention, the effector peptide is a peptide acting via intrinsic apoptosis pathway selected from the group consisting of SEQ. No. 30, No. 31, SEQ. No. 32, SEQ. No. 33, SEQ. No. 34, SEQ. No. 35, SEQ. No. 36, SEQ. No. 37, SEQ, No. 38, SEQ. No. 39, No. 40, SEQ. No. 41, SEQ. No. 42, SEQ. No. 43, SEQ. No. 44, SEQ. No. 45, SEQ. No. 46, and SEQ. No 47, or SEQ. No. 151, SEQ. No. 152, SEQ. No. 153, SEQ. No. 154, SEQ. No. 155, SEQ. No. 156, SEQ. No. 157, SEQ. No. 158 SEQ. No. 159, SEQ. No. 160, No. 161, SEQ. No. 162, SEQ. No. 163, SEQ. No. 164, SEQ. No. 165 and SEQ. No. 166.

The effector peptide of SEQ. No. 30 of the above group is the peptide derived from the BH3 domain of Bax protein which inhibits anti-apoptototic factors, and specifically the 16-amino acid peptide presented by:

SEQ. No. 30
KKLSECLKRI GDELDS

It is believed that peptides based on sequences of BH3 domains of Bax protein are able to effectively bind to the anti-apoptotic proteins Bcl-2 and Bcl-XL. The anti-apoptotic activity of Bcl-2 and Bcl-XL protein is based on their interaction with BH3 domains present in factors responsible for the initiation of apoptosis (Bax, Bak, Bad). Binding of BH3 domain results in prevention of interaction of proteins Bcl-2 and Bcl-XL with their natural ligands and inhibition of their activity, and thereby contributes to initiation of the promotion of apoptosis.

The effector peptide of SEQ. No. 31 of the above group is the 15-amino acids peptide comprising the BH3 domain of Bid protein, presented by:

(SEQ. No. 31)
RNIARHLAQV GDSMD.

Bid protein belongs to a Bcl-2 family and is responsible inter alia for activation of pro-apoptotic factor Bax. It is believed that the 16-amino acid peptide comprising the BH3 domain of Bid protein incorporated into the fusion protein of the invention will effectively induce apoptosis.

The effector peptide of SEQ. No. 32 of the above group is a peptide homologue of ribonuclease A (RNase A), presented by:

(SEQ. No. 32)
KETA AKFERQHMDS STSAASSSNY CNQMMKSRNL TKDRCKPVNT FVHESLADVQ

AVCSQKNVAC KNGQTNCYQS YSTMSITDCR ETGSSKYPNC AYKTTQANKH

IIVACEGNPY VPVHFDASV.

-

Ribonucleases are small proteins with potential antineoplastic properties, which upon binding to negatively charged cell membranes enter the cell via endocytosis, and then leak into cytosol, where they act as an enzyme to cause degradation of RNA. Starting from a concentration of 10 nM they arrest cell cycle and cause apoptosis.

The effector peptide of SEQ. No. 33, of the above described group is the cytochrome C molecule presented by:

(SEQ. No. 33)
GDVEK GKKIFIMKCS QCHTVEKGGK HKTGPNLHGL FGRKTGQAPG YSYTAANKNK

GIIWGEDTLM EYLENPKKYI PGTKMIFVGI KKKEERADLI AYLKKATNE.

The release of cytochrome C from mitochondria to cytoplasm is one of the main signals inducing apoptosis via so called mitochondrial path. The protein is part of apoptosome complex, which activates caspase 9.

The effector peptide of SEQ. No. 34, of the above described group is granzyme B, presented by:

```
                                                                      (SEQ. No. 34)
IIGGHVAKPH SRPYMAYLMI WDQKSLKRCG GFLIRDDFVL TAAHCWGSSINVTLGAHNIK

EQEPTQQFIP VKRAIPHPAY NPKNFSNDIM LLQLERKAKR

TRAVQPLRLP SNKAQVKPGQ TCSVAGWGQT APLGKHSHTL QEVKMTVQED

RKCESDLRHY YDSTIELCVG DPEIKKTSFK GDSGGPLVCN KVAQGIVSYG

RNNGMPPRAC TKVSSFVHWI KKTMKRY.
```

Granzymes, also called fragmentins in the literature, are serine proteases typical for cellular granularity of Tc lymphocytes and NK cells. In human, currently 5 different granzymes are identified: A, B, H, K (tryptase) and M (metioninase). Studies have confirmed that these enzymes are the elements of the cytotoxic reaction exerted by lymphocytes against target cells. These enzymes have been shown to activate the perforin—a protein generating pores in cell membranes and thereby mediate the cytotoxic response. Furthermore, it is believed that these enzymes are directly involved in induction of apoptosis in target cells. Granzyme B activates selected procaspases into their active forms (e.g. caspase)), and also releases via proteolysis the active form of Bid protein (a protein belonging to the Bcl-2 protein family), which initiates intracellular pathway of apoptosis by incorporation into the mitochondrial membranes and generation of pores in membranes, followed by release of apoptosis-inducing factors (cytochrome C, caspase 9, Apaf). By binding to histones Granzyme B may also participate in the relaxation of chromatin structure, which causes its relaxation and increases the access to DNA for endonucleases.

The effector peptide of SEQ. No. 35 of the above group is the fragment of Nur77 protein presented by:

```
                              (SEQ. No. 35)
FSRSLHSLL.
```

Nuclear receptor Nur77 is a very potent inducer of apoptosis. One of the mechanisms of its action is the ability to bind to Bcl-2 protein, an important anti-apoptotic factor. This interaction causes conformational changes in the structure of Bcl-2, which convert it into an inducer of apoptosis. The fragment presented above is a 9-amino acid region from the sequence of Nur77 identified as responsible for binding and conversion of Bcl-2 and induction of apoptosis in cells. (Kolluri et al, Cancer Cell 14: 285-298, 2008).

The effector peptide of SEQ. No. 36 of the above group is an 15-amino acid peptide comprising the BH3 domain of Bak protein, presented by

```
                              (SEQ. No. 36)
GQVGRQLAII GDDIN.
```

It is believed that this short peptide incorporated into the fusion protein of the invention will effectively induce apoptotic signal.

The effector peptide of SEQ. No. 37 of the above group is the BH3 domain of the protein PUMA/BBC3, presented by

```
                              SEQ. No. 37
EEQWAREIGA QLRRMADDLN AQYE.
```

PUMA/BBC3 (p53 upregulated modulator of apoptosis/Bcl-2-binding component 3) is a member of a Bcl-2 proteins family (BH3-only subfamily). It mediates apoptosis in the manner but dependent and independent on p53. Direct interactions of PUMMA/BBC3 with all known pro-survival Bcl-2 proteins cause their inactivation, mitochondrial dysfunction, and thus activation of caspases and cell death. PUMA also affects indirectly the restoration of proapoptotic activity of molecules such as Bak and Bax. The BH3 domain is responsible for binding of PUMA with pro-survival proteins.

The effector peptide of SEQ. No. 38 of the above group is a protein PUMA/BBC3, presented by

```
                                                            (SEQ. No. 38)
ARAR QEGSSPEPVE GLARDGPRPF PLGRLVPSAV SCGLCEPGLA AAPAAPTLLP

AAYLCAPTAP PAVTAALGGS RWPGGPRSRP RGPRPDGPQP SLSLAEQHLE

SPVPSAPGAL AGGPTQAAPG VRGEEEQWAR EIGAQLRRMA DDLNAQYERR

RQEEQQRHRP SPWRVLYNLI MGLLPLPRGH RAPEMEPN.
```

It is believed that both the protein PUMA/BBC3 and its BH3 domain when incorporated into the fusion protein of the invention will effectively induce apoptotic signals.

The effector peptide of SEQ. No. 39 of the above group is 8-amino acid fragment of the protein SMAC/Diablo, presented by

```
                              (SEQ. No. 39)
AVPIAQKP.
```

SMAC/DIABLO (Second mitochondria-derived activator of Caspase/Direct IAP Binding Protein with Low PI) is an activator of caspases released from mitochondria. Its N-terminal motif competitively binds to IAP proteins, preventing their BIR 2 and BIR 3 domains from inactivation of caspases.

It is believed that this short peptide when incorporated into the fusion protein of the invention will effectively induce apoptotic signal.

The effector peptide of SEQ. No. 40 of the above group is buforin IIb peptide presented by

```
(SEQ. No. 40)
RAGLQFPVGR LLRRLLRRLL.
```

Buforin IIb is a peptide derived from histone H2A, which is able to independent penetration of the cell membrane and has antibacterial properties (Park et al, Biochem Biophys. Res. Commun., 244: 253-257, 1998). Studies on its utility as an anticancer agent showed that it is able to bind selectively to numerous cancer cells, penetrate the cells and accumulate in the nucleus, inducing apoptosis via the mitochondrial pathway (Lee et al, Cancer Letters, 271:47-55, 2008).

The effector peptide of SEQ. No. 41 of the above group is onconase peptide presented by

```
(SEQ. No. 41)
QDWLT FQKKHITNTR DVDCDNIMST NLFHCKDKNT FIYSRPEPVK AICKGIIASK

NVLTTSEFYL SDCNVTSRPC KYKLKKSTNK FCVTCENQAP VHFVGVGSC.
```

Onconase or P-30 is the protein originally derived from lysates of frog *Rana pipiens* oocytes. It is a single-stranded protein with the mass of 12 kDa, structural homolog of RNase A. The research on this protein showed that it has a remarkable cytotoxic activity against tumour cells (Y Wu, S M Mikulski, W Ardelt, S M Rybak and R J Youle, The Journal of Biological Chemistry 268, 10686-10693). The research on the mechanism of action of onconase showed that upon the internalization process it enters into the cell, where carries out the degradation process of 28S and 18S ribosomal rRNA, which leads to inhibition of protein synthesis and cell death.

The effector peptide of SEQ. No. 42 of the above group is the 20-amino acid N-terminal fragment of p14ARF protein, which is the inhibitor of pro-survival Mdm2 protein, presented by

```
(SEQ. No. 42)
VRRFLVTLRI RRACGPPRV.
```

P14ARF is the protein that regulates the activity of Mdm2 protein, which binds to the tumour suppressor p53 and is responsible for its degradation and thereby possibility of survival of transformed cells. P14ARF protein by binding to Mdm2 prevents its interaction with p53. It is reported that a short peptide derived from p14ARF is sufficient to block the interaction between Mdm2 and p53 and prevent the degradation of the latter (Midgley et al, Oncogene 19: 2312-2323, 2000).

The effector peptide of SEQ. No. 43 of the above group is the 11-amino acid peptide binding to Mdm2 presented by

```
(SEQ. No. 43)
PRFMDTWEGL N.
```

The above peptide shows sequence homology to the sequence of p53 and significant efficiency of inhibition of Mdm2-p53 interactions (Böttger et al, Oncogene 13:2141-2147, 1996), thereby preventing the degradation of p53.

The effector peptide of SEQ. No. 44 of the above group is the 17-amino acid fragment of the lunasin peptide presented by

```
(SEQ. No. 44)
CEKHIMEKIQ GRGDDDD.
```

Lunasin is a 43-amino acid peptide derived from soybeans (*Glycine max*) with proven anti-carcinogenic potential. The general mechanism of action of this molecule consists in inhibition of histone acetylation. It is known that molecules that possess deacetylase activity act also as co-suppressors of transcription process (Leong et al, Cancer Lett, 18: 42-48, 2007).

The effector peptide of SEQ. No. 45 of the above group is the BH3 domain of Bik protein presented by

```
(SEQ. No. 45)
LALRLAC IGDEMDVS.
```

Bik protein interacts with cellular and viral factors initiating the survival signals (e.g. Bcl-2), thereby stimulating apoptosis. Like many other proapoptotic proteins, it contains a BH3 domain necessary for interaction with Bcl-2. A peptide derived from this protein comprising the BH3 domain may initiate apoptosis by activating other pro-apoptotic proteins or by inhibiting anti-apoptotic proteins (Del Gaizo Moore, V, et al, Blond, 111: 2300-2309, 2008).

The effector peptide of SEQ. No. 46 of the above group is the synthetic peptide—a proteasome inhibitor presented by

```
(SEQ. No. 46)
AGAGGGAGG AGAGGGAGGA G.
```

This peptide consists of a series of repetitions of Gly and Ala residues, and is proteasome inhibitor capable of potentation of TRAIL-induced apoptosis by induction of overexpression of the TRAIL receptor DR5.

The effector peptide of SEQ. No. 47 of the above group is the domain of the C-terminal fragment of proteasome S5a presented by

```
(SEQ. No. 47)
MTISQQEFG RTGLPDLSSM TEEEQIAYAM QMSLQGAEFG

QAESADIDAS SAMDTSEPAK EEDDYDVMQD PEFLQSVLEN

LPGVDPNNEA IRNAMGSLAS QATKDGKKDK KEEDK.
```

This domain from the proteasome S5a fragment contains UIMs motifs that directly participate in ubiquitin binding and thus have the ability to induce apoptosis.

The effector peptide of SEQ. No. 151 of the above group is the azurin derived peptide.

Azurin, a copper-containing redox protein, released by the pathogenic bacterium *Pseudomonas aeruginosa*, is highly cytotoxic to many cancer cell lines. It so enters into the cytosol and travels to the nucleus. It's activity strictly depends on the presence of active form of p53 in cancer cells. Azurin has been shown to bind p53 and post-translationally increase the p53 and Bax level. This apparent antagonistic action with respect to the Mdm2-p53 functional interaction suggests that binding of Azurin to p53 might interfere with the Mdm2-p53 association and thus prevent degradation of p53. Upon binding, it triggers the release of mitochondrial cytochrome C into cytosol. This process activates the caspase cascade (including caspase-9 and caspase-7), thereby initiating the apoptotic process (Punj V, et at Oncogene. 2004 Mar. 25; 23(13):2367-78, Funari G et al. J Mol Recognit. 2010 July August; 23(4): 343-51). Detailed analysis of activity of peptides derived from azurin sequence revealed the region of 28 amino acids responsible for efficient cell penetration and triggering apoptosis (Yamada i wsp., Cell Microbiol, 7:1418-1431, 2005).

The effector peptide of SEQ. No. 152 of the above group is the full length azurin peptide.

The effector peptide of SEQ. No. 153 of the above group is the peptide designed from aPP protein and BH3 domain of Bax protein.

Chimeras of aPP protein and redesigned pro-apoptotic Bak protein were reported in EP1309680 as highly potent and specific ligands for human Bcl-2 and Bcl-X. (See also Chin J W, Schepartz A. Design and evolution of a miniature Bcl-2 binding protein Angew Chem Int Ed Engl. 2001 Oct. 15; 40(20):3806-3809).

The effector peptide of SEQ. No. 154 of the above group is an another peptide designed from aPP protein and BH3 domain of Bax protein.

The effector peptide of SEQ. No. 155 of the above described group is the Reticulon RTN1-C derived peptide.

RTN1-C protein is a membrane protein localized in the ER and expressed in the nervous system, and its biological role is not completely clarified. The C-terminal region of RTN1-C, corresponding to the fragment from residues 186 to 208 is able to bind the nucleic acids and to interact with histone deacetylase (HDAC) enzymes decreasing their activity.

The effector peptide of SEQ. No. 156 of the above group is the full length human Reticulon 3 (isoform a). Reticulons (RTNs) form a group of integral membrane proteins that have no homology to other known apoptosis-related domains. Reticulon 3 isoform a is overexpressed in tumor cell lines, turning them to be sensitive to TRAIL-mediated apoptosis.

The effector peptide of SEQ. No. 157 of the above group is the modified constutively active caspase-3 (single chain) (Srinivasula S M, Ahmad M, MacFarlane M, Luo Z, Huang Z, Fernandes-Alnemri T, Alnemri E S. Generation of constitutively active recombinant caspases-3 and -6 by rearrangement of their subunits. J Biol Chem. 1998 Apr. 24; 273(17):10107-11).

The effector peptide of SEQ. No. 158 of the above group is the SAC domain from Par-4 protein (prostate apoptosis response protein par-4).

Par-4 is a tumor suppressor protein with a pro-apoptotic function. The cancer-specific pro-apoptotic action of Par-4 resides in its centrally located SAC domain. The function of the molecule is achieved by two distinct means: activation of molecular components of the cell-death machinery (translocation of Fas and FasL to the plasma membrane), and inhibition of pro-survival factor (NE-κB pathway). (Zhao Y, Rangnekar V M. Apoptosis and tumor resistance conferred by Par-4. Cancer Biol Ther. 2008 December; 7(12):1867-74. Epub 2008 Dec. 8. Review).

The effector peptide of SEQ. No. 159 of the above group is the Noxa protein. Noxa encodes a Bcl-2 homology 3 (BH3)—only member of the Bcl-2 family of proteins; this member contains the BH3 region but not other BH domains. Noxa is a mediator of p53-dependent apoptosis and undergoes BH3 motif-dependent localization to mitochondria and interacts with anti-apoptotic Bcl-2 family members, resulting in the activation of caspase-9.

The effector peptide of SEQ. No. 160, of the above described group is the 10 AA (KLLNLISKLF) fragment of Noxa protein required for mitochondrial location (MTD—mitochondrial targeting domain or CKP—Cell Killing Peptide). It was described in WO2006/001582 and in Young-Woo Seo et al. in The Journal of Biological Chemistry Vol. 278, No. 48, Issue of November 28, pp. 48292-48299, 2003.

The effector peptide of SEQ. No. 161 of the above group is the short hybrid peptide Antp-TPR described in WO2010055929. Antp-TPR is an engineered hybrid peptide targeting Hsp90, which has selective cytotoxic activity towards cancer cells due to inhibition of the interaction of Hsp90 with the TPR2A domain of Hop.

The effector peptide of SEQ. No. 162, of the above described group is the peptide inhibitor of the SH2 domain of Stat3 protein.

SH2 domain of Stat proteins is responsible for the series of events that lead to promoting cell growth and differentiation via normal STAT signalling in response to growth factors and cytokines.

The effector peptide of SEQ. No. 163 of the above group is the peptide GQVGRQLAIIGDDINR derived from BH3 domain of Bak protein (Bcl-2 family) (Castelli M, Reiners J J, Kessel D. A mechanism for the proapoptotic activity of ursodeoxycholic acid: effects on Bcl-2 conformation. Cell Death Differ. 2004 August; 11(8):906-14). The Bak protein is a pro-apoptotic member of the Bcl-2 family which is involved in apoptosis initiation.

The effector peptide of SEQ. No. 164 of the above group is the peptide KNLWAAQRYGRELRRMSDEFEGSFKGL derived from BH3 domain of Bad protein (Bcl-2 family) (Wang J L, Zhang Z J, Choksi S, Shan S, Lu Z, Croce C M, Alnemri E S, Korngold R, Huang Z. Cell permeable Bcl-2 binding peptides: a chemical approach to apoptosis induction in tumor cells. Cancer Res. 2000 Mar. 15; 60(6): 1498-502).

The effector peptide of SEQ. No. 165 of the above group is the peptide ATAP from Bft1 protein.

ATAP (amphipathic tail-anchoring peptide) (residues 147-175 from Bfl1, a bifunctional Bcl2 family protein), targets specifically to mitochondria and induces caspase-dependent apoptosis that does not require Bax or Bak.

The effector peptide of SEQ. No. 166 of the above group is another ATAP peptide from Bfl1 protein. The ATAP protein is fused to MTS domain from HCCS1 (Ko J K, Choi K H, Pan Z, Lin P, Weisleder N, Kim C W, Ma J. The tail-anchoring domain of Bfl1 and HCCS1 targets mitochondrial membrane permeability to induce apoptosis. J Cell Sci. 2007 Aug. 15; 120(Pt 16):2912-23. Epub 2007 Jul. 31).

As described herein above, the first variant of the pro-apoptotic effector peptide of domain (b) may be a peptide exerting its apoptotic activity via intrinsic apoptosis pathway (intracellularly), that induces apoptosis directly by activating signalling cascade components of mitochondrial pathway of apoptosis, or by direct induction of mitochondrial apoptosis in cells.

In one embodiment of the first variant, one group of pro-apoptotic effector peptides of domain (b) exerting its activity via intrinsic pathway may be peptides that inhibit and/or modulate intracellular anti-apoptotic or pro-survival factors, such as anti-apoptotic proteins Bcl-2 and Bcl-XL, upon binding thereof.

Exemplary effector peptides of the above group are peptides represented by SEQ. No. 30, present in the fusion proteins of Examples 1, SEQ. No. 37 present in the fusion proteins of Examples 11 and 47, SEQ. No. 45 incorporated in the fusion protein of Example 21, SEQ. No. 158 present in the fusion proteins of Examples 42 and 43, and SEQ. No. 159 incorporated in the fusion protein of Example 44.

In another embodiment of this first variant, a group of pro-apoptotic effector peptides of domain (b) exerting its activity via intrinsic pathway may be peptides exerting direct destructive effect inside the cell to arrest the cell cycle.

Said direct destructive effect inside the cell in a mitochondrial intrinsic pathway may be initiated by the effector peptide on different levels of the caspase cascade leading to cell death.

Examples of said direct destructive effect of the effector peptide in a mitochondrial intrinsic pathway are degradation of nucleic acids, particularly whole cellular RNA or DNA and induction of degradative nucleases. Such an effect may be exerted for example by ribonucleases, such as ribonucleases of superfamily of pancreatic RNAse A, including human pancreatic RNAse, human angiogenin (ribonuclease 5, hAng), human eosinophil-derived neurotoxin (EDN) and bovine ribonuclease, as well as their homologs and variants. Examples of RNAse homologs are onconase, ribonucleases isolated from Rana catesbiana and Rana japonica.

Exemplary effector peptides of the above group acting by degradation of nucleic acids are peptides represented by SEQ. No. 32, present in the fusion proteins of Examples 3, 4 and 27, SEQ. No. 41, present in the fusion proteins of Examples 16, 17 and 46, and SEQ. No. 157, present in the fusion protein of Example 41.

Another example of said direct destructive effect of the effector peptide in a mitochondrial intrinsic pathway is caspase activation. Such an effect may be exerted for example by cytochrome c (SEQ. No. 33), present in the fusion proteins of Examples 5 and 6, granzyme B (SEQ. No. 34), present in the fusion proteins of Examples 7 and 8, or peptide derived form protein Smac/DIABLO (SEQ. No. 39), present in the fusion proteins of Examples 14, 21, 33, 34 and 35.

Another example of said direct destructive effect of the effector peptide in a mitochondrial intrinsic pathway is proteasome inhibition, due to influence of the stabilisation of proapoptotic proteins on restoration of p53 functions.

Exemplary effector peptides of the above group acting by proteasome inhibition are peptides represented by SEQ. No. 46 incorporated in the fusion protein of Example 22, and SEQ. No. 47 incorporated in the fusion protein of Example 23.

Another example of said direct destructive effect of the effector peptide in a mitochondrial intrinsic pathway is modulation of histone proteins due enhancement of the influence of expression of proapoptotic proteins on restoration of p53 functions.

Exemplary effector peptides of the above group acting by modulation of histone proteins are buforin IIb represented by SEQ. No. 40 incorporated in the fusion protein of Example 15 and lunasin represented by SEQ. No. 44 incorporated in the fusion protein of Example 20.

Another example of said direct destructive effect of the effector peptide in a mitochondrial intrinsic pathway is restoration of p-53 functions, such as by inhibition of its degradation. Prevention of p-53 degradation may be achieved by inhibition of the negative regulator of p-53, such as murine double minute 2 (MDM2) to disrupt its negative regulation. This may be achieved by MDM2 binding peptides, which compete with MDM2 for binding to p-53, such as Azurin, a copper-containing redox protein, a cycle cell regulator p14ARF, or SuperTIP (ThioredoxinInsert Protein, mdm-2-binding peptide within the active site loop of the bacterial thioredoxin protein), or their fragments.

Exemplary effector peptides of the above group acting by restoration of p-53 functions are peptides represented by SEQ. No. 42 incorporated in the fusion protein of Example 18, SEQ. No. 43 incorporated in the fusion protein of Example 19, SEQ. No. 151 present in the fusion proteins of Examples 29, 30 and 31, and SEQ. No. 152 incorporated in the fusion protein of Example 32.

Another example of said direct destructive effect of the effector peptide in a mitochondrial intrinsic pathway is influencing, i.e. activation, inhibition or modulation of Bcl-2 proteins family, such as proteins Bax, Bak, Bok, Bid, Bim, Bad, Bmf, Hrk, Noxa, Puma, Bik, BNIP3 and Spike, more particularly BH3 only—proteins family, including Bid, Bim, Bad, Bmf, Hrk, Noxa, Puma, Bik, BNIP3 and Spike. In particular, fragments of BH3 domains of Bcl-2 family members will be advantageous effector peptides. Other group of effector peptides are fragments of the family of nuclear receptors RXR (Retinoid X Receptor), such as for example nuclear receptor Nur77.

Exemplary effector peptides of the above group acting by influencing Bcl-2 proteins family are peptides represented by SEQ. No. 30 incorporated in the fusion protein of Example 1, SEQ. No. 31 present in the fusion proteins of Examples 2, 4 and 8, SEQ. No. 32 incorporated in the fusion protein of Example 3, SEQ. No. 35 incorporated in the fusion protein of Example 9, SEQ. No. 36 incorporated in the fusion protein of Example 10, SEQ. No. 37 present in the fusion proteins of Examples 11 and 47, SEQ. No. 38 present in the fusion proteins of Examples 12 and 13, SEQ. No. 159 incorporated in the fusion protein of Example 44, SEQ. No. 160 incorporated in the fusion protein of Example 45, SEQ. No. 163 incorporated in the fusion protein of Example 51, SEQ. No. 164 present in the fusion proteins of Examples 52 and 53, SEQ. No. 165 incorporated in the fusion protein of Example 54, and SEQ. No. 166 incorporated in the fusion protein of Example 55.

Another example of said direct destructive effect of the effector peptide in a mitochondrial intrinsic pathway is converging apoptotic signal induced by TRAIL binding to TRAIL receptors, particularly by caspase activation.

Another example of said direct destructive effect of the effector peptide in a mitochondrial intrinsic pathway is promoting apoptosome formation.

Exemplary effector peptides of the above group acting by promoting apoptosome formation are peptides represented by SEQ. No. 30 incorporated in the fusion protein of Example 1, SEQ. No. 31 incorporated in the fusion protein of Example 2, SEQ. No. 33 present in the fusion proteins of Examples 5 and 6, SEQ. No. 35 incorporated in the fusion protein of Example 9, SEQ. No. 36 incorporated in the fusion protein of Example 10, SEQ. No. 37 incorporated in the fusion protein of Example 47, SEQ. No. 39 present in the fusion proteins of Examples 33, 34 and 35, SEQ. No. 40 incorporated in the fusion protein of Example 14, SEQ. No. 45 incorporated in the fusion protein of Example 21, SEQ. No. 153 present in the fusion proteins of Examples 36 and 37, SEQ. No. 154 incorporated in the fusion protein of Example 38, SEQ. No. 157 incorporated in the fusion protein of Example 41, SEQ. No. 158 present in the fusion proteins of Examples 42 and 43, SEQ. No. 159 incorporated in the fusion protein of Example 44, SEQ. No. 160 incorporated in the fusion protein of Example 45, SEQ. No. 163 incorporated in the fusion protein of Example 51, and SEQ. No. 164 present in the fusion proteins of Examples 52 and 53.

Another example of said direct destructive effect of the effector peptide in a mitochondrial intrinsic pathway is promoting mitochondrial outer membrane (MOMP) permeabilization, due to which proteins released by mitochondrium can act on caspase activation level.

Exemplary effector peptides of the above group acting by promoting MOMP permeabilization are peptides represented by SEQ. No. 30 incorporated in the fusion protein of Example 1, SEQ. No. 31 present in the fusion proteins of Examples 2 and 48, SEQ. No. 33 present in the fusion proteins of Examples 5 and 6, SEQ. No. 39 present in the fusion proteins of Examples 14, 33, 34 and 35, SEQ. No. 40 incorporated in the fusion protein of Example 15, SEQ. No. 41 incorporated in the fusion protein of Example 46, and SEQ. No. 45 incorporated in the fusion protein of Example 21.

As described herein above, the second variant of the pro-apoptotic effector peptide of domain (b) of the invention is the group of pro-apoptotic effector peptides acting via extrinsic pathway (extracellularly), which for their effect require binding to receptors present on the surface of the cancer cell.

The following TNF-ligands (TNF—tumour necrosis factor) or TNF-analogs as extracellularly acting peptides were used as the comparative effector peptides:

```
                                    (SEQ. No. 48)
VANPQAEGQL decapeptide;

                                    (SEQ. No. 49)
LANGVE hexapeptide,
or

                                    (SEQ. No. 50)
Septapeptide CPSEGLC.
```

Decapeptide represented by SEQ. No. 48 has been described as analog/agonist of TNF in JP 60,226,816.

Hexapeptide represented by SEQ. No. 49 derives from TNF and has been described in DE 3,841,768.

Septapeptide represented by SEQ. No. 50 is the five-amino acid peptide, which is a part of the TNF cytokine derived from the surface of the interaction of this cytokine with its cellular receptors: TNFR55 and TNFR75, which is flanked at the C-terminus and the N-terminus by two cysteine residues. Cysteine residues stabilize peptide cyclization via formation of a sulphide bridge between the amino acids. The aim of cyclization is so stabilization of the peptide and improvement of its activity.

Upon binding to TRAIL receptors present on the surface of cancer cells, the fusion protein will exert a double effect. Domain (a), that is a functional fragment of TRAIL, will exert its known agonistic activity—i.e. binding to death receptors on the cell surface and activation of the extrinsic pathway of apoptosis. After internalization via endocytosis of the fusion protein comprising pro-apoptotic peptide acting intracellularly, the domain (b) will be able to potentially exert its action intracellularly parallel to the activity of TRAIL domain. In this way, anti-cancer activity of TRAIL can be potentiated by activation of other elements and mechanisms of apoptosis.

The comparative fusion protein incorporating pro-apoptotic peptide acting extracellularly should potentially additionally initiate apoptosis pathway by binding to and activating pro-apoptotic receptors other than TRAIL receptors.

In one of the embodiments of the invention, domains (a) and (b) of the fusion protein can be linked directly with each other.

In another embodiment, domain (a) and domain (b) are linked by a domain (c) comprising the sequence of a cleavage site recognized by proteases present in the cell environment, especially in the tumour cell environment.

A protease cleavage site can be selected from:

- a sequence recognized by the metalloprotease MMP, in particular sequences PLGLAG (SEQ. No. 51), PLGIAGE (SEQ. No. 171) or PLGLAGQ (SEQ. No. 173),
- a sequence recognized by urokinase uPA, in particular RVVR sequence (SEQ. No. 52), and
- a sequence recognized by furin, in particular sequence RKKR (SEQ. No. 53), or sequence RKKRVKR (SEQ. No. 172), and their combinations.

In particular, the protease cleavage site is a combination of the sequence recognized by the metalloprotease MMP and a sequence recognized by urokinase uPA, located next to each other in any order.

In one embodiment, the domain (c) is a combination of MMP/uPA SEQ. No 51/Sekw. No. 52, that is the sequence PLGLAGRVVR, or a combination of uPA/MMP SEQ. No 52/SEQ. No. 51, that is the sequence RVVRPLGLAG.

Proteases metalloprotease MMP, urokinase and/or furin are overexpressed in the tumour environment. The presence of the sequence recognized by the protease enables the cleavage of the domain (a) from the domain (b) upon internalization of the construct, i.e. the release of the functional domain (b) and thus its activation.

The presence of the protease cleavage site, by allowing quick release of the effector peptide, increases the chances of transporting the peptide to the place of its action, before random degradation of the fusion protein by proteases present in the cell occurs.

Additionally, to the domain (b) of the effector peptide of the fusion protein of the invention may be attached a transporting domain (d), selected from the to group consisting of:

(d1) a sequence directing to the endoplasmic reticulum,
(d2) a polyarginine sequence transporting through the cell membrane, comprised of 6, 7, 8 or 9 Arg residues,
(d3) a translocation domain of *Pseudomonas aeruginosa* (SEQ. No. 54),
(d4) a membrane transporting domain,
(d5) a nuclear localization domain, and
(d6) a mitochondrial targeting domain,
and combinations thereof.

The combination of domains (d1) (d2) and (d3) may comprise, in particular the combination of (d1)/(d2), (d1)/(d3) or (d1)/(d2)/(d3).

The combination of domains (d1), (d2), (d3), (d4), and (d5) may comprise, in particular also the combination of (d1)/(d2), (d1)/(d3), (d1)/(d4), (d1)/(d5) and (d1)/(d2)/(d3), (d3)/(d5), (d2)/(d5), (d1)/(d3)/(d5), (d2)/(d3)/(d6).

Furthermore, the combination of domains (d1), (d2), (d3), (d4), and (d5) may include domains located next to each other and connected to one end of the domain (b) and/or domains linked to different ends of the domain (b).

It should be understood that in the case when the fusion protein has both the transporting domain (d) attached to the domain (b) and the domain (c) of the cleavage site between the domains (a) and (b), then the domain (c) is located in such a manner that after cleavage of the construct the transporting domain (d) remains attached to the domain (b). In other words, if the fusion protein contains both the transporting domain (d) and the cleavage site domain (c), then the domain (d) is located between the domain (b) and the domain (c), or is located at the end of the domain (b) opposite to the place of attachment of domain (d). The invention does not comprise such a variant in which the domain (d) is located between the domain (c) a domain (a), that is the case when after cleavage of the construct the transporting domain remains attached to the TRAIL domain.

The transporting sequence may be attached at the N-terminus or at the C-terminus of the domain (b). In some embodiments, the transporting sequence may be also terminal part of the whole construct, such as C-terminal part or N-terminal part, depending on the manner of attachment of domains (a) and (b).

Translocation domain of *Pseudomonas aeruginosa* is capable of translocation through the lysosomal membrane into the cytoplasm and can be used to introduce the effector peptide to the tumour cell compartments. The translocation domain sequence of *Pseudomonas aeruginosa* is well known and is represented by:

```
                                         (SEQ. No. 54)
PEGGSLA ALTAHQACHL PLETFTRHRQ PRGWEQLEQC

GYPVQRLVAL YLAARLSWNQ VDQVIANALA SPGSGGDLGE

AIRESPEQAR LALTLAAAES ERFVRQGTGN DEAGAANGPA D
```

The sequence (d1) directing to endoplasmic reticulum may be any signal sequence directing to endoplasmic reticulum known in the art, such as for example, but not limited to, KDEL, HDEL, RDEL, DDEL, ADEL, SDEL, KEDL. Sequence (d1) is preferably selected from the sequences KDEL (SEQ. No. 55) and KEDL (SEQ. No. 56).

Preferably, the directing sequence (d1) is located at the C-terminus of the fusion protein of the invention and forms C-terminal part thereof.

The membrane transporting domain (d4) may be any signal sequence transporting through the plasma membrane known in the art, such as for example and not limited to, KPRRPY or K PRRPYR.

The nuclear localization sequence (d5) may be any signal sequence directing into nucleus known in the art, such as for example and not limited to, EEEAAGRKRKKRT (SEQ. No. 168), FFFAAGRKRKKRT, NNNAAGRKRKKRT, YYYAAGRKRKKRT, AAKKK, or GR KRKKRT.

The mitochondrial targeting domain (d6) may be any signal sequence directing to mitochondrium known in the art, such as for example and not limited to RVSFCRPGWSA-MARSRLTATSVSQVQENGFVK (SEQ. No. 166), fragment MLATRVFSLVGKRAISTSVCVR of human cytochrome oxidase subunit IV (hCOXIV1), or the ornithine transcarbamylase leader peptide.

Apart from the main functional elements of the fusion protein, transporting domains and the cleavage site domains, the fusion proteins of the invention so may contain domain (e), i.e. a polycysteine motif facilitating trimer stabilisation, as, for example, and not limited to, CAACAAAC sequence (SEQ. No. 177) or CAAECAAAC (SEQ. No. 178).

Furthermore, the polycysteine domain (e) may by connected to one end of the domain (b) and/or linked to different ends of the domain (b).

It should be understood that in the case when the fusion protein has both the polycysteine domain (e) attached to the domain (b) and the domain (c) of the cleavage site between the domains (a) and (b), then the domain (c) is located in such a way that after cleavage of the construct the polycysteine domain (e) remains attached to the domain (a). In other words, if the fusion protein contains both polycysteine domain (e) and cleavage site domain (c), then domain (e) is located between domain (a) and domain (c), or is placed at the end of the domain (a) opposite to the place of attachment of domain (d). The invention does not comprise such a variant in which domain (e) would be located between domain (c) and domain (b), that is the case when after cleavage of the construct the polycysteine domain would remain attached to the effector peptide domain.

Apart from the main functional elements of the fusion protein, transporting domains and the cleavage site domain(s), the fusion proteins of the invention may contain a neutral sequence/sequences of a flexible steric linker (spacer) comprised of alanine, glycine, glutamine, cysteine, histidine and serine residues. Such linkers/spacers are well known and described in the literature. Their incorporation into the sequence of the fusion protein is intended to provide the correct folding of proteins produced by the process of its overexpression in the host cells.

In particular, the flexible steric linker may be selected from the group consisting of GGSG (SEQ. No. 57), GGGS (SEQ. No. 58), GGGGS (SEQ. No. 59), GGSGG (SEQ. No. 60), GGGSGG (SEQ. No. 61), GGGSGGG (SEQ. No. 62), GGGSGGGS (SEQ. No. 63), GGGSGGGGS (SEQ. No. 64), ASGG (SEQ. No. 65), GGGSASGG (SEQ. No. 66) SGCGS (SEQ. No. 169), GGGGSGGGG (SEQ. No. 180), GGSHG (SEQ. No. 182), SGGCGGS (SEQ. No. 183) and AACAA (SEQ. No. 184).

In one of the embodiments, between domain (a) and domain (b) there is additionally (f) domain of the sequence suitable for attachment to the fusion protein of the invention of a PEG molecule (PEG linker).

Such a linker can be a known sequence AlaSerGlyCysGlyProGlu (ASGCGPE in a one-letter convention), designated in the attached Sequence Listing as the SEQ. No. 170. PEG linker can be also chosen from between AlaAlaCysAlaAla (AACAA), SerGlyGlyCysGlyGlySer (SGGCGGS) i (SGCGS), designated in the attached Sequence Listing as, respectively, SEQ. No. 178, SEQ. No. 177 and SEQ. No. 179.

In another embodiment domains (a) (b) (c) (d) (e) and (f) may be additionally separated by up to three amino acids residues, formed of amino acid residues, particularly selected from the group consisting of Glycine and Glutamine.

Furthermore, in some embodiments the fusion protein may contain as a C-terminal part of the whole construct a non-functional fragment of hTRAIL, such as the sequence hTRAIL95-121, preceded by the sequence allowing its cleavage from the construct, advantageously the protease cleavage site, preferably the sequence recognized by thrombin. Incorporation of such small non-functional fragment of hTRAIL confers greater hydrophilcity to the whole construct, thus improving solubility of the protein during the expression process. After the purification steps hTRAIL95-121 will be cleaved by thrombin. In such a case, hTRAIL95-121 will not be present in the fusion protein used for the preparation of the pharmaceutical composition.

Any sequence recognized by thrombin known in the at may be used, in particular sequence LVPRGS (SEQ. No. 174).

Such additional hTRAIL95-121 sequence is especially advantageous in the case of lipophilic effector peptides, and when domain (a) begins with the aminoacid 114 and higher in the sequence of the whole TRAIL.

Particular embodiments of the fusion protein of the invention are fusion proteins comprising an intracellularly acting proapoptotic peptide, selected from the group consisting of the proteins represented by:

SEQ. No. 1, SEQ. No. 2, SEQ. No. 3, SEQ. No. 4, SEQ., No. 5, SEQ. No. 6, SEQ. No. 7, SEQ. No. 8, SEQ. No. 9, SEQ. No. 10, SEQ. No. 11, SEQ. No. 12, SEQ. No. 13, SEQ. No. 14, SEQ. No. 15, SEQ. No. 16, SEQ. No. 17, SEQ. No. 18, SEQ. No. 19, SEQ. No. 20, SEQ. No. 21, SEQ. No. 22, SEQ. No 23, SEQ. No. 93, SEQ. No. 94, SEQ. No. 95, SEQ. No. 96, SEQ., No. 97, SEQ. No. 98, SEQ. No. 99, SEQ. No. 100, SEQ. No. 101, SEQ. No. 102, SEQ. No. 103, SEQ. No. 104, SEQ. No. 105, SEQ. No. 106, SEQ. No. 107, SEQ. No. 108, SEQ. No.

109, SEQ. No. 110, SEQ. No. 111, SEQ. No. 112, SEQ. No. 113, SEQ. No. 114, SEQ. No 115, SEQ. No. 116, SEQ. No. 117, SEQ. No. 118, SEQ. No. 119, SEQ. No. 120 and SEQ. No. 121.

Other specific embodiments of the fusion protein of the invention are fusion proteins comprising an extracellularly acting pro-apoptotic peptide selected from the group consisting of proteins represented by SEQ. No. 24, SEQ. No. 25 and SEQ. No. 26.

A detailed description of the structure of representative fusion proteins mentioned above are shown in FIGS. 1 to 5 and 9 to 13, and in the Examples presented herein below.

In accordance with the present invention, by the fusion protein it is meant a single protein molecule containing two or more proteins or fragments thereof, covalently linked via peptide bond within their respective peptide chains, without additional chemical linkers.

The fusion protein can also be alternatively described as a protein construct or a chimeric protein. According to the present invention, the terms "construct" or "chimeric protein", if used, should be understood as referring to the fusion protein as defined above.

For a person skilled in the art it will be apparent that the fusion protein thus defined can be synthesized by known methods of chemical synthesis of peptides and proteins.

The fusion protein can be synthesized by methods of chemical peptide synthesis, especially using the techniques of peptide synthesis in solid phase using suitable resins as carriers. Such techniques are conventional and known in the art, and described inter alia in the monographs, such as for example Bodanszky and Bodanszky, The Practice of Peptide Synthesis, 1984, Springer-Verlag, New York, Stewart et al., Solid Phase Peptide Synthesis, 2nd Edition, 1984, Pierce Chemical Company.

The fusion protein can be synthesized by the methods of chemical synthesis of peptides as a continuous protein. Alternatively, the individual fragments (domains) of protein may be synthesized separately and then combined together in one continuous peptide via a peptide bond, by condensation of the amino terminus of one peptide fragment from the carboxyl terminus of the second peptide. Such techniques are conventional and well known.

For verification of the structure of the resulting peptide known methods of the analysis of amino acid composition of peptides may be used, such as high resolution mass spectrometry technique to determine the molecular weight of the peptide. To confirm the peptide sequence protein sequencers can also be used, which sequentially degrade the peptide and identify the sequence of amino acids.

Preferably, however, the fusion protein of the invention is a recombinant protein, generated by methods of gene expression of a polynucleotide sequence encoding the fusion protein in host cells.

A further aspect of the invention is the polynucleotide sequence, particularly DNA sequence encoding a fusion protein as defined above.

Preferably, the polynucleotide sequence, particularly DNA, according to the invention, encoding the fusion protein as defined above, is a sequence optimized for expression in *E. coli*.

Another aspect of the invention is also an expression vector containing the polynucleotide sequence, particularly DNA sequence of the invention as defined above.

Another aspect of the invention is also a host cell comprising an expression vector as defined above.

A preferred host cell for expression of fusion proteins of the invention is an *E. coli* cell.

Methods for generation of recombinant proteins, including fusion proteins, are well known. In brief, this technique consists in generation of polynucleotide molecule, for example DNA molecule encoding the amino acid sequence of the target protein and directing the expression of the target protein in the host. Then, the target protein encoding polynucleotide molecule is incorporated into an appropriate expression vector, which ensures an efficient expression of the polypeptide. Recombinant expression vector is then introduced into host cells for transfection/transformation, and as a result a transformed host cell is produced. This is followed by a culture of transformed cells to overexpress the target protein, purification of obtained proteins, and optionally cutting off by cleavage the tag sequences used for expression or purification of the protein.

Suitable techniques of expression and purification are described, for example in the monograph Goeddel, Gene Expression Technology, Methods in Enzymology 185, Academic Press, San Diego, Calif. (1990), and A. Staron et al., Advances Mikrobiol., 2008, 47, 2, 1983-1995.

As expression vectors for the introduction and replication of DNA sequences in host cells can be used cosmids, plasmids or modified viruses. Typically plasmids are used as expression vectors. Suitable plasmids are well known and commercially available.

Expression vector of the invention comprises a polynucleotide molecule encoding the fusion protein of the invention and the necessary regulatory sequences for transcription and translation of the coding sequence incorporated into a suitable host cell. Selection of regulatory sequences is dependent on the type of host cells and can be easily carried out by a person skilled in the art. Examples of such regulatory sequences are transcriptional promoter and enhancer or RNA polymerase binding sequence, ribosome binding sequence, containing the transcription initiation signal, inserted before the coding sequence, and transcription terminator sequence, inserted after the coding sequence. Moreover, depending on the host cell and the vector used, other sequences may be introduced into the expression vector, such as the origin of replication, additional DNA restriction sites, enhancers, and sequences allowing induction of transcription.

The expression vector will also comprise a marker gene sequence, which confers defined phenotype to the transformed cell and enables specific so selection of transformed cells. Furthermore, the vector may also contain a second marker sequence which allows to distinguish cells transformed with recombinant plasmid containing inserted coding sequence of the target protein from those which have taken up the plasmid without insert. Most often, typical antibiotic resistance markers are used, however, any other reporter genes known in the field may be used, whose presence in a cell (in vivo) can be easily determined using autoradiography techniques, spectrophotometry or bio- and chemi-luminescence. For example, depending on the host cell, reporter genes such as β-galactosidase, β-gluckuronidase, luciferase, chloramphenicol acetyltransferase or green fluorescent protein may be used.

Furthermore, the expression vector may contain signal sequence, transporting proteins to the appropriate cellular compartment, e.g. periplasma, where folding is facilitated. Additionally a sequence encoding a label/tag, such as HisTag attached to the N-terminus or GST attached to the C-terminus, may be present, which facilitates subsequent purification of the protein produced using the principle of affinity, via affinity chromatography on a nickel column. Additional sequences that protect the protein against proteolytic degradation in the host cells, as well as sequences that increase its solubility may also be present.

Auxiliary element attached to the sequence of the target protein may block its activity, or be detrimental for another reason, such as for example due to toxicity. Such element must be removed, which may be accomplished by enzymatic or chemical cleavage.

In particular, a six-histidine tag HisTag or other markers of this type attached to allow protein purification by affinity chromatography should be removed, because of its described effect on the liver toxicity of soluble TRAIL protein.

Heterologous expression systems based on various well-known host cells may be used, including prokaryotic cells: bacterial, such as *Escherichia coli* or *Bacillus subtilis*, yeasts such as *Saccharomyces cervisiae* or *Pichia pastoris*, and eukaryotic cell lines (insect, mammalian, plant).

Preferably, due to the ease of culturing and genetic manipulation, and a large amount of obtained product, the *E. coli* expression system is used. Accordingly, the polynucleotide sequence containing the target sequence encoding the fusion protein of the invention will be optimized for expression in *E. coli*, i.e. it will contain in the coding sequence codons optimal for expression in *E. coli*, selected from the possible sequence variants known in the state of art. Furthermore, the expression vector will contain the above-described elements suitable for *E. coli* attached to the coding sequence.

Accordingly, in a preferred embodiment of the invention a polynucleotide sequence comprising a sequence encoding a fusion protein of the invention, optimized for expression in *E. coli* is selected from the group of polynucleotide sequences consisting of:

SEQ. No. 67, SEQ. No. 68, SEQ. No. 69, SEQ. No. 70, SEQ. No. 71, SEQ. No. 72, SEQ. No. 73, SEQ. No. 74, SEQ. No. 75, SEQ. No. 76, SEQ. No. 77, SEQ. No. 78, SEQ. No. 79, SEQ. No. 80, SEQ. No. 81, SEQ. No. 82, SEQ. No. 83, SEQ. No. 84, SEQ. No. 85, SEQ. No. 86, SEQ. No. 87, SEQ. No. 88), SEQ. No. 89, SEQ. No. 90, SEQ. No. 91, SEQ. No. 92, SEQ. No. 122, SEQ. No. 123, SEQ. No. 124, SEQ. No. 125, SEQ. No. 126, SEQ. No. 127, SEQ. No. 128, SEQ. No. 129, SEQ. No. 130, SEQ. No. 131, SEQ. No. 132, SEQ. No. 133, SEQ. No. 134, SEQ. No. 135, SEQ. No. 136, SEQ. No. 137, SEQ. No. 138, SEQ. No. 139, SEQ. No. 140, SEQ. No. 141, SEQ. No. 142, SEQ. No. 143), SEQ. No. 144, SEQ. No. 145, SEQ. No. 146, SEQ. No. 147; SEQ. No. 148, SEQ. No. 149, and SEQ. No. 150;

which encode a fusion protein having an amino acid sequence corresponding to amino acid sequences selected from the group consisting of amino acid sequences, respectively:

SEQ. No. 1, SEQ. No. 2, SEQ. No. 3, SEQ. No. 4, SEQ. No. 5, SEQ. No. 6, SEQ. No. 7, SEQ. No. 8, SEQ. No. 9, SEQ. No. 10, SEQ. No. 11, SEQ. No. 12, SEQ. No. 13, SEQ. No. 14, SEQ. No. 15, SEQ. No. 16, SEQ. No. 17, SEQ. No. 18, SEQ. No. 19, SEQ. No. 20, SEQ. No. 21, SEQ. No. 22), SEQ. No. 23, SEQ. No. 24, SEQ. No. 25, SEQ. No. 26, SEQ No. 93, SEQ. No. 94, SEQ. No. 95, SEQ. No. 96, SEQ. No. 97, SEQ. No. 98, SEQ. No. 99, SEQ. No. 100, SEQ. No. 101, SEQ. No. 102, SEQ. No. 103, SEQ. No. 104, SEQ. No. 105, SEQ. No. 106, SEQ. No. 107, SEQ. No. 108, SEQ. No. 109, SEQ. No. 110, SEQ. No. 111, SEQ. No. 112, SEQ. No. 113, SEQ. No. 114, SEQ. No. 115, SEQ. No. 116, SEQ. No. 117 and SEQ. No. 118, SEQ. No. 119, SEQ. No. 120 and SEQ. No 121.

In a preferred embodiment, the invention provides also an expression vector suitable for transformation of *E. coli*, comprising the polynucleotide sequence selected from the group of polynucleotide sequences SEQ. No. 67 to SEQ. No. 92 and SEQ. No. 122 to SEQ. No. 150 indicated above, as well as *E. coli* cells transformed with such an expression vector.

Transformation, i.e. introduction of a DNA sequence into bacterial host cells, particularly *E. coli*, is usually performed on the competent cells, prepared to take up the DNA for example by treatment with calcium ions at low temperature (4° C.), and then subjecting to the heat-shock (at 37-42° C.) or by electroporation. Such techniques are well known and are usually determined by the manufacturer of the expression system.

The procedure of overexpression of fusion proteins of the invention in *E. coli* expression system will be further described below.

The invention also provides a pharmaceutical composition containing the fusion protein of the invention as defined above as an active ingredient and a suitable pharmaceutically acceptable carrier, diluent and conventional auxiliary components.

The pharmaceutical composition will contain an effective amount of the fusion protein of the invention and pharmaceutically acceptable auxiliary components dissolved or dispersed in a carrier or diluent, and preferably will be in the form of a pharmaceutical composition formulated in a unit dosage form or formulation containing a plurality of doses.

Pharmaceutical forms and methods of their formulation as well as other components, carriers and diluents are known to the skilled person and described in the literature. For example, they are described in the monograph Remington's Pharmaceutical Sciences, ed. 20, 2000, Mack Publishing Company, Easton, USA.

The terms "pharmaceutically acceptable carrier, diluent, and auxiliary ingredient" comprise any solvents, dispersion media, surfactants, antioxidants, stabilizers, preservatives (e.g. antibacterial agents, antifungal agents), isotoning agents, known in the art. The pharmaceutical composition so of the invention may contain various types of carriers, diluents and excipients, depending on the chosen route of administration and desired dosage form, such as liquid, solid and aerosol forms for oral, parenteral, inhaled, topical, and whether that selected form must be sterile for administration route such as by injection.

The preferred route of administration of the pharmaceutical composition according to the invention is parenteral, including injection routes such as intravenous, intramuscular, subcutaneous, intraperitoneal, intratumourous, or by single or continuous intravenous infusions.

In one embodiment, the pharmaceutical composition of the invention may be administered by injection directly to the tumour. In another embodiment, the pharmaceutical composition of the invention may be administered intravenously. In yet another embodiment, the pharmaceutical composition of the invention can be administered subcutaneously or intraperitoneally.

A pharmaceutical composition for parenteral administration may be a solution or dispersion in a pharmaceutically acceptable aqueous or non-aqueous medium, buffered to an appropriate pH and isoosmotic with body fluids, if necessary, and may also contain antioxidants, buffers, bacteriostatic agents and soluble substances, which make the composition compatible with the tissues or blood of recipient. Other components, which may included in the composition, are for example water, alcohols such as ethanol, polyols such as glycerol, propylene glycol, liquid polyethylene glycol, lipids such as triglycerides, vegetable oils, liposomes. Proper fluidity and the particles size of the substance may be provided by coating substances, such as lecithin, and surfactants, such as hydroxypropylcellulose polysorbates, and the like. Suitable isotoning agents for liquid parenteral compositions are, for example, sugars such as glucose, and sodium chloride, and combinations thereof.

Alternatively, the pharmaceutical composition for administration by injection or infusion may be in a powder form, such as a lyophilized powder for reconstitution immediately prior to use in a suitable carrier such as, for example, sterile pyrogen-free water.

The pharmaceutical composition of the invention for parenteral administration may also have the form of nasal administration, including solutions, sprays or aerosols. Preferably, the form for intranasal administration will be an aqueous solution and will be isotonic or buffered o maintain the pH from about 5.5 to about 6.5, so as to maintain a character similar to nasal secretions. Moreover, it will contain preservatives or stabilizers, such as in the well-known intranasal preparations.

The composition may contain various antioxidants which delay oxidation of one or more components. Furthermore, in order to prevent the action of microorganisms, the composition may contain various antibacterial and antifungal agents, including, for example, and not limited to, parabens, chlorobutanol, thimerosal, sorbic acid, and similar known substances of this type.

In general, the pharmaceutical composition of the invention can include, for example at least about 0.01 wt % of active ingredient. More particularly, the composition may contain the active ingredient in the amount from 1% to 75% by weight of the composition unit, or for example from 25% to 60% by weight, but not limited to the indicated values.

The actual amount of the dose of the composition according to the present invention administered to patients, including man, will be determined by physical and physiological factors, such as body weight, severity of the condition, type of disease being treated, previous or concomitant therapeutic interventions, the patient and the route of administration. A suitable unit dose, the total dose and the concentration of active ingredient in the composition is to be determined by the treating physician.

The composition may for example be administered at a dose of about 1 microgram/kg of body weight to about 1000 mg/kg of body weight of the patient, for example in the range of 5 mg/kg of body weight to 100 mg/kg of body weight or in the range of 5 mg/kg of body weight to 500 mg/kg of body weight.

The fusion protein and the compositions containing it exhibit anticancer or antitumor and can be used for the treatment of cancer diseases.

The invention also provides the use of the fusion protein of the invention as defined above for treating cancer diseases in mammals, including humans.

The invention also provides a method of treating cancer diseases in mammals, including humans, comprising administering to a subject in need of such so treatment an anticancer effective amount of the fusion protein of the invention as defined above, optionally in the form of appropriate pharmaceutical composition.

The fusion protein of the invention can be used for the treatment of hematologic malignancies, such as leukaemia, granulomatosis, myeloma and other hematologic malignancies. The fusion protein can also be used for the treatment of solid tumours, such as breast cancer, lung cancer, including non-small cell lung cancer, colon cancer, pancreatic cancer, ovarian cancer, bladder cancer, prostate cancer, kidney cancer, brain cancer, and the like.

Appropriate route of administration of the fusion protein in the treatment of cancer will be in particular parenteral route, which consists in administering the fusion protein of the invention in the form of injections or infusions, in the composition and form appropriate for this administration route.

The invention will be described in more detail in the following general procedures and examples of specific fusion proteins.

General Procedure for Overexpression of the Fusion Protein

Preparation of Plasmid

Amino acid sequence of the target fusion protein was used as a template to generate a DNA sequence encoding it, comprising codons optimized for expression in *Escherichia coli*. Such a procedure allows to increase the efficiency of a further step of target protein synthesis in *Escherichia coli*. Resulting nucleotide sequence was then automatically synthesized. Additionally, the cleavage sites of restriction enzymes NdeI (at the 5'-end of leading strand) and XhoI (at the 3'-end of leading strand) were added to the resulting gene encoding the target protein. These were used to clone the gene into the vector pET28a (Novagen). They may be also be used for cloning the gene encoding the protein to other vectors. Target protein expressed from this construct was equipped at the N-terminus with a polyhistidine tag (six histidines), preceded by a site recognized by thrombin, which subsequently served to its purification via affinity chromatography, The correctness of the resulting construct was confirmed firstly by restriction analysis of isolated plasmids using the enzymes NdeI and XhoI, followed by automatic sequencing of the entire reading frame of the target protein. The primers used for sequencing were complementary to the sequences of T7 promoter (5'-TAATACGACTCACTATAGG-3') (SEQ ID NO: 185) and T7 terminator (5'-GCTAGTTATTCCTCAGCGG-3') (SE ID NO: 186) present in the vector.

Resulting plasmid was used for overexpression of the target fusion protein in a commercial *E. coli* strain, which was transformed according to the manufacturer's recommendations. Colonies obtained on the selection medium (LB agar, kanamycin 50 μg/ml, 1% glucose) were used for preparing an overnight culture in LB liquid medium supplemented with kanamycin (50 μg/ml) and 1% glucose. After about 15 h of growth in shaking incubator, the cultures were used to inoculate the appropriate culture.

Overexpression and Purification of Fusion Proteins—General Procedure A

LB medium with kanamycin (30 μg/ml) and 100 uM zinc sulfate was inoculated with overnight culture. The culture was incubated at 37° C. until the optical density (OD) at 600 nm reached 0.60-0.80. Then IPTG was added to the final concentration in the range of 0.25-1 mM. After incubation (3.5-20 h) with shaking at 25° C. the culture was centrifuged for 25 min at 6,000 g.

Bacterial pellets were resuspended in a buffer containing 50 mM $KH_2PO_4$, 0.5 M NaCl, 10 mM imidazole, pH 7.4. The suspension was sonicated on ice for 8 minutes (40% amplitude, 15-second pulse, 10 s interval). The resulting extract was clarified by centrifugation for 40 minutes at 20.000 g, 4° C. Ni-Sepharose (GE Healthcare) resin was pre-treated by equilibration with buffer, which was used for preparation of the bacterial cells extract. The resin was then incubated overnight at 4° C. with the supernatant obtained after centrifugation of the extract. Then it was loaded into chromatography column and washed with 15 to 50 volumes of buffer 50 mM $KH_2PO_4$, 0.5 M NaCl, 20 mM imidazole, pH 7.4. The obtained protein was eluted from the column using imidazole gradient in 50 mM $KH_2PO_4$ buffer with 0.5 M NaCl, pH 7.4. Obtained fractions were analyzed by SDS-PAGE. Appropriate fractions were combined and dialyzed overnight at 4° C. against 50 mM Tris buffer, pH 7.2, 150 mM NaCl, 500 mM L-arginine, 0.1 mM $ZnSO_4$, 0.01% Tween 20, and at the same time Histag was cleaved with thrombin (1:50). After the cleavage, thrombin was separated from the target fusion protein using Benzamidine Sepharose™ resin. The purity of the product was analyzed by SDS-PAGE electrophoresis (Maniatis et al, Molecular Cloning. Cold Spring Harbor, N.Y., 1982).

Overexpression and Purification of Fusion Proteins—General Procedure B

LB medium with kanamycin (30 μg/ml) and 100 μM zinc sulfate was inoculated with overnight culture. Cultures were incubated at 37° C. until optical density (OD) at 600 nm reached 0.60-0.80. Then IPTG was added to the final concentration in the range 0.5-1 mM. After 20 h incubation with shaking at 25° C. the culture was centrifuged for 25 min at 6,000 g.

Bacterial cells after overexpression were disrupted in a French Press in a buffer containing 50 mM $KH_2PO_4$, 0.5 M NaCl, 10 mM imidazole, 5 mM beta-mercaptoethanol, 0.5 mM PMSF (phenylmethylsulphonyl fluoride), pH 7.8. Resulting extract was clarified by centrifugation for 50 minutes at 8.000 g. The Ni-Sepharose resin was incubated overnight with the obtained supernatant. Then the resin with bound protein was packed into the chromatography column. To wash-out the fractions containing non-binding proteins, the column was washed with 15 to 50 volumes of buffer 50 mM $KH_2PO_4$, 0.5 M NaCl, 10 mM imidazole, 5 mM beta-mercaptoethanol, 0.5 mM PMSF (phenylmethylsulphonyl fluoride), pH 7.8. Then, to wash-out the majority of proteins binding specifically with the bed, the column was washed with a buffer containing 50 mM $KH_2PO_4$, 0.5 M NaCl, 500 mM imidazole, 10% glycerol, 0.5 mM PMSF, pH 7.5. Obtained fractions were analyzed by SDS-PAGE (Maniatis et al, Molecular Cloning. Cold Spring Harbor, N.Y., 1982). The fractions containing the target protein were combined and cleaved with thrombin (1 U per 4 mg of protein, 8 h at 16° C.) to remove polyhistidine tag. Then the fractions were dialyzed against formulation buffer (500 mM L-arginine, 50 mM Tris, 2.5 mM $ZnSO_4$, pH 7.4), Characterization of Fusion Proteins Using 2-D Electrophoresis In order to further characterize obtained proteins and to select precisely chromatographic conditions, isoelectric points of the proteins were determined. For this purpose, two-dimensional electrophoresis (2-D) method was used, in two stages according to the following schedule.

Step 1. Isoelectrofocusing of Proteins in a pH Gradient and Denaturing Conditions.

Protein preparations at concentrations of 1-2 mg/ml were precipitated by mixing in a 1:1 ratio with a precipitation solution containing 10% trichloro-acetic acid and 0.07% beta-mercaptoethanol in acetone. The mixture was incubated for 30 min at −20° C. and then centrifuged for 25 min at 15,000 g and 4° C. The supernatant was removed and the pellet was washed twice with cold acetone with 0.07% beta-mercaptoethanol. Then the residues of acetone were evaporated until no detectable odour. The protein pellet was suspended in 250 ml of rehydration buffer 8M urea, 1% CHAPS, 15 mM DTT, 0.5% ampholyte (GE Healthcare) with a profile of pH 3-11 or 6-11, depending on the strip subsequently used. The protein solution was placed in a ceramic chamber for isoelectrofocusing, followed by 13 cm DryStrip (GE Healthcare) with appropriate pH profile (3-11 or 6-11). The whole was covered with a layer of mineral oil. The chambers were placed in the Ettan IPGphor III apparatus, where isoelectrofocusing was conducted according to the following program assigned to the dimensions of the strip and the pH profile:

16 h dehydration at 20° C.

Focusing in the electric field at a fixed pH gradient

| Time | Voltage |
|---|---|
| 1 h | 500 V |
| 1 h | gradient 500-1000 V |
| 2 h 30 min | gradient 1000-8000 V |
| 30 min | 8000 V |

Then, the strip containing the focused proteins was washed for 1 min in deionised water, stained with Coomassie Brilliant and then decolorized and archived as an image to mark the location of proteins. Discolored strip was equilibrated 2×15 min with a buffer of the following composition: 50 mM Tris-HCl pH 8.8, 6M urea, 1% DTT, 2% SDS, 30% glycerol.

Step 2. Separation in a Second Direction by SDS-Page.

The strip was placed over the 12.5% polyacrylamide gel containing a single well per standard size and then separation was performed in an apparatus for SDS-PAGE, at a voltage of 200V for 3 hours. The gel was stained with Coomassie Brilliant then archived with the applied scale. Proteins were identified by determining its weight on the basis of the standard of size, and its IPI was read for the scale of 6-11 on the basis of the curves provided by the manufacturer (GE Healthcare) (ratio of pH to % of length of the strip from the end marked as anode) or a scale of 3-11 on the basis of the curve determined experimentally by means of isoelectrofocusing calibration kit (GE Healthcare).

Representative examples of the fusion proteins of the invention are described below.

EXAMPLE 1

The Fusion Protein of SEQ. No. 1

The protein of SEQ. No. 1 is a fusion protein having the length of 194 amino acids and the mass of 22.7 kDa, in which at the N-terminus of TRAIL121-281 sequence the 16-amino acid peptide derived from the BH3 domain of Bax protein (SEQ. No. 30) is attached as the effector peptide. At the C-terminus of the 16-amino acid sequence of the effector peptide there is attached the polyarginine sequence of 7 Arg/R residues. Polyarginine sequence aids in penetration of the cell membrane and transportation of the fusion protein into the cell. Between the polyarginine sequence and TRAIL domain there are incorporated sequentially next to each other sequences recognized by urokinase uPA (SEQ. No. 52) and metalloprotease MMP (SEQ. No. 51), due to which the effector peptide upon internalization of the fusion protein will be cleaved in the tumour environment.

Structure of the fusion protein is presented schematically in FIG. 1 and its amino acid sequence and the DNA encoding sequence comprising codons optimized for expression in *E. coli* are, respectively, SEQ. No. 1 and SEQ. No. 67 as shown below.

```
Amino acid sequence:
                                                  SEQ. No. 1
  1  KKLSECLKRI GDELDSRRRR RRRRVVRPLG LAGRVAAHIT GTRGRSNTLS

 51  SPNSKNEKAL GRKINSWESS RSGHSFLSNL HLRNGELVIH EKGFYYIYSQ
```

-continued

```
101 TYFRFQEEIK ENTKNDKQMV QYIYKYTSYP DPILLMKSAR NSCWSKDAEY

151 GLYSIYQGGI FELKENDRIF VSVTNEHLID MDHEASFFGA FLVG
```

DNA sequence:

SEQ. No. 67

```
  1 GCCCACCAGA AATGCACCAA AAAAGCTGGC TTCATGATCC ATATCAATCA

    GATGTTCATT GGTCACGCTC ACAAAAATGC GATCATTTTC TTTCAGTTCA

101 AAAATGCCAC CCTGATAAAT GCTATACAGG CCATATTCTG CATCTTTGCT

    CCAACAGCTA TTACGTGCGC TTTTCATCAG CAGAATCGGA TCCGGATAGC

201 TGGTATATTT ATAAATGTAC TGCACCATTT GTTTATCATT TTTGGTATTT

    TCTTTAATTT CTTCCTGAAA GCGAAAATAG GTCTGGCTAT AAATATAATA

301 AAAGCCTTTT TCATGAATCA CCAGTTCACC ATTACGCAGA TGCAGATTGC

    TCAGAAAGCT ATGACCGCTA CGGCTGCTTT CCCAGCTATT AATTTTGCGA

401 CCCAGGGCTT TTTCATTTTT GCTATTCGGG CTGCTCAGGG TATTGCTACG

    ACCACGGGTG CCGGTAATAT GTGCTGCAAC ACGACCTGCC AGACCCAGCG

501 GACGAACAAC ACGACGACGG CGACGACGAC GACGGCTATC CAGTTCATCA

    CCAATACGTT TCAGGCATTC GCTCAGTTTT TT
```

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* strains BL21 (DE3) and Tuner (DE3) pLysS, both from Novagen. The protein was separated by electrophoresis in accordance with the general procedure described above.

EXAMPLE 2

The Fusion Protein of SEQ. No. 2

The fusion protein of SEQ. No. 2 is a protein having the length of 193 amino acids and the mass of 22.5 kDa, in which at the N-terminus of 121-281TRAIL sequence the 16-amino acid peptide derived from the Bid protein (SEQ. No. 31) is attached as the effector peptide. Additionally, to the C-terminus of the effector protein there is attached polyarginine sequence consisting of seven Arg residues. Polyarginine sequence aids in penetration of the cell membrane and transportation of the fusion protein into the cell. Between the polyarginine sequence and the sequence of TRAIL sequences recognized by metalloprotease MMP (SEQ. No. 51) and urokinase uPA (SEQ. No. 52) are incorporated sequentially next to each other, due to which upon internalization of the fusion protein the effector peptide will be cleaved in the tumour environment.

Structure of the fusion protein is shown schematically in FIG. 1 and its amino acid sequence and the DNA encoding sequence comprising codons optimized for expression in *E. coli* are, respectively, SEQ. No. 2 and SEQ. No. 68 as shown below.

Amino acid sequence:

SEQ. No. 2

```
  1 RNIARHLAQV GDSMDRRRRR RRRVVRPLGL AGRVAAHITG TRGRSNTLSS

 51 PNSKNEKALG RKINSWESSR SGHSFLSNLH LRNGELVIHE KGFYYIYSQT

101 YFRFQEEIKE NTKNDKQMVQ YIYKYTSYPD PILLMKSARN SCWSKDAEYG

151 LYSIYQGGIF ELKENDRIFV SVTNEHLIDM DHEASFFGAF LVG
```

DNA sequence:

SEQ. No. 68

```
  1 CGTAATATTG CACGTCATCT GGCACAGGTT GGTGATAGCA TGGACCGTCG

    TCGTCGTCGC CGTCGTCGTG TTGTTCGTCC GCTGGGTCTG GCAGGTCGTG

101 TTGCAGCACA TATTACCGGC ACCCGTGGTC GTAGCAATAC CCTGAGCAGC

    CCGAATAGCA AAAATGAAAA AGCCCTGGGT CGCAAAATTA ATAGCTGGGA

201 AAGCAGCCGT AGCGGTCATA GCTTTCTGAG CAATCTGCAT CTGCGTAATG

    GTGAACTGGT GATTCATGAA AAAGGCTTTT ATTATATTTA TAGCCAGACC
```

-continued

```
301 TATTTTCGCT TTCAGGAAGA AATTAAAGAA AATACCAAAA ATGATAAACA

    AATGGTGCAG TACATTTATA AATATACCAG CTATCCGGAT CCGATTCTGC

401 TGATGAAAAG CGCACGTAAT AGCTGTTGGA GCAAAGATGC AGAATATGGC

    CTGTATAGCA TTTATCAGGG TGGCATTTTT GAACTGAAAG AAAATGATCG

501 CATTTTTGTG AGCGTGACCA ATGAACATCT GATTGATATG GATCATGAAG

    CCAGCTTTTT TGGTGCATTT CTGGTGGGC
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain BL21 (DE3) from Novagen. The protein was separated by electrophoresis in accordance with the general procedure described above.

EXAMPLE 3

The Fusion Protein of SEQ. No. 3

The fusion protein of SEQ. No. 3 is a protein having the length of 303 amino acids and the mass of 34.2 kDa, in which at the C-terminus of the 121-281TRAIL sequence the homologue of ribonuclease RNase A (SEQ. No. 32) is attached as an effector peptide. Between the polyarginine sequence and the sequence of TRAIL sequences recognized by metalloprotease MMP (SEQ. No. 51) and urokinase uPA (SEQ. No. 52) are sequentially incorporated next to each other, due to which upon internalization of the fusion protein the effector peptide will be cleaved in the tumour environment.

The protein also contains, between the TRAIL domain sequence and the sequence of cleavage sites, flexible glycine-serine linker GGSG (SEQ. No. 57). Furthermore, at the C-terminus of the effector peptide, the protein contains the sequence KEDL (SEQ. No. 56) directing to the endoplasmic reticulum, being also a C-terminal part of the entire construct.

Structure of the fusion protein is shown schematically in FIG. 1 and its amino acid sequence and the DNA encoding sequence comprising codons optimized for expression in *E. coli* are, respectively, SEQ. No. 3 and SEQ. No. 69 as shown below.

```
Amino acid sequence:
                                                SEQ. No. 3
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGSGPLGLA GRVVRKETAA AKFERQHMDS STSAASSSNY

201 CNQMMKSRNL TKDRCKPVNT FVHESLADVQ AVCSQKNVAC KNGQTNCYQS

251 YSTMSITDCR ETGSSKYPNC AYKTTQANKH IIVACEGNPY VPVHFDASVK

301 EDL

DNA sequence:
                                                SEQ. No. 69
  1 CGTGTTGCAG CACATATTAC CGGCACCCGT GGTCGTAGCA ATACCCTGAG

    CAGCCCGAAT AGCAAAAATG AAAAAGCCCT GGGTCGCAAA ATTAATAGCT

101 GGGAAAGCAG CCGTAGCGGT CATAGCTTTC TGAGCAATCT GCATCTGCGT

    AATGGTGAAC TGGTGATTCA TGAAAAAGGC TTTTATTATA TTTATAGCCA

201 GACCTATTTT CGCTTTCAGG AAGAAATTAA AGAAAATACC AAAAATGACA

    AACAAATGGT GCAGTATATC TACAAATACA CCAGCTATCC GGATCCGATT

301 CTGCTGATGA AAAGCGCACG TAATAGCTGT TGGAGCAAAG ATGCAGAATA

    TGGCCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTA GCGGTCCGCT

501 GGGTCTGGCA GGTCGTGTTG TTCGTAAAGA AACCGCAGCA GCCAAATTTG

    AACGTCAGCA CATGGATAGC AGCACCAGCG CAGCAAGCAG CAGCAATTAT
```

-continued

```
601 TGCAATCAGA TGATGAAAAG CCGCAATCTG ACCAAAGATC GTTGTAAACC

    GGTGAATACC TTTGTTCATG AAAGCCTGGC AGATGTTCAG GCAGTTTGCA

701 GCCAGAAAAA TGTGGCCTGT AAAAATGGTC AGACCAATTG CTATCAGAGC

    TATAGCACCA TGAGCATTAC CGATTGTCGT GAAACCGGTA GCAGCAAATA

801 TCCGAATTGC GCCTATAAAA CCACCCAGGC CAATAAACAT ATTATTGTGG

    CCTGTGAAGG CAATCCGTAT GTTCCGGTTC ATTTTGATGC CAGCGTGAAA

901 GAAGATCTG
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strain BL21 (DE3) from Novagen. The protein was separated by electrophoresis in accordance with the general procedure described above.

EXAMPLE 4

The Fusion Protein of SEQ. No. 4

The protein of SEQ. No. 4 is a fusion protein having the length of 293 amino acids and the mass of 33.2 kDa, in which at the C-terminus of TRAIL 121-281 sequence the homologue of ribonuclease RNase A (SEQ. No. 32) is attached as an effector peptide. Between the effector peptide and the sequence of TRAIL there is a flexible glycine-serine linker GGGSGGGS (SEQ. No. 63).

Structure of the fusion protein is shown schematically in FIG. 1 and its amino acid sequence and the DNA encoding sequence comprising codons optimized for expression in *E. coli* are, respectively, SEQ. No. 4 and SEQ. No. 70 as shown below.

```
Amino acid sequence:
                                                        SEQ. No. 4
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGGSGGGSK ETAAAKFERQ HMDSSTSAAS SSNYCNQMMK

201 SRNLTKDRCK PVNTFVHESL ADVQAVCSQK NVACKNGQTN CYQSYSTMSI

251 TDCRETGSSK YPNCAYKTTQ ANKHIIVACE GNPYVPVHFD ASV
```

```
DNA sequence:
                                                       SEQ. No. 70
  1 CGTGTTGCAG CACATATTAC CGGCACCCGT GGTCGTAGCA ATACCCTGAG

    CAGCCCGAAT AGCAAAAATG AAAAAGCACT GGGTCGCAAA ATTAATAGCT

101 GGGAAAGCAG CCGTAGCGGT CATAGCTTTC TGAGCAATCT GCATCTGCGT

    AATGGTGAAC TGGTGATTCA TGAAAAAGGC TTTTATTATA TTTATAGCCA

201 GACCTATTTT CGCTTTCAAG AAGAAATTAA AGAAAATACC AAAAATGATA

    AGCAGATGGT GCAGTATATC TATAAATATA CCAGCTATCC GGATCCGATT

301 CTGCTGATGA AAAGCGCACG TAATAGCTGT TGGAGCAAAG ATGCAGAATA

    TGGTCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTG GTAGCGGTGG

501 TGGTAGTAAA GAAACCGCAG CAGCAAAATT TGAACGTCAG CACATGGATA

    GCAGCACCAG CGCAGCAAGC AGCAGCAATT ATTGTAATCA GATGATGAAA

601 AGCCGCAATC TGACCAAAGA TCGTTGTAAA CCGGTGAATA CCTTTGTTCA

    TGAAAGCCTG GCAGATGTTC AGGCAGTTTG TAGCCAGAAA AATGTTGCCT
```

-continued

```
701 GTAAAAATGG TCAGACCAAT TGCTATCAGA GCTATAGCAC CATGAGCATT

    ACCGATTGTC GTGAAACCGG TAGCAGCAAA TATCCGAATT GTGCATATAA

801 AACCACCCAG GCCAATAAAC ATATTATTGT TGCCTGTGAA GGCAATCCGT

    ATGTTCCGGT TCATTTTGAT GCAAGCGTT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains BL21DE3pLysSRIL from Stratagene and Tuner (DE3) from Novagen. The protein was separated by electrophoresis in accordance with the general procedure described above.

EXAMPLE 5

The Fusion Protein of SEQ. No. 5

The protein of SEQ. No. 5 is a fusion protein having the length of 283 amino acids and the mass of 31 kDa, in which at the C-terminus of 121-281TRAIL sequence the sequence of cytochrome C (SEQ. No. 33) is attached as an effector peptide. Between the sequence of TRAIL domain and the sequence of effector protein the sequences recognized by metalloprotease MMP (SEQ. No. 51) and urokinase uPA (SEQ. No. 52) are incorporated sequentially next to each other, due to which upon internalization of the fusion protein the effector peptide will be cleaved in the tumour environment. The protein also contains, between the TRAIL domain sequence and the sequence of cleavage sites, the flexible glycine-serine linker GGSG (SEQ. No. 57). Furthermore, at the C-terminus of the effector peptide the protein contains the sequence KEDL (SEQ. No. 56) directing to the endoplasmic reticulum, which is a C-terminal part of the entire construct.

Structure of the fusion protein is shown schematically in FIG. 1 and its amino acid sequence and the DNA encoding sequence comprising codons optimized for expression in *E. coli* are, respectively, SEQ. No. 5 and SEQ. No. 71 as shown below.

```
Amino acid sequence:
                                                   SEQ. No. 5
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGSGPLGLA GRVVRGDVEK GKKIFIMKCS QCHTVEKGGK

201 HKTGPNLHGL FGRKTGQAPG YSYTAANKNK GIIWGEDTLM EYLENPKKYI

251 PGTKMIFVGI KKKEERADLI AYLKKATNEK EDL

DNA sequence:
                                                   SEQ. No. 71
  1 CAGATCTTCT TTTTCATTGG TGGCTTTTTT CAGATAGGCA ATCAGATCTG

    CGCGTTCTTC TTTTTTTTTA ATGCCCACAA AAATCATTTT CGTACCCGGA

101 ATATATTTTT TCGGATTTTC CAGATATTCC ATCAGGGTAT CTTCACCCCA

    AATAATGCCT TTGTTTTTAT TGGCTGCGGT ATAGCTATAA CCCGGTGCCT

201 GACCGGTTTT ACGACCAAAC AGACCATGCA GATTCGGACC GGTTTTATGT

    TTGCCACCTT TTTCAACGGT ATGACACTGG CTGCATTTCA TAATAAAAAT

301 TTTTTTGCCT TTTTCCACAT CACCACGAAC AACACGACCT GCCAGACCCA

    GCGGACCGCT ACCACCACCA ACCAGAAATG CACCAAAAAA GCTGGCTTCA

401 TGATCCATAT CAATCAGATG TTCATTGGTC ACGCTCACAA AAATGCGATC

    ATTTTCTTTC AGTTCAAAAA TGCCACCCTG ATAAATGCTA TACAGGCCAT

501 ATTCTGCATC TTTGCTCCAA CAGCTATTAC GTGCGCTTTT CATCAGCAGA

    ATCGGATCCG GATAGCTGGT ATATTTATAA ATGTACTGCA CCATTTGTTT

601 ATCGTTTTTG GTATTTTCTT TAATTTCTTC CTGAAAGCGA AAATAGGTCT

    GGCTATAAAT ATAATAAAAG CCTTTTTCAT GAATCACCAG TTCACCATTA
```

-continued

```
701 CGCAGATGCA GATTGCTCAG AAAGCTATGA CCGCTACGGC TGCTTTCCCA

    GCTATTAATT TTGCGACCCA GGGCTTTTTC ATTTTTGCTA TTCGGGCTGC

801 TCAGGGTATT GCTACGACCA CGGGTGCCGG TAATATGTGC TGCAACACGC AT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 6

The Fusion Protein of SEQ. No. 6

The protein of SEQ. No. 6 is a fusion protein having the length of 407 amino acids and the mass of 45.2 kDa, in which at the C-terminus of 121-281TRAIL sequence the sequence of cytochrome C (SEQ. No. 33) is attached as an effector peptide. Between the sequence of TRAIL domain and the effector peptide there are the sequence recognized by furin (SEQ. No. 53) and the translocation domain from *Pseudomonas aeruginosa* (SEQ. No. 54). The protein also contains flexible linkers: between the sequence of TRAIL sequence and the sequence of cleavage site recognized by furin there is the flexible glycine-serine linker GGGS (SEQ. No. 58), between the sequence of cleavage site recognized by furin and the translocation domain from *Pseudomonas aeruginosa* the flexible glycine-serine linker ASGG (SEQ. No. 65), and between the sequence of translocation domain and the sequence of cytochrome C the flexible glycine-serine linker GGGSGGG (SEQ. No. 62). Furthermore, at the C-terminus of the effector peptide domain, the protein contains a sequence KEDL (SEQ. No. 56) directing to the endoplasmic reticulum, which is a C-terminal part of the entire construct.

Figure 2:
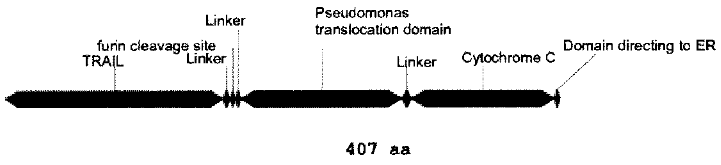
FIG. 2 presents a schematic structure of fusion proteins of the invention according to Ex. 6, Ex. 7, Ex. 8, Ex. 9 and Ex. 10.
Figure 2:
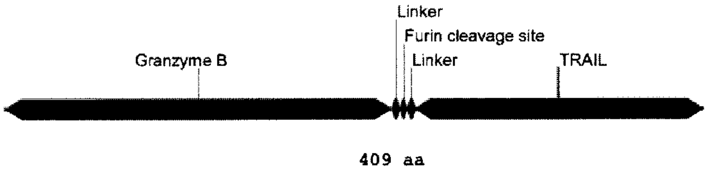
Figure 2:
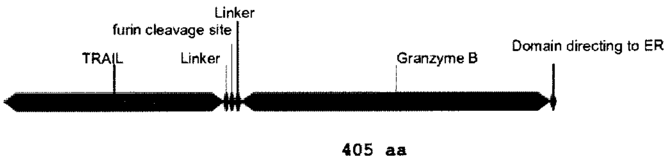
Figure 2:
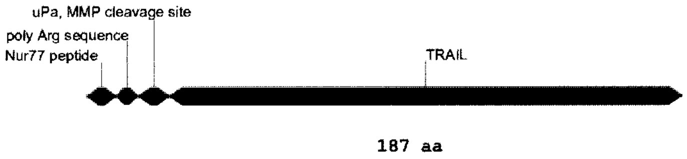
Figure 2:

Structure of the fusion protein is shown schematically in FIG. 2 and its amino acid sequence and the DNA encoding sequence comprising codons optimized for expression in *E. coli* are, respectively, SEQ. No. 6 and SEQ. No. 72 as shown below.

```
Amino acid sequence:
                                                    SEQ. No. 6
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGGSRKKRA SGGPEGGSLA ALTAHQACHL PLETFTRHRQ

201 PRGWEQLEQC GYPVQRLVAL YLAARLSWNQ VDQVIANALA SPGSGGDLGE

251 AIRESPEQAR LALTLAAAES ERFVRQGTGN DEAGAANGPA DGGGSGGGMG

301 DVEKGKKIFI MKCSQCHTVE KGGKHKTGPN LHGLFGRKTG QAPGYSYTAA

351 NKNKGIIWGE DTLMEYLENP KKYIPGTKMI FVGIKKKEER ADLIAYLKKA

401 TNEKDEL

DNA sequence:
                                                   SEQ. No. 72
  1 CGTGTTGCAG CACATATTAC CGGCACCCGT GGTCGTAGCA ATACCCTGAG

    CAGCCCGAAT AGCAAAAATG AAAAAGCACT GGGTCGCAAA ATTAATAGCT

101 GGGAAAGCAG CCGTAGCGGT CATAGCTTTC TGAGCAATCT GCATCTGCGT

    AATGGTGAAC TGGTGATTCA TGAAAAAGGC TTTTATTATA TTTATAGCCA

201 GACCTATTTT CGCTTTCAAG AAGAAATTAA AGAAAATACC AAAAATGACA

    AACAAATGGT GCAGTATATC TATAAATATA CCAGCTATCC GGATCCGATT

301 CTGCTGATGA AAAGCGCACG TAATAGCTGT TGGAGCAAAG ATGCAGAATA

    TGGTCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTG GTAGCCGTAA

501 AAAACGTGCA AGCGGTGGTC CGGAAGGTGG TAGCCTGGCA GCACTGACCG

    CACATCAGGC ATGTCATCTG CCGCTGGAAA CCTTTACCCG TCATCGTCAG
```

-continued

```
601 CCTCGTGGTT GGGAACAGCT GGAACAGTGT GGTTATCCGG TTCAGCGTCT

    GGTTGCACTG TATCTGGCAG CACGTCTGAG CTGGAATCAG GTTGATCAGG

701 TTATTGCAAA TGCACTGGCA AGTCCGGGTA GCGGTGGTGA TCTGGGTGAA

    GCAATTCGTG AAAGTCCGGA ACAGGCACGT CTGGCACTGA CCCTGGCAGC
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 7

The Fusion Protein of SEQ. No. 7

The protein of SEQ. No. 7 is a fusion having the length of 409 amino acids and the mass of 46.1 kDa, in which at the N-terminus of the sequence of TRAIL114-281 the sequence of granzyme B (SEQ. No. 34) is attached as an effector peptide. Between the sequence of TRAIL domain and the sequence of the effector peptide granzyme B there is the sequence of the furin cleavage site (SEQ. No. 53), additionally flanked by the flexible glycine-serine linkers GGGGS (SEQ. No. 59).

Structure of the fusion protein is shown schematically in FIG. 2 and its amino acid sequence and the DNA encoding sequence comprising codons optimized for expression in *E. coli* are, respectively, SEQ. No. 7 and SEQ. No. 73 as shown below.

```
Amino acid sequence:
                                                        SEQ. No. 7
  1 IIGGHVAKPH SRPYMAYLMI WDQKSLKRCG GFLIRDDFVL TAAHCWGSSI

 51 NVTLGAHNIK EQEPTQQFIP VKRAIPHPAY NPKNFSNDIM LLQLERKAKR

101 TRAVQPLRLP SNKAQVKPGQ TCSVAGWGQT APLGKHSHTL QEVKMTVQED

151 RKCESDLRHY YDSTIELCVG DPEIKKTSFK GDSGGPLVCN KVAQGIVSYG

201 RNNGMPPRAC TKVSSFVHWI KKTMKRYGGG GSRKKRGGGG SVRERGPQRV

251 AAHITGTRGR SNTLSSPNSK NEKALGRKIN SWESSRSGHS FLSNLHLRNG

301 ELVIHEKGFY YIYSQTYFRF QEEIKENTKN DKQMVQYIYK YTSYPDPILL

351 MKSARNSCWS KDAEYGLYSI YQGGIFELKE NDRIFVSVTN EHLIDMDHEA

401 SFFGAFLVG

DNA sequence:
                                                        SEQ. No. 73
  1 CGTGTTGCAG CACATATTAC CGGCACCCGT GGTCGTAGCA ATACCCTGAG

    CAGCCCGAAT AGCAAAAATG AAAAAGCCCT GGGTCGTAAA ATTAATAGCT

101 GGGAAAGCAG CCGTAGCGGT CATAGCTTTC TGAGCAATCT GCATCTGCGT

    AATGGCGAAC TGGTGATTCA TGAAAAAGGC TTTTATTATA TTTATAGCCA

201 GACCTATTTT CGCTTTCAGG AAGAAATTAA AGAAAATACC AAAAATGATA

    AACAAATGGT GCAGTATATC TATAAATATA CCAGCTATCC GGATCCGATT

301 CTGCTGATGA AAAGCGCACG TAATAGCTGT TGGAGCAAAG ATGCCGAATA

    TGGTCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTG GTAGCCGTAA

501 AAAACGTGGT GGTGGCGGTT CTATTATTGG TGGTCATGTT GCAAAACCGC

    ATAGCCGTCC GTATATGGCA TATCTGATGA TTTGGGATCA GAAAAGCCTG

601 AAACGTTGTG GTGGCTTTCT GATTCGTGAT GATTTTGTTC TGACCGCAGC

    ACATTGTTGG GGTAGCAGCA TTAATGTTAC CCTGGGTGCC CATAATATTA
```

-continued

```
701 AAGAACAGGA ACCGACCCAG CAGTTTATTC CGGTTAAACG TGCAATTCCG

    CATCCGGCAT ATAATCCGAA AAATTTTAGC AATGATATCA TGCTGCTGCA

801 GCTGGAACGT AAAGCAAAAC GTACCCGTGC AGTTCAGCCG CTGCGTCTGC

    CGAGCAATAA AGCACAGGTT AAACCGGGTC AGACCTGTAG CGTTGCAGGT

901 TGGGGTCAGA CCGCACCGCT GGGTAAACAT TCTCATACCC TGCAAGAGGT

    TAAAATGACC GTCCAAGAGG ATCGTAAATG CGAAAGCGAT CTGCGCCATT

1001 ATTATGATAG CACCATTGAA CTGTGTGTGG GCGATCCGGA AATCAAAAAA

     ACCAGCTTTA AAGGTGATAG CGGTGGTCCG CTGGTTTGTA ATAAAGTTGC

1101 CCAGGGTATT GTTAGCTATG GTCGTAATAA TGGTATGCCG CCGCGTGCAT

     GTACCAAAGT TAGCAGCTTT GTGCATTGGA TTAAAAAAAC GATGAAACGC

1201 TATAAAGATG AACTG
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 8

The Fusion Protein of SEQ. No. 8

The protein of SEQ. No. 8 is a fusion protein having the length of 405 amino acids and the mass of 45.7 kDa, in which at the C-terminus of TRAIL 121-281 sequence the sequence of granzyme B (SEQ. No. 34) is attached as an effector peptide. Between the sequence of TRAIL and the sequence of the effector peptide there is the sequence of furin cleavage site (SEQ. No. 53), additionally separated from the sequences of both granzyme B and TRAIL with flexible glycine-serine linkers GGGS (Sekw. Nr 58) and GGGGS (SEQ. No. 59), respectively. Furthermore, at the C-terminus of the effector peptide, the protein contains the sequence KDEL directing the endoplasmic reticulum, which is the C-terminal part of the entire construct.

Structure of the fusion protein is shown schematically in FIG. 2 and its amino acid sequence and the DNA encoding sequence comprising codons optimized for expression in *E. coli* are, respectively, SEQ. No. 8 and SEQ. No. 74 as shown below.

```
Amino acid sequence:
                                                      SEQ. No. 8
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGGSRKKRG GGGSIIGGHV AKPHSRPYMA YLMIWDQKSL

201 KRCGGFLIRD DFVLTAAHCW GSSINVTLGA HNIKEQEPTQ QFIPVKRAIP

251 HPAYNPKNFS NDIMLLQLER KAKRTRAVQP LRLPSNKAQV KPGQTCSVAG

301 WGQTAPLGKH SHTLQEVKMT VQEDRKCESD LRHYYDSTIE LCVGDPEIKK

351 TSFKGDSGGP LVCNKVAQGI VSYGRNNGMP PRACTKVSSF VHWIKKTMKR

401 YKDEL

DNA sequence:
                                                      SEQ. No. 74
  1 CGTGTTGCAG CACATATTAC CGGCACCCGT GGTCGTAGCA ATACCCTGAG

    CAGCCCGAAT AGCAAAAATG AAAAAGCACT GGGTCGCAAA ATTAATAGCT

101 GGGAAAGCAG CCGTAGCGGT CATAGCTTTC TGAGCAATCT GCATCTGCGT

    AATGGTGAAC TGGTGATTCA TGAAAAAGGC TTTTATTATA TTTATAGCCA

201 GACCTATTTT CGCTTTCAAG AAGAAATTAA AGAAAACACC AAAAATGATA

    AACAAATGGT GCAGTATATT TACAAATATA CCAGCTATCC GGATCCGATT
```

-continued

```
301 CTGCTGATGA AAAGCGCACG TAATAGCTGT TGGAGCAAAG ATGCAGAATA

    TGGTCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTG GTAGCCGTAA

501 AAAACGTGGT GGTGGCGGTA GTATTATTGG TGGTCATGTT GCAAAACCGC

    ATAGCCGTCC GTATATGGCA TATCTGATGA TTTGGGATCA GAAAAGCCTG

601 AAACGTTGTG GTGGTTTTCT GATTCGTGAT GATTTTGTTC TGACCGCAGC

    ACATTGTTGG GGTAGCAGCA TTAATGTTAC CCTGGGTGCC CATAATATTA

701 AAGAACAAGA ACCGACCCAG CAGTTTATTC CGGTTAAACG TGCAATTCCG

    CATCCGGCAT ATAATCCGAA AAATTTTAGC AATGATATTA TGCTGCTGCA

801 GCTGGAACGC AAAGCAAAAC GTACCCGTGC AGTTCAGCCG CTGCGTCTGC

    CGAGCAATAA AGCACAGGTT AAACCGGGTC AGACCTGTAG CGTTGCAGGT

901 TGGGGTCAGA CCGCACCGCT GGGTAAACAT TCACATACCC TGCAAGAGGT

    GAAAATGACC GTTCAAGAGG ATCGTAAATG CGAAAGCGAT CTGCGCCATT

1001 ATTATGATAG CACCATTGAA CTGTGTGTTG GTGATCCGGA AATTAAAAAA

    ACCAGCTTTA AAGGCGATAG CGGTGGTCCG CTGGTTTGTA ATAAAGTTGC

1101 ACAGGGTATT GTGAGCTATG GTCGTAATAA TGGTATGCCT CCGCGTGCAT

    GTACCAAAGT TAGCAGCTTT GTGCATTGGA TTAAAAAAAC GATGAAACGC

1201 TATAAAGATG AACTG
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) pLysS from Novagen. The protein was separated by electrophoresis in accordance with the general procedure described above.

EXAMPLE 9

The Fusion Protein of SEQ. No. 9

The protein of SEQ. No. 9 is a fusion protein having the length of 187 amino acids and the mass of 21.9 kDa, in which at the N-terminus of TRAIL121-281 sequence the 9-amino acid peptide derived from Nur77 protein (SEQ. No. 35) is attached as an effector peptide, the polyarginine sequence consisting of seven Arg residues being additionally attached at the C-terminus of the effector peptide. Between the effector peptide and the sequence of TRAIL there is a sequence of cleavage sites for metalloprotease MMP (SEQ. No. 51) and urokinase uPA (SEQ. No. 52).

Structure of the fusion protein is shown schematically in FIG. 2 and its amino acid sequence and the DNA encoding sequence comprising codons optimized for expression in *E. coli* are, respectively, SEQ. No. 9 and SEQ. No. 75 as shown below.

Amino acid sequence:

```
                                                    SEQ. No. 9
  1 FSRSLHSLLR RRRRRRRVVR PLGLAGRVAA HITGTRGRSN TLSSPNSKNE

 51 KALGRKINSW ESSRSGHSFL SNLHLRNGEL VIHEKGFYYI YSQTYFRFQE

101 EIKENTKNDK QMVQYIYKYT SYPDPILLMK SARNSCWSKD AEYGLYSIYQ

151 GGIFELKEND RIFVSVTNEH LIDMDHEASF FGAFLVG
```

DNA sequence:

```
                                                    SEQ. No. 75
  1 TTTAGCCGTA GCCTGCATAG CCTGCTGCGT CGTCGTCGTC GCCGTCGTCG

    TGTTGTTCGT CCGCTGGGTC TGGCAGGTCG TGTTGCAGCA CATATTACCG

101 GCACCCGTGG TCGTAGCAAT ACCCTGAGCA GCCCGAATAG CAAAAATGAA

    AAAGCCCTGG GTCGCAAAAT TAATAGCTGG GAAAGCAGCC GTAGCGGTCA
```

-continued

```
201 TAGCTTTCTG AGCAATCTGC ATCTGCGTAA TGGTGAACTG GTGATTCATG

    AAAAAGGCTT TTATTATATT TATAGCCAGA CCTATTTTCG CTTTCAGGAA

301 GAAATTAAAG AAAATACCAA AAATGATAAA CAAATGGTGC AGTACATTTA

    TAAATATACC AGCTATCCGG ATCCGATTCT GCTGATGAAA AGCGCACGTA

401 ATAGCTGTTG GAGCAAAGAT GCAGAATATG GCCTGTATAG CATTTATCAG

    GGTGGCATTT TTGAACTGAA AGAAAATGAT CGCATTTTTG TGAGCGTGAC

501 CAATGAACAT CTGATTGATA TGGATCATGA AGCCAGCTTT TTTGGTGCAT

    TTCTGGTGGG C
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Rosetta (DE3) from Novagen. The protein was separated by electrophoresis in accordance with the general procedure described above.

EXAMPLE 10

The Fusion Protein of SEQ. No. 10

The protein of SEQ. No. 10 is a fusion protein having the length of 193 amino acids and the mass of 22.4 kDa, in which at the N-terminus of the sequence TRAIL121-281 the 16-amino acid peptide containing the BH3 domain of Bak protein (SEQ. No. 36) is attached as an effector peptide, the membrane penetrating polyarginine sequence, consisting of seven Arg residues being additionally attached at the C-terminus of the effector peptide. Between the sequence of the effector peptide and the sequence of TRAIL there are sequences of the cleavage sites for metalloprotease MMP (SEQ. No. 51) and urokinase uPA (SEQ. No. 52).

Structure of the fusion protein is shown schematically in FIG. 2 and its amino acid sequence and the DNA encoding sequence comprising codons optimized for expression in *E. coli* are, respectively, SEQ. No. 10 and SEQ. No. 76 as shown below.

```
Amino acid sequence:
                                                    SEQ. No. 10
  1 GQVGRQLAII GDDINRRRRR RRRVVRPLGL AGRVAAHITG TRGRSNTLSS

 51 PNSKNEKALG RKINSWESSR SGHSFLSNLH LRNGELVIHE KGFYYIYSQT

101 YFRFQEEIKE NTKNDKQMVQ YIYKYTSYPD PILLMKSARN SCWSKDAEYG

151 LYSIYQGGIF ELKENDRIFV SVTNEHLIDM DHEASFFGAF LVG

DNA sequence:
                                                    SEQ. No. 76
  1 GGTCAGGTTG GTCGTCAGCT GGCAATTATT GGTGATGATA TTAACCGTCG

    TCGTCGTCGC CGTCGTCGTG TTGTTCGTCC GCTGGGTCTG GCAGGTCGTG

101 TTGCAGCACA TATTACCGGC ACCCGTGGTC GTAGCAATAC CCTGAGCAGC

    CCGAATAGCA AAAATGAAAA AGCCCTGGGT CGCAAAATTA ATAGCTGGGA

201 AAGCAGCCGT AGCGGTCATA GCTTTCTGAG CAATCTGCAT CTGCGTAATG

    GTGAACTGGT GATTCATGAA AAAGGCTTTT ATTATATTTA TAGCCAGACC

301 TATTTTCGCT TTCAGGAAGA AATTAAAGAA AATACCAAAA ATGATAAACA

    AATGGTGCAG TACATTTATA AATATACCAG CTATCCGGAT CCGATTCTGC

401 TGATGAAAAG CGCACGTAAT AGCTGTTGGA GCAAAGATGC AGAATATGGC

    CTGTATAGCA TTTATCAGGG TGGCATTTTT GAACTGAAAG AAAATGATCG

501 CATTTTTGTG AGCGTGACCA ATGAACATCT GATTGATATG GATCATGAAG

    CCAGCTTTTT TGGTGCATTT CTGGTGGGC
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strains BL21 (DE3) and Tuner (DE3) pLysS from Novagen. The protein was separated by electrophoresis in accordance with the general procedure described above

EXAMPLE 11

The Fusion Protein of SEQ. No. 11

The protein of SEQ. No. 11 is a fusion protein having the length of 204 amino acids and the mass of 24.3 kDa, in which at the N-terminus of the sequence of TRAIL 121-281 the BH3 domain of the PUMA/BBC3 molecule (SEQ. No. 37) is attached as an effector peptide, the polyarginine sequence comprising 9 Arg residues being additionally attached at the C-terminus of the effector peptide. Between sequence of the effector peptide and the sequence of TRAIL the construct contains also sequences of cleavage sites recognized by proteases uPA (SEQ. No. 52) and MMP (SEQ. No. 51).

Figure 3:
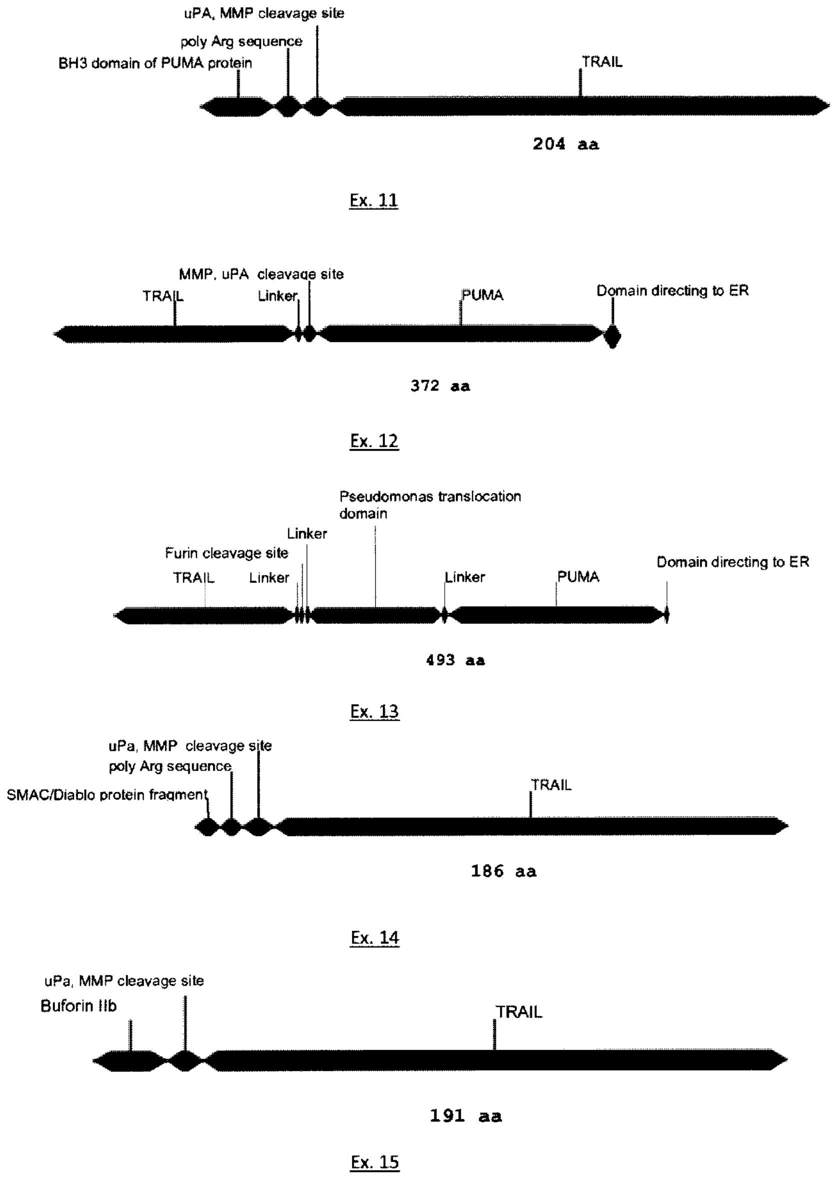
FIG. 3 presents a schematic structure of fusion proteins of the invention according to Ex. 11, Ex. 12, Ex. 13, Ex. 14 and Ex. 15.

Structure of the fusion protein is shown schematically in FIG. 3 and its amino acid sequence and the DNA encoding sequence comprising codons optimized for expression in *E. coli* are, respectively, SEQ. No. 11 and SEQ. No. 77 as shown below.

The amino acid sequence presented above was used as a template to generate to its coding DNA sequence presented above. A plasmid containing the coding sequence of DNA was generated and overexpression of the fusion protein was carried out in accordance with the general procedures described above. Overexpression was performed according to the general procedure A, using *E. coli* strains BL21 (DE3) and Tuner (DE3) pLysS from Novagen. The protein was separated by electrophoresis in accordance with the general procedure described above

EXAMPLE 12

The Fusion Protein of SEQ. No. 12

The protein of SEQ. No. 12 is a fusion protein having the length of 372 amino acids and the mass of 41 kDa, in which at the C-terminus of the sequence of TRAIL121-281 the PUMA protein (SEQ. No. 38) is attached as an effector peptide. Between the sequence of TRAIL the and the sequence of the effector peptide there is a sequence of cleavage sites recognized by metalloprotease MMP (SEQ. No. 51) and urokinase uPA (SEQ. No. 52), which additionally is separated from the sequence of TRAIL by the flexible glycine-serine linker GGSGG (SEQ. No. 60). Furthermore, at the C-terminus the effector peptide comprises the KEDL sequence (SEQ. No. 56) directing to the endoplasmic reticulum, and forming a C-terminal part of the entire construct.

Structure of the fusion protein is shown schematically in FIG. 3 and its amino acid sequence and the DNA encoding sequence comprising codons optimized for expression in *E. coli* are, respectively, SEQ. No. 12 and SEQ. No. 78 as shown below.

```
Amino acid sequence:
                                                  SEQ. No. 11
  1 EEQWAREIGA QLRRMADDLN AQYERRRRRR RRRRVVRPLG LAGRVAAHIT

 51 GTRGRSNTLS SPNSKNEKAL GRKINSWESS RSGHSFLSNL HLRNGELVIH

101 EKGFYYIYSQ TYFRFQEEIK ENTKNDKQMV QYIYKYTSYP DPILLMKSAR

151 NSCWSKDAEY GLYSIYQGGI FELKENDRIF VSVTNEHLID MDHEASFFGA

201 FLVG

DNA sequence:
                                                  SEQ. No. 77
  1 GAAGAACAGT GGGCACGTGA AATTGGTGCA CAGCTGCGTC GTATGGCAGA

    TGATCTGAAT GCACAGTATG AACGTCGTCG TCGTCGCCGT CGGCGTCGTC

101 GTGTTGTTCG TCCGCTGGGT CTGGCAGGTC GTGTTGCAGC ACATATTACC

    GGCACCCGTG GTCGTAGCAA TACCCTGAGC AGCCCGAATA GCAAAAATGA

201 AAAAGCACTG GGTCGCAAAA TCAATAGCTG GGAAAGCAGC CGTAGCGGTC

    ATAGCTTTCT GAGCAATCTG CATCTGCGTA ATGGTGAACT GGTGATTCAT

301 GAAAAAGGCT TTTATTATAT TTATAGCCAG ACCTATTTTC GCTTTCAAGA

    AGAGATTAAA GAAAATACCA AAAATGATAA ACAAATGGTG CAGTATATTT

401 ACAAATACAC CAGCTATCCG GACCCGATTC TGCTGATGAA AAGCGCACGT

    AATAGCTGTT GGAGCAAAGA TGCAGAATAT GGTCTGTATA GCATTTATCA

501 GGGTGGCATC TTTGAGCTGA AAGAAAATGA TCGCATCTTT GTTAGCGTGA

    CCAACGAACA TCTGATCGAT ATGGATCATG AAGCCAGCTT TTTTGGTGCA
```

Amino acid sequence:

SEQ. No. 12

```
  1 RVAAHITGTR GRSNTLSSPN SKNEKALGRK INSWESSRSG HSFLSNLHLR
 51 NGELVIHEKG FYYIYSQTYF RFQEEIKENT KNDKQMVQYI YKYTSYPDPI
101 LLMKSARNSC WSKDAEYGLY SIYQGGIFEL KENDRIFVSV TNEHLIDMDH
151 EASFFGAFLV GGGSGGPLGL AGRVVRARAR QEGSSPEPVE GLARDGPRPF
201 PLGRLVPSAV SCGLCEPGLA AAPAAPTLLP AAYLCAPTAP PAVTAALGGS
251 RWPGGPRSRP RGPRPDGPQP SLSLAEQHLE SPVPSAPGAL AGGPTQAAPG
301 VRGEEEQWAR EIGAQLRRMA DDLNAQYERR RQEEQQRHRP SPWRVLYNLI
351 MGLLPLPRGH RAPEMEPNKE DL
```

DNA sequence:

SEQ. No. 78

```
   1 CGTGTTGCAG CACATATTAC CGGCACCCGT GGTCGTAGCA ATACCCTGAG
     CAGCCCGAAT AGCAAAAATG AAAAAGCACT GGGTCGCAAA ATCAATAGCT
 101 GGGAAAGCAG CCGTAGCGGT CATAGCTTTC TGAGCAATCT GCATCTGCGT
     AATGGTGAAC TGGTGATTCA TGAAAAAGGC TTTTATTATA TTTATAGCCA
 201 GACCTATTTT CGCTTTCAAG AAGAGATTAA AGAAAATACC AAAAATGATA
     AACAAATGGT GCAGTACATT TACAAATATA CCAGCTATCC GGACCCGATT
 301 CTGCTGATGA AAAGCGCACG TAATAGCTGT TGGAGCAAAG ATGCAGAATA
     TGGTCTGTAT AGCATTTATC AGGGTGGCAT CTTTGAGCTG AAAGAAAATG
 401 ATCGCATCTT TGTTAGCGTG ACCAACGAAC ATCTGATCGA TATGGATCAT
     GAAGCCAGCT TTTTTGGTGC ATTTCTGGTT GGTGGTGGTA GCGGTGGTCC
 501 GCTGGGTCTG GCAGGTCGTG TTGTTCGTGC CCGTGCGCGT CAAGAAGGTA
     GCAGTCCGGA ACCGGTTGAA GGTCTGGCAC GTGATGGTCC GCGTCCGTTT
 601 CCGCTGGGTC GTCTGGTTCC GAGCGCAGTT AGCTGTGGTC TGTGTGAACC
     GGGTCTGGCA GCCGCACCGG CAGCACCGAC ACTGCTGCCT GCAGCATATC
 701 TGTGTGCACC GACCGCACCG CCTGCAGTTA CCGCAGCACT GGGTGGTAGC
     CGTTGGCCTG GTGGTCCGCG TAGTCGTCCG CGTGGTCCTC GTCCGGATGG
 801 TCCGCAGCCG AGCCTGAGCC TGGCAGAACA GCATCTGGAA AGTCCGGTGC
     CGAGCGCACC GGGTGCACTG GCAGGCGGTC CTACACAGGC AGCACCGGGT
 901 GTTCGTGGTG AAGAGGAACA GTGGGCACGT GAAATTGGTG CACAGCTGCG
     TCGTATGGCA GATGATCTGA ATGCACAGTA TGAACGTCGT CGTCAAGAAG
1001 AACAGCAGCG TCATCGTCCG AGCCCGTGGC GTGTTCTGTA TAATCTGATT
     ATGGGTCTGC TGCCGCTGCC TCGTGGTCAT CGTGCACCGG AAATGGAACC
1101 GAATAAAGAA GATCTG
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains B.21 (DE3) from Novagen i BL21DE3pLysSRIL from Stratagene. The protein was separated by electrophoresis in accordance with the general procedure described above.

EXAMPLE 13

The Fusion Protein of SEQ. No. 13

The protein of SEQ. No. 13 is a fusion protein having the length of 493 amino acids and the mass of 53.4 kDa, in which at the C-terminus of the 121-281 TRAIL the sequence of PUMA protein (SEQ. No. 38) is attached as an effector peptide. Furthermore, between the sequence of TRAIL and the sequence of PUMA protein there is a sequence of translocation domain from *Pseudomonas aeruginosa* (SEQ. No. 54), which is further separated from the sequence of TRAIL by consecutive sequences of: flexible glycine-serine linker GGGGS (SEQ. No. 59), furin cleavage site (SEQ. No. 53) and flexible alanine-glycine-serine linker ASGG (SEQ. No. 65), and from the PUMA protein by flexible glycine-serine linker GGSGG (SEQ. No. 60). Furthermore, at the C-terminus of the effector peptide the fusion protein contains the sequence KEDL (SEQ. No. 56) directing to the endoplasmic reticulum, which is the C-terminal part of the entire construct.

Structure of the fusion protein is shown schematically in FIG. 3 and its amino acid sequence and the DNA encoding sequence comprising codons optimized for expression in *E. coli* are, respectively, SEQ. No. 13 and SEQ. No. 79 as shown below.

```
Amino acid sequence:
                                                    SEQ. No. 13
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGGSRKKRA SGGPEGGSLA ALTAHQACHL PLETFTRHRQ

201 PRGWEQLEQC GYPVQRLVAL YLAARLSWNQ VDQVIANALA SPGSGGDLGE

251 AIRESPEQAR LALTLAAAES ERFVRQGTGN DEAGAANGPA DGGSGGGARA

301 RQEGSSPEPV EGLARDGPRP FPLGRLVPSA VSCGLCEPGL AAAPAAPTLL

351 PAAYLCAPTA PPAVTAALGG SRWPGGPRSR PRGPRPDGPQ PSLSLAEQHL

401 ESPVPSAPGA LAGGPTQAAP GVRGEEEQWA REIGAQLRRM ADDLNAQYER

451 RRQEEQQRHR PSPWRVLYNL IMGLLPLPRG HRAPEMEPNK DEL

DNA sequence:
                                                    SEQ. No. 79
   1 CGTGTTGCAG CACATATTAC CGGCACCCGT GGTCGTAGCA ATACCCTGAG

     CAGCCCGAAT AGCAAAAATG AAAAAGCACT GGGTCGCAAA ATTAATAGCT

 101 GGGAAAGCAG CCGTAGCGGT CATAGCTTTC TGAGCAATCT GCATCTGCGT

     AATGGTGAAC TGGTGATTCA TGAAAAAGGC TTTTATTATA TTTATAGCCA

 201 GACCTATTTT CGCTTTCAAG AAGAAATTAA AGAAAATACC AAAAATGATA

     AGCAGATGGT GCAGTATATC TATAAATATA CCAGCTATCC GGATCCGATT

 301 CTGCTGATGA AAAGCGCACG TAATAGCTGT TGGAGCAAAG ATGCAGAATA

     TGGTCTGTAT AGCATTTATC AGGGTGGCAT TTTTGAACTG AAAGAAAATG

 401 ATCGCATTTT TGTGAGCGTG ACCAATGAAC ATCTGATTGA TATGGATCAT

     GAAGCCAGCT TTTTTGGTGC ATTTCTGGTT GGTGGTGGTG GTAGCCGTAA

 501 AAAACGTGCA AGCGGTGGTC CGGAAGGTGG TAGCCTGGCA GCACTGACCG

     CACATCAGGC ATGTCATCTG CCGCTGGAAA CCTTTACCCG TCATCGTCAG

 601 CCTCGTGGTT GGGAACAGCT GGAACAGTGT GGTTATCCGG TTCAGCGTCT

     GGTTGCACTG TATCTGGCAG CACGTCTGAG CTGGAATCAG GTTGATCAGG

 701 TTATTGCAAA TGCACTGGCA AGTCCGGGTA GCGGTGGTGA TCTGGGTGAA

     GCAATTCGTG AAAGTCCGGA ACAGGCACGT CTGGCACTGA CCCTGGCAGC

 801 AGCAGAAAGC GAACGTTTTG TTCGTCAGGG CACCGGTAAT GATGAAGCCG

     GTGCAGCAAA TGGTCCGGCA GATGGTGGTA GTGGTGGTGG TGCACGTGCT

 901 CGTCAAGAAG GTAGCAGTCC GGAACCGGTT GAAGGTCTGG CACGTGACGG

     TCCGCGTCCG TTTCCGCTGG GTCGTCTGGT TCCGAGCGCA GTTAGCTGTG

1001 GTCTGTGTGA ACCGGGTCTG GCAGCCGCAC CGGCAGCACC GACACTGCTG

     CCTGCAGCAT ATCTGTGTGC ACCGACCGCA CCGCCTGCAG TTACCGCAGC

1101 ACTGGGTGGT AGTCGTTGGC CTGGTGGTCC GCGTAGTCGT CCGCGTGGTC

     CGCGTCCGGA TGGTCCGCAG CCGAGTCTGA GCCTGGCAGA ACAGCATCTG
```

-continued

```
1201 GAAAGTCCTG TGCCGAGCGC ACCGGGTGCA CTGGCAGGCG GTCCGACACA

     GGCAGCACCT GGTGTTCGTG GTGAAGAAGA ACAGTGGGCA CGCGAAATTG

1301 GTGCACAGCT GCGTCGTATG GCAGATGATC TGAATGCACA GTATGAACGT

     CGTCGTCAAG AAGAACAGCA GCGTCATCGT CCGAGCCCGT GGCGTGTTCT

1401 GTATAATCTG ATTATGGGTC TGCTGCCGCT GCCTCGTGGT CATCGTGCAC

     CGGAAATGGA ACCGAATAAA GATGAACTG
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains BL21 (DE3) from Novagen and BL21DE3pLysSRIL from Stratagene. The protein was separated by electrophoresis in accordance with the general procedure described above.

EXAMPLE 14

The Fusion Protein of SEQ. No. 14

The protein of SEQ. No. 14 is a fusion protein having the length of 186 amino acids and the mass of 21.5 kDa, in which at the N-terminus of the sequence TRAIL 121-281 the 8-amino acid fragment of the protein SMAC/Diablo (SEQ. No. 39) is attached as an effector peptide, the polyarginine sequence consisting of seven Arg residues being additionally attached to the C-terminus of the effector peptide. Furthermore, between the polyarginine sequence and the sequence of TRAIL the protein contains sequences of cleavage sites recognized by protease uPA (SEQ. No. 52) and MMP (SEQ. No. 51).

Structure of the fusion protein is shown schematically in FIG. 3 and its amino acid sequence and the DNA encoding sequence comprising codons optimized for expression in *E. coli* are, respectively, SEQ. No. 14 and SEQ. No. 80 as shown below.

```
Amino acid sequence:
                                                      SEQ. No. 14
  1AVPIAQKPRR RRRRRRVVRP LGLAGRVAAH ITGTRGRSNT LSSPNSKNEK

 51ALGRKINSWE SSRSGHSFLS NLHLRNGELV IHEKGFYYIY SQTYFRFQEE

101IKENTKNDKQ MVQYIYKYTS YPDPILLMKS ARNSCWSKDA EYGLYSIYQG

151GIFELKENDR IFVSVTNEHL IDMDHEASFF GAFLVG

DNA sequence:
                                                      SEQ. No. 80
  1GCAGTTCCGA TTGCACAGAA ACCGCGTCGT CGTCGTCGCC GTCGTCGTGT

   TGTTCGTCCG CTGGGTCTGG CAGGTCGTGT TGCAGCACAT ATTACCGGCA

101CCCGTGGTCG TAGCAATACC CTGAGCAGCC CGAATAGCAA AAATGAAAAA

   GCCCTGGGTC GCAAAATCAA TAGCTGGGAA AGCAGCCGTA GCGGTCATAG

201CTTTCTGAGC AATCTGCATC TGCGTAATGG TGAACTGGTG ATTCATGAAA

   AAGGCTTTTA CTATATCTAT AGCCAGACCT ACTTCCGCTT TCAGGAAGAA

301ATTAAAGAAA ATACCAAAAA TGATAAACAA ATGGTGCAGT ATATCTATAA

   ATATACCAGC TATCCGGATC CGATTCTGCT GATGAAAAGC GCACGTAATA

401GCTGTTGGAG CAAAGATGCA GAATATGGCC TGTATAGCAT TTATCAGGGT

   GGCATTTTTG AACTGAAAGA AAATGATCGC ATTTTTGTGA GCGTGACCAA

501TGAACATCTG ATTGATATGG ATCATGAAGC CAGCTTTTTT GGTGCATTTC

   TGGTGGGT
```

The amino acid sequence presented above was used as a template to generate its coding DNA sequence presented above. A plasmid containing the coding sequence of DNA was generated and overexpression of the fusion protein was ID carried out in accordance with the general procedures described above. Overexpression was performed according to the general procedure B, using *E. coli* strains BL21 (DE3) or Tuner (DE3) from Novagen. The protein was separated by electrophoresis in accordance with the general procedure described above.

EXAMPLE 15

The Fusion Protein of SEQ. No. 15

The protein of SEQ. No. 15 is a fusion protein having the length of 191 amino acids and the mass of 22.2 kDa, in which at the N-terminus of the sequence TRAIL 121-281 buforin IIb (SEQ. No. 40) is attached as an effector peptide. Furthermore, between the effector peptide and the sequence of TRAIL the protein contains sequences of cleavage sites recognized by proteases uPA (SEQ. No. 52) and MMP (SEQ. No. 51).

Structure of the fusion protein is shown schematically in FIG. 3 and its amino acid sequence and the DNA encoding sequence comprising codons optimized for expression in *E. coli* are, respectively, SEQ. No. 15 and SEQ. No. 81 as shown below.

```
Amino acid sequence:
                                                  SEQ. No. 15
  1 RAGLQFPVGR LLRRLLRRLL RVVRPLGLAG RVAAHITGTR GRSNTLSSPN

 51 SKNEKALGRK INSWESSRSG HSFLSNLHLR NGELVIHEKG FYYIYSQTYF

101 RFQEEIKENT KNDKQMVQYI YKYTSYPDPI LLMKSARNSC WSKDAEYGLY

151 SIYQGGIFEL KENDRIFVSV TNEHLIDMDH EASFFGAFLV G

DNA sequence:
                                                  SEQ. No. 81
  1 CGTGCAGGTC TGCAGTTTCC GGTTGGACGT CTGTTACGTC GCCTGCTGCG

    TCGTCTGCTG CGCGTTGTTC GTCCGCTGGG TCTGGCAGGT CGTGTTGCAG

101 CACATATTAC CGGCACCCGT GGTCGTAGCA ATACCCTGAG CAGCCCGAAT

    AGCAAAAATG AAAAAGCACT GGGTCGCAAA ATCAATAGCT GGGAAAGCAG

201 CCGTAGCGGT CATAGCTTTC TGAGCAATCT GCATCTGCGT AATGGTGAAC

    TGGTGATTCA TGAAAAAGGC TTTTATTATA TTTATAGCCA GACCTATTTT

301 CGCTTTCAAG AAGAGATTAA AGAAAATACC AAAAATGATA AACAAATGGT

    GCAGTACATT TACAAATATA CCAGCTATCC GGACCCGATT CTGCTGATGA

401 AAAGCGCACG TAATAGCTGT TGGAGCAAAG ATGCAGAATA TGGTCTGTAT

    AGCATTTATC AGGGTGGCAT CTTTGAGCTG AAAGAAAATG ATCGCATCTT

501 TGTTAGCGTG ACCAACGAAC ATCTGATCGA TATGGATCAT GAAGCCAGCT

    TTTTTGGTGC ATTTCTGGTG GGTCTGGTTC CGCGTGGTAG CGGTAGCAGC

601 CATCATCATC ATCACCATAG CAGCGGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 16

The Fusion Protein of SEQ. No. 16

The protein of SEQ. No. 16 is a fusion protein having the length of 279 amino acids and mass of 31.7 kDa, in which at the C-terminus of the TRAIL 121-281 sequence protein onconase (SEQ. No. 41) is attached as an effector peptide. Between the sequence of TRAIL and the sequence of the effector peptide there is a sequence of cleavage sites recognized by proteases MMP (SEQ. No. 51) and uPA (SEQ. No. 52), additionally separated from the sequence of TRAIL by the flexible glycine-serine linker GGGS (SEQ. No. 58).

Figure 4:
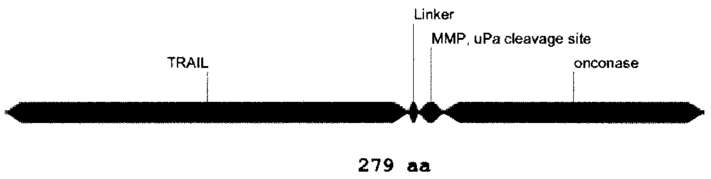
FIG. 4 presents a schematic structure of fusion proteins of the invention according to Ex. 16, Ex. 17, Ex. 18, Ex. 19 and Ex. 20.
Figure 4:
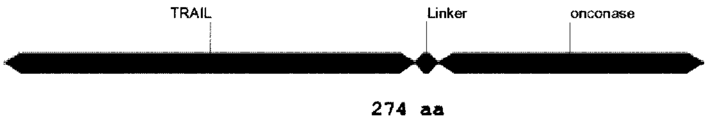
Figure 4:
Figure 4:
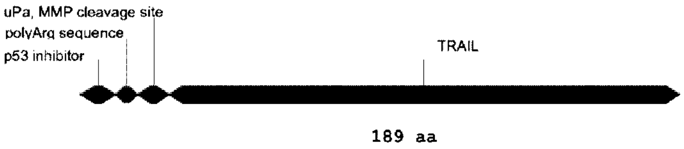
Figure 4:
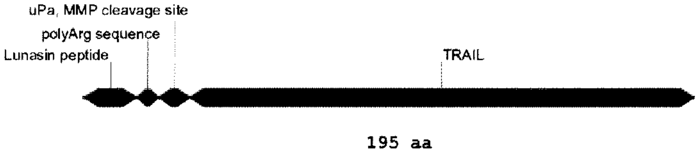

Structure of the fusion protein is shown schematically in FIG. 4 and its amino acid sequence and the DNA encoding sequence comprising codons optimized for expression in *E. coli* are, respectively, SEQ. No. 16 and SEQ. No. 82 as shown below.

```
Amino acid sequence:
                                                  SEQ. No. 16
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGSGPLGLA GRVVRQDWLT FQKKHITNTR DVDCDNIMST

201 NLFHCKDKNT FIYSRPEPVK AICKGIIASK NVLTTSEFYL SDCNVTSRPC

251 KYKLKKSTNK FCVTCENQAP VHFVGVGSC
```

-continued

DNA sequence:

SEQ. No. 82

```
  1 CGTGTTGCAG CACATATTAC CGGCACCCGT GGTCGTAGCA ATACCCTGAG
    CAGCCCGAAT AGCAAAAATG AAAAAGCACT GGGTCGCAAA ATTAATAGCT
101 GGGAAAGCAG CCGTAGCGGT CATAGCTTTC TGAGCAATCT GCATCTGCGT
    AATGGTGAAC TGGTGATTCA TGAAAAAGGC TTTTATTATA TTTATAGCCA
201 GACCTATTTT CGCTTTCAAG AAGAAATTAA AGAAAATACC AAAAATGATA
    AGCAGATGGT GCAGTATATC TATAAATATA CCAGCTATCC GGATCCGATT
301 CTGCTGATGA AAAGCGCACG TAATAGCTGT TGGAGCAAAG ATGCAGAATA
    TGGTCTGTAT AGCATTTATC AGGGTGGCAT TTTTGAACTG AAAGAAAATG
401 ATCGCATTTT TGTGAGCGTG ACCAATGAAC ATCTGATTGA TATGGATCAT
    GAAGCCAGCT TTTTTGGTGC ATTTCTGGTT GGTGGTGGTA GCGGTCCGCT
501 GGGTCTGGCA GGTCGTGTTG TTCGTCAGGA TTGGCTGACC TTTCAGAAAA
    AACATATTAC CAATACCCGT GATGTGGATT GCGATAATAT TATGAGCACC
601 AACCTGTTTC ATTGCAAAGA TAAAAATACC TTTATTTATA GCCGTCCGGA
    ACCGGTTAAA GCAATTTGTA AAGGTATTAT TGCCAGCAAA AATGTGCTGA
701 CCACGAGCGA ATTCTATCTG AGCGATTGTA ATGTTACCAG CCGTCCGTGT
    AAATATAAAC TGAAAAAAAG CACCAATAAA TTTTGCGTGA CCTGCGAAAA
801 TCAGGCACCG GTTCATTTTG TTGGTGTTGG TAGCTGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 17

The Fusion Protein of SEQ. No. 17

The protein of SEQ. No. 17 is a fusion protein having the length of 274 amino acids and the mass of 31 kDa, in which at the C-terminus of the TRAIL 121-281 sequence protein onconase (SEQ. No. 41) is attached as an effector peptide, the sequence of the effector peptide being additionally separated from the sequence of TRAIL by the flexible glycine-serine linker, GGGGSGGGGS (SEQ. No. 64).

Structure of the fusion protein is shown schematically in FIG. 4 and its amino acid sequence and the DNA encoding sequence comprising codons optimized for expression in *E. coli* are, respectively, SEQ. No. 17 and SEQ. No. 83 as shown below.

Amino acid sequence:

SEQ. No. 17

```
  1 RVAAHITGTR GRSNTLSSPN SKNEKALGRK INSWESSRSG HSFLSNLHLR
 51 NGELVIHEKG FYYIYSQTYF RFQEEIKENT KNDKQMVQYI YKYTSYPDPI
101 LLMKSARNSC WSKDAEYGLY SIYQGGIFEL KENDRIFVSV TNEHLIDMDH
151 EASFFGAFLV GGGGSGGGGS QDWLTFQKKH ITNTRDVDCD NIMSTNLFHC
201 KDKNTFIYSR PEPVKAICKG IIASKNVLTT SEFYLSDCNV TSRPCKYKLK
251 KSTNKFCVTC ENQAPVHFVG VGSC
```

DNA sequence:

SEQ. No. 83

```
  1 CGTGTTGCAG CACATATTAC CGGCACCCGT GGTCGTAGCA ATACCCTGAG
    CAGCCCGAAT AGCAAAAATG AAAAAGCACT GGGTCGCAAA ATTAATAGCT
101 GGGAAAGCAG CCGTAGCGGT CATAGCTTTC TGAGCAATCT GCATCTGCGT
    AATGGTGAAC TGGTGATTCA TGAAAAAGGC TTTTATTATA TTTATAGCCA
```

-continued

```
201GACCTATTTT CGCTTTCAAG AAGAAATTAA AGAAAATACC AAAAATGATA

   AGCAGATGGT GCAGTATATC TATAAATATA CCAGCTATCC GGATCCGATT

301CTGCTGATGA AAAGCGCACG TAATAGCTGT TGGAGCAAAG ATGCAGAATA

   TGGTCTGTAT AGCATTTATC AGGGTGGCAT TTTTGAACTG AAAGAAAATG

401ATCGCATTTT TGTGAGCGTG ACCAATGAAC ATCTGATTGA TATGGATCAT

   GAAGCCAGCT TTTTTGGTGC ATTTCTGGTT GGTGGTGGTG GTAGCGGTGG

501TGGTGGCAGC CAGGATTGGC TGACCTTTCA GAAAAAACAT ATTACCAATA

   CCCGTGATGT GGATTGCGAT AATATTATGA GCACCAACCT GTTTCATTGC

601AAAGATAAAA ATACCTTTAT TTATAGCCGT CCGGAACCGG TTAAAGCAAT

   TTGTAAAGGT ATTATTGCCA GCAAAAATGT GCTGACCACG AGCGAATTCT

701ATCTGAGCGA TTGTAATGTT ACCAGCCGTC CGTGTAAATA TAAACTGAAA

   AAAAGCACCA ATAAATTTTG CGTGACCTGC GAAAATCAGG CACCGGTTCA

801TTTTGTTGGT GTTGGTAGCT GT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 18

The Fusion Protein of SEQ. No. 18

The protein of SEQ. No. 18 is a fusion protein having the length of 197 amino acids and the mass of 23.2 kDa, in which at the N-terminus of the TRAIL 121-281 sequence a 20-amino acid peptide containing the N-terminal domain of the protein p14ARF (SEQ. No. 42) is attached as an effector peptide, the polyarginine sequence consisting of six Arg residues being additionally attached at the C-terminus of the effector peptide. Furthermore, between the polyarginine sequence and the sequence of TRAIL there is a sequence of protease cleavage sites uPA (SEQ. No. 52) and MMP (SEQ. No. 51).

Structure of the fusion protein is shown schematically in FIG. 4 and its amino acid sequence and the DNA encoding sequence comprising codons optimized for expression in *E. coli* are, respectively, SEQ. No. 18 and SEQ. No. 84 as shown below.

```
Amino acid sequence:
                                                   SEQ. No. 18
  1VRRFLVTLRI RRACGPPRVR RRRRRRRVVR PLGLAGRVAA HITGTRGRSN

 51TLSSPNSKNE KALGRKINSW ESSRSGHSFL SNLHLRNGEL VIHEKGFYYI

101YSQTYFRFQE EIKENTKNDK QMVQYIYKYT SYPDPILLMK SARNSCWSKD

151AEYGLYSIYQ GGIFELKEND RIFVSVTNEH LIDMDHEASF FGAFLVG

DNA sequence:
                                                   SEQ. No. 84
  1GTTCGTCGTT TTCTGGTTAC CCTGCGTATT CGTCGTGCAT GTGGTCCTCC

   GCGTGTGCGT CGTCGTCGTC GCCGTCGTCG TGTTGTTCGT CCTCTGGGTC

101TGGCAGGTCG CGTTGCAGCA CATATTACCG GCACCCGTGG TCGTAGCAAT

   ACCCTGAGCA GCCCGAATAG CAAAAATGAA AAAGCCCTGG GTCGCAAAAT

201TAATAGCTGG GAAAGCAGCC GTAGCGGTCA TAGCTTTCTG AGCAATCTGC

   ATCTGCGTAA TGGTGAACTG GTGATTCATG AAAAAGGCTT TTATTATATT

301TATAGCCAGA CCTATTTTCG CTTTCAGGAA GAAATTAAAG AAAATACCAA

   AAATGATAAA CAAATGGTGC AGTATATCTA TAAATATACC AGCTATCCGG

401ATCCGATTCT GCTGATGAAA AGCGCACGTA ATAGCTGTTG GAGCAAAGAT

   GCAGAATATG GCCTGTATAG CATTTATCAG GGTGGCATTT TTGAACTGAA
```

```
501 AGAAAATGAT CGCATTTTTG TGAGCGTGAC CAATGAACAT CTGATTGATA

    TGGATCATGA AGCCAGCTTT TTTGGTGCAT TTCTGGTTGG T
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 19

The Fusion Protein of SEQ. No. 19

The protein of SEQ. No. 19 is a fusion protein having the length of 189 amino acids and the mass of 22.3 kDa, in which at the N-terminus of the TRAIL 121-281 sequence the 11-amino acid peptide binding to Mdm2 (SEQ. No. 43) is attached as an effector peptide, the polyarginine sequence consisting of seven Arg residues being additionally attached at the C-terminus of the effector peptide. Furthermore, between the polyarginine sequence and the sequence of TRAIL there are sequences of cleavage sites recognized by proteases uPA (SEQ. No. 52) and MMP (SEQ. No. 51).

Structure of the fusion protein is shown schematically in FIG. 4 and its amino acid sequence and the DNA encoding sequence comprising codons optimized for expression in *E. coli* are, respectively, SEQ. No. 19 and SEQ. No. 85 as shown below.

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains BL21 (DE3) or Tuner (DE3) from Novagen. The protein was separated by electrophoresis in accordance with the general procedure described above.

EXAMPLE 20

The Fusion Protein of SEQ. No. 20

The protein of SEQ. No. 20 is a fusion protein having the length of 195 amino acids and the mass of 22.9 kDa, in which at the N-terminus of the TRAIL 121-281 sequence the peptide derived from lunasin (SEQ. No. 44) is attached as an effector peptide. Between the effector peptide and the sequence of TRAIL there are, in given order, the polyarginine sequence consisting of seven Arg residues and sequences of cleavage sites for proteases uPA (SEQ. No. 52) and MMP (SEQ. No. 51).

Structure of the fusion protein is shown schematically in FIG. 4 and its amino acid sequence and the DNA encoding sequence comprising codons optimized for expression in *E. coli* are, respectively, SEQ. No. 20 and SEQ. No. 86 as shown below.

```
Amino acid sequence:
                                                         SEQ. No. 19
  1 PRFMDTWEGL NRRRRRRRRV VRPLGLAGRV AAHITGTRGR SNTLSSPNSK

 51 NEKALGRKIN SWESSRSGHS FLSNLHLRNG ELVIHEKGFY YIYSQTYFRF

101 QEEIKENTKN DKQMVQYIYK YTSYPDPILL MKSARNSCWS KDAEYGLYSI

151 YQGGIFELKE NDRIFVSVTN EHLIDMDHEA SFFGAFLVG

DNA sequence:
                                                         SEQ. No. 85
  1 CCTCGTTTTA TGGATACCTG GGAAGGTCTG AATCGCCGTC GGCGTCGTCG

    GCGTCGTGTT GTTCGTCCGC TGGGTCTGGC AGGTCGTGTT GCAGCACATA

101 TTACCGGCAC CCGTGGTCGT AGCAATACCC TGAGCAGCCC GAATAGCAAA

    AATGAAAAAG CACTGGGTCG CAAAATTAAT AGCTGGGAAA GCAGCCGTAG

201 CGGTCATAGC TTTCTGAGCA ATCTGCATCT GCGTAATGGT GAACTGGTGA

    TTCATGAAAA AGGCTTTTAT TATATTTATA GCCAGACCTA TTTTCGCTTT

301 CAGGAAGAAA TTAAAGAAAA TACCAAAAAT GATAAACAAA TGGTGCAGTA

    CATTTACAAA TATACCAGCT ATCCGGATCC GATTCTGCTG ATGAAAAGCG

401 CACGTAATAG CTGTTGGAGC AAAGATGCAG AATATGGTCT GTATAGCATT

    TATCAGGGTG GCATTTTTGA ACTGAAAGAA AATGATCGCA TTTTTGTGAG

501 CGTGACCAAT GAACATCTGA TTGATATGGA TCATGAAGCC AGCTTTTTTG

    GTGCATTTCT GGTTGGT
```

```
Amino acid sequence:
                                                    SEQ. No. 20
  1 CEKHIMEKIQ GRGDDDDRRR RRRRRVVRPL GLAGRVAAHI TGTRGRSNTL

 51 SSPNSKNEKA LGRKINSWES SRSGHSFLSN LHLRNGELVI HEKGFYYIYS

101 QTYFRFQEEI KENTKNDKQM VQYIYKYTSY PDPILLMKSA RNSCWSKDAE

151 YGLYSIYQGG IFELKENDRI FVSVTNEHLI DMDHEASFFG AFLVG

DNA sequence:
                                                    SEQ. No. 86
  1 TGTGAAAAAC ATATTATGGA AAAAATTCAG GGTCGCGGTG ATGATGATGA

    TCGCCGTCGG CGTCGTCGGC GTCGTGTTGT TCGTCCGCTG GGTCTGGCAG

101 GTCGTGTTGC AGCACATATT ACCGGCACCC GTGGTCGTAG CAATACCCTG

    AGCAGCCCGA ATAGCAAAAA TGAAAAAGCA CTGGGTCGCA AAATTAATAG

201 CTGGGAAAGC AGCCGTAGCG GTCATAGCTT TCTGAGCAAT CTGCATCTGC

    GTAATGGTGA ACTGGTGATT CATGAAAAAG GCTTTTATTA TATTTATAGC

301 CAGACCTATT TTCGCTTTCA GGAAGAAATT AAAGAAAATA CCAAAAATGA

    TAAACAAATG GTGCAGTACA TTTACAAATA TACCAGCTAT CCGGATCCGA

401 TTCTGCTGAT GAAAAGCGCA CGTAATAGCT GTTGGAGCAA AGATGCAGAA

    TATGGTCTGT ATAGCATTTA TCAGGGTGGC ATTTTTGAAC TGAAAGAAAA

501 TGATCGCATT TTTGTGAGCG TGACCAATGA ACATCTGATT GATATGGATC

    ATGAAGCCAG CTTTTTTGGT GCATTTCTGG TTGGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains BL21 (DE3) or Tuner (DE3) from Novagen. The protein was separated by electrophoresis in accordance with the general procedure described above.

EXAMPLE 21

The Fusion Protein of SEQ. No. 21

The protein of SEQ. No. 21 is a fusion protein having the length of 218 amino acids and the mass of 25.5 kDa, in which at the N-terminus of the TRAIL 121-281 sequence there is attached as an effector peptide a fragment of the 8-amino acid protein Smac/Diablo (SEQ. No. 39) with attached to its C-terminus polyarginine sequence consisting of seven Arg residues. Furthermore, to the C-terminus of the TRAIL 121-281 sequence there is attached as a second effector peptide the peptide containing the BH3 domain of Bik protein (SEQ. No. 45), the second effector peptide having attached at its N-terminus polyarginine sequence consisting of seven Arg residues. Between the sequence of TRAIL and both effector peptides with attached polyarginine sequences there are sequences of cleavage sites recognized by metalloprotease MMP (SEQ. No. 51) and urokinase uPA (SEQ. No. 52).

Structure of the fusion protein is shown schematically in FIG. 4 and its amino acid sequence and the DNA encoding sequence comprising codons optimized for expression in *E. coli* are, respectively, SEQ. No. 21 and SEQ. No. 87 as shown below.

```
Amino acid sequence:
                                                    SEQ. No. 21
  1 AVPIAQKPRR RRRRRRVVRP LGLAGRVAAH ITGTRGRSNT LSSPNSKNEK

 51 ALGRKINSWE SSRSGHSFLS NLHLRNGELV IHEKGFYYIY SQTYFRFQEE

101 IKENTKNDKQ MVQYIYKYTS YPDPILLMKS ARNSCWSKDA EYGLYSIYQG

151 GIFELKENDR IFVSVTNEHL IDMDHEASFF GAFLVGPLGL AGRVVRRRRR

201 RRRLALRLAC IGDEMDVS

DNA sequence:
                                                    SEQ. No. 87
  1 GCAGTTCCGA TTGCACAGAA ACCGCGTCGT CGTCGTCGCC GTCGTCGTGT

    TGTTCGTCCT CTGGGTCTGG CAGGTCGCGT TGCAGCACAT ATTACCGGCA
```

-continued

```
101 CCCGTGGTCG TAGCAATACC CTGAGCAGCC CGAATAGCAA AAATGAAAAA

    GCCCTGGGTC GCAAAATTAA TAGCTGGGAA AGCAGCCGTA GCGGTCATAG

201 CTTTCTGAGC AATCTGCATC TGCGTAATGG TGAACTGGTG ATTCATGAAA

    AAGGCTTTTA TTATATTTAT AGCCAGACCT ATTTTCGCTT TCAGGAAGAA

301 ATTAAAGAAA ATACCAAAAA TGATAAACAA ATGGTGCAGT ATATCTATAA

    ATATACCAGC TATCCGGATC CGATTCTGCT GATGAAAAGC GCACGTAATA

401 GCTGTTGGAG CAAAGATGCA GAATATGGCC TGTATAGCAT TTATCAGGGT

    GGCATTTTTG AACTGAAAGA AAATGATCGC ATTTTTGTGA GCGTGACCAA

501 TGAACATCTG ATTGATATGG ATCATGAAGC CAGCTTTTTT GGTGCATTTC

    TGGTTGGTCC GCTGGGCCTG GCTGGCCGTG TGGTTCGCCG GCGCCGTCGC

601 CGTCGCCGCC TGGCACTGCG TCTGGCATGT ATTGGTGATG AAATGGATGT

    GAGC
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Rosetta (DE3) from Novagen. The protein was separated by electrophoresis in accordance with the general procedure described above.

EXAMPLE 22

The Fusion Protein of SEQ. No. 22

The protein of SEQ. No. 22 is a fusion protein having the length of 199 amino acids and the mass of 22.3 kDa, in which at the C-terminus of the TRAIL 121-281 sequence there is attached as an effector peptide the synthetic peptide sequence consisting of Gly, Ala repetitions (SEQ. No. 46), having also attached to its C-terminus the polyarginine sequence consisting of eight Arg residues, the latter forming also the C-terminal part of the entire construct. Furthermore, between the effector peptide and the sequence of TRAIL there is a sequence of cleavage sites recognized by metalloprotease MMP (SEQ. No. 51) and urokinase uPA (SEQ. No. 52).

Structure of the fusion protein is shown schematically in FIG. 4 and its amino acid sequence and the DNA encoding sequence comprising codons optimized for expression in *E. coli* are, respectively, SEQ. No. 22 and SEQ. No. 88 as shown below.

```
Amino acid sequence:
                                                    SEQ. No. 22
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GRVVRPLGLA GAGAGGGAGG AGAGGGAGGA GRRRRRRRR

DNA sequence:
                                                    SEQ. No. 88
  1 CGTGTTGCAG CACATATTAC CGGCACCCGT GGTCGTAGCA ATACCCTGAG

    CAGCCCGAAT AGCAAAAATG AAAAAGCACT GGGTCGCAAA ATTAATAGCT

101 GGGAAAGCAG CCGTAGCGGT CATAGCTTTC TGAGCAATCT GCATCTGCGT

    AATGGTGAAC TGGTGATTCA TGAAAAAGGC TTTTATTATA TTTATAGCCA

201 GACCTATTTT CGCTTTCAAG AAGAAATTAA AGAAAACACC AAAAATGATA

    AACAAATGGT GCAGTATATT TACAAATATA CCAGCTATCC GGATCCGATT

301 CTGCTGATGA AAAGCGCACG TAATAGCTGT TGGAGCAAAG ATGCAGAATA

    TGGTCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTG GTAGCGGTGG
```

-continued

```
501 TGGTCGTGTT GTTCGTCCGC TGGGTCTGGC TGGTGCCGGT GCCGGTGGTG

    GTGCAGGCGG TGCTGGTGCG GGTGGCGGAG CCGGTGGTGC AGGTCGTCGT

601 CGTCGCCGTC GTCGGCGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains BL21 (DE3) or Tuner (DE3) from Novagen. The protein was separated by electrophoresis in accordance with the general procedure described above.

EXAMPLE 23

The Fusion Protein of SEQ. No. 23

The protein of SEQ. No. 23 is a fusion protein having the length of 289 amino acids and the mass of 32.6 kDa, in which at the C-terminus of the 121-281 TRAIL sequence the C-terminal domain of the proteasome component S5a containing UIMs motifs (SEQ. No. 46) is attached as an effector peptide. Furthermore, between the effector peptide and the TRAIL sequence there is the sequence of furin cleavage site (SEQ. No. 53), additionally separated from the TRAIL sequence by flexible glycine-serine linker GGGSGG (SEQ. No. 61), and at the C-terminus of the effector peptide there is located the KEDL sequence directing to endoplasmic reticulum (SEQ. No. 56), the latter being the C-terminal part of the entire construct.

Figure 5:
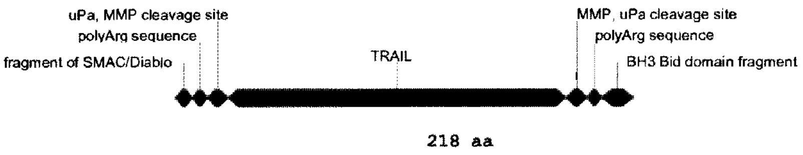
FIG. 5 presents a schematic structure of fusion proteins of the invention according to Ex. 21, Ex. 22, and Ex. 23, as well as comparative fusion proteins of Ex. 24, Ex. 25 and Ex. 26.
Figure 5:
Figure 5:
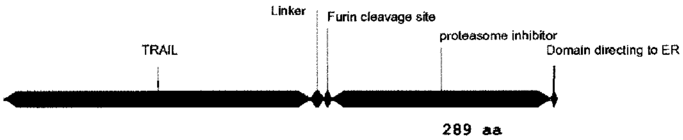
Figure 5:
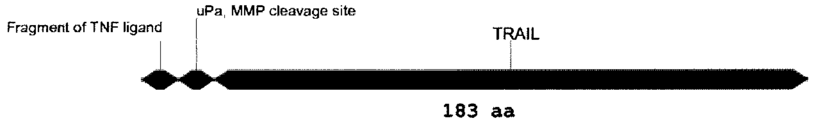
Figure 5:
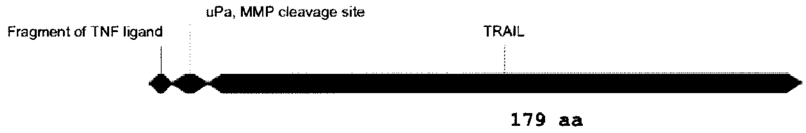
Figure 5:

Structure of the fusion protein is shown schematically in FIG. 5 and its amino acid sequence and the DNA encoding sequence comprising codons optimized for expression in *E. coli* are, respectively, SEQ. No. 23 and SEQ. No. 89 as shown below.

```
Amino acid sequence:
                                                        SEQ. No. 23
  1 RVAAHITGTR GRSNTLSSPN SKNEKALGRK INSWESSRSG HSFLSNLHLR

 51 NGELVIHEKG FYYIYSQTYF RFQEEIKENT KNDKQMVQYI YKYTSYPDPI

101 LLMKSARNSC WSKDAEYGLY SIYQGGIFEL KENDRIFVSV TNEHLIDMDH

151 EASFFGAFLV GGGGSGGRKK RMTISQQEFG RTGLPDLSSM TEEEQIAYAM

201 QMSLQGAEFG QAESADIDAS SAMDTSEPAK EEDDYDVMQD PEFLQSVLEN

251 LPGVDPNNEA IRNAMGSLAS QATKDGKKDK KEEDKKEDL

DNA sequence:
                                                        SEQ. No. 89
  1 CGTGTTGCAG CACATATTAC CGGCACCCGT GGTCGTAGCA ATACCCTGAG

    CAGCCCGAAT AGCAAAAATG AAAAAGCACT GGGTCGCAAA ATTAATAGCT

101 GGGAAAGCAG CCGTAGCGGT CATAGCTTTC TGAGCAATCT GCATCTGCGT

    AATGGTGAAC TGGTGATTCA TGAAAAAGGC TTTTATTATA TTTATAGCCA

201 GACCTATTTT CGCTTTCAAG AAGAAATTAA AGAAAACACC AAAAATGATA

    AACAAATGGT GCAGTATATT TACAAATATA CCAGCTATCC GGATCCGATT

301 CTGCTGATGA AAAGCGCACG TAATAGCTGT TGGAGCAAAG ATGCAGAATA

    TGGTCTGTAT AGCATTTATC AGGGTGGCAT TTTTGAACTG AAAGAAAATG

401 ATCGCATTTT TGTGAGCGTG ACCAATGAAC ATCTGATTGA TATGGATCAT

    GAAGCCAGCT TTTTTGGTGC ATTTCTGGTT GGTGGTGGTG GTAGCGGTGG

501 TCGTAAAAAA CGTATGACCA TTAGCCAGCA AGAATTTGGT CGTACCGGTC

    TGCCGGATCT GAGCAGCATG ACCGAAGAAG AACAAATTGC CTACGCAATG

601 CAGATGAGCC TGCAGGGTGC AGAATTTGGT CAGGCAGAAA GCGCAGATAT

    TGATGCAAGC AGCGCAATGG ATACCAGCGA ACCGGCAAAA GAAGAAGACG

701 ATTACGACGT TATGCAGGAT CCGGAATTTC TGCAGAGCGT TCTGGAAAAT

    CTGCCGGGTG TTGATCCGAA TAATGAAGCA ATTCGTAATG CAATGGGTAG

801 CCTGGCAAGC CAAGCAACCA AAGATGGCAA AAAAGATAAA AAAGAGGAAG

    ACAAAAAAGA AGATCTG
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure B, using *E. coli* strains BL21 (DE3) or Tuner (DE3) from Novagen. The protein was separated by electrophoresis in accordance with the general procedure described above.

EXAMPLE 24

The Fusion Protein of SEQ. No. 24 (Comparative)

The protein of SEQ. No. 24 is a fusion protein having the length of 183 amino acids and the mass of 21 kDa, in which at the N-terminus of the 119-281 TRAIL sequence the decapeptide derived from the TNF ligand (SEQ. No. 48) is attached as an effector peptide. Furthermore, between the sequence of the effector peptide and the sequence of TRAIL there are sequences of cleavage sites recognized by proteases uPA (SEQ. No. 52) and MMP (SEQ. No. 51).

Structure of the fusion protein is shown schematically in FIG. 5 and its amino acid sequence and the DNA encoding sequence comprising codons optimized for expression in *E. coli* are, respectively, SEQ. No. 24 and SEQ. No. 90 as shown below.

```
Amino acid sequence: SEQ. No. 24
  1    VANPQAEGQL RVVRPLGLAG PQRVAAHITG TRGRSNTLSS PNSKNEKALG

 51    RKINSWESSR SGHSFLSNLH LRNGELVIHE KGFYYIYSQT YFRFQEEIKE

101    NTKNDKQMVQ YIYKYTSYPD PILLMKSARN SCWSKDAEYG LYSIYQGGIF

151    ELKENDRIFV SVTNEHLIDM DHEASFFGAF LVG

DNA sequence: SEQ. No. 90
  1    GTTGCAAATC CGCAGGCAGA AGGTCAGCTG CGCGTTGTTC GTCCGCTGGG
       TCTGGCAGGT CCGCAGCGTG TTGCAGCACA TATTACCGGC ACCCGTGGTC

101    GTAGCAATAC CCTGAGCAGC CCGAATAGCA AAAATGAAAA AGCCCTGGGT
       CGTAAAATTA ATAGCTGGGA AAGCAGCCGT AGCGGTCATA GCTTTCTGAG

201    CAATCTGCAT CTGCGTAATG GCGAACTGGT GATTCATGAA AAAGGCTTTT
       ATTATATTTA TAGCCAGACC TATTTTCGCT TTCAGGAAGA AATTAAAGAA

301    AATACCAAAA ATGATAAACA AATGGTGCAG TATATCTATA AATATACCAG
       CTATCCGGAT CCGATTCTGC TGATGAAAAG CGCACGTAAT AGCTGTTGGA

401    GCAAAGATGC CGAATATGGT CTGTATAGCA TTTATCAGGG TGGCATTTTT
       GAACTGAAAG AAAATGATCG CATTTTTGTG AGCGTGACCA ATGAACATCT

501    GATTGATATG GATCATGAAG CCAGCTTTTT TGGTGCATTT CTGGTTGGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain BL21 (DE3) from Novagen. The protein was separated by electrophoresis in accordance with the general procedure described above.

EXAMPLE 25

The Fusion Protein of SEQ. No. 25 (Comparative)

The protein of SEQ. No. 25 is a fusion protein having the length of 179 amino acids and the mass of 20.7 kDa, in which at the N-terminus of the TRAIL 119-281 sequence the 6-amino acid peptide derived from TNF (SEQ. No. 49) is attached as an effector peptide. Furthermore, between the sequence of the effector peptide and the sequence of TRAIL there are sequences of cleavage sites recognized by proteases uPA (SEQ. No. 52) and MMP (SEQ. No. 51).

Structure of the fusion protein is shown schematically in FIG. 5 and its amino acid sequence and the DNA encoding sequence comprising codons optimized for expression in *E. coli* are, respectively, SEQ. No. 25 and SEQ. No. 91 as shown below.

Amino acid sequence:

SEQ. No. 25

```
  1 LANGVERVVR PLGLAGPQRV AAHITGTRGR SNTLSSPNSK NEKALGRKIN
 51 SWESSRSGHS FLSNLHLRNG ELVIHEKGFY YIYSQTYFRF QEEIKENTKN
101 DKQMVQYIYK YTSYPDPILL MKSARNSCWS KDAEYGLYSI YQGGIFELKE
151 NDRIFVSVTN EHLIDMDHEA SFFGAFLVG
```

DNA sequence:

SEQ. No. 91

```
  1 CTGGCAAATG GTGTTGAACG TGTTGTTCGT CCGCTGGGTC TGGCAGGTCC
    GCAGCGTGTT GCAGCACATA TTACCGGCAC CCGTGGTCGT AGCAATACCC
101 TGAGCAGCCC GAATAGCAAA AATGAAAAAG CCCTGGGTCG TAAAATTAAT
    AGCTGGGAAA GCAGCCGTAG CGGTCATAGC TTTCTGAGCA ATCTGCATCT
201 GCGTAATGGC GAACTGGTGA TTCATGAAAA AGGCTTTTAT TATATTTATA
    GCCAGACCTA TTTTCGCTTT CAGGAAGAAA TTAAAGAAAA TACCAAAAAT
301 GATAAACAAA TGGTGCAGTA TATCTATAAA TATACCAGCT ATCCGGATCC
    GATTCTGCTG ATGAAAAGCG CACGTAATAG CTGTTGGAGC AAAGATGCCG
401 AATATGGTCT GTATAGCATT TATCAGGGTG GCATTTTTGA ACTGAAAGAA
    AATGATCGCA TTTTTGTGAG CGTGACCAAT GAACATCTGA TTGATATGGA
501 TCATGAAGCC AGCTTTTTTG GTGCATTTCT GGTTGGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 26

The Fusion Protein of SEQ. No. 26 (Comparative)

The protein of SEQ. No. 26 is a fusion protein having the length of 180 amino acids and the mass of 20.8 kDa, in which at the N-terminus of the TRAIL119-281 sequence there is attached as an effector peptide the 5-amino acid fragment of the TNF cytokine (SEQ. No 50) with additional one Cys residue at its both C-terminus and N-terminus. Furthermore, between the sequence of the effector peptide and the sequence of TRAIL there are sequences of cleavage sites recognized by proteases uPA (SEQ. No. 52) and MMP (SEQ. No. 51).

Structure of the fusion protein is shown schematically in FIG. 5 and its amino acid sequence and the DNA encoding sequence comprising codons optimized for expression in *E. coli* are, respectively, SEQ. No. 26 and SEQ. No. 92 as shown below.

Amino acid sequence:

SEQ. No. 26

```
  1 CPSEGLCRVV RPLGLAGPQR VAAHITGTRG RSNTLSSPNS KNEKALGRKI
 51 NSWESSRSGH SFLSNLHLRN GELVIHEKGF YYIYSQTYFR FQEEIKENTK
101 NDKQMVQYIY KYTSYPDPIL LMKSARNSCW SKDAEYGLYS IYQGGIFELK
151 ENDRIFVSVT NEHLIDMDHE ASFFGAFLVG
```

DNA sequence:

SEQ. No. 92

```
  1 TGTCCGAGCG AAGGTCTGTG TCGTGTTGTT CGTCCGCTGG GTCTGGCAGG
    TCCGCAGCGT GTTGCAGCAC ATATTACCGG CACCCGTGGT CGTAGCAATA
101 CCCTGAGCAG CCCGAATAGC AAAAATGAAA AAGCCCTGGG TCGTAAAATT
    AATAGCTGGG AAAGCAGCCG TAGCGGTCAT AGCTTTCTGA GCAATCTGCA
201 TCTGCGTAAT GGCGAACTGG TGATTCATGA AAAAGGCTTT TATTATATTT
    ATAGCCAGAC CTATTTTCGC TTTCAGGAAG AAATTAAAGA AAATACCAAA
```

-continued

```
301 AATGATAAAC AAATGGTGCA GTATATCTAT AAATATACCA GCTATCCGGA

    TCCGATTCTG CTGATGAAAA GCGCACGTAA TAGCTGTTGG AGCAAAGATG

401 CCGAATATGG TCTGTATAGC ATTTATCAGG GTGGCATTTT TGAACTGAAA

    GAAAATGATC GCATTTTTGT GAGCGTGACC AATGAACATC TGATTGATAT

501 GGATCATGAA GCCAGCTTTT TTGGTGCATT TCTGGTTGGT
```

The amino acid sequence presented above was used as a template to generate its coding DNA sequence presented above. A plasmid containing the coding sequence of DNA was generated and overexpression of the fusion protein was carried out in accordance with the general procedures described above. Overexpression was performed according to the general procedure A, using *E. coli* strain Tuner (DE3) from Novagen. The protein was separated by electrophoresis in accordance with the general procedure described above.

EXAMPLE 27

The Fusion Protein of SEQ. No. 93

The protein of SEQ. No. 93 is a fusion protein having the length of 459 amino acids and the mass of 50.4 kDa, in which at the C-terminus of the TRAIL95-281 sequence there is attached as an effector peptide the full length human RNAse A (SEQ. No 32) flanked at its C-terminus by the sequence directing to endoplasmic reticulum (KDEL) and at its N-terminus by the flexible glycine-serine linker (SEQ No. 175). Additionally, to stabilize its trimeric structure, the sequence of TRAIL has attached at its N-terminus the polycysteine linker (SEQ. No. 179) flanked at its N-terminus by glycine residue. Furthermore, between the sequence of TRAIL and the sequence of the effector peptide and there are located in a given order the flexible glycine-serine linker (SEQ. No. 59), the linker for pegylation (SEQ. No. 170), the sequence of cleavage site recognized by furin (SEQ. No. 53), the flexible glycine-serine linker (SEQ No. 65) and the modified *Pseudomonas aeruginosa* translocation domain (helix F deletion) (SEQ. No 176).

Figure 6:
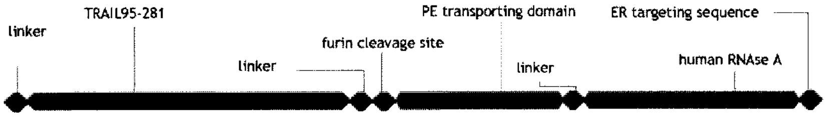
FIG. 6 presents a schematic structure of fusion proteins of the invention according to Ex. 27, Ex. 28, Ex. 29, Ex. 30 and Ex. 31.
Figure 6:
Figure 6:
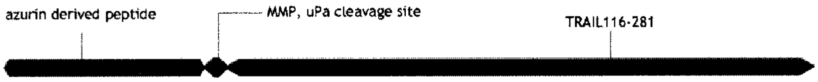
Figure 6:
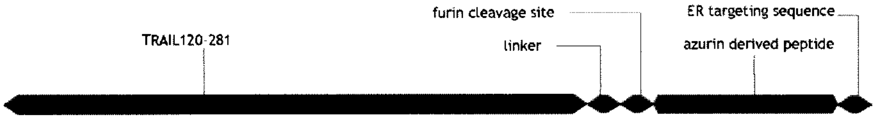
Figure 6:
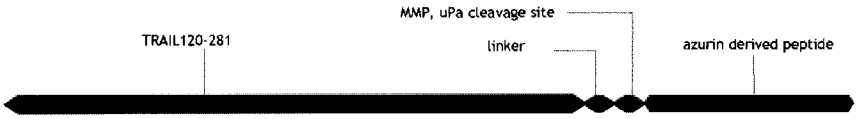

Structure of the fusion protein is shown schematically in FIG. 6 and its amino acid sequence and the DNA encoding sequence comprising codons optimized for expression in *E. coli* are, respectively, SEQ. No. 93 and SEQ. No. 122.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 28

The Fusion Protein of SEQ. No. 94

The protein of SEQ. No. 94 is a fusion protein having the length of 213 amino acids and the mass of 24.7 kDa, in which at the N-terminus of the TRAIL95-281 sequence the Nur77 derived peptide (SEQ. No 35) is attached as an effector peptide. The sequence of the effector peptide has attached at its N-terminus the poly-arginine transporting domain consisting of 7 Arg residues. Between the sequence of the effector peptide and the sequence of TRAIL there is a sequence of cleavage sites recognized by proteases MMP (SEQ. No. 51) and uPA (SEQ. No. 52).

Structure of the fusion protein is shown schematically in FIG. 6 and its amino acid sequence and the DNA encoding sequence comprising codons optimized for expression in *E. coli* are, respectively, SEQ. No. 93 and SEQ. No. 122.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 29

The fusion protein of SEQ. No. 95

The protein of SEQ. No. 95 is a fusion protein having the length of 204 amino acids and the mass of 23.1 kDa, in which at the N-terminus of the sequence of TRAIL116-281 the azurin derived peptide (SEQ. No 151) is attached as an effector peptide. Between the sequence of the effector peptide and the sequence of TRAIL there is located the sequence of cleavage sites recognized by proteases MMP (SEQ. No. 51) and uPA (SEQ. No. 52).

Structure of the fusion protein is shown schematically in FIG. 6 and its amino acid sequence and the DNA encoding sequence comprising codons optimized for expression in *E. coli* are, respectively, SEQ. No. 95 and SEQ. No. 124.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 30

The Fusion Protein of SEQ. No. 96

The protein of SEQ. No. 96 is a fusion protein having the length of 205 amino acids and the mass of 23.3 kDa, in which at the C-terminus of the sequence of TRAIL120-281 the azurin derived peptide (SEQ. No 151) is attached as an effector peptide. Furthermore, between the sequence of TRAIL and the sequence of the effector peptide there is a sequence of cleavage site recognized by furin protease (SEQ. No. 172), additionally separated from the TRAIL sequence by the flexible glycine-serine linker GGGS (SEQ. No. 58). The C-terminus of the effector peptide is flanked by the sequence KEDL directing to endoplasmic reticulum (SEQ. No. 56), which forms the C-terminal part of the entire construct.

Structure of the fusion protein is shown schematically in FIG. 6 and its amino acid sequence and the DNA encoding sequence comprising codons optimized for expression in *E. coli* are, respectively, SEQ. No. 96 and SEQ. No. 125.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 31

The Fusion Protein of SEQ. No. 97

The protein of SEQ. No. 97 is a fusion protein having the length of 207 amino acids and the mass of 23.1 kDa, in which at the C-terminus of the sequence of TRAIL120-281 the azurin derived peptide (SEQ. No 151) is attached as an effector peptide. Furthermore, between the sequence of TRAIL and the so sequence of the effector peptide there is located the sequence of cleavage sites recognized by proteases MMP (SEQ. No. 51) and uPA (SEQ. No. 52), additionally separated from the sequence of TRAIL by the flexible glycine-serine linker GGGSGGG (SEQ. No. 62).

Structure of the fusion protein is shown schematically in FIG. 6 and its amino acid sequence and the DNA encoding sequence comprising codons optimized for expression in *E. coli* are, respectively, SEQ. No. 97 and SEQ. No. 126.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 32

The Fusion Protein of SEQ. No. 98

The protein of SEQ. No. 97 is a fusion protein having the length of 327 amino acids and the mass of 36.2 kDa, in which at the C-terminus of the sequence of TRAIL120-281 the full length azurin peptide (SEQ. No 152) is attached as an effector peptide. Furthermore, between the sequence of TRAIL and the sequence of the effector peptide there is located the sequence of cleavage sites recognized by proteases MMP (SEQ. No. 51) and uPA (SEQ. No. 52), additionally separated from the sequence of TRAIL sequence by the flexible glycine-serine linker GGGSGGG (SEQ. No. 62).

Figure 7:
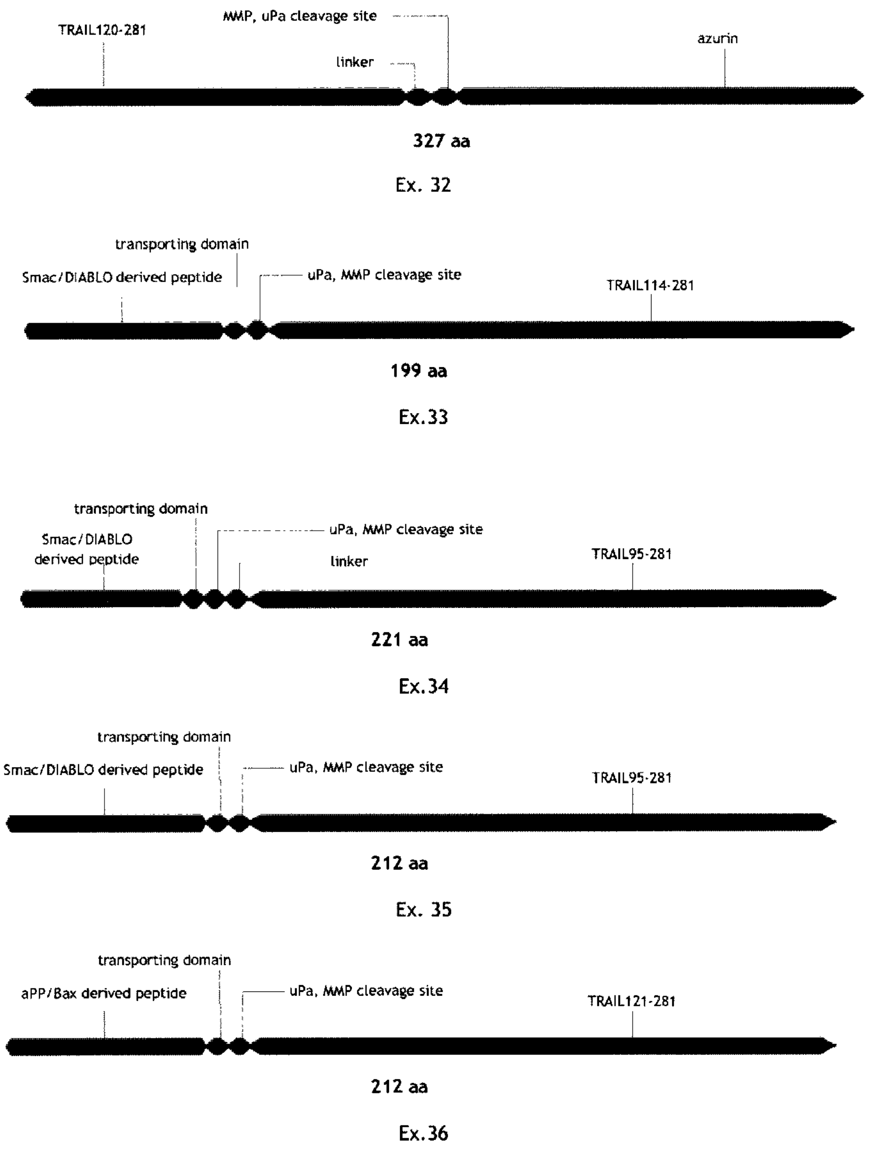
FIG. 7 presents a schematic structure of fusion proteins of the invention according to Ex. 32, Ex. 33, Ex. 34, Ex. 35 and Ex. 36.

Structure of the fusion protein is shown schematically in FIG. 7 and its amino acid sequence and the DNA encoding sequence comprising codons optimized for expression in *E. coli* are, respectively, SEQ. No. 98 and SEQ. No. 127.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 33

The Fusion Protein of SEQ. No. 99

The protein of SEQ. No. 99 is a fusion protein having the length of 199 amino acids and the mass of 22.9 kDa, in which at the N-terminus of the sequence of TRAIL114-281 the Smac/DIABLO derived octameric peptide (SEQ. No 39) is attached as an effector peptide. The sequence of the effector peptide has attached at its C-terminus the poly-arginine transporting domain consisting of 7 Arg residues. Furthermore, between the sequence of TRAIL and the sequence of the effector peptide there is located the sequence of cleavage sites recognized by proteases uPA (SEQ. No. 52) and MMP (SEQ. No. 51).

Structure of the fusion protein is shown schematically in FIG. 7 and its amino acid sequence and the DNA encoding sequence comprising codons optimized for expression in *E. coli* are, respectively, SEQ. No. 99 and SEQ. No. 128.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 34

The Fusion Protein of SEQ. No. 100

The protein of SEQ. No. 100 is a fusion protein having the length of 221 amino acids and the mass of 25.2 kDa, in which at the N-terminus of the sequence of TRAIL95-281 the Smac/DIABLO derived octameric peptide (SEQ. No 39) is attached as an effector peptide. The sequence of TRAIL has attached at its N-terminus the polycysteine linker (SEQ. No. 177) for stabilizing its trimeric structure. The sequence of the effector peptide has attached at its C-terminus the poly-arginine transporting domain consisting of 7 Arg residues. Furthermore, between the sequence of the effector peptide and the sequence of TRAIL there is located the sequence of cleavage sites recognized by proteases uPA (SEQ. No. 52) and MMP (SEQ. No. 51).

Structure of the fusion protein is shown schematically in FIG. 7 and its amino acid sequence and the DNA encoding sequence comprising codons optimized for expression in *E. coli* are, respectively, SEQ. No. 100 and SEQ. No. 129.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 35

The Fusion Protein of SEQ. No. 101

The protein of SEQ. No. 101 is a fusion protein having the length of 212 amino acids and the mass of 24.5 kDa, in which at the N-terminus of the sequence of TRAIL95-281 the Smac/DIABLO derived octameric peptide (SEQ. No 39) is attached as an effector peptide. The sequence of the effector peptide has attached at its C-terminus the poly-arginine transporting domain consisting of 7 Arg residues. Furthermore, between the sequence of TRAIL and the sequence of the effector peptide there is located the sequence of cleavage sites recognized by proteases uPA (SEQ. No. 52) and MMP (SEQ. No. 51).

Structure of the fusion protein is shown schematically in FIG. 7 and its amino acid sequence and the DNA encoding sequence comprising codons optimized for expression in *E. coli* are, respectively, SEQ. No. 101 and SEQ. No. 130.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 36

The Fusion Protein of SEQ. No. 102

The protein of SEQ. No. 102 is a fusion protein having the length of 212 amino acids and the mass of 24.5 kDa, in which at the N-terminus of the sequence of TRAIL121-281 the peptide designed from aPP protein and BH3 domain of Bax protein (SEQ. No 153) is attached as an effector peptide. The sequence of the effector peptide has attached at its C-terminus the poly-arginine transporting domain consisting of 6 Arg residues. Furthermore, between the sequence of TRAIL and the sequence of the effector peptide there are located the sequences of cleavage sites recognized by proteases uPA (SEQ. No. 52) and MMP (SEQ. No. 51).

Structure of the fusion protein is shown schematically in FIG. 7 and its amino acid sequence and the DNA encoding sequence comprising codons optimized for expression in *E. coli* are, respectively, SEQ. No. 102 and SEQ. No. 131.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 37

The Fusion Protein of SEQ. No. 103

The protein of SEQ. No. 103 is a fusion protein having the length of 247 amino adds and the mass of 28.1 kDa, in which at the N-terminus of the sequence of TRAIL95-281 the peptide designed from aPP protein and BH3 domain of Bax protein (SEQ. No 153) is attached as an effector peptide. The sequence of the effector peptide has attached at its C-terminus the poly-arginine transporting domain consisting of 6 Arg residues. The sequence of TRAIL has attached at its N-terminus the polycysteine linker (SEQ. No. 177) to stabilize its trimeric structure. Furthermore, between the sequence of the effector peptide and the sequence of TRAIL there is located the sequence of cleavage sites recognized by proteases uPA (SEQ. No. 52) and MMP (SEQ. No. 51).

Figure 8:
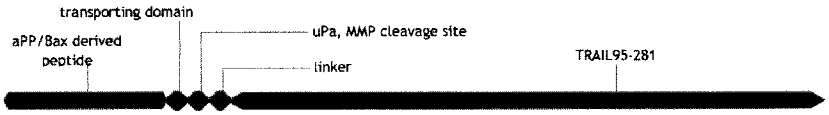
FIG. 8 presents a schematic structure of fusion proteins of the invention according to Ex. 37, Ex. 38, Ex. 39, Ex. 40 and Ex. 41.
Figure 8:
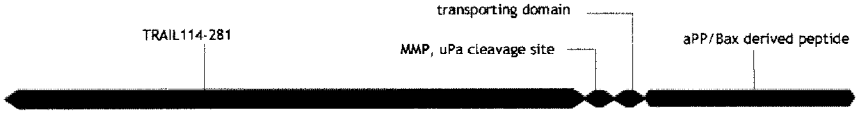
Figure 8:
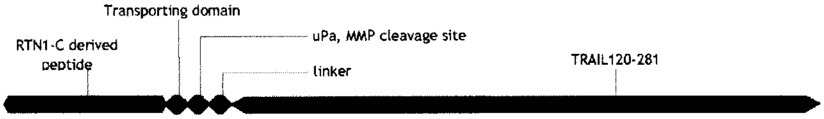
Figure 8:
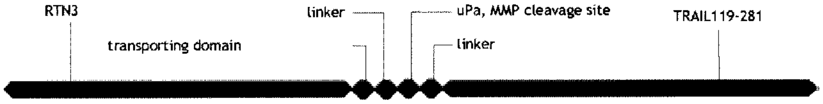
Figure 8:
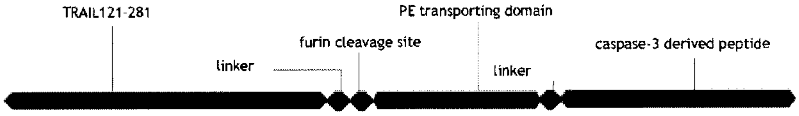

Structure of the fusion protein is shown schematically in FIG. 8 and its amino acid sequence and the DNA encoding sequence comprising codons optimized for expression in *E. coli* are, respectively, SEQ. No. 103 and SEQ. No. 132.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 38

The Fusion Protein of SEQ. No. 104

The protein of SEQ. No. 104 is a fusion protein having the length of 212 amino acids and the mass of 24.4 kDa, in which at the C-terminus of the sequence of TRAIL114-281 the peptide designed from aPP protein and BH3 domain of Bax protein (SEQ. No 153) is attached as an effector peptide. Furthermore, between the sequence of TRAIL and the sequence of the effector peptide there is located the sequence of cleavage sites recognized by proteases MMP (SEQ. No. 51) and uPA (SEQ. No. 52).

Structure of the fusion protein is shown schematically in FIG. 8 and its amino acid sequence and the DNA encoding sequence comprising codons optimized for expression in *E. coli* are, respectively, SEQ. No. 104 and SEQ. No. 133.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 39

The Fusion Protein of SEQ. No. 105

The protein of SEQ. No. 105 is a fusion protein having the length of 221 amino acids and the mass of 24.8 kDa, in which at the N-terminus of the sequence of TRAIL120-281 Reticulon RTN1-C derived peptide (SEQ. No 155) is attached as an effector peptide. The sequence of the effector peptide has attached at its C-terminus the nucleus localizing sequence (SEQ. No. 168). Additionally, to stabilize its trimeric structure, the sequence of TRAIL has attached at its N-terminus the polycysteine linker (SEQ. No. 179) flanked by two and three glycine residues, respectively at its N- and C-terminus. Furthermore, between the sequence of the effector peptide and the sequence of TRAIL there is located the sequence of cleavage sites recognized by proteases uPA (SEQ. No. 52) and MMP (SEQ. No. 51).

Structure of the fusion protein is shown schematically in FIG. 8 and its amino acid sequence and the DNA encoding sequence comprising codons optimized for expression in *E. coli* are, respectively, SEQ. No. 105 and SEQ. No. 134.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 40

The Fusion Protein of SEQ. No. 106

The protein of SEQ. No. 106 is a fusion protein having the length of 435 amino acids and the mass of 48 kDa, in which at the N-terminus of the sequence of TRAIL119-281 the Reticulon RTN1-C derived peptide (SEQ. No 156) is attached as an effector peptide. The sequence of the effector peptide has attached at its C-terminus the poly-arginine transporting domain consisting of 8 Arg residues. Additionally, to stabilize its trimeric structure, the sequence of TRAIL has attached at its N-terminus the polycysteine linker (SEQ. No. 178). Furthermore, between the sequence of the effector peptide and the sequence of TRAIL there is located the sequence of cleavage sites recognized by proteases uPA (SEQ. No. 52) and MMP (SEQ. No. 51), this sequence of cleavage sites being flanked by a linker sequence GGSGG (SEQ. No. 60), respectively at the N- and C-terminus.

Structure of the fusion protein is shown schematically in FIG. 8 and its amino acid sequence and the DNA encoding sequence comprising codons optimized for expression in *E. coli* are, respectively, SEQ. No. 106 and SEQ. No. 135.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 41

The Fusion Protein of SEQ. No. 107

The protein of SEQ. No. 107 is a fusion protein having the length of 580 amino acids and the mass of 65 kDa, in which at the C-terminus of the sequence of TRAIL121-281 constitutively active caspase-3 (single chain) (SEQ. No 157) is attached as an effector peptide. Furthermore, between the sequence of TRAIL and the sequence of the effector peptide there is located the transporting domain derived from *Pseudomonas* (SEQ No. 176). The transporting domain and the sequence of the effector peptide are connected via flexible linker GGGSGGG (SEQ. No. 62). The transporting domain is separated from the sequence of TRAIL by the sequence of the cleavage site recognized by furin (SEQ. No. 53), this sequence of cleavage site being flanked at its N- and C-terminus by two linker sequences GGGGS (SEQ. No. 59) and ASGG (SEQ. No. 65), respectively.

Structure of the fusion protein is shown schematically in FIG. 8 and its amino acid sequence and the DNA encoding sequence comprising codons optimized for expression in *E. coli* are, respectively, SEQ. No. 107 and SEQ. No. 136.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 42

The Fusion Protein of SEQ. No. 108

The protein of SEQ. No. 108 is a fusion protein having the length of 247 amino acids and the mass of 28.5 kDa, in which at the N-terminus of the sequence of TRAIL119-281 SAC domain from Par-4 (SEQ. No 158) is attached as an effector peptide. The sequence of the effector peptide has attached at its C-terminus the poly-arginine transporting domain consisting of 7 Arg residues. Additionally, the sequence of TRAIL has attached at its N-terminus the flexible glycine-serine linker GGSGG (SEQ. No. 60). Furthermore, between the sequence of TRAIL and sequence of the effector peptide there is located the sequence of cleavage sites recognized by proteases uPA (SEQ. No. 52) and MMP (SEQ. No. 173).

Figure 9:
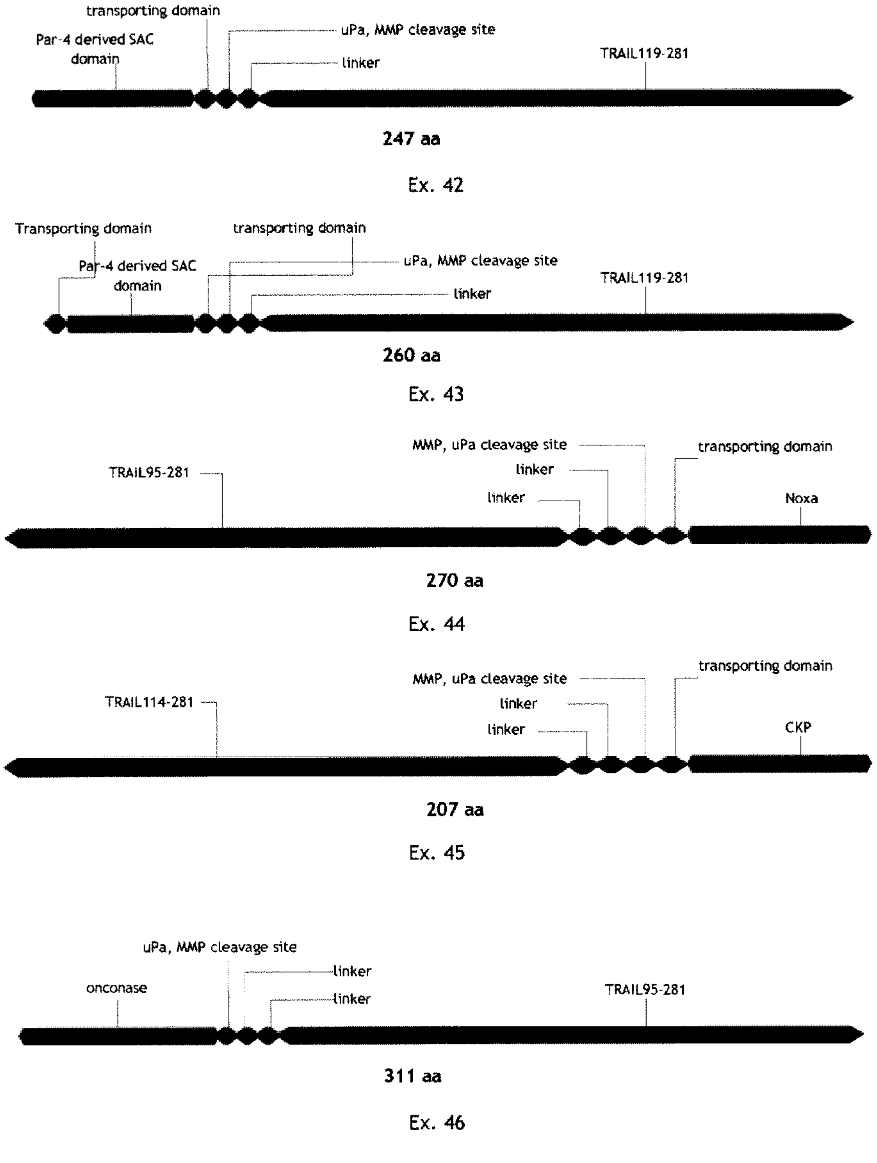
FIG. 9 presents a schematic structure of fusion proteins of the invention according to Ex. 42, Ex. 43, Ex. 44, Ex. 45 and Ex. 46.

Structure of the fusion protein is shown schematically in FIG. 9 and its amino acid sequence and the DNA encoding sequence comprising codons optimized for expression in *E. coli* are, respectively, SEQ. No. 108 and SEQ. No. 137.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 43

The Fusion Protein of SEQ. No. 109

The protein of SEQ. No. 109 is a fusion protein having the length of 247 amino acids and the mass of 28.5 kDa, in which at the N-terminus of the sequence of TRAIL119-281 the SAC domain from Par-4 (SEQ. No 158) is attached as an effector peptide. The sequence of the effector peptide has attached at its C-terminus the poly-arginine transporting domain consisting of 7 Arg residues, and at its N-terminus the NLS (Nuclear Localization Signal) sequence from Oct6 transcription factor (SEQ. No. 168). The sequence of TRAIL has attached at its N-terminus the flexible glycine-serine linker GGSGG (SEQ. No. 60). Furthermore, between the sequence of the effector peptide and the sequence of TRAIL there is located the sequence of cleavage sites recognized by proteases uPA (SEQ. No. 52) and MMP (SEQ. No. 173).

Structure of the fusion protein is shown schematically in FIG. 9 and its amino acid sequence and the DNA encoding sequence comprising codons optimized for expression in *E. coli* are, respectively, SEQ. No. 109 and SEQ. No. 138.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 44

The Fusion Protein of SEQ. No. 110

The protein of SEQ. No. 110 is a fusion protein having the length of 270 amino acids and the mass of 30.8 kDa, in which at the C-terminus of the sequence of TRAIL95-281 Noxa protein (SEQ. No 159) is attached as an effector peptide. The sequence of the effector peptide has attached at its N-terminus the poly-arginine transporting domain consisting of 7 Arg residues. Additionally, to stabilize its trimeric structure, the sequence of TRAIL has attached at its C-terminus the polycysteine linker (SEQ. No. 177), separated from the sequence of TRAIL by the flexible glycine-serine linker GGSG (SEQ. No. 57). Furthermore, between the sequence of TRAIL and the sequence of the effector peptide there is located the sequence of cleavage sites recognized by proteases MMP (SEQ. No. 51) and uPA (SEQ. No. 52).

Structure of the fusion protein is shown schematically in FIG. 9 and its amino acid sequence and the DNA encoding sequence comprising codons optimized for expression in *E. coli* are, respectively, SEQ. No. 110 and SEQ. No. 139.

The amino acid sequence of the structure described above was used as template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 45

The Fusion Protein of SEQ. No. 111

The protein of SEQ. No. 111 is a fusion protein having the length of 207 amino acids and the mass of 23.7 kDa, in which at the C-terminus of the sequence of TRAIL114-281 the MTD/CKP peptide derived from Noxa protein (SEQ. No 160) is attached as an effector peptide. The sequence of the effector peptide has attached at its N-terminus the poly-arginine transporting domain consisting of 7 Arg residues. To stabilize its trimeric structure, the sequence of TRAIL has attached at its C-terminus the polycysteine linker (SEQ. No. 177), this linker being separated from the sequence of TRAIL by the flexible glycine-serine linker GGSG (SEQ. No. 57). Furthermore, between the sequence of TRAIL and the sequence of the effector peptide there is located the sequence of cleavage sites recognized by proteases MMP (SEQ. No. 51) and uPA (SEQ. No. 52).

Structure of the fusion protein is shown schematically in FIG. 9 and its amino acid sequence and the DNA encoding sequence comprising codons optimized for expression in *E. coli* are, respectively, SEQ. No. 111 and SEQ. No. 140.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 46

The Fusion Protein of SEQ. No. 112

The protein of SEQ. No. 112 is a fusion protein having the length of 311 amino acids and the mass of 35 kDa, in which at the N-terminus of the sequence of TRAIL95-281 peptide onconase (SEQ. No 41) is attached as an effector peptide. Furthermore, between the sequence of the effector peptide and the sequence of TRAIL there is located the sequence of cleavage sites recognized by proteases uPA (SEQ. No. 52) and MMP (SEQ. No. 51), additionally separated from the sequence of TRAIL by two flexible glycine-serine linkers GGGGS (SEQ. No. 59).

Structure of the fusion protein is shown schematically in FIG. 9 and its amino acid sequence and the DNA encoding sequence comprising codons optimized for expression in *E. coli* are, respectively, SEQ. No. 112 and SEQ. No. 141.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 47

The Fusion Protein of SEQ. No. 113

The protein of SEQ. No. 113 is a fusion protein having the length of 230 amino so acids and the mass of 27 kDa, in which at the N-terminus of the sequence of TRAIL95-281 BH3 domain from PUMA protein (SEQ. No 37) is attached as an effector peptide. The sequence of the effector peptide has attached at its C-terminus the poly-arginine transporting domain consisting of 9 Arg residues. Furthermore, between the sequence of TRAIL and the sequence of the effector peptide there is located the sequence of cleavage sites recognized by proteases uPA (SEQ. No. 52) and MMP (SEQ. No. 51).

Figure 10:
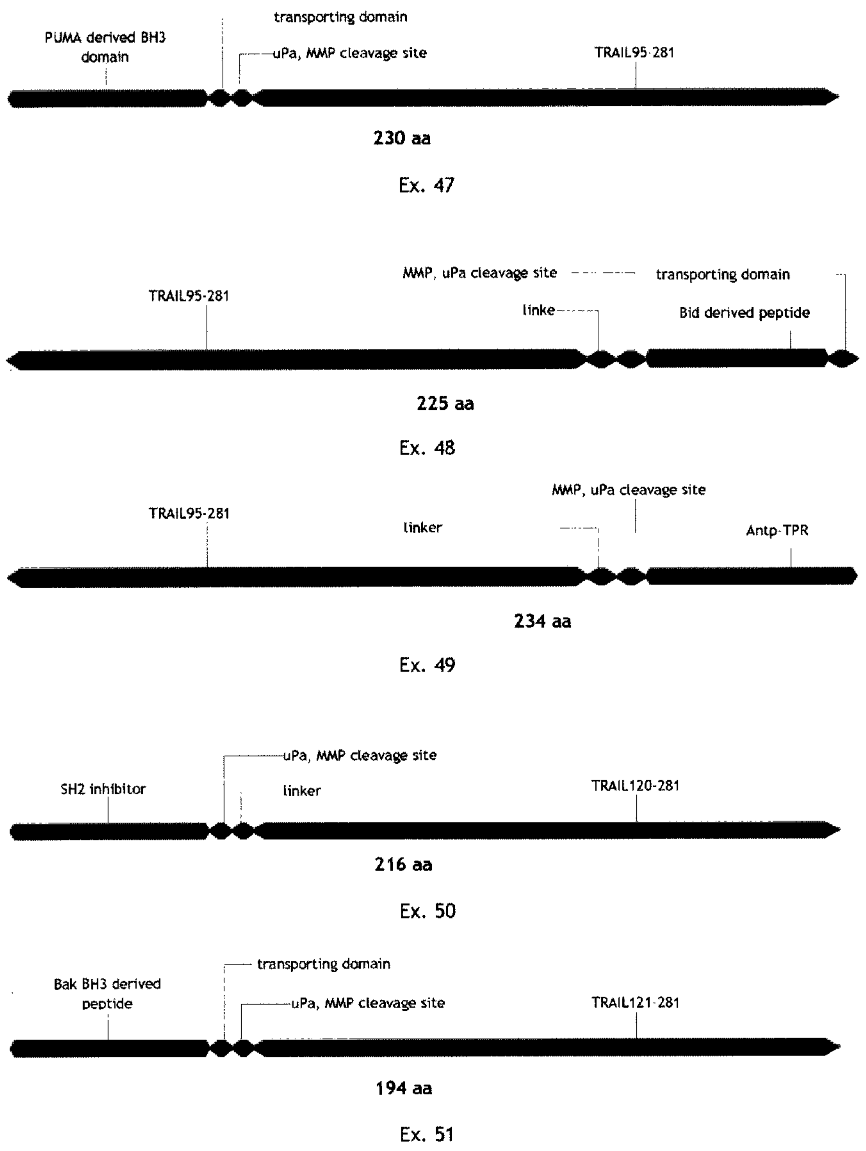
FIG. 10 presents a schematic structure of fusion proteins of the invention according Ex. 47, Ex. 48, Ex. 49, Ex. 50 and Ex. 51.

Structure of the fusion protein is shown schematically in FIG. 10 and its amino acid sequence and the DNA encoding sequence comprising codons optimized for expression in *E. coli* are, respectively, SEQ. No. 113 and SEQ. No. 142.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 48

The Fusion Protein of SEQ. No. 114

The protein of SEQ. No. 114 is a fusion protein having the length of 225 amino acids and the mass of 25.7 kDa, in which at the C-terminus of the sequence of TRAIL95-281 the short peptide derived from Bid protein (SEQ. No 31) is attached as an effector peptide. The sequence of the effector peptide has attached at its C-terminus the transporting domain KPRRPY (SEQ. No. 167). To stabilize its trimeric structure, the sequence of TRAIL has attached at its C-terminus the polycysteine linker (SEQ. No. 177). Furthermore, between the sequence of TRAIL and the sequence of the effector peptide there is located the sequence of cleavage sites recognized by proteases MMP (SEQ. No. 51) and uPA (SEQ. No. 52).

Structure of the fusion protein is shown schematically in FIG. 10 and its amino acid sequence and the DNA encoding sequence comprising codons optimized for expression in *E. coli* are, respectively, SEQ. No. 114 and SEQ. No. 143.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 49

The Fusion Protein of SEQ. No. 115

The protein of SEQ. No. 115 is a fusion protein having the length of 234 amino acids and the mass of 26.7 kDa, in which at the C-terminus of the sequence of TRAIL95-281 the short hybrid peptide Antp-TPR (SEQ. No 161) is attached as an effector peptide. Furthermore, between the sequence of TRAIL and the sequence of the effector peptide there is located the sequence of cleavage so sites recognized by proteases MMP (SEQ. No. 51) and uPA (SEQ. No. 52), additionally separated from the TRAIL sequence by polycysteine linker (SEQ. No. 177) to stabilize its trimeric structure, followed by two glycine residues.

Structure of the fusion protein is shown schematically in FIG. 10 and its amino acid sequence and the DNA encoding sequence comprising codons optimized for expression in *E. coli* are, respectively, SEQ. No. 115 and SEQ. No. 144.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 50

The Fusion Protein of SEQ. No. 116

The protein of SEQ. No. 116 is a fusion protein having the length of 216 amino acids and the mass of 24.3 kDa, in which at the N-terminus of the sequence of TRAIL120-281 peptide inhibitor of the SH2 domain of Stat3 protein (SEQ. No 162) is attached as an effector peptide. Additionally, to stabilize its trimeric structure, at the N-terminus of the sequence of TRAIL there is attached the polycysteine linker (SEQ. No. 179), the linker being flanked at its N- and C-terminus by three glycine residues and GSG motif, respectively. Furthermore, between the sequence of the effector peptide and the sequence of TRAIL there is located the sequence of cleavage sites recognized by proteases uPA (SEQ. No. 52) and MMP (SEQ. No. 51).

Structure of the fusion protein is shown schematically in FIG. 10 and its amino acid sequence and the DNA encoding sequence comprising codons optimized for expression in *E. coli* are, respectively, SEQ. No. 116 and SEQ. No. 145.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 51

The Fusion Protein of SEQ. No. 117

The protein of SEQ. No. 117 is a fusion protein having the length of 194 amino acids and the mass of 22.8 kDa, in which at the N-terminus of the sequence of TRAIL121-281 the peptide derived from BH3 domain of Bak protein (SEQ. No 163) is attached as an effector peptide. The sequence of the effector peptide has attached at its C-terminus the poly-arginine transporting domain consisting of 7 Arg residues. Furthermore, between the sequence of the effector peptide and the sequence of TRAIL there is located the sequence of cleavage sites recognized by proteases uPA (SEQ. No. 52) and MMP (SEQ. No. 51).

Structure of the fusion protein is shown schematically in FIG. 10 and its amino acid sequence and the DNA encoding sequence comprising codons optimized for expression in *E. coli* are, respectively, SEQ. No. 117 and SEQ. No. 146.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 52

The Fusion Protein of SEQ. No. 118

The protein of SEQ. No. 118 is a fusion protein having the length of 257 amino acids and the mass of 30 kDa, in which at the N-terminus of the sequence of TRAIL121-281 the peptide derived from BH3 domain of Bad protein (SEQ. No 164) is attached as an effector peptide. The sequence of the effector peptide has attached at its C-terminus the poly-arginine transporting domain consisting of 8 Arg residues. Between the sequence of the effector peptide so and the sequence of TRAIL there is located the sequence of cleavage sites recognized by proteases uPA (SEQ. No. 52) and MMP (SEQ. No. 51). At the C-terminus of the sequence of TRAIL121-281 there is the flexible linker GGSHG (SEQ. No. 182), followed by the sequence of the cleavage site recognized by thrombin protease (SEQ. No. 174) and, as a C-terminal part of the whole construct, the sequence of TRAIL95-121.

Figure 11:
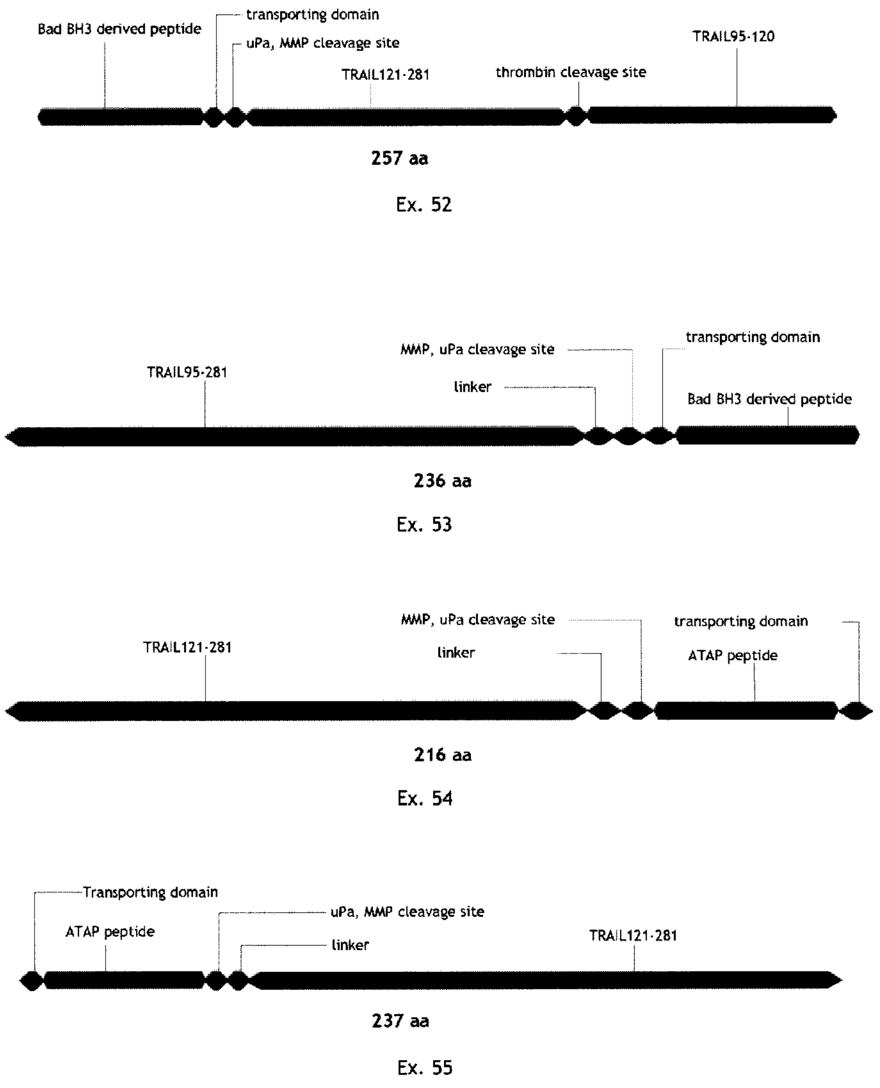
FIG. 11 presents a schematic structure of fusion proteins of the invention according Ex. 52, Ex. 53, Ex. 54, and Ex. 55.

Structure of the fusion protein is shown schematically in FIG. 11 and its amino acid sequence and the DNA encoding sequence comprising codons optimized for expression in *E. coli* are, respectively, SEQ. No. 118 and SEQ. No. 147.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 53

The Fusion Protein of SEQ. No. 119

The protein of SEQ. No. 119 is a fusion protein having the length of 236 amino acids and the mass of 27.5 kDa, in which at the C-terminus of the sequence of TRAIL95-281 the peptide derived from BH3 domain of Bad protein (SEQ. No 164) is attached as an effector peptide. The sequence of the effector peptide has attached at its N-terminus the poly-arginine transporting domain consisting of 7 Arg residues. Furthermore, between the sequence of TRAIL and the sequence of the effector peptide there is located the sequence of cleavage sites recognized by proteases MMP (SEQ. No. 51) and uPA (SEQ. No. 52), C-terminus of the sequence of TRAIL95-281 being additionally separated from the sequence of cleavage sites by the linker consisting of GGS residues.

Structure of the fusion protein is shown schematically in FIG. 11 and its amino acid sequence and the DNA encoding sequence comprising codons optimized for expression in *E. coli* are, respectively, SEQ. No. 119 and SEQ. No. 148.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 54

The Fusion Protein of SEQ. No. 120

The protein of SEQ. No. 120 is a fusion protein having the length of 216 amino acids and the mass of 24.7 kDa, in which at the C-terminus of the sequence of TRAIL121-281 the ATAP peptide from Bfl1 protein (SEQ. No 165) is attached as an effector peptide. The sequence of the effector peptide has attached at its N-terminus the membrane transporting domain KPRRPYR (SEQ. No. 181). Furthermore, between the sequence of TRAIL and the sequence of the effector peptide there is located the sequence of cleavage sites recognized by proteases MMP (SEQ. No. 51) and uPA (SEQ. No. 52), additionally separated from the sequence of TRAIL by flexible glycine-serine linker GGGGSGGGG (SEQ. No. 180).

Structure of the fusion protein is shown schematically in FIG. 11 and its amino acid sequence and the DNA encoding sequence comprising codons optimized for expression in *E. coli* are, respectively, SEQ. No. 120 and SEQ. No. 149.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

EXAMPLE 55

The Fusion Protein of SEQ. No. 121

The protein of SEQ. No. 120 is a fusion protein having the length of 237 amino acids and the mass of 27 kDa, in which at the N-terminus of the sequence of TRAIL121-281 the ATAP peptide from Bfl1 protein (SEQ. No 165) is attached as an effector peptide. The sequence of the effector peptide has attached at its N-terminus the mitochondrial targeting sequence (SEQ. No. 166). Furthermore, between the sequence of the effector peptide and the sequence of TRAIL there is located the sequence of cleavage sites recognized by proteases uPA (SEQ. No. 52) and MMP (SEQ. No. 51), additionally separated from the sequence of TRAIL by the flexible glycine-serine linker GGSGG (SEQ. No. 60).

Structure of the fusion protein is shown schematically in FIG. 11 and its amino acid sequence and the DNA encoding sequence comprising codons optimized for expression in *E. coli* are, respectively, SEQ. No. 121 and SEQ. No. 150.

The amino acid sequence of the structure described above was used as a template to generate its coding DNA sequence. A plasmid containing the coding sequence of DNA was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

Examination of the Anti-Tumour Activity of the Fusion Proteins

Examination of the anti-tumour activity of the fusion proteins was carried out in vitro in a cytotoxicity assay on tumour cell lines and in vivo in mice. For comparison purposes, the hTRAIL114-281 protein (hereinafter also designated as simply TRAIL) was used.

1. Tests on Cell Lines In Vitro

Cell Lines

The cells of human colorectal cancer Colo205 (ATCC #CCL-222), small cell lung cancer A549 (ATCC #CCL-185), pancreatic cancer BxPC3 (ATCC #CRL-1687), prostate cancer DU145 (ATCC #HTB-81) and PC3 (ATCC #CRL-1435), and human large cell lung cancer NCI-H460-Luc2 (Caliper #124316) were maintained in RPMI 1640 medium (Hyclone, Logan, Utah, USA) supplemented with 10% fetal calf serum. Human ovarian cancer cells OVCAR-3 (ATCC #HTB-161) were maintained in RPMI 1640 medium (Hyclone, Logan, Utah, USA) supplemented with 20% fetal calf serum and 0.01 mg/ml insulin. Bladder cancer cells UM-UC-3 (ATCC #CRL-1749), lung cancer cells SK-MES-1 (ATCC #HTB-58), breast cancer cells MCF-7 (ATCC #HTB-22), HT1080 connective tissue cancer cells (ATCC #CCL-121), liver hepatoma HepG2 cells (ATCC #HB-8065) were maintained in MEM culture medium (Hyclone, Logan, Utah, USA) supplemented with 10% fetal calf serum (Hyclone, Logan, Utah, USA). Connective tissue tumour cells HT1080 were maintained also during the experiment in the conditioned medium, harvested from 2-day normal culture of these cells. The cells of human colorectal cancer HCT-116 (ATCC #CCL-247) and HT-29 (HTB-38), ovarian cancer SK-OV-3 (ATCC #HTB-77), uterus cancer MES-SA (ATCC #CRL-1976) and its clone resistant to doxorubicin MES-SA/Dx5 (ATCC #CRL-1977) were maintained in McCoy's medium (Hyclone, Logan, Utah, USA) supplemented with 10% fetal calf serum. Bladder cancer cells SW780 (ATCC #CRL-2169), breast cancer cells MDA-MB-231 (ATCC #HTB-26) and human pancreatic carcinoma epithelial-like cell line PANC-1, CLS (Cell Lines Service #300228 were maintained in DMEM (Hyclone, Logan, Utah, USA) supplemented with 10% fetal calf serum. HUVEC cells from the umbilical vein (ATCC #CRL-1730) were maintained in M199 medium (Hyclone, Logan, Utah, USA) supplemented with 20% fetal calf serum, growth factors 0.02 mg/ml ECGS (Sigma), 0.1 mg/ml heparin (Sigma), these cells were grown on a medium coated with 0.1% gelatin. MCF10A breast cells (ATCC #CRL-10317) were maintained in DMEM: F12 (1:1) (Sigma, USA) supplemented with 5% horse serum, 0.5 mg/ml hydrocortisone, 10 μg/ml insulin, 20 ng/ml growth factor EGF (all Sigma, USA). All media were additionally supplemented with 2 mM L-glutamine and antibiotics (100 U/ml penicillin and 100 mg/ml streptomycin (Hyclone, Logan, Utah, USA)). Cells were maintained at 37° C. in 5% $CO_2$/air in the case of growth media RPMI, MEM, McCoy and DMEM: F12, and in 10% $CO_2$/air in the case of DMEM. Cells were routinely checked for the presence of *Mycoplasma* by PCR technique using the kit Venor®GeM *Mycoplasma* PCR Detection Kit (Minerva Biolabs, Berlin, Germany).

MTT Cytotoxicity Test

MTT assay is a calorimetric assay used to measure cell proliferation, viability and cytotoxicity. It consists in decomposition of a yellow tetrazolium salt MTT (4,5-dimethyl-2-thiazolyl)-2,5-diphenyltetrazolium bromide) to the water-insoluble purple dye formazan by the enzyme succinate-tetrazolium reductase present in the mitochondria. MTT reduction occurs only in living cells. Data analysis consists in determining the $IC_{50}$ concentration of the protein (in ng/ml), at which the 50% reduction in the number of cells occurs in the population treated compared with the control cells. Results were analyzed using GraphPad Prism 5.0.

The test was performed according to the literature descriptions (Cells, J E, (1998). Cell Biology, a Laboratory Handbook, second edition, Academic Press, San Diego; Yang, Y., Koh, L W, Tsai, J H., (2004); Involvement of viral and chemical factors with oral cancer in Taiwan, Jpn J Clin Oncol, 34 (4), 176-183).

Cell culture medium was diluted to a defined density ($10^4$-$10^5$ cells per 100 μl). Then 100 μl of appropriately diluted cell suspension was applied to a 96-well plate in triplicates. Thus prepared cells were incubated for 24 h at 37° C. in 5% or 10% $CO_2$, depending on the medium used, then to the cells (in 100 μl of medium) was added further 100 μl of the medium containing various concentrations of tested proteins. Cells were incubated with tested proteins over the next 72 hours which is equivalent to 3-4 times of a cell division, after which the medium with the test protein was added with 20 ml of working solution of MIT [5 mg/ml] and incubated for 3 h at 37° C. in 5% $CO_2$. Then the medium with a solution of MTT was removed, and formazan crystals were dissolved by adding 100 μl of DMSO. After mixing, the absorbance was measured at 570 nm (reference filter 690 nm).

The results of in vitro cytotoxicity tests are summarized in Tables 1, 1a, 1b and Table 2 as $IC_{50}$ values (ng/ml), which correspond to a protein concentration at which the cytotoxic effect of fusion proteins is observed at the level of 50% with respect to control cells incubated with solvent only. Each experiment represents the average value of at least two independent experiments conducted in triplicates. As a criterion of lack of activity of protein preparations the $IC_{50}$ limit of 2000 ng/ml was adopted. Fusion proteins with an $IC_{50}$ value above 2000 were considered inactive.

Cells for this test were selected so as to include the tumour cell lines naturally resistant to TRAIL protein (the criterion of natural resistance to TRAIL: $IC_{50}$ for TRAIL protein >2000), tumour cell lines sensitive to TRAIL protein and resistant to doxorubicin line MES-SA/DX5 as a cancer line resistant to conventional anticancer medicaments.

Undifferentiated HUVEC cell line was used as a healthy control cell line for assessment of the impact/toxicity of the fusion proteins on non-cancer cells.

The results obtained confirm the possibility of overcoming the resistance of the cell lines to TRAIL by administration of certain fusion proteins of the invention to cells naturally resistant to TRAIL. When administering fusion proteins of the invention into the cells sensitive to TRAIL, in some cases a clear and strong potentiation of the potency of TRAIL action was observed, manifesting in reduced $IC_{50}$ values of the fusion protein compared with the $IC_{50}$ for the TRAIL alone. Furthermore, cytotoxic activity of the fusion protein of the invention was obtained on the cells resistant to classical anticancer medicament doxorubicin, in some cases being stronger than activity of TRAIL.

The $IC_{50}$ values above 2000 obtained for the non-cancer cell lines show the absence of toxic effects associated with the use of proteins of the invention for healthy cells, which indicates potential low systemic toxicity of the protein.

TABLE 1

Cytotoxic activity of the fusion proteins of the invention and comparative proteins

| | Continuous incubation of preparations with cells over 72 h (test MTT, ng/ml) | | | | | | | | | | | |
|---|---|---|---|---|---|---|---|---|---|---|---|---|
| | MES-SA | | MES-SA/Dx5 | | HCT116 | | SK-MES-1 | | A549 | | MCF10A | |
| Protein | $IC_{50}$ | ±SD | $IC_{50}$ | ±SD | $IC_{50}$ | ±SD | $IC_{50}$ | ±SD | $IC_{50}$ | ±SD | $IC_{50}$ | ±SD |
| TRAIL 114-281 | >2000 | | 32.2 | 2.40 | 173 | 31.3 | 12.2 | 2.33 | >2000 | | >2000 | |
| Ex. 1 | 6.98 | 1.01 | 7.05 | 0.63 | 39.2 | 11.00 | 2.79 | 0.70 | >2000 | | 386 | 52.5 |
| Ex. 2 | 3.19 | 0.41 | 2.62 | 1.61 | 35.1 | 23.70 | 6.43 | 1.22 | >2000 | | >2000 | |
| Ex. 5 | 646 | 166.9 | 378 | 94.3 | 757 | 446.3 | 1114 | 108.2 | 719 | 91.7 | 912 | 2.4 |
| Ex. 9 | >2000 | | 1720 | 312.7 | >2000 | | 791.9 | 95.8 | >2000 | | >2000 | |
| Ex. 14 | 8.99 | 8.73 | 0.53 | 0.265 | 7.73 | 5.45 | 0.45 | 0.091 | >2000 | | >2000 | |

TABLE 1-continued

Cytotoxic activity of the fusion proteins of the invention and comparative proteins

| | Continuous incubation of preparations with cells over 72 h (test MTT, ng/ml) | | | | | | | | | | | |
|---|---|---|---|---|---|---|---|---|---|---|---|---|
| | MES-SA | | MES-SA/Dx5 | | HCT116 | | SK-MES-1 | | A549 | | MCF10A | |
| Protein | $IC_{50}$ | ±SD | $IC_{50}$ | ±SD | $IC_{50}$ | ±SD | $IC_{50}$ | ±SD | $IC_{50}$ | ±SD | $IC_{50}$ | ±SD |
| Ex. 18 | 312 | 110.6 | 326 | 56.1 | 937 | 144.6 | 184 | 30.5 | >2000 | | >2000 | |
| Ex. 19 | 24.9 | 21.2 | 19.9 | 1.98 | 23.9 | 2.31 | 87.6 | 32.4 | 87.2 | 45.8 | 83.1 | 19.33 |
| Ex. 20 | 259 | 60.0 | 172 | 20.9 | 223 | 110.4 | 123 | 25.6 | 296 | 3.4 | 282 | 39.9 |
| Ex. 24 (not of the invention) | >2000 | | 1760 | 367.7 | 85.6 | 19.96 | 36.8 | 7.44 | >2000 | | >2000 | |
| Ex. 25 (not of the invention) | >2000 | | 157 | 40.0 | 991 | 119.0 | 117.4 | 4.24 | >2000 | | >2000 | |
| Ex. 26 (not of the invention) | >2000 | | >2000 | | 1895 | 70.0 | 245 | 19.2 | >2000 | | >2000 | |

TABLE 1a

Cytotoxic activity of the fusion proteins of the invention

| | Continuous incubation of preparations with cells over 72 h (test MTT, ng/ml) | | | | | | | | | | | |
|---|---|---|---|---|---|---|---|---|---|---|---|---|
| | A549 | | HCT116 | | MCF10A | | MES-SA | | MES-SA/Dx5 | | SK-MES-1 | |
| Protein | $IC_{50}$ | ±SD | $IC_{50}$ | ±SD | $IC_{50}$ | ±SD | $IC_{50}$ | ±SD | $IC_{50}$ | ±SD | $IC_{50}$ | ±SD |
| TRAIL 95-281 | 10000 | | 7558 | | 10000 | | 10000 | | 29.15 | 12.66 | 33.60 | |
| Ex. 16 | 2632.50 | 219.91 | 132.65 | 37.69 | 1890.00 | 894.03 | 65.63 | 4.41 | 32.24 | 7.86 | 20.31 | 2632.50 |
| Ex. 23 | 10000 | | 223.55 | 105.29 | 10000 | | 1280.00 | 304.06 | 292.50 | 86.97 | 82.46 | 1.48 |
| Ex. 42 | 31.70 | 11.74 | 15.32 | 12.85 | 53.33 | 12.40 | 5.18 | 2.20 | 0.40 | 0.10 | 2.53 | 2.15 |
| Ex. 36 | 142.05 | 32.46 | 5.66 | 2.26 | 79.16 | 3.33 | 2392.50 | 2.12 | 0.58 | 0.10 | 3.95 | |
| Ex. 3 | 3.10 | | 9.43 | | 4573 | | 57.14 | | 10.67 | | 6.83 | |
| Ex. 35 | 889.55 | 276.41 | 14.10 | | 1273.50 | | 57.14 | | 1.18 | 0.82 | 3.93 | 0.32 |
| Ex. 51 TRP15 | 307.95 | 72.05 | 1.29 | 1.41 | 4.97 | 1.50 | 0.64 | 0.34 | 0.08 | 0.11 | 0.62 | |

TABLE 1b

Cytotoxic activity of the fusion proteins of the invention

| | Continuous incubation of preparations with cells over 72 h (test MTT, ng/ml) | | | | | | | | | |
|---|---|---|---|---|---|---|---|---|---|---|
| | HT29 | | H460 | | PLC/PRF/5 | | HepG2 | | PANC1 | |
| Protein | $IC_{50}$ | ±SD | $IC_{50}$ | ±SD | $IC_{50}$ | ±SD | $IC_{50}$ | ±SD | $IC_{50}$ | ±SD |
| TRAIL 95-281 | 10000 | | 9000 | | 10000 | | 10000 | | 10000 | |
| Ex. 3 | 108 | | 2.852 | 3.10 | | | | | | |
| Ex. 35. | 3289.50 | | 900.15 | | | | | | | |
| Exp. 51 | | | | | 9.66 | | 10.49 | | 22.91 | |

2. Analysis of Cytotoxic Activity of Selected Protein Preparations Against Extended Panel of Tumour Cell Lines Table 2 presents the results of cytotoxic activity in vitro for selected fusion proteins of the invention against a broad panel of tumour cells from different organs, corresponding to the broad range of most common cancers. Obtained $IC_{50}$ values confirm high cytotoxic activity of fusion proteins and thus their potential usefulness in the treatment of cancer.

TABLE 2

Analysis of cytotoxic activity of selected protein preparations against broad panel of tumour cell lines

| | Continuous incubation of preparations with cells over 72 h (test MTT, ng/ml) | | | | | | | |
|---|---|---|---|---|---|---|---|---|
| | TRAIL 114-281 | | Ex. 1 | | Ex. 2 | | Ex. 14 | |
| Cell line | $IC_{50}$ | ±SD | $IC_{50}$ | ±SD | $IC_{50}$ | ±SD | $IC_{50}$ | ±SD |
| UM-UC-3 | 39.05 | 5.70 | 0.44 | 0.44 | 0.55 | 0.21 | 1.72 | 0.97 |
| HCT116 | 109.1 | 24.45 | 39.20 | 11 | 11.13 | 0.69 | 3.03 | 0.42 |
| Colo205 | 7.32 | 1.46 | 2.26 | 0.30 | 1.06 | 0.06 | 0.47 | 0.09 |

TABLE 2-continued

Analysis of cytotoxic activity of selected protein preparations against broad panel of tumour cell lines

| | Continuous incubation of preparations with cells over 72 h (test MTT, ng/ml) | | | | | | | |
|---|---|---|---|---|---|---|---|---|
| | TRAIL 114-281 | | Ex. 1 | | Ex. 2 | | Ex. 14 | |
| Cell line | $IC_{50}$ | ±SD | $IC_{50}$ | ±SD | $IC_{50}$ | ±SD | $IC_{50}$ | ±SD |
| SW780 | 25.53 | 5.10 | 3.86 | 1.39 | 0.99 | 0.15 | 0.18 | 0.03 |
| A549 | >2000 | | >2000 | | >2000 | | 485.3 | 55.51 |
| MDA-MB-231 | 81.18 | 3.78 | 11.66 | 2.06 | 23.80 | | 7.89 | 2.81 |
| MES-SA/Dx5 | 495.6 | 209.19 | 7.20 | 0.84 | 17.58 | 4.7 | 0.68 | 0.12 |
| MES-SA | >2000 | | 6.99 | 1.01 | 3.40 | | 1.80 | 0.49 |
| OVCAR-3 | 447.9 | 4.60 | 1.72 | 0.84 | 1.25 | 0.48 | 1.61 | 0.42 |
| SK-MES-1 | 10.52 | 5.49 | 3.29 | 0.70 | 5.44 | 0.36 | 0.44 | 0.13 |
| BxPC-3 | 13.20 | 1.56 | 3.89 | 1.74 | 1.24 | 0.54 | 1.55 | 0.48 |
| DU145 | >2000 | | 10.76 | 1.63 | 137.8 | 120.3 | 5.89 | 2.3 |
| HUVEC | >2000 | | >2000 | | >2000 | | >2000 | |

3. Antitumour Effectiveness of Fusion Proteins In Vivo on Xenografts

Antitumour activity of protein preparations was tested in a mouse model of human colon cancer Colo205, human large cell lung cancer NCI-H460-Luc2, human lung cancer A549, and human pancreatic cancer PANC-1.

Cells

Colo205 cells (ATCC #CCL-222) were maintained in RPMI 1640 medium (Hyclone, Logan, Utah, USA) mixed in the ratio of 1:1 with Opti-MEM ((Invitrogen, Cat. 22600-134) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $28.57\times10^6$ cells/ml. Then to the cells Matrigel (BD Biocsciences, Cat. 354 248) was added to the final cells concentration $25\times10^6$ cells/ml.

H460-Luc2 cells were maintained in RPMI 1640 medium (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $50\times10^6$ cells/ml.

A549 cells were maintained in RPMI 1640 medium (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium).

Human pancreatic cancer PANC-1 cells were maintained in DMEM medium (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium).

Mice

Examination of antitumor activity of proteins of the invention was conducted on 7-9 week-old NOD SCID mice obtained from Harlan UK Ltd., Shaws Farm, Bicester, U K. In the case of A549, NCI-H460-Luc2 and PANC-1 cells the examination of antitumor activity of the proteins of the invention was conducted on 4-5 week old Crl:SHO-Prkdc$^{scid}$Hr$^{hr}$ mice obtained from Charles River Germany. Mice were kept under specific pathogen-free conditions with free access to food and demineralised water (ad libitum). All experiments on animals were carried in accordance with the guidelines: "Interdisciplinary Principles and Guidelines for the Use of Animals in Research, Marketing and Education" issued by the New York Academy of Sciences' Ad Hoc Committee on Animal Research and were approved by the IV Local Ethics Committee on Animal Experimentation in Warsaw (No. 71/2009).

The Course and Evaluation of the Experiment

On day 0 mice were grafted subcutaneously (sc) in the right side with $5\times10^6$ of Colo205 cells suspended in 0.15 ml HBSS buffer and 0.05 ml of Matrigel by means of a syringe with a 0.5×25 mm needle (Bogmark). When tumours reached the size of ~90-140 $mm^3$ (day 11), mice were randomized to obtain the average size of tumours in the group of ~115 $mm^3$ and assigned to treatment groups. The treatment groups were administered with the preparations of fusion proteins of the invention and TRAIL114-281 as a comparison. The preparations were administered intraperitoneally (ip) daily for ten days (qd×10) on days 11-20. When a therapeutic group reached the average tumour size of ~2000 $mm^3$, the mice were sacrificed through disruption of the spinal cord. The control group received TRAIL114-281.

In the case of H460, on day 0 mice were grafted subcutaneously (sc) in the right side with $5\times10^6$ of NCI-H460-Luc2 cells suspended in 0.1 ml HBSS buffer by means of a syringe with a needle 0.5×25 mm (Bogmark). When tumours reached the size of ~100-120 $mm^3$ (day 11), mice were randomized and assigned to treatment groups. The treatment groups were administered with the preparations of fusion proteins of the invention and TRAIL114-281 as a comparison. The preparations were administered intravenously (i.v.) 6 times daily every second day. On the 29$^{th}$ day of experiment the mice were sacrificed through disruption of the spinal cord. The control group received TRAIL114-281.

In the case of 4549, on day 0 mice were grafted subcutaneously (sc) in the right side with $7\times10^6$ of A549 cells suspended in 0.1 ml of mixture HBSS buffer: Martigel in a ratio 3:1 by means of a syringe with a needle 0.5×25 mm (Bogmark). When tumours reached the size of ~100-120 $mm^3$ (day 17), mice were randomized and assigned to treatment groups. The treatment groups were administered with the preparations of fusion proteins of the invention and TRAIL114-281 as a comparison. The preparations were administered intravenously (i.v.) 6 times once daily every second day. In the $34^{th}$ day of experiment the mice were sacrificed through disruption of the spinal cord. The control group received TRAIL114-281.

In the case of PANC-1, on day 0 mice were grafted subcutaneously (sc) in the right side with 7×106 of PANC-1 cells suspended in 0.1 ml of mixture HBSS buffer: Martigel in a ratio 3:1 by means of a syringe with a needle 0.5×25 mm (Bogmark). When tumours reached the size of ~95 mm3 (day 27), mice were randomized and assigned to treatment groups. The treatment groups were administered with the preparations of fusion proteins of the invention and TRAIL114-281 as a comparison. The preparations were administered intravenously (i.v.) 6 times once daily every second day. In the 43th day of experiment the mice were sacrificed through disruption of the spinal cord. The control group received TRAIL114-281.

Tumour size was measured using an electronic caliper, tumour volume was calculated using the formula: $(a^2 \times b)/2$, where a=shorter diagonal of the tumour (mm) and b=longer diagonal of the tumour (mm). Inhibition of tumour growth was calculated using the formula:

$$TGI[\%](\text{Tumour growth inhibition})=(WT/WC)\times 100-100\%$$

wherein WT refers to the average tumour volume in the treatment group, WC refers to the average tumour volume in the control group.

The experimental results are presented as a mean value±standard deviation (SD). All calculations and graphs were prepared using the program GraphPad Prism 5.0.

Figure 12:
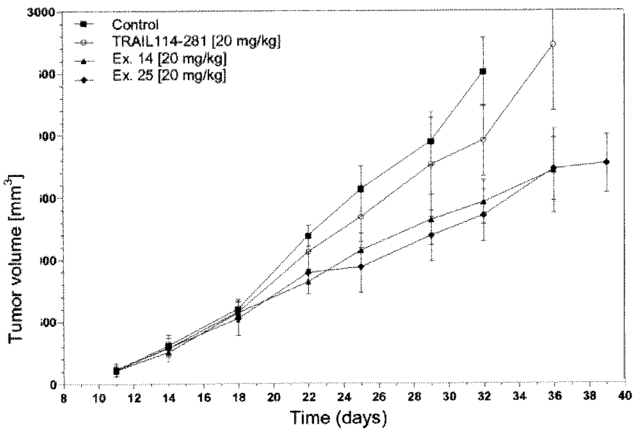
FIG. 12 presents tumour volume changes in time in SCID/NOD mice burdened with colon cancer Colo205, treated with fusion proteins of the invention compared to hTRAIL114-281.
Figure 13:
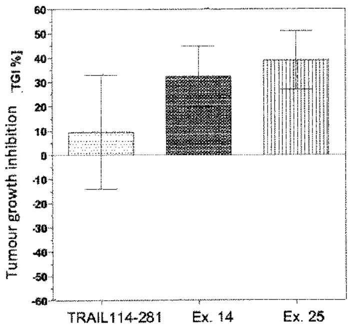
FIG. 13 presents the tumour growth inhibition values in mice burdened with colon cancer Colo205, treated with fusion proteins of the invention on the $29^{th}$ day of experiment compared to hTRAIL114-281.

The experimental results are shown in FIGS. 12 and 13 as a diagram of changes of the tumour volume in mice SCID/NOD burdened with Colo205 colon cancer treated with fusion proteins of the invention and comparatively with TRAIL114-281. The results of experiments presented in the graphs in FIGS. 12 and 13 show that administration of the fusion proteins of the invention of Example 1 and Example 14 caused tumour Colo205 growth inhibition, with TGI respectively 39% and 32% relative to the control on $29^{th}$ day of the experiment. For TRAIL114-281 used as the reference preparation, a slight inhibitory effect on tumour cell growth was obtained relative to the control, with TGI at the level of 9%. Thus, fusion proteins of the invention exert much stronger effect compared to TRAIL.

The tested fusion proteins did not cause significant side effects manifested by a decrease in body weight of mice (i.e. less than 10% of the baseline body weight). This shows low systemic toxicity of the protein.

Figure 14:
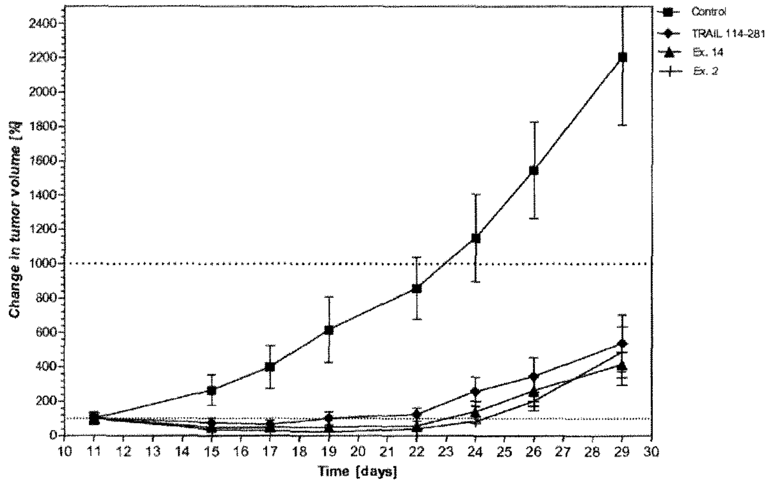
FIG. 14 presents tumour volume changes in time in mice Crl:SHO-PrkdcscidHrhr burdened with human lung cancer NCI-H460, treated with fusion proteins of the invention, compared with hTRAIL114-281.
Figure 15:
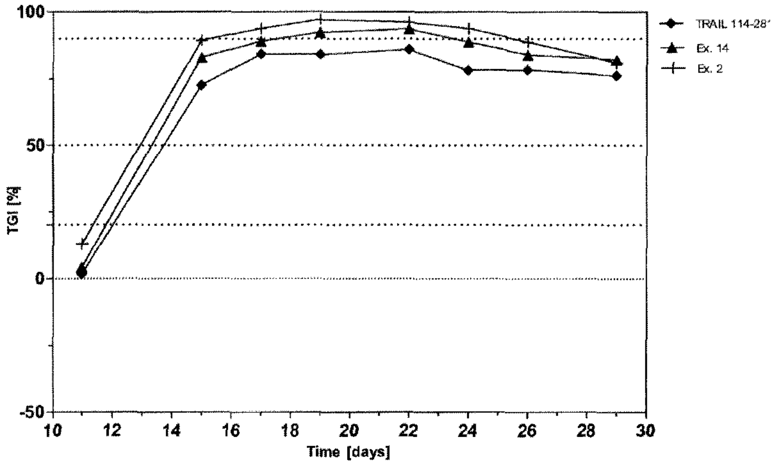
FIG. 15 presents the Tumour growth inhibition in mice burdened with human lung cancer NCI-H460, treated with fusion proteins of the invention on the 29th day of experiment, compared with hTRAIL114-281

The experimental results presented in FIGS. 14 and 15 show a diagram of changes of the tumour volume in mice Crl:SHO-PrkdcscidHrhr burdened with NCI-H460 human large cell lung cancer treated with fusion proteins of the invention and comparatively with TRAIL114-281. It can be seen that by administering fusion proteins of the invention of Example 14 and Example 2 NCI-H460 tumour growth inhibition was obtained, with TGI respectively 82% and 81% relative to the control on $29^{th}$ day of the experiment. For TRAIL114-281 used as the reference preparation, a slight inhibitory effect on tumour cell growth was obtained relative to the control, with TGI at the level of 75%. Thus, fusion proteins of the invention exert a much stronger effect against this cancer cells compared with TRAIL.

The tested fusion proteins did not cause significant side effects manifested by a decrease in body weight of mice (i.e. less than 10% of baseline body weight). This shows a low systemic toxicity of the protein.

Figure 16:
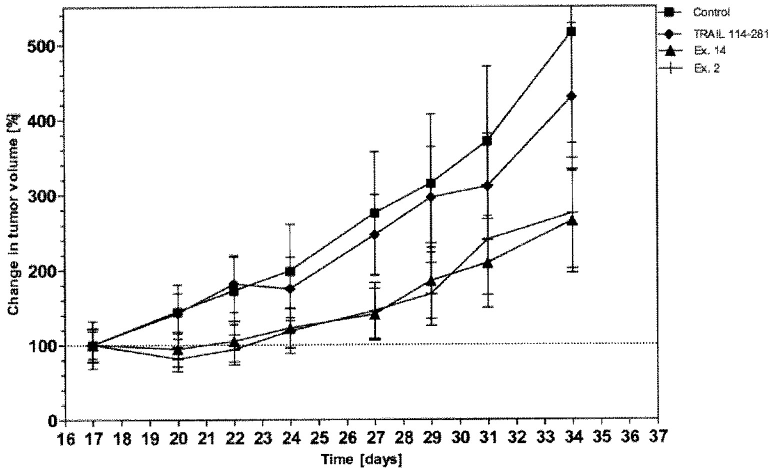
FIG. 16 presents tumour volume changes in time in mice Crl:SHO-PrkdcscidHrhr burdened with human small cell lung cancer A549, treated with fusion proteins of the invention, compared with hTRAIL114-281.
Figure 17:
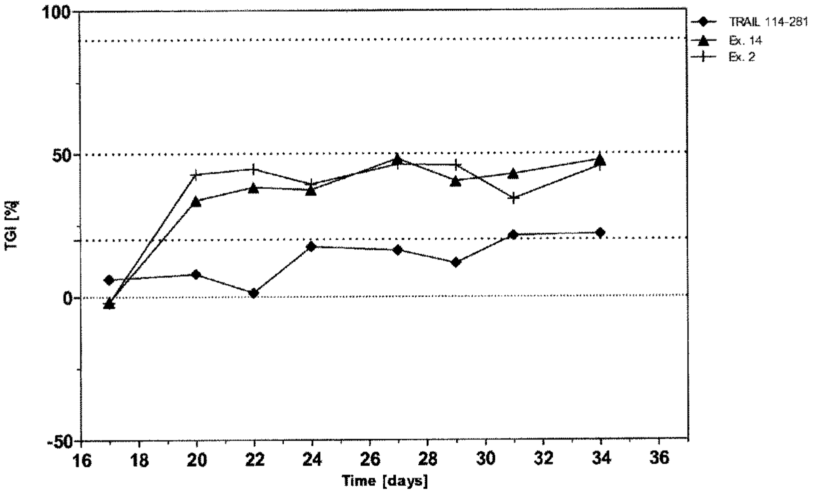
FIG. 17 presents the Tumour growth inhibition in mice burdened with human small cell lung cancer A549, treated with fusion proteins of the invention on the 34th day of experiment, compared with hTRAIL114-281

The experimental results presented in FIGS. 16 and 17 show a diagram of changes of the tumour volume in mice Crl:SHO-Prkdc$^{scid}$Hr$^{hr}$ burdened with A549 human lung cancer treated with fusion proteins of the invention and comparatively with TRAIL114-281. It can be seen that by administering fusion proteins of the invention of Example 14 and Example 24549 tumour growth inhibition was obtained, with TGI respectively 48% and 45.5% relative to the control on $29^{th}$ day of the experiment. For TRAIL114-281 used as the reference preparation, a slight inhibitory effect on tumour cell growth was obtained relative to the control, with TGI at the level of 20.7%. Thus, fusion proteins of the invention exert a much stronger effect compared with TRAIL.

Figure 18:
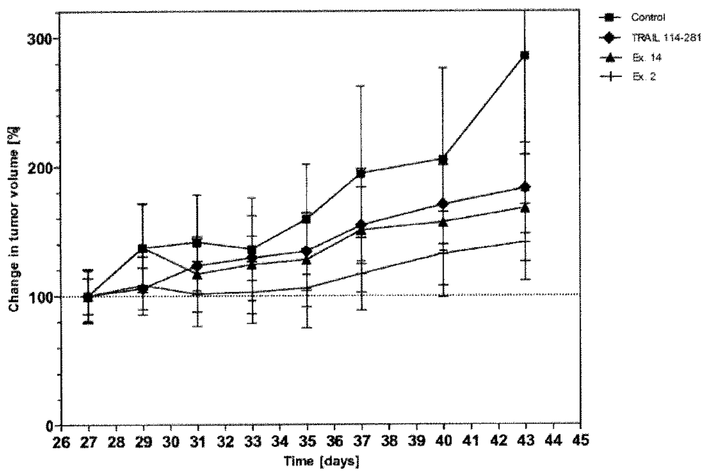
FIG. 18 presents tumour volume changes in time in mice Crl:SHO-PrkdcscidHrhr burdened with human pancreatic carcinoma, epithelial-like cell line PANC-1, treated with fusion proteins of the invention, compared with hTRAIL114-281.
Figure 19:
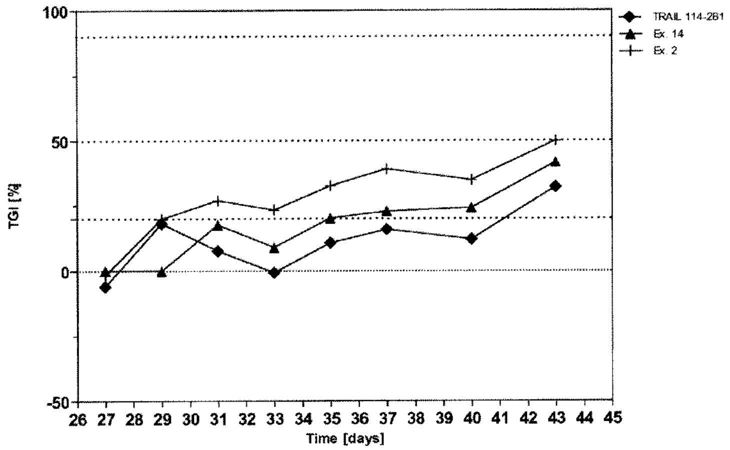
FIG. 19 presents the Tumour growth inhibition in mice burdened with human pancreatic carcinoma, epithelial-like cell line PANC-1, treated with fusion proteins of the invention on the 43th day of experiment, compared with hTRAIL114-281.

The experimental results presented in FIGS. 18 and 19 show a diagram of changes of the tumour volume in mice Crl:SHO-PrkdcscidHrhr burdened with PANC-1 human pancreatic carcinoma, epithelial-like cell treated with fusion proteins of the invention and comparatively with TRAIL114-281. It can be seen that by administering fusion proteins of the invention of Example 14 and Example 2 PANC-1 tumour growth inhibition was obtained, with TGI respectively 41.5% and 49.8% relative to the control on 43th day of the experiment. For TRAIL114-281 used as the reference preparation, a slight inhibitory effect on tumour cell growth was obtained relative to the control, with TGI at the level of 32%. Thus, fusion proteins of the invention exert a much stronger effect compared with TRAIL.

The tested fusion proteins did not cause significant side effects manifested by a decrease in body weight of mice (i.e. less than 10% of baseline body weight). This shows a low systemic toxicity of the protein.

Circular Dichroizm—Determination of Secondary Structures Content in the Preparations of Fusion Proteins of the Invention Quality of the structure the preparations of fusion proteins in terms of their structure was determined by analysis of the secondary structures using circular dichroism (CD). The CD method uses optical activity of the protein structures, manifested in rotating the plane of polarization of light and the appearance of elliptical polarization. CD spectrum of proteins in far ultraviolet (UV) provides precise data on the conformation of the main polypeptide chain.

Samples of the protein prepared in Ex. 1, Ex. 2, Ex. 14, Ex. 24, Ex. 51 and Ex. 42 after were formulation into a buffer consisting of 50 mM Tris-HCl pH 8.0, 100 mM NaCl, 10% glycerol, 0.1 mM $ZnCl_2$, 80 mM saccharose, 5 mM DTT were dialysed in the dialysis bags (Sigma-Aldrich) with cut off 12 kDa. Dialysis was performed while stirring against 100 fold excess (v/v) of buffer comparing to the protein preparations, for several hours at 4° C. After dialysis was completed, each preparation was centrifuged (25 000 rpm., 10 min., 4° C.), and the appropriate supernatants were collected. Protein concentration in the samples thus obtained was determined by Bradford method.

Measurement of the circular dichroism for proteins in the concentration range of 0.1-2.7 mg/ml was performed on Jasco J-710 spectropolarimeter, in a quartz cuvette with an optical way 0.2 mm or 1 mm. The measurement was performed under the flow of nitrogen of 7 l/min, which allowed to perform of the measurement in the wavelength range from 195 to 250 nm.

Parameters of the measurement: spectral resolution of −1 nm; half width of the light beam 1 nm; sensitivity 20 mdeg, the averaging time for one wavelength—8 s, scan speed 10 nm/min.

Figure 20:
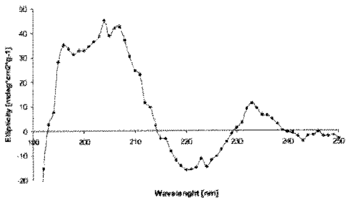
FIG. 20 shows circular dichroism spectra for fusion proteins of Ex. 1, Ex. 2, Ex. 14, Ex. 24, Ex. 51 and Ex. 42 and for rhTRAI114-281 expressed in specific ellipticity.
Figure 20:
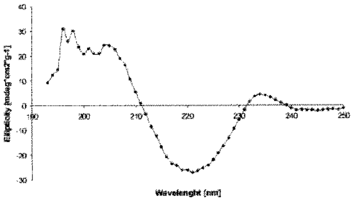
Figure 20:
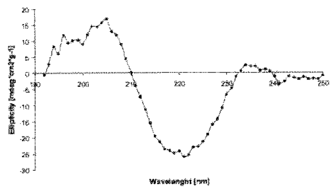
Figure 20:
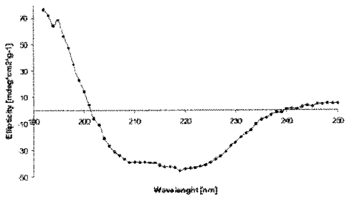
Figure 20:
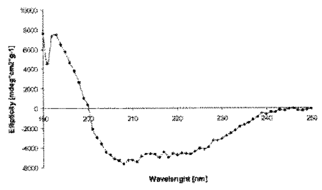
Figure 20:
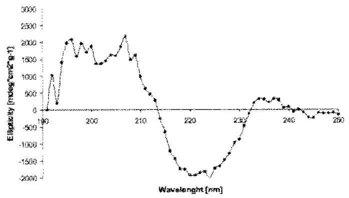
Figure 20:
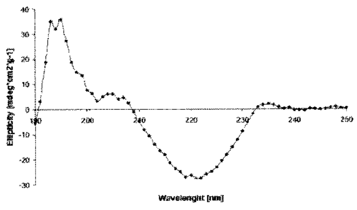

The results were presented as the average of three measurements. Circular dichroism spectra for proteins according to the Ex. 1, Ex. 2, Ex. 14, Ex. 24, Ex. 51 and Ex. 42 are presented in FIG. 20.

Obtained spectra were analyzed numerically in the range of 193-250 nm using CDPro pack. Points for which the voltage at the fotomultiplier exceeded 700 V were omitted, due to too low signal to noise ratio in this wavelength range. The data obtained served for calculations of particular secondary structures content in the analyzed proteins with use of CDPro programs package (Table 4).

TABLE 4

Content of secondary structures in the analyzed proteins

| Protein | NRMSD (Exp-Cal) | α-helix (%) | β-sheet (%) | Schift (%) | Disorder (%) |
|---|---|---|---|---|---|
| Ex. 24 | 0.720 | 4.1% | 46.7% | 26.4% | 22.8% |
| Ex. 42 | 0.100 | 18.4% | 28.7% | 22.0% | 30.8% |
| Ex. 1 | 0.105 | 20.3% | 27.4% | 22.9% | 29.3% |
| Ex. 2 | 0.035 | 14.8% | 32.2% | 21.3% | 31.6% |
| Ex. 51 | 0.302 | 4.5% | 38.6% | 22.5% | 34.4% |
| Ex. 14 | 0.220 | 3.5% | 39.0% | 21.1% | 36.3% |
| hrTRAIL* | | 1.94% | 50.97% | 7.74% | 39.35% |
| hrTRAIL114-281 | 0.389 | 4.9% | 33.7% | 23.1% | 38.3% |

*value obtained on the basis of crystalline structure 1D4V

Controls (rhTRAIL114-281) reveal a characteristic CD spectrum for the proteins with predominantly type β-sheet structures (sharply outlined ellipticity minimum at the wavelength 220 nm). This confirms the calculation of secondary structure components, which suggests a marginal number of α-helix elements. The obtained result is also consistent with data from the crystal structure of TRAIL protein, whereby the beta elements constitute more than half of its composition. In the case of hybrid proteins of Ex. 1 and Ex. 42, dichroism spectra are characterized by two minima at wavelengths 208 and 220 nm, which is characteristic for proteins with mixed secondary structure of alpha/beta type. This is probably due to attachment of a domain (e.g. BH3 from Bax) to TRAIL, which forms the alpha-helical structures, so that the mixed nature of secondary structures in the analyzed chimeric proteins can confirm their presence (for Ex. 42 due to poor quality of the spectrum it is less clear).

For preparations of Ex. 2, Ex. 51, Ex. 14 and Ex. 24 as well as for TRAIL protein, a significant content of beta-type structures was found. This is probably due to the fact that attached short peptides initially have the beta structure or are unstructuralized and therefore do not affect significantly their composition. In the case of protein of Ex. 2 a slight increase in the content of alpha structures was also observed. Similarly as with protein of Ex. 1, this may be due to the presence of BH3 domain, which creates similar forms or due to narrow range of wavelengths (high amount of noise in the far-UV excludes readings). The lack of sharply outlined range of 180-200 nm in the analyzed region of the spectrum can cause over-content of α-helix structures.

The invention claimed is:

1. A fusion protein comprising:

domain (a) which is a functional fragment of soluble human Tumor Necrosis Factor-Related Apoptosis Inducing Ligand (hTRAIL) protein sequence, wherein said fragment begins with an amino acid at a position not lower than hTRAIL95 and ends with the amino acid at position hTRAIL281 or a sequence having at least 70% homology thereto; and domain (b) which is a sequence of a pro-apoptotic effector peptide capable of effecting pro-apoptotic action via intrinsic apoptosis pathway, wherein the sequence of domain (b) is attached at the C-terminus of domain (a), at the N-terminus of domain (a), or is attached at both the C-terminus of domain (a) and at the N-terminus of domain (a).

2. The fusion protein according to claim 1, wherein the functional fragment of soluble hTRAIL protein sequence begins with an amino acid from the range hTRAIL95 to hTRAIL121, inclusive, and ends with the amino acid hTRAIL281.

3. The fusion protein according to claim 2, wherein domain (a) is selected from the group consisting of hTRAIL114-281 (SEQ ID NO: 27), hTRAIL119-281 (SEQ ID NO: 28), hTRAIL121-281 (SEQ ID NO: 29), hTRAIL116-281 and hTRAIL120-281.

4. The fusion protein according to claim 1, wherein domain (a) is the sequence hTRAIL95-281.

5. The fusion protein according to claim 1, wherein domain (b) is selected from the group consisting of:

(a) the fragment of BH3 domain of Bax protein of SEQ ID NO: 30;

(b) the fragment of Bid protein of SEQ ID NO: 31;

(c) ribonuclease A of SEQ ID NO: 32;

(d) cytochrome C of SEQ ID NO: 33;

(e) granzyme B of SEQ ID NO: 34;

(f) the fragment of Nur77 protein of SEQ ID NO: 35;

(g) BH3 domain of Bak protein of SEQ ID NO: 36;

(h) BH3 domain of PUMA/BBC3 protein of SEQ ID NO: 37;

(i) PUMA/BBC3 protein of SEQ ID NO: 38;

(j) the fragment of SMAC/Diablo protein of SEQ ID NO: 39;

(k) buforin A of SEQ ID NO: 40;

(l) onconase of SEQ ID NO: 41;

(m) the fragment of Mdm2 protein of SEQ ID NO: 42;

(n) the peptide binding to Mdm2 of SEQ ID NO: 43;

(o) a fragment of lunasin of SEQ ID NO: 44;
(p) BH3 domain of Bik protein of SEQ ID NO: 45;
(q) the peptide inhibitor of proteasome of SEQ ID NO: 46;
(r) the domain comprising proteasome binding UIM motifs of SEQ ID NO: 47;
(s) the azurin derived peptide of SEQ ID NO: 151;
(t) the full length azurine peptide of SEQ ID NO: 152;
(u) the peptide designed from aPP protein and BH3 domain of Bax protein of SEQ ID NO: 153;
(v) the peptide designed from aPP protein and BH3 domain of Bax protein of SEQ ID NO: 154;
(w) the Reticulon RTN1-C derived peptide of SEQ ID NO: 155;
(x) the full length human Reticulon 3 of SEQ ID NO: 156;
(y) the modified constitutively active caspase-3 of SEQ ID NO: 157;
(z) the SAC domain from Par-4 protein of SEQ ID NO: 158;
(z1) Noxa protein of SEQ ID NO: 159;
(z2) MTD/CKP fragment of Noxa protein of SEQ ID NO: 160;
(z3) the short hybrid peptide Antp-TPR of SEQ ID NO: 161;
(z4) the peptide inhibitor of the SH2 domain of Stat3 protein of SEQ ID NO: 162;
(z5) the peptide derived from BH3 domain of Bak protein of SEQ ID NO: 163;
(z6) the peptide derived from BH3 domain of Bad protein of SEQ ID NO: 164; and
(z7) the peptide ATAP from Bfl1 protein of SEQ ID NO: 165.

6. The fusion protein according to claim 1, that further comprises between domain (a) and domain (b) a domain (c) that comprises a protease cleavage site selected from a sequence recognized by metalloprotease MMP, a sequence recognized by urokinase uPA, a sequence recognized by furin, or combinations thereof.

7. The fusion protein according to claim 6, wherein the sequence recognized by metalloprotease MMP is SEQ ID NO: 51, SEQ ID NO: 171 or SEQ ID NO: 173, the sequence recognized by urokinase uPA is SEQ ID NO: 52, and the sequence recognized by furin is SEQ ID NO: 53 or SEQ ID NO: 172.

8. The fusion protein according to claim 6, wherein domain (c) is a combination of sequences recognized by metalloprotease MMP and urokinase uPA located next to each other.

9. The fusion protein according to claim 6, wherein domain (c) is a sequence recognized by furin.

10. The fusion protein according to claim 6, wherein a polyarginine sequence (d2) is located between domains (b) and (c).

11. The fusion protein according to claim 6, wherein a *Pseudomonas aeruginosa* translocation domain (d3) is located between domains (a) and (c).

12. The fusion protein according to claim 1, wherein domain (b) is additionally linked with a transporting domain (d), selected from the group consisting of:
(d1) a sequence for directing to the endoplasmic reticulum,
(d2) a polyarginine sequence for transporting through a cell membrane, comprising 6, 7, 8 or 9 Arg residues,
(d3) a *Pseudomonas aeruginosa* translocation domain selected from SEQ ID NO: 54 or SEQ ID NO: 176;
(d4) a membrane transporting domain,
(d5) a nuclear localization domain, and
(d6) a mitochondrial targeting domain,
and combinations thereof.

13. The fusion protein according to claim 12, wherein the sequence (d1) directing to endoplasmic reticulum is KEDL (SEQ ID NO: 55) or KDEL (SEQ ID NO: 56).

14. The fusion protein according to claim 12, wherein the sequence (d1) directing to endoplasmic reticulum is located at the C-terminus of the fusion protein.

15. The fusion protein according to claim 12, wherein the polyarginine sequence (d2) is located at the C-terminus of the fusion protein.

16. The fusion protein according to claim 1, which additionally comprises domain (e) of a glycine-serine flexible steric linker, wherein the glycine-serine linker is selected from the group consisting of GGSG (SEQ ID NO: 57), GGGS (SEQ ID NO: 58), GGGGS (SEQ ID NO: 59), GGSGG (SEQ ID NO: 60), GGGSGG (SEQ ID NO: 61), GGGSGGG (SEQ ID NO: 62), GGGSGGGS (SEQ ID NO: 63), GGGSGGGGS (SEQ ID NO: 64), ASGG (SEQ ID NO: 65), GGGSASGG (SEQ ID NO: 66), GGSHG (SEQ ID NO: 182), SGCGS (SEQ ID NO: 169), GGGGSGGGG (SEQ ID NO: 180), SGGCGGS (SEQ ID NO: 183) and AACAA (SEQ ID NO: 184).

17. The fusion protein according to claim 1, having the amino acid sequence selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16, SEQ ID NO: 17; SEQ ID NO: 18; SEQ ID NO: 19; SEQ ID NO: 20; SEQ ID NO: 21; SEQ ID NO: 22, SEQ ID NO: 23; SEQ ID NO: 24; SEQ ID NO: 25, SEQ ID NO: 26, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO 113, SEQ ID NO: 114, SEQ ID NO: 115, SEQ ID NO: 116, SEQ ID NO: 117, SEQ ID NO: 118, SEQ ID NO: 119, SEQ ID NO: 120, and SEQ ID NO: 121.

18. The fusion protein according to claim 1, that further comprises at the C-terminus of the fusion protein a protease cleavage site followed by the sequence hTRAIL95-121, such that the sequence of the protease cleavage site allows cleavage of the sequence hTRAIL95-121 from the fusion protein.

19. A pharmaceutical composition, comprising as an active ingredient the fusion protein as defined in claim 1 in combination with a pharmaceutically acceptable carrier.

20. A method of treatment of cancer in a mammal, comprising administration to the mammal in a need thereof an anti-cancer effective amount of the fusion protein as defined in claim 1 or a pharmaceutical composition comprising the fusion protein.

* * * * *